(12) United States Patent
Sinclair et al.

(10) Patent No.: US 8,846,724 B2
(45) Date of Patent: *Sep. 30, 2014

(54) COMPOSITIONS FOR TREATING OBESITY AND INSULIN RESISTANCE DISORDERS

(75) Inventors: David A. Sinclair, Chestnut Hill, MA (US); Maria Alexander-Bridges, West Newton, MA (US)

(73) Assignees: President and Fellows of Harvard College, Cambridge, MA (US); The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/192,011

(22) Filed: Jul. 27, 2011

(65) Prior Publication Data

US 2012/0029065 A1 Feb. 2, 2012

Related U.S. Application Data

(63) Continuation of application No. 11/174,000, filed on Jul. 1, 2005, now Pat. No. 8,017,634, which is a continuation-in-part of application No. 11/027,779, filed on Dec. 29, 2004, now abandoned.

(60) Provisional application No. 60/588,643, filed on Jul. 16, 2004, provisional application No. 60/533,712, filed on Dec. 29, 2003.

(51) Int. Cl.

| | | |
|---|---|---|
| A61K 31/44 | (2006.01) |
| A61K 31/35 | (2006.01) |
| A61K 31/155 | (2006.01) |
| A61K 31/12 | (2006.01) |
| A61K 31/05 | (2006.01) |
| A61K 31/7048 | (2006.01) |
| A61K 31/353 | (2006.01) |
| A61K 31/00 | (2006.01) |

(52) U.S. Cl.
CPC .............. A61K 31/12 (2013.01); A61K 31/05 (2013.01); A61K 31/7048 (2013.01); A61K 31/353 (2013.01); A61K 31/00 (2013.01); Y10S 514/866 (2013.01); Y10S 514/909 (2013.01)
USPC ........... 514/356; 514/456; 514/635; 514/866; 514/909

(58) Field of Classification Search
USPC ........................... 514/356, 456, 635, 866, 909
See application file for complete search history.

(56) References Cited

U.S. PATENT DOCUMENTS

| | | | |
|---|---|---|---|
| 3,174,901 A * | 3/1965 | Sterne ........................... 514/635 |
| 4,591,600 A | 5/1986 | Creuzet et al. |
| 4,598,089 A | 7/1986 | Hadvary et al. |
| 5,500,367 A | 3/1996 | Hain et al. |
| 5,689,046 A | 11/1997 | Schroder et al. |
| 5,689,047 A | 11/1997 | Hain et al. |
| 5,747,536 A | 5/1998 | Cavazza |
| 5,827,898 A | 10/1998 | Khandwala et al. |
| 5,874,399 A | 2/1999 | Samal |
| 5,874,444 A | 2/1999 | West |
| 5,945,106 A | 8/1999 | Sinnott |
| 5,985,647 A | 11/1999 | Schroder et al. |
| 6,008,260 A | 12/1999 | Pezzuto et al. |
| 6,020,129 A | 2/2000 | Schroder et al. |
| 6,022,901 A | 2/2000 | Goodman |
| 6,048,903 A | 4/2000 | Toppo |
| 6,063,820 A | 5/2000 | Cavazza |
| 6,063,988 A | 5/2000 | Hain et al. |
| 6,080,701 A | 6/2000 | Jeandet et al. |
| 6,124,125 A | 9/2000 | Kemp et al. |
| 6,132,740 A | 10/2000 | Hu |
| 6,147,121 A | 11/2000 | Breton et al. |
| 6,184,248 B1 | 2/2001 | Lee et al. |
| 6,190,716 B1 | 2/2001 | Galbreath, Jr. |
| 6,197,834 B1 | 3/2001 | Docherty |
| 6,211,247 B1 | 4/2001 | Goodman |
| 6,245,814 B1 | 6/2001 | Nag et al. |
| 6,264,995 B1 | 7/2001 | Newmark et al. |
| 6,270,780 B1 | 8/2001 | Carson et al. |
| 6,300,377 B1 | 10/2001 | Chopra |
| 6,319,523 B1 | 11/2001 | Zhou |
| 6,331,633 B1 | 12/2001 | Neogi et al. |
| 6,333,441 B1 | 12/2001 | Sato et al. |
| 6,355,692 B2 | 3/2002 | Docherty |
| 6,358,517 B1 | 3/2002 | Pillai et al. |
| 6,359,017 B1 | 3/2002 | Bruckner et al. |
| 6,361,815 B1 | 3/2002 | Zheng et al. |
| 6,368,617 B1 | 4/2002 | Hastings et al. |
| 6,387,416 B1 | 5/2002 | Newmark et al. |
| 6,410,596 B1 | 6/2002 | Hopp et al. |
| 6,414,037 B1 | 7/2002 | Pezzuto et al. |
| 6,416,806 B1 | 7/2002 | Zhou |

(Continued)

FOREIGN PATENT DOCUMENTS

| | | |
|---|---|---|
| CA | 2 544 781 A1 | 5/2005 |
| CA | 2 548 671 A1 | 7/2005 |

(Continued)

OTHER PUBLICATIONS

Doklady Akademi Nauk Respubliki Tadzhikistan, vol. 35, No. 4, pp. 186-189 (1992).*

(Continued)

*Primary Examiner* — Kevin E Weddington

(74) *Attorney, Agent, or Firm* — Wolf, Greenfield & Sacks, P.C.

(57) ABSTRACT

Provided herein are methods and compositions for modulating the activity or level of a sirtuin, thereby treating or preventing obesity or an insulin resistance disorder, such as diabetes in a subject. Exemplary methods comprise contacting a cell with a sirtuin activating compound or an inhibitory compound to thereby increase or decrease fat accumulation, respectively.

21 Claims, 48 Drawing Sheets

(56) References Cited

U.S. PATENT DOCUMENTS

| | | |
|---|---|---|
| 6,423,747 B1 | 7/2002 | Lanzendorfer et al. |
| 6,426,061 B1 | 7/2002 | Li et al. |
| 6,440,433 B1 | 8/2002 | Breton et al. |
| 6,448,450 B1 | 9/2002 | Nag et al. |
| 6,469,055 B2 | 10/2002 | Lee et al. |
| 6,475,530 B1 | 11/2002 | Kuhrts |
| 6,479,466 B1 | 11/2002 | Redfield et al. |
| 6,486,203 B1 | 11/2002 | Dannenberg |
| 6,500,451 B2 | 12/2002 | Adams |
| 6,515,020 B1 | 2/2003 | Cavazza |
| 6,537,969 B1 | 3/2003 | Blass |
| 6,541,522 B2 | 4/2003 | Inman et al. |
| 6,544,564 B1 | 4/2003 | Farley |
| 6,552,085 B2 | 4/2003 | Inman et al. |
| 6,552,213 B1 | 4/2003 | Deshpande et al. |
| 6,572,882 B1 | 6/2003 | Vercauteren et al. |
| 6,573,299 B1 | 6/2003 | Petrus |
| 6,576,660 B1 | 6/2003 | Liao et al. |
| 6,605,296 B1 | 8/2003 | Stuckler |
| 6,615,843 B2 | 9/2003 | Pera |
| 6,624,197 B1 | 9/2003 | Nag et al. |
| 6,638,543 B2 | 10/2003 | Kang et al. |
| 6,638,545 B1 | 10/2003 | Rombi |
| 6,656,925 B2 | 12/2003 | Petrus |
| 6,844,163 B1 | 1/2005 | Matsuzawa et al. |
| 7,119,110 B2 | 10/2006 | Bagchi et al. |
| 7,544,497 B2 | 6/2009 | Sinclair et al. |
| 7,977,049 B2 | 7/2011 | Sinclair et al. |
| 8,017,634 B2 | 9/2011 | Sinclair et al. |
| 8,242,171 B2 | 8/2012 | Sinclair et al. |
| 2001/0020043 A1 | 9/2001 | Docherty |
| 2001/0039296 A1 | 11/2001 | Bagchi et al. |
| 2001/0056071 A1 | 12/2001 | Pelliccia et al. |
| 2002/0002200 A1 | 1/2002 | Nag et al. |
| 2002/0009482 A1 | 1/2002 | Adams |
| 2002/0028852 A1 | 3/2002 | Ghai et al. |
| 2002/0051799 A1 | 5/2002 | Pruche et al. |
| 2002/0052407 A1 | 5/2002 | Lee et al. |
| 2002/0058701 A1 | 5/2002 | Inman et al. |
| 2002/0058707 A1 | 5/2002 | Hopp et al. |
| 2002/0091087 A1 | 7/2002 | Zhang et al. |
| 2002/0110604 A1 | 8/2002 | Babish et al. |
| 2002/0111383 A1 | 8/2002 | Hassen |
| 2002/0119952 A1 | 8/2002 | Petrus |
| 2002/0120008 A1 | 8/2002 | Benzer et al. |
| 2002/0142017 A1 | 10/2002 | Simonnet |
| 2002/0146424 A1 | 10/2002 | Benza et al. |
| 2002/0146472 A1 | 10/2002 | Chen et al. |
| 2002/0148478 A1 | 10/2002 | Pera |
| 2002/0155075 A1 | 10/2002 | Collington |
| 2002/0164385 A1 | 11/2002 | Dannenberg et al. |
| 2002/0173472 A1 | 11/2002 | Pezzuto et al. |
| 2002/0173549 A1 | 11/2002 | Wurtman et al. |
| 2002/0182196 A1 | 12/2002 | McCleary |
| 2002/0192310 A1 | 12/2002 | Bland et al. |
| 2003/0004142 A1 | 1/2003 | Prior et al. |
| 2003/0004143 A1 | 1/2003 | Prior et al. |
| 2003/0031693 A1 | 2/2003 | Breton et al. |
| 2003/0044474 A1 | 3/2003 | C. Tao et al. |
| 2003/0044946 A1 | 3/2003 | Longo |
| 2003/0054053 A1 | 3/2003 | Young et al. |
| 2003/0054357 A1 | 3/2003 | Young et al. |
| 2003/0055108 A1 | 3/2003 | Young |
| 2003/0055114 A1 | 3/2003 | Young |
| 2003/0064913 A1 | 4/2003 | Sonis |
| 2003/0078212 A1 | 4/2003 | Li et al. |
| 2003/0082116 A1 | 5/2003 | Badejo et al. |
| 2003/0082203 A1 | 5/2003 | Farley |
| 2003/0082597 A1 | 5/2003 | Cannon et al. |
| 2003/0082647 A1 | 5/2003 | Reenan et al. |
| 2003/0084912 A1 | 5/2003 | Pera |
| 2003/0086986 A1 | 5/2003 | Bruijn et al. |
| 2003/0118536 A1 | 6/2003 | Rosenbloom |
| 2003/0118617 A1 | 6/2003 | Soby et al. |
| 2003/0124101 A1 | 7/2003 | Gu et al. |
| 2003/0124161 A1 | 7/2003 | Biatry et al. |
| 2003/0129247 A1 | 7/2003 | Ju et al. |
| 2003/0133992 A1 | 7/2003 | Bagchi et al. |
| 2003/0145354 A1 | 7/2003 | Milkowski et al. |
| 2003/0149261 A1 | 8/2003 | Schramm et al. |
| 2003/0152617 A1 | 8/2003 | Yatvin |
| 2003/0161830 A1 | 8/2003 | Jackson et al. |
| 2003/0161902 A1 | 8/2003 | Duncan |
| 2003/0165854 A1 | 9/2003 | Cunningham et al. |
| 2003/0180719 A1 | 9/2003 | Herget et al. |
| 2003/0182302 A1 | 9/2003 | Li |
| 2003/0185912 A1 | 10/2003 | Rosenbloom |
| 2003/0186898 A1 | 10/2003 | Maurya et al. |
| 2003/0190337 A1 | 10/2003 | Bissett |
| 2003/0190381 A1 | 10/2003 | Bland et al. |
| 2003/0191064 A1 | 10/2003 | Kopke |
| 2003/0199581 A1 | 10/2003 | Seligson et al. |
| 2003/0203973 A1 | 10/2003 | Cooper et al. |
| 2003/0207325 A1 | 11/2003 | Guarente et al. |
| 2003/0224077 A1 | 12/2003 | Mahe et al. |
| 2003/0228269 A1 | 12/2003 | DeRosa et al. |
| 2003/0232782 A1 | 12/2003 | Escalante-Semerena et al. |
| 2004/0002499 A1 | 1/2004 | Aggarwal |
| 2004/0005574 A1 | 1/2004 | Guarente et al. |
| 2004/0009197 A1 | 1/2004 | DeRosa et al. |
| 2004/0014682 A1 | 1/2004 | Ravagnan et al. |
| 2004/0014721 A1 | 1/2004 | Hensley et al. |
| 2004/0015020 A1 | 1/2004 | Deshpande et al. |
| 2004/0018987 A1 | 1/2004 | Hoffman et al. |
| 2004/0028607 A1 | 2/2004 | Verdin et al. |
| 2004/0067894 A1 | 4/2004 | Carola et al. |
| 2004/0209952 A1 | 10/2004 | Kim et al. |
| 2004/0249938 A1 | 12/2004 | Bunch |
| 2004/0259938 A1 | 12/2004 | Nag et al. |
| 2004/0265861 A1 | 12/2004 | Goldfarb |
| 2005/0020511 A1 | 1/2005 | Li et al. |
| 2005/0038125 A1 | 2/2005 | Smit et al. |
| 2005/0049208 A1 | 3/2005 | Kaufmann et al. |
| 2005/0070470 A1 | 3/2005 | Coy et al. |
| 2005/0096256 A1 | 5/2005 | Sinclair |
| 2005/0136429 A1 | 6/2005 | Guarente et al. |
| 2005/0136537 A1 | 6/2005 | Sinclair |
| 2005/0171027 A1 | 8/2005 | Sinclair et al. |
| 2005/0267023 A1 | 12/2005 | Sinclair et al. |
| 2006/0002914 A1 | 1/2006 | Milbrandt et al. |
| 2006/0014705 A1 | 1/2006 | Howitz et al. |
| 2006/0025337 A1 | 2/2006 | Sinclair et al. |
| 2006/0084085 A1 | 4/2006 | Sinclair et al. |
| 2006/0084135 A1 | 4/2006 | Howitz et al. |
| 2006/0111435 A1 | 5/2006 | Sinclair et al. |
| 2006/0229265 A1 | 10/2006 | Milburn et al. |
| 2006/0257502 A1 | 11/2006 | Liu |
| 2006/0276393 A1 | 12/2006 | Milburn et al. |
| 2006/0276416 A1 | 12/2006 | Sinclair et al. |
| 2007/0160586 A1 | 7/2007 | Alt et al. |
| 2008/0194803 A1 | 8/2008 | Sinclair et al. |
| 2010/0035885 A1 | 2/2010 | Sinclair |
| 2011/0082189 A1 | 4/2011 | Sinclair et al. |
| 2012/0021924 A1 | 1/2012 | Sinclair |
| 2012/0022013 A1 | 1/2012 | Sinclair et al. |
| 2012/0164670 A1 | 6/2012 | Hubbard et al. |

FOREIGN PATENT DOCUMENTS

| | | |
|---|---|---|
| CA | 2 599 987 A1 | 9/2006 |
| CA | 2 599 989 A1 | 9/2006 |
| CA | 2 599 992 A1 | 9/2006 |
| CN | 1343100 A | 4/2002 |
| DE | 102 30 961 A1 | 2/2004 |
| EP | 1 064 931 A1 | 1/2001 |
| EP | 1 440 688 A1 | 7/2004 |
| JP | 09-143070 | 6/1997 |
| JP | 2002-080362 | 3/2002 |
| JP | 2003-524577 | 8/2003 |
| JP | 2003-252784 A | 9/2003 |
| JP | 2004-18376 A | 1/2004 |
| WO | WO 97/07790 A1 | 3/1997 |
| WO | WO 98/41113 A2 | 9/1998 |
| WO | WO 98/57928 A1 | 12/1998 |

(56) References Cited

FOREIGN PATENT DOCUMENTS

| | | |
|---|---|---|
| WO | WO 99/22728 A1 | 5/1999 |
| WO | WO 99/59561 A2 | 11/1999 |
| WO | WO 00/21526 A1 | 4/2000 |
| WO | WO 00/53176 A1 | 9/2000 |
| WO | WO 00/59522 A1 | 10/2000 |
| WO | WO 00/69430 A1 | 11/2000 |
| WO | WO 01/98291 A2 | 12/2001 |
| WO | WO 02/13811 A2 | 2/2002 |
| WO | WO 02/14252 A2 | 2/2002 |
| WO | WO 02/17959 A2 | 3/2002 |
| WO | WO 02/49575 A2 | 6/2002 |
| WO | WO 02/49994 A2 | 6/2002 |
| WO | WO 02/102981 A2 | 12/2002 |
| WO | WO 03/009838 A1 | 2/2003 |
| WO | WO 03/031404 A2 | 4/2003 |
| WO | WO 03/037316 A1 | 5/2003 |
| WO | WO 03/039535 A1 | 5/2003 |
| WO | WO 03/103583 A2 | 12/2003 |
| WO | WO 2004/016726 A2 | 2/2004 |
| WO | WO 2004/041758 A1 | 5/2004 |
| WO | WO 2004/096198 | 11/2004 |
| WO | WO 2004/105517 A1 | 12/2004 |
| WO | WO 2005/002527 A2 | 1/2005 |
| WO | WO 2005/002555 A2 | 1/2005 |
| WO | WO 2005/002672 A2 | 1/2005 |
| WO | WO 2005/004814 A2 | 1/2005 |
| WO | WO 2005/026112 A2 | 3/2005 |
| WO | WO 2005/053609 A2 | 6/2005 |
| WO | WO 2005/065667 A2 | 7/2005 |
| WO | WO 2006/078941 A2 | 7/2006 |
| WO | WO 2006/094236 A1 | 9/2006 |

OTHER PUBLICATIONS

Office Action mailed Jun. 4, 2007 for U.S. Appl. No. 11/027,779.
[No Author Listed], Aging Research's Family Feud, Science, Feb. 27, 2004;303:1276-1279.
[No Author Listed], American Federation for Aging Research, The Latest Research on Caloric Restriction and Animal and Human Longevity, Jul. 8, 2003.
[No Author Listed], Contents and Abstracts of Latest Issue of BBB. Biosciences, Biotechnology and Biochemistry. 2000;64(11):34 pages.
[No Author Listed], Grape Expectations, The Boston Globe Editorial, Aug. 29, 2003.
[No Author Listed], Guarente Describes Investigation into Longevity Gene at Dean's Distinguished Lecture Series, Harvard Public Health Nov, Feb. 20, 2004:1-3.
[No Author Listed], Harvard Medical School, Molecules Discovered That Extend Life in Yeast, Human Cells, Science Blog, Aug. 2003.
[No Author Listed], Nicholas Wade, Study Spurs Hope of Finding Way to Increase Human Life, The New York Times, Aug. 25, 2003.
[No Author Listed], Resveratrol: Definition from Answers.com. 34 pages. Last accessed from http://www.answers.com/resveratrol on Nov. 19, 2010.
[No Author Listed], Study Sheds Light on Wine's Benefits, Reuters, Aug. 25, 2003.
[No Author Listed], Syndrome X, An Insulin Resistance Disorder. Healthyroads. Last Accessed on Mar. 9, 2007 from http://healthyroads.com/mylibrary/data/ash_ref/htm/art_syndromexaninsulinresistancedisorder.com. 4 pages.
[No Author Listed], The Health Benefits of Red Wine & Resveratrol. Advanced Health & Life Extension. Accessed Last on Dec. 29, 2009 from http://www.advanced-health.com/redwine.html. 5 pages.
[No Author Listed], To Red Wine, Long Life, Newsday.com , Aug. 26, 2003.
Aguilaniu et al., Asymmetric inheritance of oxidatively damaged proteins during cytokinesis. Science 2003 299:1751-1753.
Aiston et al., Glucose 6-phosphate causes translocation of phosphorylase in hepatocytes and inactivates the enzyme synergistically with glucose. Biochem J., 2004;377:195-204.

Anderson et al., Manipulation of a nuclear NAD+ salvage pathway delays aging without altering steady-state NAD+ levels, J Biol Chem. May 24, 2002;277(21):18881-90. Epub Mar 7, 2002.
Anderson et al., Nicotinamide and PNCI govern lifespan extension by caloric restriction in *Saccharomyces cerevisiae*, Nature. May 8, 2003;423(6936):181-5.
Anderson et al., Yeast life-span extension by calorie restriction is independent of NAD fluctuation,. Science. Dec. 19, 2003;302(5653):2124-6. Epub Nov. 6, 2003.
Araki et al., Increased nuclear NAD biosynthesis and SIRT1 activation prevent axonal degeneration. Science. Aug. 13, 2004;305:1010-1013.
Arichi et al., Effects of stilbene components of the roots of *Polygonum cuspidatum* Sieb. et Zucc. on lipid metabolism. Chem Pharm Bull (Tokyo). May 1982;30(5):1766-70.
Bagchi et al., Phytoestrogen, resveratrol and women's health, research communications in pharmacology and toxicology, vol. 5., Nos. 1&2, 2000 XP-001018765.
Bastianetto et al., Reversatrol and red wine constituents: evaluation of their neuroprotective properties. Pharmaceutical News, 2001:8(5):33-38.
Bauer et al., Resveratrol improves health and survival of mice on a high-calorie diet. Nature Articles. Nature Publishing Group, 2006. pp. 1-6.
Bauer et al., Therapeutic potential of resveratrol: the in vivo evidence. Nature Reviews. Jun. 2006;5:493-506.
Bedalov et al., Identification of a small molecule inhibitor of Sir2p. PNAS, Dec. 18, 2001;98:15113-15118.
Bedalov et al., NAD to the rescue. Science Aug. 13, 2004;305:954-955.
Benguria et al., Sir2p suppresses recombination of replication forks stalled at the replication fork barrier of ribosomal DNA in *Saccharomyces cerrevisiae*. Nucleic Acids Research. 2003;31(3):893-898.
Bergeron et al., Effect of 5-aminoimidazole-4-carboxamide-1-13-D-ribofuranoside infusion on in vivo glucose and lipid metabolism in lean and obese zucker rats. Diabetes, May 2001;50:1076-1082.
Berkow et al., Merck Manual of Diagnosis and Therapy, 1987, Merck Manual of Diagnosis and Therapy, Rahway, Merck & Co., US, XP002141064:pp. 2392.
Bieganowski et al., Discoveries of nicotinamide riboside as a nutrient and conserved NRK genes establish a preiss-handler independent route to NAD+ in fungi and humans. Cell, May 4, 2004;117:495-502.
Bitterman et al., Longevity regulation in *Saccharomyces cerevisia*: linking metabolism, genome stability, and heterochromatin. Microbiol Mol Biol Rev. Sep. 2003;6793):376-99.
Bitterman et al., Inhibition of silencing and accelerated aging by nicotinamide, a putative negative regulator of yeast sir2 and human SIRT I. J Biol Chem. Nov. 22, 2002;277(47):45099-107. Epub Sep. 23, 2002.
Borra et al., Mechanism of human SIRT1 activation by resveratrol. J Biol Chem. Apr. 29, 2005; 280(17):17 187-95. Epub Mar. 4, 2005.
Brachmann et al., The SIR2 gene family, conserved from bacteria to humans, functions in silencing, cell cycle progression, and chromosome stability. Genes & Development 1995 9:2888-2902.
Brandolini et al., Capillary electrophoresis determination, synthesis, and stability of resveratrol and related 3-O-B-D-glucopyranosides. Journal of Agricultural and Food Chemistry, 2002;50:7407-7411.
Brehm, The skinny of fat: MIT researchers establish first link between eating and aging, Massachusetts Institute of Technology, Jun. 2, 2004.
Brunet et al., Stress-dependent regulation of FOXO transcription factors by the SIRT1 deacetylase. Science. Mar. 26, 2004;303(5666):2011-5. Epub Feb. 19, 2004.
Bryk et al., Transcriptional silencing of Tyl elements in the RDNI locus of yeast. Genes & Development 1997 11:255-269.
Campisi, Aging, chromatin, and food restriction-connecting the dots. Science, Sep. 22, 2000;289:2062-2063.
Chua et al., Mammalian SIRT1 limits replicative life span in response to chronic genotoxic street. Cell Metabolism, Jul. 2005;2:67-76.
Cohen et al., Acetylation of the C terminus of Ku70 by CBP and PCAF controls bax-mediated apoptosis. Mol Cell. Mar. 12, 2004;13:627-638.

(56) References Cited

OTHER PUBLICATIONS

Cohen et al., Calorie restriction promotes mammalian cell survival by inducing the SIRT1 deacetylase. Science, Jul. 16, 2004;305:390-392.
Coronado et al., Alfalfa root flavonoid production is nitrogen regulated. Plant Physiol. 1995;108:533-542.
Couzin-Frankel, Genetics. Aging genes: the sirtuin story unravels. Science. Dec. 2, 2011;334(6060):1194-8.
Dai et al., SIRT1 activation by small molecules: kinetic and biophysical evidence for direct interaction of enzyme and activator. J Biol Chem. Oct. 22, 2010;285(43):32695-703. Epub Aug. 11, 2010. Supplemental Materials.
Dajas et al., Cell culture protection and in vivo neuroprotective capacity of flavonoids. Neurotox Res. 2003;5(6):425-32. Abstract.
De Cabo et al., An in vitro model of caloric restriction. Experimental Gerontology, 2003;38:631-639.
Defossez et al., Elimination of replication block protein fob1 extends the life span of yeast mother cells. Molecular Cell;1999 3:447-455.
Denu, Linking chromatin function with metabolic networks:SIR2 family of NAD+-dependent deacetylases. Trends in Biochemical Sciences. 2003;28(1):41-48.
Dong, Molecular mechanism of the chemopreventive effect of resveratrol. Mutation Research. 2003;523-524:145-150.
Ferguson, Role of plant polyphenols in genomic stability. Mutation Research. 2002;475:89-111.
Flam, PA Scientists may be on to antiaging compound. Philadelphia Inquirer; Sep. 10, 2003.
Frye et al., Phylogenetic classification of prokaryotic and eukaryotic Sir2-like proteins. Biochemical and Biophysical Research Communications. 2000;273:793-798.
Fukuhara et al., Visfatin: A Protein Secreted by Visceral Fat that Mimics the Effects of Insulin. Sciencexpress/www.sciencexpress. org/2004_December_16:1/10.1126.
GenBank Accession No. BCO20691. Jun. 29, 2004. Homo sapiens pre-B-cell colony enhancing factor I.
GenBank Accession No. NP_005737. Oct. 28, 2004. pre-B-cell colony enhancing factor 1 isoform a.
GenBank Accession No. NP_877591. Oct. 27, 2004. pre-B-Cell colony enhancing factor 1 isoforrn b.
Glossmann et al., Quercetin inhibits tyrosine phosphorylation by the cyclic nucleotide-independent, transforming protein kinase, pp60. Naunyn-Schmiedeberg's Arch Pharmacol. 1981; 317:100-102.
Godfroid, Eulogy of wine. Presse Med. Dec. 20, 1997;26(40):1971-4.
Gottlieb et al., A new role for a yeast transcriptional silencer gene, SIR2, in regulation of recombination in ribosomal DNA. Cell;1989 56:771-776.
Graefe et al., Pharmacokinetics and bioavailability of the flavonol quercetin in humans. Intl. J. of Clin Pharmacology and Therapeutics, 1999;37(5):219-233.
Grozinger et al., Identification of a class of small molecule inhibitors of the sirtuin family of NAD-dependent deacetylases by phenotypic screening. J Biol. Chem. Oct. 19, 2001;276(42):38837-38843.
Guarente et al., Genetic pathways that regulate ageing in model organisms. Nature.2000;408:255-262.
Hekimi et al., Genetics and the specificity of the aging process. Science. 2003;299:1351-1354.
Hendrickson, A dietary magic bullet? Harvard team says pill will fight effects of high-fat eating. The Journal of New England Technology, Mass. High Tech, Dec. 8-14, 2003.
Herzenberg et al., The history and future of the fluorescence activated cell sorter and flow cytometry:a view from Stanford. Clinical Chemistry. 2002;48:10 1819-1827.
Hildebrandt, Pschyrembel Klinisches Woerterbuch, 1998, XP002141063:47-49.
Hirao et al., Identification of selective inhibitors of NAD+-dependent deacetylases using phenotypic screens in yeast. J Biol. Chem. Dec. 26, 2003;278(52):52773-58782.
Holla et al., New bis-aminomercaptotriazoles and bis-triazolothiadiazoles as possible anticancer agents. Eur. J. Med. Chem. 2002;37:511-517.
Holzenberger et al., IGF-1 receptor regulates lifespan and resistance to oxidative stress in mice. Nature. 2003;421:182-187.
Howitz et al., Small molecule activators of sirtuins extend *Sacdharomyces cerevisiae* lifespan. Nature, Sep. 11, 2003;425:191-196.
Hu et al., Antioxidants may contribute in the fight against ageing: an in vitro model. Mechanisms of Aging and Development, 2000;121:217-230.
Ignatowicz et al., Resveratrol, A natural chemopreventive agent against degenerative diseases. Pol J Pharmacol, 2001;53:557-569.
Imai et al., Transcriptional silencing and longevity protein Sir2 is an NAD-dependent histone deacetylase. Nature. 2000;403:795-800.
Iwashita et al., Effect of flavonoids on the differentiation of 3T3-L1 adipoctes. Food Science and Technology Rsearch. 2001;7(2):154-160.
Jai et al., Pre-B cell colony-enhancing factor inhibits neutrophil apoptosis in experimental inflammation and clinical sepsis. J. Clin. Invest., 2004;113:1318-1327.
Jang et al., Cancer chemopreventive activity of resveratrol, a natural product derived from grapes. Science. 1997;275:218-220.
Jazwinski, Metabolic control and gene dysregulation in yeast aging. Annals New York Academy of Sciences. 2000;908:21-30.
Johnstone et al., Histone deacetylase inhibitors in cancer therapy: is transcription the primary target? Cancer Cell, Jul. 2003;4:13-18.
Kaeberlein et al., Grapes versus gluttony. Nature News & Views. Nature Publishing Group, 2006. pp. 1-2.
Kaeberlein et al., High osmolarity extends life span in *Saccharomyces cerevisiae* by a mechanism related to calorie restriction. Molecular and Cellular Biology, Nov. 2002;22(22):8056-8066.
Kaeberlein et al., Substrate-specific activation of sirtuins by resveratrol. J. Biol. Chem. 2005;280(17):17038-17045.
Kaeberlein et al., The SIR2/3/4 complex and SIR2 alone promote longevity in *Saccharomyces cerevisiae* by two different mechanisms. Genes & Development, 1999;13:2570-2580.
Kenyon, A conserved regulatory system for aging. Cell. 2001;105:165-168.
Khanna et al., Dermal would healing properties of redox-active grape seed proanthocyanidins. Free Radical Biology & Medicine, 2002;33(8):1089-1096.
Kimura et al., Pharmacological studies on resveratrol. Methods Find Exp Clin Pharmacol, 2003;25(4):297-310.
Koppes et al., Moderate alcohol consumption lowers the risk of type 2 diabetes. Diabetes Care. Mar. 2005; 28(3):719-725.
Koubova et al., How does calorie restriction work? Genes & Development, 2003;17:313-321.
Kris-Etherton et al., Bioactive compounds in foods: their role in the prevention of cardiovascular disease and cancer. Am. J. Med. 2002;113(9B):71S-88S.
Kuppusamy et al., Effects of flavonoids on cyclic AMP phosphodiesterase and lipid mobilization in rat adipocytes. Biochem Pharmacol. Oct. 6, 1992;44(7):1307-15.
Kuppusamy et al., Potentiation of beta-adrenoceptor agonist-mediated lipolysis by quercetin and fisetin in isolated rat adipocytes. Biochem Pharmacol. Feb. 9, 1994;47(3):521-9.
Lacey et al., Glenn launches labs for aging research. Harvard Medical School Communications, Harvard University Gazette. Mar. 17, 2005.
Lamming et al., Small molecules that regulate lifespan: evidence for xenohormesis. Mol Microbiol. 2004;53(4):1003-9.
Landry et al., The silencing protein SIR2 and its homologs are NAD-dependent protein deacetylases. Proc. Natl.Acad. Sci. USA. 2000;97(11):5807-5811.
Langley et al., Human SIR2 deacetylates p53 and antagonizes PML/p53-induced cellular senescence. The EMBO Jurnal. 2002;21(10):2383-2396.
Lasalandra, Wine, less dine: age study eyes low-calorie diet . . . and a glass of red. Boston Herald, Aug. 25, 2003.
Laurenson et al., Silencers, silencing, and heritable transcriptional states. Microbiological Reviews.1992;56(4):543-560.
Ledford, Much ado about ageing. Nature. Mar. 2010;464:480-481.
Lin et al., Requirement of NAD and SIR2 for life-span extension by calorie restriction in *Saccharomyces cerevisiae*. Science, Sep. 22, 2000;289:2126-2128.

(56) References Cited

OTHER PUBLICATIONS

Longo et al., Evolutionary medicine: from dwarf model systems to healthy centenarians. Science. 2003;299:1342-1346.
Lui et al., Antimalarial alkoxylated and hydroxylated chalones: structure—activity relationship analysis. J. Med. Chem. 2004;(4):4443-4452.
Luo et al., Negative control of p53 by Sir2alpha promotes cell survival under stress. Cell. Oct. 19, 2001;107(2):137-48.
Mai et al., Histone deacetylation in eipgenetics:an attractive target for anticancer therapy. Medicinal Research Reviews, 2005;25:261-309.
Marcotte et al., Fluorescence assay of SIRT protein deacetylases using an acetylated peptide substrate and a secondary trypsin reaction. Analytical Biochemistry 332(2004):90-99.
Michael, Compound in Blueberries May Prevent Heart Disease and Type 2 Diabetes. Healthy Living NYC; 2005.
Middleton et al., The effects of plant flavonoids on mammalian cells: implications for inflammation, heart disease,and cancer. Pharmacol Rev. 2000;52:673-751.
Mills et al., *MECI*-dependent redistribution of the Sir3 silencing protein from telomeres to DNA double-strand breaks. Cell. May 28, 1999;(97) 609-620.
Milne, J.C. et al., .Small molecule activators of SIRT1 as therapeutics for the treatment of type 2 diabetes. Nature 2007; 450: 712-716; and Supplementary Information pp. 1-17.
Monod et al., On the nature of allosteric transitions:a plausible model. J. Mol. Biol. 1965;12:88-118.
Morino et al., Specific regulation of HSPs in human tumor cell lines by flavonoids. In Vivo, 1997;11:265-270.
Motta et al., Mammalian SIRT-1 represses forkhead transcription factors. Cell, Feb. 20, 2004;116(4):551-63. Epub Feb. 5, 2004.
Nemoto et al., Nutrient availability regulates SIRT1 through a forkhead-dependent pathway. Science, Dec. 17, 2004;306:2105-2108.
Nicolini et al., Anti-apoptotic effect of trans-resveratrol on paclitaxel-induced apoptosis in the human neuroblastoma SH-SY5Y cell line. Neuroscience Letters. 2001;302:41-44.
Nothwehr et al., A Retention factor keeps death at bay. Nature Cell Biology, Apr. 11, 2003;5:281-283.
Oganesyan et al., Study of structure-activity (SA) interrelations in the flavonoid series: synthesis of chalcone derivatives and quantitative SA analysis. Khimiko-Farmatsevticheskii Zhurnal. 1986;20(6):696-702.
Ognjanovic et al., Genomic organization-of the gene coding for human pre-B-cell colony enhancing factor and expression in human fetal membranes. Journal of Molecular Endocrinology, 2001;16:107-117.
Oliver et al., Inhibition of mast cell Fc R1-mediated signaling and effector function by the syk-selective inhibitor, piceatannol. J. Biol. Chem. 1994;269(47):29697-29703.
Pacholec et al., SRT1720, SRT2183 and SRT1460 do not activate Sirt2 with native substrates. Poster 30. FASEB Summer Research Conferences. Arizona. Jun. 21-26, 2009.
Pacholec et al., SRT1720, SRT2183, SRT1460, and resveratrol are not direct activators of SIRT1. J Biol Chem. Mar. 12, 2010;285(11):8340-51. Epub Jan. 8, 2010. Supplemental Materials Included.
Pandey et al., Analysis of histone acetyltransferase and histone deacetylase families of *Arabidopsis thaliana* suggests functional diversification of chromatin modification among multicellular eukaryotes. Nucleic Acids Research.2002;30(23):5036-5055.
Parfiit et al., Antineopiastics and Immunosuppressants. Pharmaceutical Press, London, 1995, XP002329271, Martindale 32" ed.
Park et al., Effects of mutations in DNA repair genes on formation of ribosomal DNA circles and life span in *Saccharomyces cerevisiae*. Molecular and Cellular Biology. 1999;19(5):3848-3856.
Perez et al., Synthesis and characterization of complexes of p-isopropyl benzaldehyde and methyl 2-pyridyl ketone thiosemicarbazones with Zn(II) and Cd(II) metallic centers. Cytotoxic activity and induction of apoptosis in pam-ras cells. J. of Inorganic Biochemistry, 1999;75:255-261.

Picard et al., Sirt1 promotes fat mobilization in white adipocytes by repressing PPAR. Nature, Jun. 17, 2004;429(6993):771-6. Epub Jun. 2, 2004.
Polgreen, Selling Red Wine as Good (and Good for You), The New York Times, Aug. 26, 2003.
Pont et al., Relation between the chemical structure and the biological activity of hydroxystilbenes against botrytis cinerea. J. Phytopathology;1990 130:1-8.
Procu et al., The emerging therapeutic potential of sirtuin-interacting drugs: from cell death to lifespan extension. Trends in Pharmacological Sciences, Feb. 2005;26(2): 94-103.
Pugh et al., Controlling caloric consumption: protocols for rodents and rhesus monkeys. Neurobiology of Aging, Apr. 20, 1999:157-165.
Raffaelli et al., Identification of a novel human nicotinamide mononucleotide adenylyltransferease. Biochem Biophys Res Commun Oct. 4, 2002;297 (Abstract only).
Regev-Shoshani et al., Glycosylation of resveratrol protects it from enzymatic oxidation. Biochemical Journal Aug. 15, 2003;374:157. e-pub Apr. 16, 2003.
Revollo et al., The NAD biosynthesis pathway mediated by nicotinamide phosphoribosyltransferase regulates Sir2 activity in mammalian cells. The Journal of Biological Chemistry, Dec. 3, 2004;279(49):50754-50763.
Rogina et al., Longevity regulation by drosophila Rpd3 deacetylase and caloric restriction. Science, Nov. 29, 2002;298:1745.
Rowland, Do life spans of biblical proportions await us?, The Atlanta Journal Constitution, Sep. 2, 2003.
Samal et al., Cloning and Characterization of the cDNA Encoding a novel Human Pre-B-Cell Colony-Enhancing Factor, Molecular and Cellular Biology, Feb. 1994;14(2):1431-1437.
Sampson, Compound Identified in Grapes May Fight Cancer and Diabetes, htt://prohealth.com. May 27, 2002.
Sandmeier et al., Telomeric and rNDA silencing in saccharomyces cerevisiae are dependent on a nuclear NAD+.salvage pathway,. Genetics, Mar. 2002;160:877-889.
Sawada et al., Cytoprotective membrane-permeable peptides designed from the Bax-binding domain of Ku70. Nat Cell Biol. Apr. 2003;5(4):352-7.
Sawada et al., Ku70 suppresses the apoptotic translocation of Bax to mitochondria. Nat Cell Biol. Apr. 2003;5(4):320-9. Abstract.
Shimokawa et al., Life span extension by reduction of the growth hormone-insulin-like growth factor-1 axis:relation to caloric restriction. FASEB J. 2003;17:1108-1109.
Sinclair, Sirtuins for healthy neurons. Nat Genet. Apr. 2005; 37(4):339-40.
Sinclair, Extrachrornosomal rDNA circles—a cause of aging in yeast. Cell. 1997;91:1033-1042.
Sinclair, Paradigms and pitfalls of yeast longevity research. Mechanisms of Ageing and Development. 2002;123:857-867.
Smith et al., A phylogenetically conserved NAD+-dependent protein deacetylase activity in the Sir2 protein family. Proc. Natl. Acad. Sci. USA, Jun. 6, 2000;97(12):6658-6663.
Smith et al., An unusual form of transcriptional silencing in yeast ribosomal DNA. Genes & Development. 1997;11:241-254.
Smith, In Lab, seeking secret of youth, Chemical abundant in red wine appears to slow aging in study, The Boston Globe, Aug. 25, 2003.
Soleas et al., Resveratrol: a molecule whose time has come? and gone?. Clinical Biochemistry. 1997;30(2):91-113.
Solomon et al , Inhibition of SIRT1 catalytic activity increases p53 acetylation but does not alter cell survival following DNA damage. Mol. Cell. Biol. 2006;26(1):28-38.
South, Resveratrol & Quercetin—pro Heart & anti-Cancer, Offshore Pharmacy, Jun. 26, 2003 or earlier.
Stojanovi et al., Efficiency and mechanism of the antioxidant action of trans-resveratrol and its analogues in the radical liposome oxidation. Archives of Biochemistry and Biophysics. 2001;391(1):79-89.
Subramanian et al., Ku70 acetylation mediates neuroblastorna cell death induced by histone deacetylase inhbitors. PNAS, Mar. 29, 2005;102(13):4842-4847.
Sun et al., The "French Paradox" and beyond: neuroprotective effects of polyphenols. Free Radic Biol Med.2002; 15;32(4):314-8.

(56) References Cited

OTHER PUBLICATIONS

Tanasescu et al., Alcohol consumption and risk of coronary heart disease among individuals with type 2 diabetes. Curr. Diab. Rep. Oct. 1, 2001; (2):187-91.

Tanner et al., Silent information regulator 2 family of NAD-dependent histone/protein deacetylases generates a unique product, 1-0-acetyl-ADP-ribose. Proc. Natl. Acad. Sci. USA. 2000;97(26):14178-14182.

Tanny et al., An enzymatic activity in the yeast Sir2 protein that is essential for gene silencing. Cell. 1999;99:735-745.

Tanny et al., Coupling of histone deacetylation to NAD breakdown by the yeast silencing protein Sir2: evidence for acetyl transfer from substrate to an NAD breakdown product. Proc. Natl. Acad. Sci. USA. 2001;98(2):415-420.

Tartar et al., The endocrine regulation of aging by insulin-like signals. Science. 2003; 299:1346-1351.

Tissenbaum et al., Increased dosage of a sir-2 gene extends lifespan in *Caenorhabditis elegans*. Nature. 2001;410:227-230.

Vaziri et al., hSIR2SIRT1 functions as an NAD-Dependent p53 deacetylase. Cell, 2001 Oct. 2001;107:149-159.

Vergnes et al., Cytoplasmic SIR2 homologue overexpression promotes survival of *Leishmania* parasites by preventing programmed cell death. Gene. 2002;296:139-150.

Vessal et al., Antidiabetic effects of quercetin in streptozocin-induced diabetic rats. Comp Biochem Physiol C Toxicol Pharmacol. Jul. 2003;135C(3):357-64.

Wasowicz, Red wine ingredient may extend life. United Press International, Aug. 28, 2003.

Weiss, Enzymes Found to Delay Aging Process, The Washington Post, Aug. 25, 2003.

Windholz et al., Glutaric acid. The Merck Index, An Encyclopedia of Chemicals, Drugs and Biologicals. 10th Edition. 1983:642 Abstract 4334.

Wood et al., Sirtuin activators mimic caloric restriction and delay ageing in metazoans. Nature. Aug. 5, 2004;430(7000):686-9. Epub Jul. 14, 2004.

Wu et al., Ginkgo biloba extract EGb 761 increases stress resistance and extends life span of *Caenorhabditis elegans*. Cell Mol Biol,(Noisy-le-grand). 2002; 48(6):725-31.

Yoshida et al., Histone deacetylase as a new target for cancer chemotherapy. Cancer Chemother Pharmacol, 2001;48(1):520-526.

Zern et al., Grape polyphenols decrease plasma triglycerides and cholesteral accumulation in the aorta of ovariectomized guinea pigs. J. Nutr., 2003;133:2268-2272.

Zhang et al., Crystal structures of *E. coli* nicotinate mononucleotide adenylyltransferase and its complex with deamido-NAD. Structure, Jan. 2002;10:69-79.

Zhao et al., Structural basis for nicotinamide cleavage and ADP-ribose transfer by Nad+-dependant Sir2 histone/protein deacetylases. PNAS, Jun. 8, 2004;101(23):8563-8. Epub May 18, 2004.

Zhou et al., Role of AMP-activated protein kinase in mechanism of metformin action. The Journal of Clinical Investigation, Oct. 2001;108(8):1167-1174.

Park et al., Resveratrol ameliorates aging-related metabolic phenotypes by inhibiting cAMP phosphodiesterases. Cell. Feb. 3, 2012;148(3):421-33. doi:10.1016/j.ce11.2012.01.017.

Tennen et al., Finding a target for resveratrol. Cell. Feb. 3, 2012;148(3):387-9. doi: 10.1016/j.cell.2012.01.032.

Iacopini et al., Catechin, epicatechin, quercetin, rutin and resveratrol in red grape: Content in vitro antioxidant activity and interactions. J Food Comp Analy. 2008;21:589-98.

\* cited by examiner

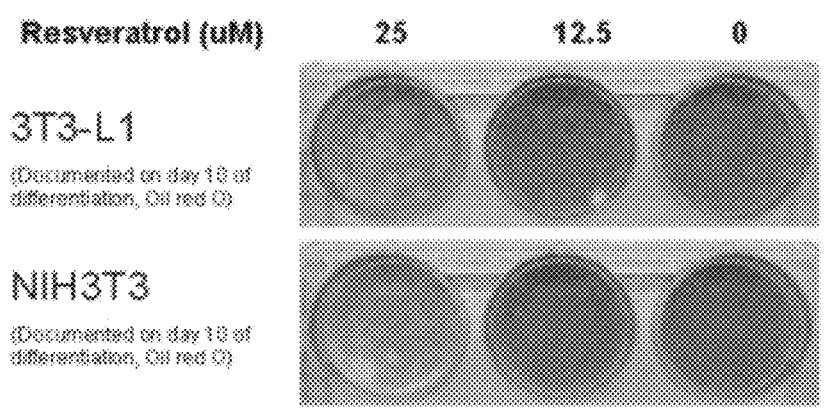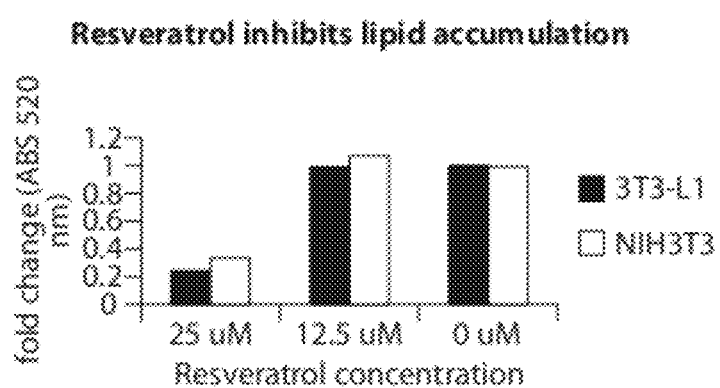
Figure 12

Figure 21

Table 1. Stimulation of SIRT1 Catalytic Rate by Plant Polyphenols (100 µM).

| Compound | Ratio to Control Rate Mean ± SE | Structure |
|---|---|---|
| Resveratrol (3,5,4'-Trihydroxy-trans-stilbene) | 13.4 ± 1.0 | 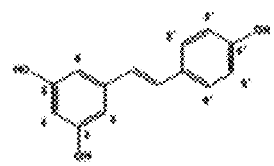 |
| Butein (3,4,2',4'-Tetrahydroxychalcone) | 8.53 ± 0.88 | 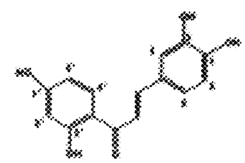 |
| Piceatannol (3,5,3',4'-Tetrahydroxy-trans-stilbene) | 7.90 ± 0.50 | 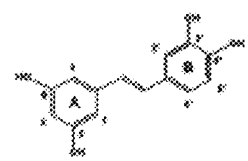 |
| Isoliquiritigenin (4,2',4'-Trihydroxychalcone) | 7.57 ± 0.84 | 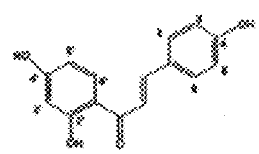 |
| Fisetin (3,7,3',4'-Tetrahydroxyflavone) | 6.58 ± 0.69 | 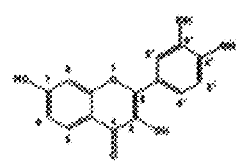 |
| Quercetin (3,5,7,3',4'-Pentahydroxyflavone) | 4.59 ± 0.47 | 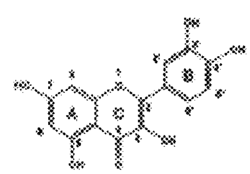 |

Figure 22

Supplementary Table 1. Effects of Stilbenes and Chalcones (100 µM) on SIRT1 Rate.

| Compound | Ratio to Control Rate Mean ± SE | Replicates | Structure Skeleton |
|---|---|---|---|
| Resveratrol (3,5,4'-Trihydroxy-trans-stilbene) | 13.4 ± 1.0 | 10 | |
| Piceatannol (3,5,3',4'-Tetrahydroxy-trans-stilbene) | 7.90 ± 0.50 | 7 | 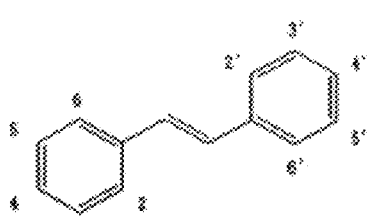 STILBENES (trans) |
| Deoxyrhapontin (3,5-Dihydroxy-4'-methoxystilbene 3-O-β-D-glucoside) | 1.84 ± 0.21 | 6 | |
| trans-Stilbene | 1.48 ± 0.18 | 6 | |
| Rhapontin 3,3',5-Trihydroxy-4'-methoxystilbene 3-O-β-D-glucoside | 1.40 ± 0.37 | 6 | |
| cis-Stilbene | 1.14 ± 0.29 | 6 | |
| Butein (3,4,2',4'-Tetrahydroxychalcone) | 8.53 ± 0.89 | 6 | 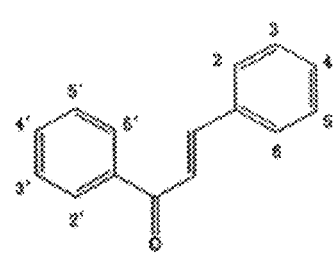 CHALCONES |
| 4,2',4'-Trihydroxychalcone | 7.57 ± 0.64 | 6 | |
| 3,4,2',4',6'-Pentahydroxychalcone | 2.80 ± 0.32 | 6 | |
| Chalcone | 1.34 ± 0.17 | 6 | |

Figure 23

Supplementary Table 2. Effects of Flavones (100 μM) on SIRT1 Rate (Part I).

| Compound | Ratio to Control Rate Mean ± SE | Replicates | Structure Skeleton |
|---|---|---|---|
| Fisetin (3,7,3',4'-Tetrahydroxyflavone) | 6.56 ± 0.69 | 9 | |
| 5,7,3',4',5'-Pentahydroxyflavone | 6.05 ± 0.88 | 6 | |
| Luteolin (5,7,3',4'-Tetrahydroxyflavone) | 5.66 ± 0.80 | 6 | |
| 3,6,3',4'-Tetrahydroxyflavone | 5.45 ± 0.57 | 12 | PLAVONES structure |
| Quercetin (3,5,7,3',4'-Pentahydroxyflavone) | 4.59 ± 0.47 | 16 | |
| 7,3',4',5'-Tetrahydroxyflavone | 3.62 ± 0.56 | 6 | |
| Kaempferol (3,5,7,4'-Tetrahydroxyflavone) | 3.55 ± 0.66 | 6 | |
| 6-Hydroxyapigenin (5,6,7,4'-Tetrahydroxyflavone; Scutellarein) | 3.06 ± 0.29 | 6 | |
| Apigenin (5,7,4'-Trihydroxyflavone) | 2.77 ± 0.40 | 6 | |
| 3,6,2',4'-Tetrahydroxyflavone | 2.10 ± 0.22 | 6 | |
| 7,4'-Dihydroxyflavone | 1.91 ± 0.17 | 6 | |

Figure 24

Supplementary Table 3. Effects of Flavones (100 µM) on SIRT1 Rate (Part II).

| Compound | Ratio to Control Rate Mean ± SE | Replicates | Structure Skeleton |
|---|---|---|---|
| 7,8,3',4'-Tetrahydroxyflavone | 1.91 ± 0.39 | 6 | |
| 3,6,2',3'-Tetrahydroxyflavone | 1.74 ± 0.27 | 6 | |
| 4'-Hydroxyflavone | 1.73 ± 0.12 | 6 | |
| 5,4'-Dihydroxyflavone | 1.58 ± 0.15 | 6 | |
| 6,7-Dihydroxyflavone | 1.51 ± 0.18 | 6 | |
| Morin (3,5,7,2',4'-Pentahydroxyflavone) | 1.461 ± 0.071 | 6 | |
| Flavone | 1.41 ± 0.23 | 6 | |
| 6-Hydroxyflavone | 1.23 ± 0.19 | 6 | |
| Myricetin (Cannabiscetin; 3,5,7,3',4',5'-Hexahydroxyflavone) | 0.898 ± 0.070 | 12 | |
| 3,7,3',4',5'-Pentahydroxyflavone | 0.828 ± 0.074 | 12 | |
| Gossypetin (3,5,7,8,3',4'-Hexahydroxyflavone) | 0.723 ± 0.062 | 6 | |

FLAVONES

Figure 25

Supplementary Table 4. Effects of Isoflavones, Flavanones and Anthocyanidins (100 µM) on SIRT1 Rate

| Compound | Ratio to Control Rate Mean ± SE | Replicates | Structure Skeleton |
|---|---|---|---|
| Daidzein (7,4'-Dihydroxyisoflavone) | 2.28 ± 0.74 | 2 | ISOFLAVONES |
| Genistein (5,7,4'-Trihydroxyisoflavone) | 1.109 ± 0.028 | 2 | |
| Naringenin (5,7,4'-Trihydroxyflavanone) | 2.10 ± 0.23 | 6 | FLAVANONES |
| 3,5,7,3',4'-Pentahydroxyflavanon e | 1.97 ± 0.22 | 5 | |
| Flavanone | 1.92 ± 0.24 | 6 | |
| Pelargonidin chloride (3,5,7,4'-Tetrahydroxyflavylium chloride) | 1.586 ± 0.037 | 2 | ANTHOCYANIDINS (Flavylium Chloride Salts) |
| Cyanidin chloride (3,5,7,3',4'-Pentahydroxyflavylium chloride) | 0.451 ± 0.015 | 2 | |
| Delphinidin chloride (3,5,7,3',4',5'-Hexahydroxyflavylium chloride) | 0.4473 ± 0.0071 | 2 | |

Figure 26

Supplementary Table 6. Effects of Catechins (Flavan-3-ols) (100 µM) on SIRT1 Rate.

| Compound | Ratio to Control Rate Mean ± SE | Replicates | Structure Skeleton/Structure |
|---|---|---|---|
| (-)-Epicatechin (Hydroxy Sites: 3,5,7,3',4') | 1.53 ± 0.31 | 4 | |
| (-)-Catechin (Hydroxy Sites: 3,5,7,3',4') | 1.41 ± 0.21 | 4 | CATECHINS (Flavan-3-ols) |
| (-)-Gallocatechin (Hydroxy Sites: 3,5,7,3',4',5') | 1.36 ± 0.25 | 4 | |
| (+)-Catechin (Hydroxy Sites: 3,5,7,3',4') | 1.31 ± 0.19 | 4 | |
| (+)-Epicatechin (Hydroxy Sites: 3,5,7,3',4') | 1.26 ± 0.20 | 4 | |
| (-)-Epigallocatechin (Hydroxy Sites: 3,5,7,3',4',5') | 0.41 ± 0.11 | 4 | |
| (-)-Epigallocatechin Gallate (Hydroxy Sites: 3*,5,7,3',4',5'; *Position of gallate ester) | 0.32 ± 0.12 | 4 | (-)-EPIGALLOCATECHIN GALLATE |

Figure 27

Supplementary Table 6. Effects of Free Radical Protective Compounds (100 μM) on SIRT1 Rate.

| Compound | Ratio to Control Rate Mean ± SE | Replicates | Protective Mechanism |
|---|---|---|---|
| Hinokitiol (b-Thujaplicin; 2-hydroxy-4-isopropyl-2,4,6-cycloheptatrien-1-one) | 2.48 ± 0.15 | 2 | Iron Chelator |
| L-(+)-Ergothioneine ((S)-α-Carboxy-2,3-dihydro-N,N,N-trimethyl-2-thioxo-1H-imidazole-4-ethanaminium inner salt) | 2.06 ± 0.48 | 2 | Antioxidant, Peroxynitrite Scavenger |
| Caffeic Acid Phenyl Ester | 1.80 ± 0.16 | 2 | Iron Chelator |
| MCI-186 (3-Methyl-1-phenyl-2-pyrazolin-5-one) | 1.2513 ± 0.0080 | 2 | Radical Scavenger and Antioxidant |
| HBED (N,N'-Di-(2-hydroxybenzyl)ethylenediamine-N,N'-diacetic acid·HCl·H2O) | 1.150 ± 0.080 | 2 | Iron Chelator |
| Ambroxol (trans-4-(2-Amino-3,5-dibromobenzylamino) cyclohexane·HCl) | 1.076 ± 0.0028 | 2 | Radical Scavenger |
| U-83836E ((-)-2-((4-(2,6-di-1-Pyrrolidinyl-4-pyrimidinyl)-1-piperazinyl)methyl)-3,4-dihydro-2,5,7,8-tetramethyl-2H-1-benzopyran-6-ol·2HCl) | 1.030 ± 0.055 | 2 | "Lazaroid" aminosteroid, Peroxidation inhibitor |
| Trolox (6-Hydroxy-2,5,7,8-tetramethylchroman-2-carboxylic acid) | 0.985 ± 0.019 | 2 | Antioxidant |

Figure 28

Supplementary Table 7. Effects of Miscellaneous Compounds (100 µM) on SIRT1 Catalytic Rate.

| Compound | Ratio to Control Rate Mean ± SE | Replicates | Structure & Activities |
|---|---|---|---|
| Dipyridamole (2,6-bis(Diethanolamino)-4,8-dipiperidino-pyrimido[5,4-d]pyrimidine) | 3.54 ± 0.20 | 2 | 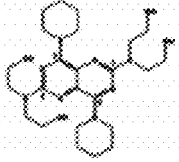 Inhibitor of Adenosine Transport, Phosphodiesterase, 5-Lipoxygenase |
| Nicotinamide | 0.428 ± 0.019 | 42 |  Sirtuin Reaction Product/Inhibitor |
| NF279 | 0.0035 ± 0.0011 | 3 | 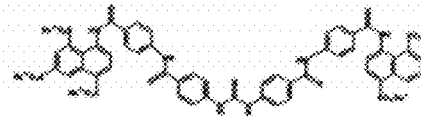 Purinergic Receptor Antagonist |
| NF023 | -0.0016 ± 0.0015 | 3 | 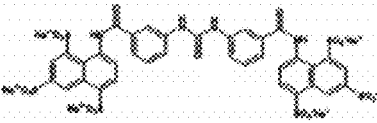 G-protein Antagonist |
| Suramin | -0.0002 ± 0.0010 | 3 | 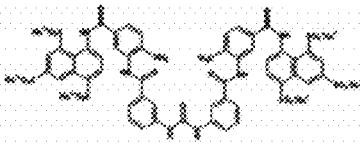 G-protein Antagonist, Reverse Transcriptase Inhibitor |

Figure 29
Supplementary Table 8. Effects of Various Modulators on SIRT1 Rate.
| Compound, (Concentration) | Ratio to Control Rate Mean ± SE | Replicates | Structure |
|---|---|---|---|
| ZM 336372, (100 µM) | 3.5 ± 1.1 | 3 | 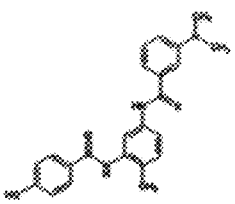 |
| Camptothecin, (10 µM) | 2.92 ± 0.41 | 3 | 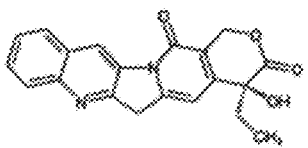 |
| Coumestrol, (10 µM) | 2.30 ± 0.31 | 2 | 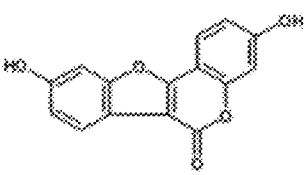 |
| NDGA, (100 µM) | 1.738 ± 0.068 | 3 | 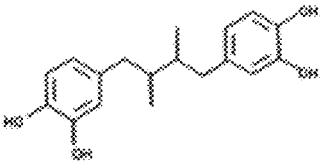 |
| Esculetin, (10 µM) | 1.737 ± 0.082 | 3 | 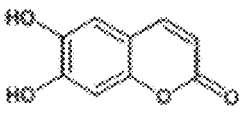 |
| Sphingosine | 0.069 ± 0.028 | 3 |  |

Figure 30

Table 9. SIRT1 Rate Effects of New Resveratrol Analogs (100 µM).

| Compound | Ratio to Control Rate Mean ± SE | N | Structure | Stability in Solution t½, hrs. |
|---|---|---|---|---|
| BML-230 (3,5-Dihydroxy-4'-thiomethyl-trans-stilbene) | 11.6 ± 1.9 | 12 | 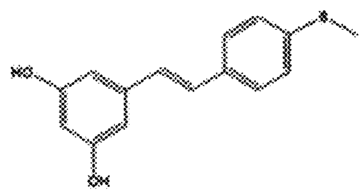 | |
| Resveratrol (3,5,4'-Trihydroxy-trans-stilbene) | 10.7 ± 0.4 | 49 | 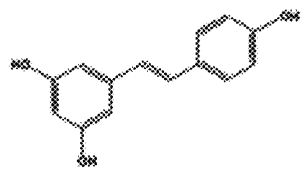 | 59 (ethanol), 20 (water) |
| BML-217 (3,5-Dihydroxy-4'-chloro-trans-stilbene) | 10.6 ± 0.4 | 3 | 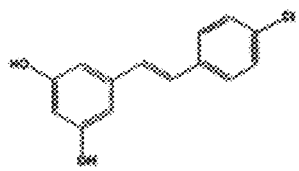 | |
| Pinosylvin (3,5-Dihydroxy-trans-stilbene) | 9.95 ± 0.46 | 3 | 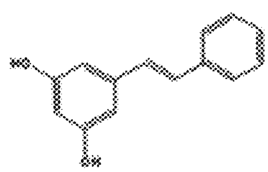 | |
| BML-226 (3,5-Dihydroxy-4'-ethyl-trans-stilbene) | 9.373 ± 0.014 | 3 | | |
| BML-212 (3,5-Dihydroxy-4'-fluoro-trans-stilbene) | 8.20 ± 0.69 | 3 | 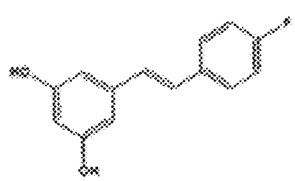 | 68 (ethanol) |

Figure 31

Table 10. SIRT1 Rate Effects of New Resveratrol Analogs (100 µM).

| Compound | Ratio to Control Rate Mean ± SE | N | Structure | Stability in Solution $t_{1/2}$, hrs. |
|---|---|---|---|---|
| BML-228 (3,5-Dihydroxy-4'-methyl-*trans*-stilbene) | 7.72 ± 0.12 | 3 | 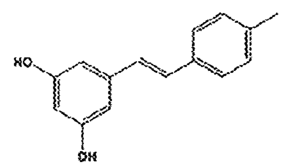 | |
| BML-232 (3,5-Dihydroxy-4'-azido-*trans*-stilbene) | 7.24 ± 0.12 | 3 | 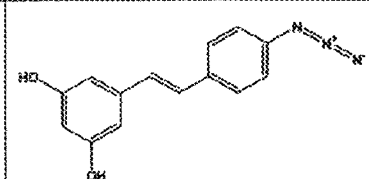 | |
| BML-229 (3,5-Dihydroxy-4'-nitro-*trans*-stilbene) | 6.78 ± 0.22 | 3 | 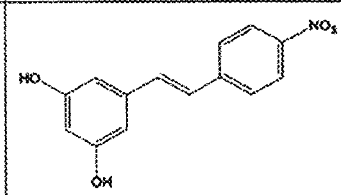 | |
| BML-231 (3,5-Dihydroxy-4'-isopropyl-*trans*-stilbene) | 6.01 ± 0.15 | 3 | 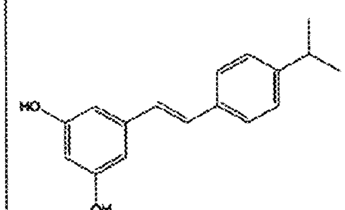 | |
| BML-233 3,5-Dihydroxy-4'-methoxy-*trans*-stilbene | 5.48 ± 0.33 | 6 | 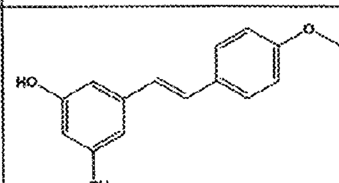 | |

Figure 32

Table 11. SIRT1 Rate Effects of New Resveratrol Analogs (100 μM).

| Compound | Ratio to Control Rate Mean ± SE | N | Structure | Stability in Solution t½, hrs. |
|---|---|---|---|---|
| Rhapontin aglycone (3,5,3'Trihydroxy-4'-methoxy-*trans*-stilbene) | 4.060 ± 0.069 | 3 | 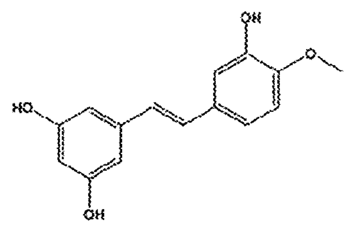 | |
| BML-227 (3,4'-Dihydroxy-5-acetoxy-*trans*-stilbene) | 3.340 ± 0.093 | 3 | 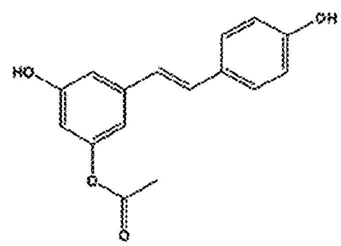 | |
| BML-221 (3,5-Dihydroxy-4'-acetoxy-*trans*-stilbene) | 3.05 ± 0.54 | 6 | 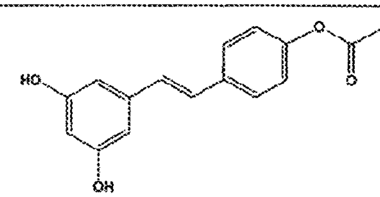 | 504 (ethanol) |
| BML-218 (E)-1-(3,5-Dihydroxyphenyl)-2-(2-napthyl)ethene | 3.05 ± 0.37 | 6 | 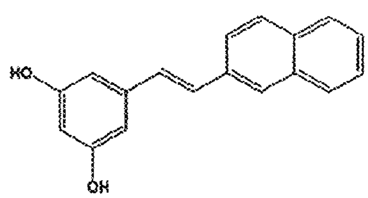 | |
| BML-216 3-Hydroxystilbene | 2.357 ± 0.074 | 3 | 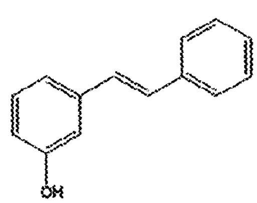 | |

Figure 33
Table 12. SIRT1 Rate Effects of New Resveratrol Analogs (100 µM).
| Compound | Ratio to Control Rate Mean ± SE | N | Structure | Stability in Solution t₁/₂, hrs. |
|---|---|---|---|---|
| BML-226 (3,5-Dimethoxymethoxy-4'-thiomethyl-*trans*-stilbene) | 2.316 ± 0.087 | 3 | 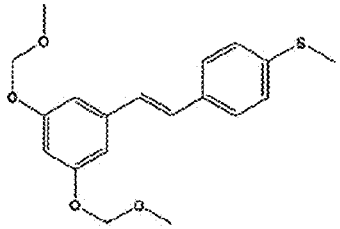 | |
| BML-222 (3,5-Dihydroxy-4'-acetamide-*trans*-stilbene) | 1.88 ± 0.11 | 3 | 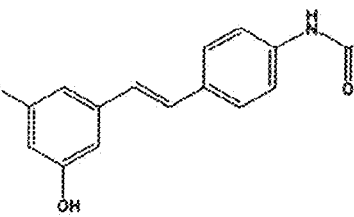 | |
| BML-215 3,4-Dihydroxy-*trans*-stilbene | 1.64 ± 0.10 | 6 | 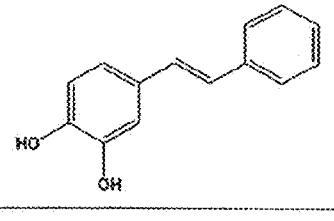 | |
| BML-224 (E)-1-(3,5-Dihydroxyphenyl)-2-(cyclohexyl) ethene | 1.297 ± 0.042 | 3 | 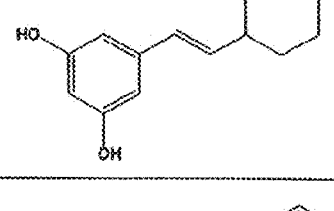 | |
| 3,4-Dimethoxy-*trans*-stilbene | 1.127 ± 0.019 | 3 | 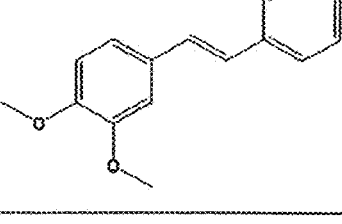 | |

Figure 34
Table 13. SIRT1 Rate Effects of New Resveratrol Analogs (100 µM).
| Compound | Ratio to Control Rate Mean ± SE | N | Structure | Stability in Solution $t_{1/2}$, hrs. |
|---|---|---|---|---|
| Dihydroresveratrol (1-(3,5-Dihydroxyphenyl)-2-(4-hydroxyphenyl)ethane) | 1.08 ± 0.14 | 4 | 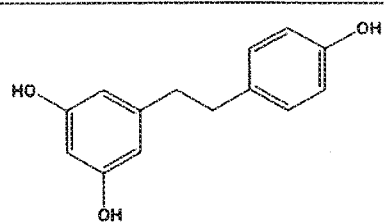 | |
| 4-Hydroxy-*trans*-stilbene | 0.943 ± 0.039 | 3 | 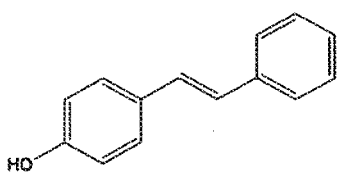 | |
| BML-219 *N*-phenyl-(3,5-dihydroxy)benzamide | 0.902 ± 0.014 | 3 | 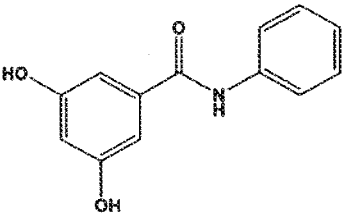 | |
| 3,5-Dihydroxy-4'-nitro-*trans*-stilbene | 0.870 ± 0.019 | 3 | 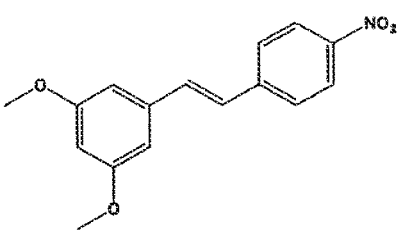 | |
| 4-Methoxy-*trans*-stilbene | 0.840 ± 0.089 | 3 | 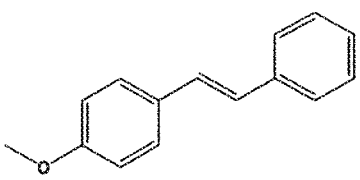 | |

Figure 35

Table 14. Resveratrol Analog Synthetic Intermediates

| Compound | Benzylphosphonate | Aldehyde | Structure |
|---|---|---|---|
| BML-217 (3,5-Dihydroxy-4'-chloro-*trans*-stilbene) | Diethyl 3-5-dimethoxybenzyl phosphonate | 4-Chlorobenzaldehyde | 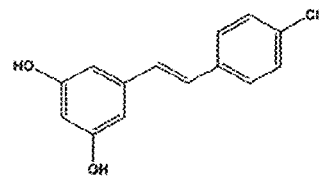 |
| Resveratrol (3,5,4'-Trihydroxy-*trans*-stilbene) | N/A | N/A | 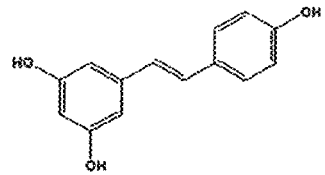 |
| Pinosylvin (3,5-Dihydroxy-*trans*-stilbene) | Diethyl benzyl phosphonate | 3,5-Dimethoxy benzaldehyde | 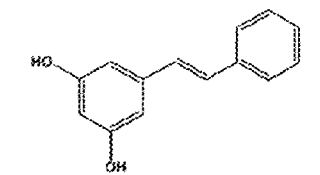 |
| BML-225 (3,5-Dihydroxy-4'-ethyl-*trans*-stilbene) | Diethyl 3-5-dimethoxybenzyl phosphonate | 4-Ethylbenzaldehyde | 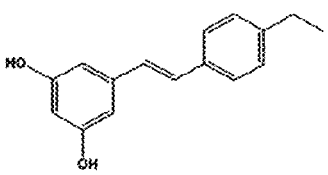 |
| BML-212 (3,5-Dihydroxy-4'-fluoro-*trans*-stilbene) | Diethyl 4-fluoro benzylphosphonate | 3,5-Dimethoxy benzaldehyde | 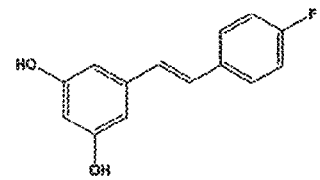 |
| BML-228 (3,5-Dihydroxy-4'-methyl-*trans*-stilbene) | Diethyl 3-5-dimethoxybenzyl phosphonate | 4-Methylbenzaldehyde | 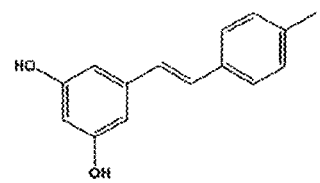 |

Figure 36

Table 15. Resveratrol Analog Synthetic Intermediates

| Compound | Benzylphosphonate | Aldehyde | Structure |
|---|---|---|---|
| BML-232 (3,5-Dihydroxy-4'-azido-*trans*-stilbene) | Diethyl 4-azido benzylphosphonate | 3,5-Dimethoxymethoxy benzaldehyde | 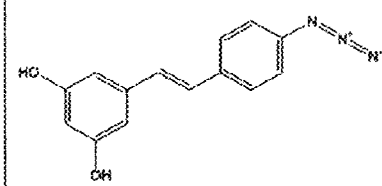 |
| BML-230 (3,5-Dihydroxy-4'-thiomethyl-*trans*-stilbene) | Diethyl 4-methylthio benzylphosphonate | 3,5-Dimethoxymethoxy benzaldehyde | 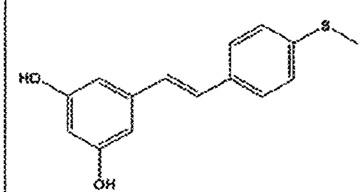 |
| BML-229 (3,5-Dihydroxy-4'-nitro-*trans*-stilbene) | Diethyl 3-5-dimethoxybenzyl phosphonate | 4-Nitrobenzaldehyde | 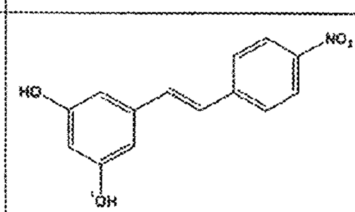 |
| BML-231 (3,5-Dihydroxy-4'-isopropyl-*trans*-stilbene) | Diethyl 3-5-dimethoxybenzyl phosphonate | 4-Isopropyl benzaldehyde | 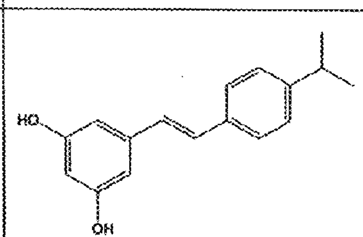 |
| 3,5-Dihydroxy-4'-methoxy-*trans*-stilbene | N/A | N/A | 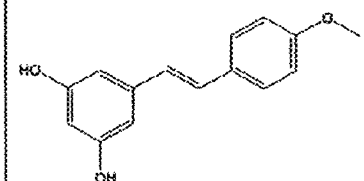 |

Figure 37

Table 16. Resveratrol Analog Synthetic Intermediates

| Compound | Benzylphosphonate | Aldehyde | Structure |
|---|---|---|---|
| Rhapontin aglycone (3,5,3'Trihydroxy-4'-methoxy-*trans*-stilbene) | N/A | N/A | 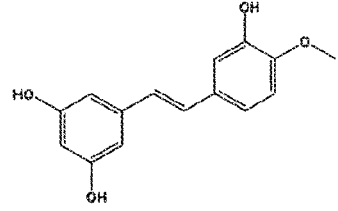 |
| BML-227 (3,4'-Dihydroxy-5-acetoxy-*trans*-stilbene) | N/A | N/A | 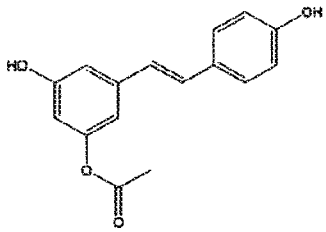 |
| BML-221 (3,5-Dihydroxy-4'-acetoxy-*trans*-stilbene) | N/A | N/A | 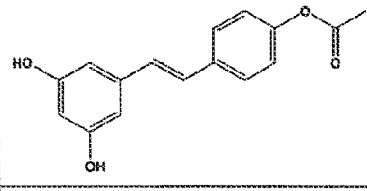 |
| BML-218 (E)-1-(3,5-Dihydroxyphenyl)-2-(2-napthyl) ethene | Diethyl 3-5-dimethoxybenzyl phosphonate | 2-Naphthaldehyde | 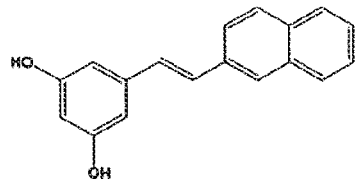 |
| BML-216 3-Hydroxystilbene | Benzylphosphonate | 3-Methoxy benzaldehyde | 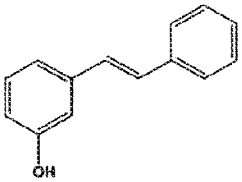 |

Figure 38

Table 17. Resveratrol Analog Synthetic Intermediates

| Compound | Benzylphosphonate | Aldehyde | Structure |
|---|---|---|---|
| BML-226 (3,5-Dimethoxymethoxy-4'-thiomethyl-trans-stilbene) | Diethyl 4-methylthio benzylphosphonate | 3,5dimethoxymethoxy benzaldehyde | 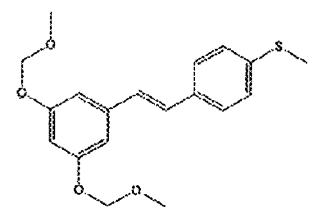 |
| BML-222 (3,5-Dihydroxy-4'-acetamide-trans-stilbene) | Diethyl 4-acetamido benzylphosphonate | 3,5-dimethoxymethoxy benzaldehyde | 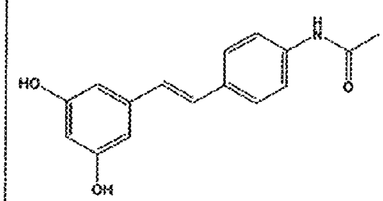 |
| BML-215 3,4-Dihydroxy-trans-stilbene | Benzylphosphonate | 3,4-Dimethoxy benzaldehyde | 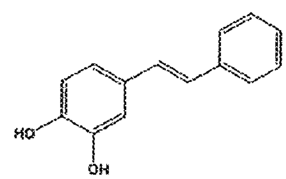 |
| BML-224 (E)-1-(3,5-Dihydroxyphenyl)-2-(cyclohexyl) ethene | 3,5-Dimethoxy benzylphosphonate | Cyclohexane carboxaldehyde | 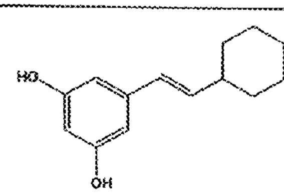 |
| 3,4-Dimethoxy-trans-stilbene | Benzylphosphonate | 3,4-Dimethoxy benzaldehyde | 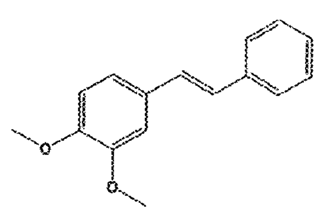 |

Figure 39

Table 18. Resveratrol Analog Synthetic Intermediates

| Compound | Benzylphosphonate | Aldehyde | Structure |
|---|---|---|---|
| Dihydroresveratrol (1-(3,5-Dihydroxyphenyl)-2-(4-hydroxyphenyl)ethane) | N/A | N/A | 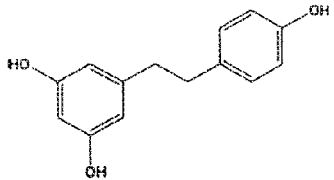 |
| BML-214 4-Hydroxy-*trans*-stilbene | Benzylphosphonate | 4-Methoxy benzaldehyde | 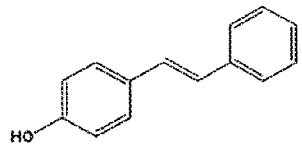 |
| BML-219 N-phenyl-(3,5-dihydroxy)benzamide | N/A | N/A | 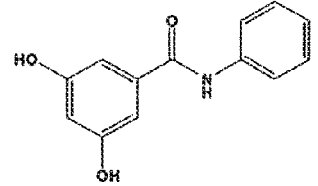 |
| 3,5-Dihydroxy-4'-nitro-*trans*-stilbene | 3,5-Dimethoxy benzylphosphonate | 4-Nitrobenzaldehdye | 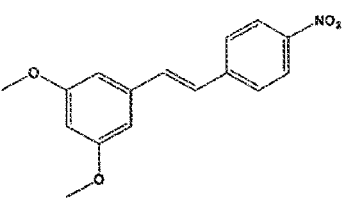 |
| 4-Methoxy-*trans*-stilbene | Benzylphosphonate | 4-Methoxy benzaldehyde | 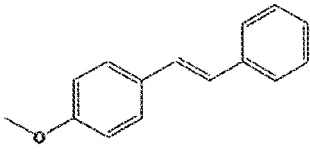 |

Figure 40

Table 20

Figure 41A

Table 21. Sirtuin activators.

| Compound | Fold Activation | Structure | Included in formula number |
|---|---|---|---|
| 2-[1-(2-hydroxyphenyl) ethylidene] hydrazine-1-carbothioamide | 1.1 | 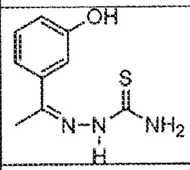 | 32 |
| prop-2-ynyl 3-(2,6-dichlorophenyl)-5-methylisoxazole-4-carboxylate | 1.1 | 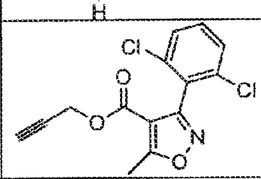 | 33 |
| 4-{3-[(3,5-dichloro-2-hydroxybenzylidene)amino]propyl}-4,5-dihydro-1H-pyrazol-5-one | 1.2 | 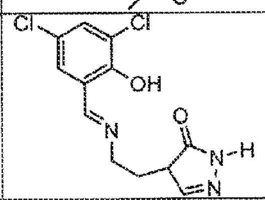 | 34 |
| 6-(phenylthio)-2-[2-(2-pyridyl)ethyl]-2,3-dihydro-1H-benzo[de]isoquinoline-1,3-dione | 1.15 | 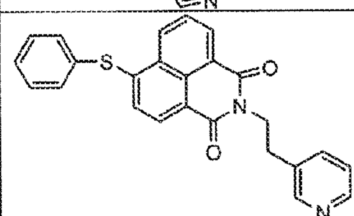 | 35 |
| 5-[(4-chloroanilino)methylene]-3-(4-chlorophenyl)-1lambda~6~,3-thiazolane-1,1,4-trione | 1.15 | 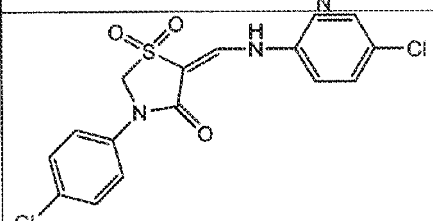 | 36 |
| 2-(4-chlorophenyl)-7-methylimidazo[1,2-a]pyridine-3-carbaldehyde O-(3-fluorobenzyl)oxime | 1.1 | 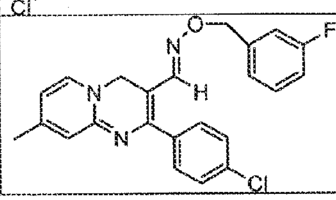 | 37 |

Figure 41B

| | | | |
|---|---|---|---|
| 2-(4-tert-butylphenoxy)-N-(3-methoxyphenyl)acetamide | 1.12 | 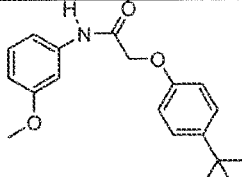 | 38 |
| 3,4,5-trimethoxy-N-(4-methyl-1,3-benzothiazol-2-yl)benzamide | 1.12 | 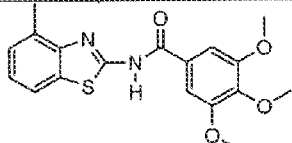 | 39 |
| 3-(1,3-benzodioxol-5-yl)-N-(pentafluorophenyl)acrylamide | 1.09 | 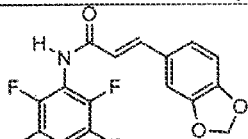 | 40 |
| 'ethyl [(4-cyano-1-morpholin-4-yl-5,6,7,8-tetrahydroisoquinolin-3-yl)thio]acetate | 1.11 | 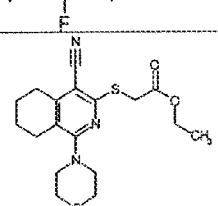 | 41 |
| 'ethyl 2-({[5-(4-methylphenyl)-7-(trifluoromethyl)-4,5,6,7-tetrahydropyrazolo[1,5-a]pyrimidin-3-yl]carbonyl}amino)-4,5,6,7-tetrahydro-1-benzothiophene-3-carboxylate | 1.1 | 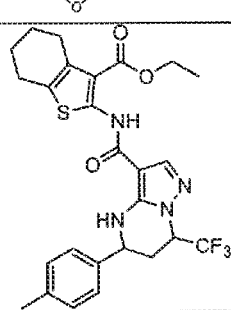 | 42 |
| '6-amino-3-(4-bromophenyl)-4-(3-hydroxy-4-methoxyphenyl)-1,4-dihydropyrano[2,3-c]pyrazole-5-carbonitrile | 1.1 | 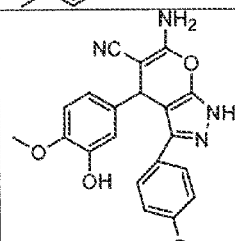 | 43 |

Figure 41C
| | | | |
|---|---|---|---|
| dimethyl 5-{[({4-oxo-5-[3-(trifluoromethyl)phenyl]-4,5-dihydro-1H-pyrazolo[3,4-d]pyrimidin-6-yl}thio)acetyl]amino}isophthalate | 1.08 | 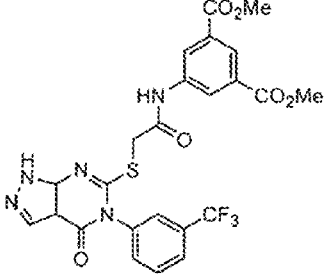 | 44 |
| N-(2-{4-(aminosulfonyl)phenyl]ethyl)-2-{[4-oxo-3-(tetrahydrofuran-2-ylmethyl)-3,4-dihydroquinazolin-2-yl]thio}acetamide | 1.05 | 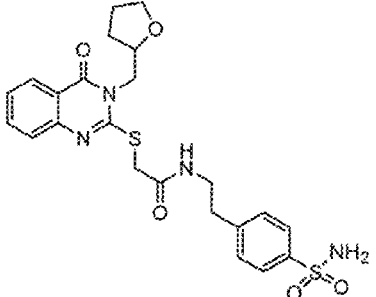 | 45 |
| N-{3-chloro-4-[(4-chloro-1-naphthyl)oxy]phenyl}-2-hydroxy-3,5-diiodobenzamide | 1.24 | 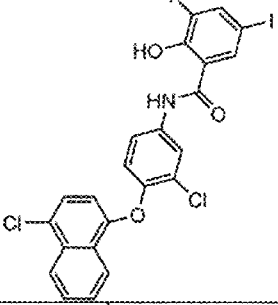 | 46 |
| | 1.2 | 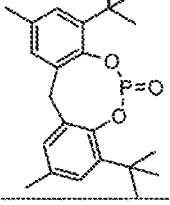 | 47 |

Figure 41D

| Name | Value | Structure | # |
|---|---|---|---|
| 'tetramethyl 5',5',9'-trimethyl-6'-(trifluoroacetyl)-5',6'-dihydrospiro[1,3-dithiole-2,1'-thiopyrano[2,3-c]quinoline]-2',3',4,5-tetracarboxylate | 1.14 | 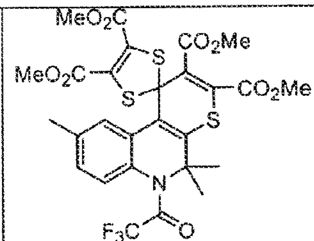 | 48 |
| 'dimethyl 2-[2,2,6-trimethyl-1-(3-methylbutanoyl)-3-thioxo-2,3-dihydroquinolin-4(1H)-ylidene]-1,3-dithiole-4,5-dicarboxylate | 1.17 | 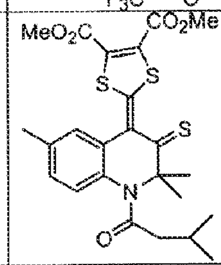 | 49 |
| 'ethyl 4-[5-[(cyanomethyl)thio]-2-thioxo[1,3]thiazolo[4',5':4,5]pyrimido[1,6-a]benzimidazol-3(2H)-yl]benzoate | 1.47 | 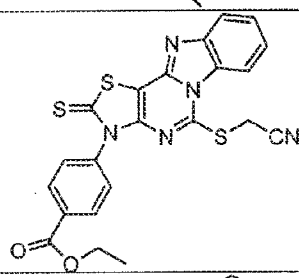 | 50 |
| '6-chloro-2,3-diphenyl-7-(trifluoromethyl)quinoxaline | 1.12 | 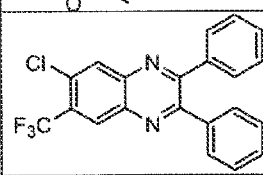 | 51 |
| '6-fluoro-2,3-bis(4-methylphenyl)quinoxaline | 1.27 | 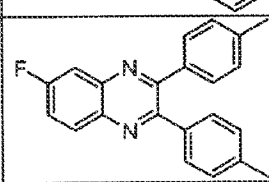 | 51 |
| | 1.1 | | 52 |

Figure 41E
| | | | |
|---|---|---|---|
| | 1.28 | 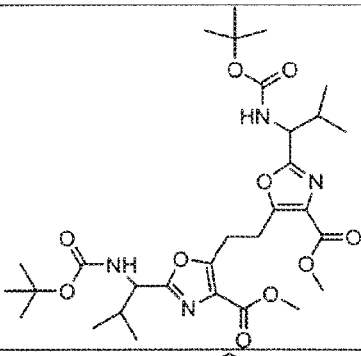 | 53 |
| Pyridine, 2-(p-chlorostyryl)-4-[[4-(diethylamino)-1-methylbutyl]amino]-, (E)- | 1.06 | 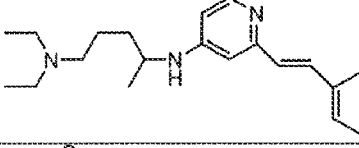 | 54 |
| Gloxazone | 1.16 | 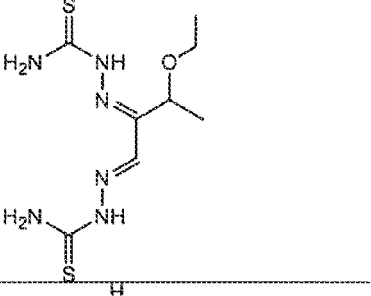 | 55 |
| | 1.25 | 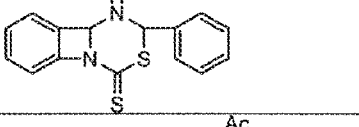 | 56 |
| | 1.1 | 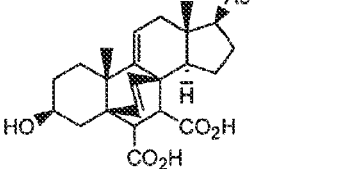 | 57 |

Figure 41F
| | | | |
|---|---|---|---|
| Ouabaine | 1.07 | 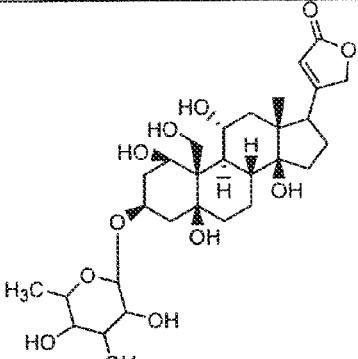 | 58 |
| | 1.16 | 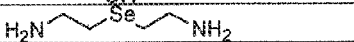 | 59 |
| | 1.06 | 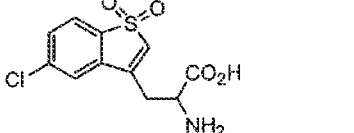 | 60 |
| Pinosylvin | 3.28 | 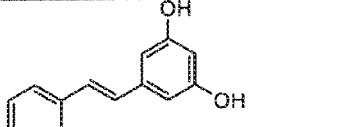 | 61 |
| Resveratrol 4"-Methyl Ether | 2.1 | 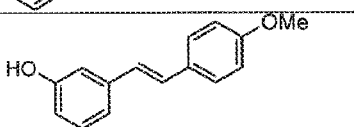 | 1 |
| Resveratrol | 2.2 | 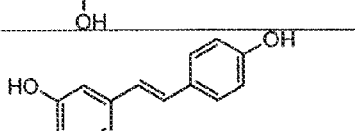 | 1 |
| Aloin | 1.2 | 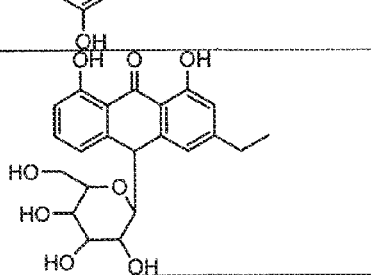 | 62 |

Figure 41G

| | | | |
|---|---|---|---|
| Piromidic Acid | 1.47 | [structure] | 63 |
| Meclocycline Sulfosalicylate | 1.12 | [structure] | 64 |
| Methacycline Hydrochloride | 1.14 | [structure] | 64 |
| Ofloxacin | 1.5 | [structure] | 65 |

Figure 42
Table 22. Sirtuin inhibitors
| Compound | Fold Activation | Structure | Included in formula number |
|---|---|---|---|
| Chlortetracycline | <1 | 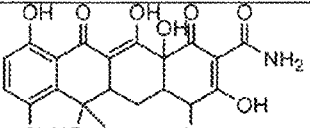 | 66 |
| | 0.27 | 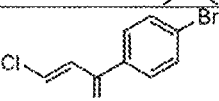 | 67 |
| Methotrexate | 0.53 | 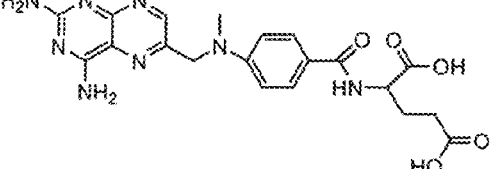 | 68 |

COMPOSITIONS FOR TREATING OBESITY AND INSULIN RESISTANCE DISORDERS

RELATED APPLICATIONS

This application is a continuation of U.S. patent application Ser. No. 11/174,000, filed Jul. 1, 2005, which is a continuation-in-part application of U.S. application Ser. No. 11/027,779, filed on Dec. 29, 2004, which claims the benefit of U.S. Provisional Application No. 60/533,712, filed on Dec. 29, 2003, and U.S. Provisional Application No. 60/588,643, filed on Jul. 16, 2004; all of which are specifically incorporated by reference herein.

GOVERNMENT SUPPORT

This invention was made with government support under Grant numbers GM068072 and 5RO1-AG19892 awarded by the National Institutes of Health. The government has certain rights in this invention.

BACKGROUND

Obesity is a chronic condition that is characterized by a body mass index (BMI) over 25. Both congenital and environmental factors, such as exercise and eating habits, contribute to the disease. For instance, the hormone leptin has been shown to be involved in fat accumulation and regulating eating behavior. Several animal models of obesity result from mutations in the leptin and/or leptin receptor gene. In addition to affecting the lifestyle of an individual, obesity can lead to a number of complications and diseases, including insulin resistance, Type II diabetes, gallbladder disease, hypertension, cardiovascular disease, hyperlipidemia, sleep apnea, coronary artery disease, knee osteoarthritis, gout, infertility, breast cancer, endometrial cancer, colon cancer and lower back pain.

Diabetes is a disease that shows an acute symptom due to a remarkably high blood sugar or ketoacidosis, or as well as chronic, general metabolic abnormalities arising from a prolonged high blood sugar status or a decrease in glucose tolerance. Both congenital and environmental factors, such as exercise and eating habits, contribute to the disease. The pathogenic causes of diabetes are insulin productive disorders, secretion disorders or reductions in activities and sensitivities of the secreted insulin. Diabetes is largely grouped into the following two types: insulin-dependent diabetes mellitus (also known as Type I diabetes) and non-insulin-dependent diabetes mellitus (also known as Type II diabetes). The incidence of Type II diabetes is remarkably increased in obese patients.

Treatments for obesity are generally directed to suppressing the appetite of the subject. Whereas a number of appetite suppressants are available (diethylpropion tenuate, mazindol, orlistat, phendimetrazine, phentermine, sibutramine), these compounds may not be effective in all subjects or may be of limited efficacy. Accordingly, new treatments for obesity are needed.

A number of treatments for diabetes are well known and include oral hypoglycemic agents such as sulfonylureas that increase insulin secretion (for example, tolbutamide, chlorpropamide and glibenclamide), biguanides (for example, metformin and buformin) that increase glucose uptake and utilization and α-glucosidase inhibitors (for example, acarbose and voglibose). In addition, thiazolidinediones, such as troglitazone, rosiglitazone and pioglitazone, are used to ameliorate insulin-resistance. However, thiazolidinedione intake is usually associated with a weight gain. Thus, there is a still a need for more effective therapies for diabetes.

Currently 8% and 15% of adults in the United States are diabetic or obese, respectively. With the number of individuals affected with diabetes, particularly with type II diabetes, and obesity on the increase, there is a dire need for medications that prevent and treat these conditions.

SUMMARY

Provided herein are methods for treating or preventing obesity and/or insulin resistance disorders, such as diabetes in a subject. In one embodiment, the method comprises administering to a subject in need thereof a therapeutically effective amount of an agent that increases the activity and/or protein level of a sirtuin, such as SIRT1 or Sir2. The agent may be a sirtuin-activating compound, or a salt or prodrug thereof. The sirtuin-activating compound preferably stimulates human Sir2, i.e., SIRT1, protein activity. The sirtuin-activating compound preferably is a compound, which has a formula selected from the group consisting of formulas 1-18, 23-47, 52 and 54-87 or a salt or prodrug thereof. Sirtuin-activating compounds may be flavones, stilbenes, flavanones, isoflavones, catechins, chalcones, tannins and anthocyanidins or analogs or derivatives thereof. Sirtuin-activating compounds may be selected from the group consisting of resveratrol, butein, piceatannol, isoliquiritgenin, fisetin, luteolin, 3,6,3',4'-tetrahydroxyfalvone, quercetin, and analogs and derivatives thereof. Preferred sirtuin activating compounds also increase the activity and/or protein level of 5'-AMP-activated protein kinase (AMPK).

In certain embodiments, the method further comprises administering to the subject a therapeutically effective amount of a second agent that: (i) increases the activity and/or protein level of 5'-AMP-activated protein kinase (AMPK); (ii) increases the activity and/or protein level of a sirtuin; (iii) is an anti-diabetic agent; or (iv) is an anti-obesity agent.

Also provided herein are methods for promoting weight gain in a subject, e.g., for treating cachexia comprising administering to a subject in need thereof a therapeutically effective amount of an agent that decreases the activity and/or protein level of a sirtuin, such as SIRT1 or Sir2. Preferably, the sirtuin-inhibitory compound is a compound selected from the group of compounds represented by formulas 19-21, 48-51, 53 and 88-90, or a salt or prodrug thereof. Preferred sirtuin inhibitory compounds also decrease or inhibit the activity and/or protein level of 5'-AMP-activating protein kinase (AMPK). In certain embodiments, the method further comprises administering to the subject a therapeutically effective amount of a second agent that: (i) decreases the activity and/or protein level of a sirtuin; (ii) decreases the activity and/or protein level of 5'-AMP-activated protein kinase (AMPK); or (iii) is an agent for promoting weight gain.

Also provided is the use of a sirtuin-activating compound, alone or in conjunction with a second agent, for the manufacture of a medicament for treating or preventing an insulin resistance disorder and the use of a sirtuin inhibitory compound, alone or in conjunction with a second agent, for the manufacture of a medicament for promoting weight gain in a subject.

BRIEF DESCRIPTION OF THE DRAWINGS

FIG. 12 shows that resveratrol inhibits lipid accumulation during mammalian adipogenesis. A. 3T3-L1 and NIH3T3 cells were differentiated into adipocytes in the presence of 25 µM, 12.5 µM or 0 µM resveratrol in vehicle (ethanol). After 10 days of differentiation, cells were fixed and stained with Oil red O. Oil red O was extracted from stained cells and quantified by measuring absorbance at 520 nm. B. Oil red O quantitation is shown as fold change relative to the 3T3-L1 sample treated with 0 µm resvratrol.

FIG. 21 shows the stimulation of SIRT 1 catalytic rate by 100 µM plant polyphenols (Table 1). Abbreviation: SE, standard error of the mean. Rate measurements with 25 µM NAD$^+$ and 25 µM p53-382 acetylated peptide substrate were performed as described in Methods. All ratio data were calculated from experiments in which the total deacetylation in the control reaction was 0.25-1.25 µM peptide or 1-5% of the initial concentration of acetylated peptide.

FIG. 22 shows the effect of 100 µM stilbenes and chalcones on SIRT 1 catalytic rate (Supplementary Table 1). Abbreviation: SE, standard error of the mean. Rate measurements with 25 µM NAD$^+$ and 25 µM p53-382 acetylated peptide substrate were performed as described in Methods. All ratio data were calculated from experiments in which the total deacetylation in the control reaction was 0.25-1.25 µM peptide or 1-5% of the initial concentration of acetylated peptide.

FIG. 23 shows the effect of 100 µM flavones on SIRT 1 catalytic rate (Supplementary Table 2). Abbreviation: SE, standard error of the mean. Rate measurements with 25 µM NAD$^+$ and 25 µM p53-382 acetylated peptide substrate were performed as described in Methods. All ratio data were calculated from experiments in which the total deacetylation in the control reaction was 0.25-1.25 μM peptide or 1-5% of the initial concentration of acetylated peptide.

FIG. 24 shows the effect of 100 μM flavones on SIRT 1 catalytic rate (Supplementary Table 3). Abbreviation: SE, standard error of the mean. Rate measurements with 25 μM NAD$^+$ and 25 μM p53-382 acetylated peptide substrate were performed as described in Methods. All ratio data were calculated from experiments in which the total deacetylation in the control reaction was 0.25-1.25 μM peptide or 1-5% of the initial concentration of acetylated peptide.

FIG. 25 shows the effect of 100 μM isoflavones, flavanones and anthocyanidins on SIRT 1 catalytic rate (Supplementary Table 4). Abbreviation: SE, standard error of the mean. Rate measurements with 25 μM NAD$^+$ and 25 μM p53-382 acetylated peptide substrate were performed as described in Methods. All ratio data were calculated from experiments in which the total deacetylation in the control reaction was 0.25-1.25 μM peptide or 1-5% of the initial concentration of acetylated peptide.

FIG. 26 shows the effect of 100 μM catechins (Flavan-3-ols) on SIRT 1 catalytic rate (Supplementary Table 5). Abbreviation: SE, standard error of the mean. Rate measurements with 25 μM NAD$^+$ and 25 μM p53-382 acetylated peptide substrate were performed as described in Methods. All ratio data were calculated from experiments in which the total deacetylation in the control reaction was 0.25-1.25 μM peptide or 1-5% of the initial concentration of acetylated peptide.

FIG. 27 shows the effect of 100 μM free radical protective compounds on SIRT 1 catalytic rate (Supplementary Table 6). Abbreviation: SE, standard error of the mean. Rate measurements with 25 μM NAD$^+$ and 25 μM p53-382 acetylated peptide substrate were performed as described in Methods. All ratio data were calculated from experiments in which the total deacetylation in the control reaction was 0.25-1.25 μM peptide or 1-5% of the initial concentration of acetylated peptide.

FIG. 28 shows the effect of 100 μM miscellaneous compounds on SIRT 1 catalytic rate (Supplementary Table 7). Abbreviation: SE, standard error of the mean. Rate measurements with 25 μM NAD$^+$ and 25 μM p53-382 acetylated peptide substrate were performed as described in Methods. All ratio data were calculated from experiments in which the total deacetylation in the control reaction was 0.25-1.25 μM peptide or 1-5% of the initial concentration of acetylated peptide.

FIG. 29 shows the effect of 100 μM of various modulators on SIRT 1 catalytic rate (Supplementary Table 8). Abbreviation: SE, standard error of the mean. Rate measurements with 25 μM NAD$^+$ and 25 μM p53-382 acetylated peptide substrate were performed as described in Methods. All ratio data were calculated from experiments in which the total deacetylation in the control reaction was 0.25-1.25 μM peptide or 1-5% of the initial concentration of acetylated peptide.

FIG. 30 shows the effect of 100 μM of new resveratrol analogs on SIRT 1 catalytic rate (Table 9).

FIG. 31 shows the effect of 100 μM of new resveratrol analogs on SIRT 1 catalytic rate (Table 10).

FIG. 32 shows the effect of 100 μM of new resveratrol analogs on SIRT 1 catalytic rate (Table 11).

FIG. 33 shows the effect of 100 μM of new resveratrol analogs on SIRT 1 catalytic rate (Table 12).

FIG. 34 shows the effect of 100 μM of new resveratrol analogs on SIRT 1 catalytic rate (Table 13).

FIG. 35 shows synthetic intermediates of resveratrol analog synthesis (Table 14).

FIG. 36 shows synthetic intermediates of resveratrol analog synthesis (Table 15).

FIG. 37 shows synthetic intermediates of resveratrol analog synthesis (Table 16).

FIG. 38 shows synthetic intermediates of resveratrol analog synthesis (Table 17).

FIG. 39 shows synthetic intermediates of resveratrol analog synthesis (Table 18).

Figure 40:
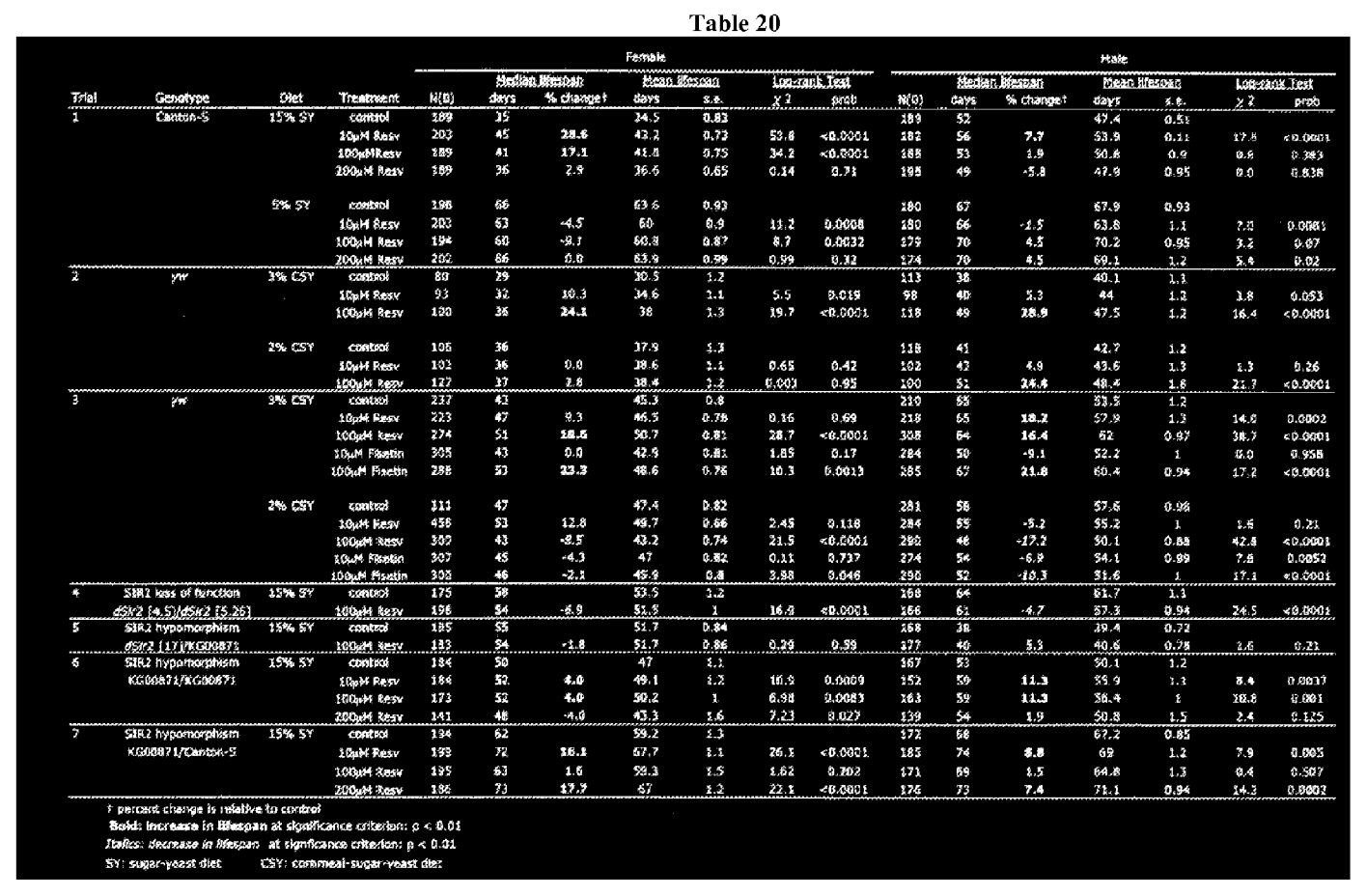

FIG. 40 shows the effect of resveratrol on *Drosophila melanogaster* (Table 20).

FIG. 41A-G shows sirtuin activators and the fold activation of SIRT1 (Table 21).

FIG. 42 shows sirtuin inhibitors and the fold inhibition of SIRT1 (Table 22).

DETAILED DESCRIPTION

Definitions

Figure 1:
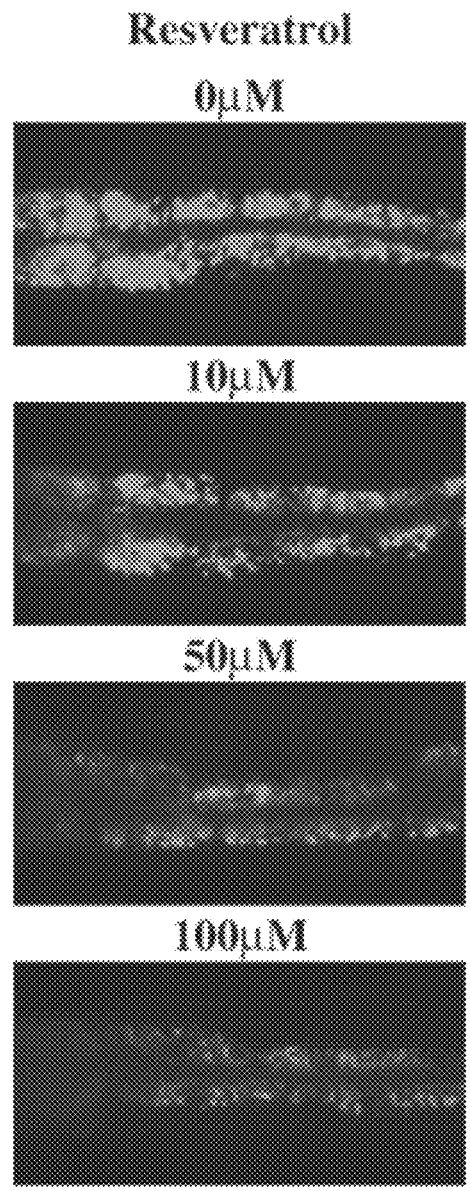
FIG. 1 is a series of photomicrographs that depict the effect of the sirtuin-activating compound resveratrol at different concentrations to induce fat mobilization as indicated by a decrease in Nile Red staining.

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

"Sirtuin activation" refers to increasing at least one activity of a sirtuin protein, preferably by at least about 10%, 50%, 100% or more. "Activating a sirtuin protein" refers to the action of producing an activated sirtuin protein, i.e., a sirtuin protein that is capable of performing at least one of its biological activities with an increase of activity of at least about 10%, 50%, 2 fold or more. Biological activities of sirtuin proteins include deacetylation, e.g., of histones and p53; extending lifespan; increasing genomic stability; silencing transcription; and controlling the segregation of oxidized proteins between mother and daughter cells.

An "activating compound," "sirtuin-activating compound," or a "sirtuin activator" refers to a compound that activates a sirtuin protein or stimulates or increases at least one activity of a sirtuin protein. In certain embodiments, a sirtuin-activating compound may have a formula selected from the group of formulas 1-18, 23-47, 52, and 54-87.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

"Sirtuin inhibition" refers to decreasing at least one activity of a sirtuin protein, preferably at least about 10%, 50%, 100% or more.

An "inhibitory compound" or "inhibiting compound" or "sirtuin inhibitory compound" refers to a compound that inhibits at least one activity of a sirtuin protein. In certain embodiments, a sirtuin inhibitory compound may have a formula selected from the group consisting of formulas 19-21, 48-51, 53 and 88-90.

A "form that is naturally occurring" when referring to a compound means a compound that is in a form, e.g., a composition, in which it can be found naturally. For example, since resveratrol can be found in red wine, it is present in red wine in a form that is naturally occurring. A compound is not in a form that is naturally occurring if, e.g., the compound has been purified and separated from at least some of the other molecules that are found with the compound in nature. A "naturally occurring compound" refers to a compound that can be found in nature, i.e., a compound that has not been designed by man. A naturally occurring compound may have been made by man or by nature.

"Sirtuin protein" refers to a member of the sirtuin deacetylase protein family or preferably to the Sir2 family, which include yeast Sir2 (GenBank Accession No. P53685), C. elegans Sir-2.1 (GenBank Accession No. NP_501912), and human SIRT1 (GenBank Accession No. NM_012238 and NP_036370 (or AF083106), set forth as SEQ ID NOs: 1 and 2, respectively) and SIRT2 (GenBank Accession No. NM_030593 and AF083107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273). Preferred sirtuins are those that share more similarities with SIRT1, i.e., hSIRT1, and/or Sir2 than with SIRT2, such as those members having at least part of the N-terminal sequence present in SIRT1 and absent in SIRT2 such as SIRT3 has.

SEQ ID NOs of the human genes referred to herein are identified in the table below:

| name | | nucleotide sequence | | amino acid sequence | |
| --- | --- | --- | --- | --- | --- |
| | | GenBank | SEQ ID NO | GenBank | SEQ ID NO |
| SIRT1 | | NM_012238 | 1 | NP_036370 | 2 |
| SIRT2 | i1 | NM_012237 | 3 | NP_036369 | 4 |
| | i2 | NM_030593 | 5 | NP_085096 | 6 |
| SIRT3 | ia | NM_012239 | 7 | NP_036371 | 8 |
| | ib | NM_001017524 | 9 | NP_001017524 | 10 |
| SIRT4 | | NM_012240 | 11 | NP_036372 | 12 |
| SIRT5 | i1 | NM_012241 | 13 | NP_036373 | 14 |
| | i2 | NM_031244 | 15 | NP_112534 | 16 |
| SIRT6 | | NM_016539 | 17 | NP_057623 | 18 |
| SIRT7 | | NM_016538 | 19 | NP_057622 | 20 |

A "direct activator" of a sirtuin is a molecule that activates a sirtuin by binding to it. A "direct inhibitor" of a sirtuin is a molecule that inhibits a sirtuin by binding to it.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "hyperinsulinemia" refers to a state in an individual in which the level of insulin in the blood is higher than normal.

The term "insulin resistance" refers to a state in which a normal amount of insulin produces a subnormal biologic response relative to the biological response in a subject that does not have insulin resistance.

An "insulin resistance disorder," as discussed herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholescystitis and cholelithiasis, gout, obstructive sleep apnea and respiratory problems, osteoarthritis, and prevention and treatment of bone loss, e.g. osteoporosis.

"Obese" individuals or individuals suffering from obesity are generally individuals having a body mass index (BMI) of at least 25 or greater. Obesity may or may not be associated with insulin resistance.

The terms "comprise" and "comprising" are used in the inclusive, open sense, meaning that additional elements may be included.

The term "including" is used to mean "including but not limited to." "Including" and "including but not limited to" are used interchangeably.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The term "recombinant" polynucleotide means a polynucleotide of genomic, cDNA, semisynthetic, or synthetic origin which either does not occur in nature or is linked to another polynucleotide in a normatural arrangement.

A "patient," "individual," "subject" or "host" refers to either a human or a non-human animal.

The term "substantially homologous" when used in connection with amino acid sequences, refers to sequences which are substantially identical to or similar in sequence with each other, giving rise to a homology of conformation and thus to retention, to a useful degree, of one or more biological (including immunological) activities. The term is not intended to imply a common evolution of the sequences.

The term "modulation" is art-recognized and refers to up regulation (i.e., activation or stimulation), down regulation (i.e., inhibition or suppression) of a response, or the two in combination or apart.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "mammal" is known in the art, and exemplary mammals include humans, primates, bovines, porcines, canines, felines, and rodents (e.g., mice and rats).

The term "bioavailable" when referring to a compound is art-recognized and refers to a form of a compound that allows for it, or a portion of the amount of compound administered, to be absorbed by, incorporated to, or otherwise physiologically available to a subject or patient to whom it is administered.

The term "pharmaceutically-acceptable salt" is art-recognized and refers to the relatively non-toxic, inorganic and organic acid addition salts of compounds, including, for example, those contained in compositions described herein.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

"Transcriptional regulatory sequence" is a generic term used throughout the specification to refer to DNA sequences, such as initiation signals, enhancers, and promoters, which induce or control transcription of protein coding sequences with which they are operable linked. In preferred embodiments, transcription of one of the recombinant genes is under the control of a promoter sequence (or other transcriptional regulatory sequence) which controls the expression of the recombinant gene in a cell-type which expression is intended. It will also be understood that the recombinant gene can be under the control of transcriptional regulatory sequences which are the same or which are different from those sequences which control transcription of the naturally-occurring forms of genes as described herein.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions. As used herein, "expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

"Treating" a condition or disease refers to curing as well as ameliorating at least one symptom of the condition or disease.

The term "cis" is art-recognized and refers to the arrangement of two atoms or groups around a double bond such that the atoms or groups are on the same side of the double bond. Cis configurations are often labeled as (Z) configurations.

The term "trans" is art-recognized and refers to the arrangement of two atoms or groups around a double bond such that the atoms or groups are on the opposite sides of a double bond. Trans configurations are often labeled as (E) configurations.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "therapeutic agent" is art-recognized and refers to any chemical moiety that is a biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic effect" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease or condition being treated, the weight and age of the subject, the severity of the disease or condition, the manner of administration and the like, which can readily be determined by one of ordinary skill in the art. For example, certain compositions described herein may be administered in a sufficient amount to produce a desired effect at a reasonable benefit/risk ratio applicable to such treatment.

The term "synthetic" is art-recognized and refers to production by in vitro chemical or enzymatic synthesis.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not minor images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "structure-activity relationship" or "(SAR)" is art-recognized and refers to the way in which altering the molecular structure of a drug or other compound alters its biological activity, e.g., its interaction with a receptor, enzyme, nucleic acid or other target and the like.

The term "aliphatic" is art-recognized and refers to a linear, branched, cyclic alkane, alkene, or alkyne. In certain embodiments, aliphatic groups in the present compounds are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, naphtalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is a rt-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

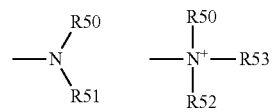

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

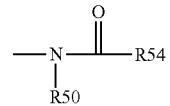

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

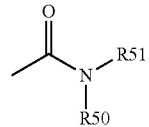

wherein R50 and R51 are as defined above. Certain embodiments of amides may not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

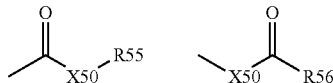

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

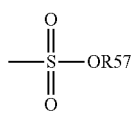

in which R57 is an electron pair, hydrogen, alkyl, cycloalkyl, or aryl.

The term "sulfate" is art recognized and includes a moiety that may be represented by the general formula:

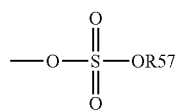

in which R57 is as defined above.

The term "sulfonamido" is art recognized and includes a moiety that may be represented by the general formula:

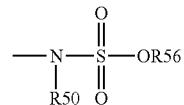

in which R50 and R56 are as defined above.

The term "sulfamoyl" is art-recognized and refers to a moiety that may be represented by the general formula:

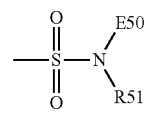

in which R50 and R51 are as defined above.

The term "sulfonyl" is art-recognized and refers to a moiety that may be represented by the general formula:

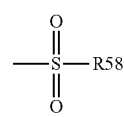

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

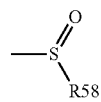

in which R58 is defined above.

The term "phosphoryl" is art-recognized and may in general be represented by the formula:

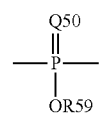

wherein Q50 represents S or O, and R 59 represents hydrogen, a lower alkyl or an aryl. When used to substitute, e.g., an alkyl, the phosphoryl group of the phosphorylalkyl may be represented by the general formulas:

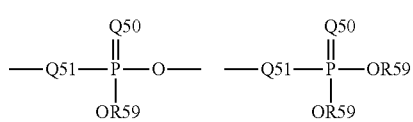

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

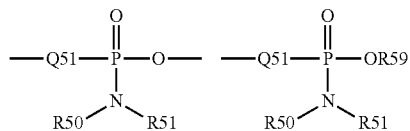

wherein Q51, R50, R51 and R59 are as defined above.

The term "phosphonamidite" is art-recognized and may be represented in the general formulas:

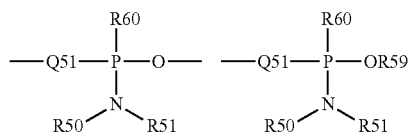

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls. The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions described herein may exist in particular geometric or stereoisomeric forms. In addition, compounds may also be optically active. Contemplated herein are all such compounds, including cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. All such isomers, as well as mixtures thereof, are encompassed herein.

If, for instance, a particular enantiomer of a compound is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. Heteroatoms such as nitrogen may have hydrogen substituents and/or any permissible substituents of organic compounds described herein which satisfy the valences of the heteroatoms. Compounds are not intended to be limited in any manner by the permissible substituents of organic compounds.

The chemical elements are identified in accordance with the Periodic Table of the Elements, CAS version, *Handbook of Chemistry and Physics*, 67th Ed., 1986-87, inside cover.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* (2$^{nd}$ ed., Wiley: New York, 1991).

The term "hydroxyl-protecting group" is art-recognized and refers to those groups intended to protect a hydrozyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—CH$_2$C$_6$H$_5$), acyl[C(O)R1] or SiR1$_3$ where R1 is C$_1$-C$_4$ alkyl, halomethyl, or 2-halo-substituted-(C$_2$-C$_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, March, *Advanced Organic Chemistry* 251-59 (McGraw Hill Book Company: New York, 1977). The Hammett constant values are generally negative for electron donating groups (σ(P)=−0.66 for NH$_2$) and positive for electron withdrawing groups (σ(P)=0.78 for a nitro group), σ(P) indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

Exemplary Sirtuin-activating Compounds and Methods of Use

The following examples show that activators of sirtuins, such as resveratrol, butein, fisetin, piceatannol, quercetin and 3,5-dihydroxy-4-'-thiomethyl-trans-stilbene stimulates fat metabolism by reducing fat accumulation (See examples 1, 8 and 9) as well as inhibit adipogenesis (example 6); that Sir2 and AMPK are necessary for resveratrol mediated fat mobilization (See examples 3 and 4); that resveratrol stimulates AMPK and ACC phosphorylation (See example 5); that resveratrol boosts insulin sensitivity of adipocytes (See example 10) and that resveratrol, like other AMPK activators, can stimulate fatty acid oxidation in lipogenic cells (See example 11).

Exemplary sirtuin-activating compounds that activate sirtuins are described in Howitz et al. (2003) *Nature* 425: 191 and include: for example, resveratrol (3,5,4'-Trihydroxy-trans-stilbene), butein (3,4,2',4'-Tetrahydroxychalcone), piceatannol (3,5,3',4'-Tetrahydroxy-trans-stilbene), isoliquiritigenin (4,2',4'-Trihydroxychalcone), fisetin (3,7,3',4'-Tetrahydroxyflavone), quercetin (3,5,7,3',4'-Pentahydroxyflavone), Deoxyrhapontin (3,5-Dihydroxy-4'-methoxystilbene 3-O-β-D-glucoside); trans-Stilbene; Rhapontin (3,3',5-Trihydroxy-4'-methoxystilbene 3-O-β-D-glucoside); cis-Stilbene; Butein (3,4,2',4'-Tetrahydroxychalcone); 3,4,2'4'6'-Pentahydroxychalcone; Chalcone; 7,8,3',4'-Tetrahydroxyflavone; 3,6,2',3'-Tetrahydroxyflavone; 4'-Hydroxyflavone; 5,4'-Dihydroxyflavone; 5,7-Dihydroxyflavone; Morin (3,5,7,2',4'-Pentahydroxyflavone); Flavone; 5-Hydroxyflavone; (−)-Epicatechin (Hydroxy Sites: 3,5,7,3',4'); (−)-Catechin (Hydroxy Sites: 3,5,7,3',4'); (−)-Gallocatechin (Hydroxy Sites: 3,5,7,3',4',5') (+)-Catechin (Hydroxy Sites: 3,5,7,3',4'); 5,7,3',4',5'-pentahydroxyflavone; Luteolin (5,7,3',4'-Tetrahydroxyflavone); 3,6,3',4'-Tetrahydroxyflavone; 7,3',4',5'-Tetrahydroxyflavone; Kaempferol (3,5,7,4'-Tetrahydroxyflavone); 6-Hydroxyapigenin (5,6,7,4'-Tetrahydroxyflavone); Scutellarein; Apigenin (5,7,4'-Trihydroxyflavone); 3,6,2',4'-Tetrahydroxyflavone; 7,4'-Dihydroxyflavone; Daidzein (7,4'-Dihydroxyisoflavone); Genistein (5,7,4'-Trihydroxyflavanone); Naringenin (5,7,4'-Trihydroxyflavanone); 3,5,7,3',4'-Pentahydroxyflavanone; Flavanone; Pelargonidin chloride (3,5,7,4'-Tetrahydroxyflavylium chloride); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole-4-ethana-minium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid.H$_2$O); Ambroxol (trans-4-(2-Amino-3,5-dibromobenzylamino) cyclohexane.HCl; and U-83836E ((−)-2-((4-(2,6-di-1-Pyrrolidinyl-4-pyrimidinyl)-1-piperazinyl)methyl)-3,4-dihydro-2,5,7,8-tetramethyl-2H-1-benzopyran-6-ol.2HCl). Analogs and derivatives thereof can also be used.

Other sirtuin-activating compounds may have any of formulas 1-18 below. In one embodiment, a sirtuin-activating compound is a stilbene or chalcone compound of formula 1:

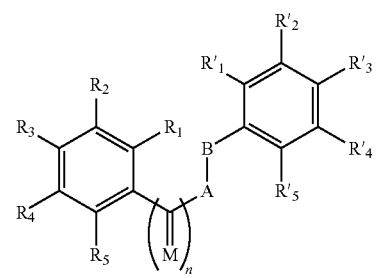

wherein, independently for each occurrence,

R$_1$, R$_2$, R$_3$, R$_4$, R$_5$, R'$_1$, R'$_2$, R'$_3$, R'$_4$, and R'$_5$ represent H, alkyl, aryl, heteroaryl, alkaryl, heteroaralkyl, halide, NO$_2$, SR, OR, N(R)$_2$, or carboxyl;

R represents H, alkyl, or aryl;

M represents O, NR, or S;

A-B represents a bivalent alkyl, alkenyl, alkynyl, amido, sulfonamido, diazo, ether, alkylamino, alkylsulfide, or hydrazine group; and n is 0 or 1;

provided that when n is 0:

when R$_2$ and R$_4$ are OR, and R$_1$, R$_3$, R$_5$, R'$_1$, R'$_2$, R'$_4$, and R'$_5$ are H, and A-B is alkenyl, R'$_3$ is not Cl, F, —CH$_3$, —CH$_2$CH$_3$, —SMe, NO$_2$, i-propyl, —OMe, or carboxyl;

when A-B is alkyl or amido, R$_2$ and R$_4$ are not both OH;

when R$_3$ is OR at least one of R'$_1$, R'$_2$, R'$_3$, R'$_4$, or R'$_5$ is not H; and R$_4$ is not carboxyl.

In a further embodiment, the compound is a compound as shown as of formula 1 with attendant definitions, wherein the n is 0. In a further embodiment, the compound is a compound as shown as formula 1 and the attendant definitions, wherein the n is 1. In a further embodiment, the compound is a compound as shown as formula 1 and the attendant definitions, wherein the A-B is ethenyl. In a further embodiment, the compound is a compound as shown as formula 1 and the attendant definitions, wherein the A-B is —CH$_2$CH(Me)CH (Me)CH$_2$—. In a further embodiment, the compound is a compound as shown as formula 1 and the attendant definitions, wherein the M is O. In a further embodiment, the compound is a compound as shown as formula 1 and the attendant definitions, wherein $R_1$, $R_2$, $R_3$, $R_4$, $R_5$, $R'_1$, $R'_2$, $R'_3$, $R'_4$, and $R'_5$ are H. In a further embodiment, the compound is a compound as shown as formula 1 and the attendant definitions, wherein $R_2$, $R_4$, and $R'_3$ are OH. In a further embodiment, the compound is a compound as shown as formula 1 and the attendant definitions, wherein $R_2$, $R_4$, $R'_2$ and $R'_3$ are OH. In a further embodiment, the compound is a compound as shown as formula 1 and the attendant definitions, wherein the $R_3$, $R_5$, $R'_2$ and $R'_3$ are OH. In a further embodiment, the compound is a compound as shown as formula 1 and the attendant definitions, wherein $R_1$, $R_3$, $R_5$, $R'_2$ and $R'_3$ are OH. In a further embodiment, the compound is a compound as shown as formula 1 and the attendant definitions, wherein $R_2$ and $R'_2$ are OH; $R_4$ is O-β-D-glucoside; and $R'_3$ is $OCH_3$. In a further embodiment, the compound is a compound as shown as formula 1 and the attendant definitions, wherein $R_2$ is OH; $R_4$ is O-β-D-glucoside; and $R'_3$ is $OCH_3$.

In a further embodiment, the compound is a compound as shown as formula 1 and the attendant definitions, wherein n is 0; A-B is ethenyl; and $R_1$, $R_2$, $R_3$, $R_4$, $R_5$, $R'_1$, $R'_2$, $R'_3$, $R'_4$, and $R'_5$ are H (trans stilbene). In a further embodiment, the compound is a compound as shown as formula 1 and the attendant definitions, wherein n is 1; A-B is ethenyl; M is O; and $R_1$, $R_2$, $R_3$, $R_4$, $R_5$, $R'_1$, $R'_2$, $R'_3$, $R'_4$, and $R'_5$ are H (chalcone). In a further embodiment, the compound is a compound as shown as formula 1 and the attendant definitions, wherein n is 0; A-B is ethenyl; $R_2$, $R_4$, and $R'_3$ are OH; and $R_1$, $R_3$, $R_5$, $R'_1$, $R'_2$, $R'_4$, and $R'_5$ are H (resveratrol). In a further embodiment, the compound is a compound as shown as formula 1 and the attendant definitions, wherein n is 0; A-B is ethenyl; $R_2$, $R_4$, $R'_2$ and $R'_3$ are OH; and $R_1$, $R_3$, $R_5$, $R'_1$, $R'_4$ and $R'_5$ are H (piceatannol). In a further embodiment, the compound is a compound as shown as formula 1 and the attendant definitions, wherein n is 1; A-B is ethenyl; M is O; $R_3$, $R_5$, $R'_2$ and $R'_3$ are OH; and $R_1$, $R_2$, $R_4$, $R'_1$, $R'_4$, and $R'_5$ are H (butein). In a further embodiment, the compound is a compound as shown as formula 1 and the attendant definitions, wherein n is 1; A-B is ethenyl; M is O; $R_1$, $R_3$, $R_5$, $R'_2$ and $R'_3$ are OH; and $R_2$, $R_4$, $R'_1$, $R'_4$, and $R'_5$ are H (3,4,2',4',6'-pentahydroxychalcone). In a further embodiment, the compound is a compound as shown as formula 1 and the attendant definitions, wherein n is 0; A-B is ethenyl; $R_2$ and $R'_2$ are OH, $R_4$ is O-β-D-glucoside, $R'_3$ is $OCH_3$; and $R_1$, $R_3$, $R_5$, $R'_1$, $R'_4$, and $R'_5$ are H (rhapontin). In a further embodiment, the compound is a compound as shown as formula 1 and the attendant definitions, wherein n is 0; A-B is ethenyl; $R_2$ is OH, $R_4$ is O-β-D-glucoside, $R_3$ is $OCH_3$; and $R_1$, $R_3$, $R_5$, $R'_1$, $R'_2$, $R'_4$, and $R'_5$ are H (deoxyrhapontin). In a further embodiment, a compound is a compound as shown as formula 1 and the attendant definitions, wherein n is 0; A-B is —$CH_2CH(Me)CH(Me)CH_2$—; $R_2$, $R_3$, $R'_2$, and $R'_3$ are OH; and $R_1$, $R_4$, $R_5$, $R'_1$, $R'_4$, and $R'_5$ are H (NDGA).

In another embodiment, a sirtuin-activating compound is a flavanone compound of formula 2:

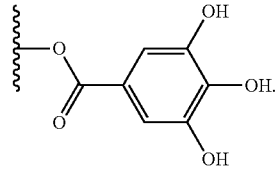

2 wherein, independently for each occurrence, $R_1$, $R_2$, $R_3$, $R_4$, $R_5$, $R'_1$, $R'_2$, $R'_3$, $R'_4$, $R'_5$, and R" represent H, alkyl, aryl, heteroaryl, alkaryl, heteroaralkyl, halide, $NO_2$, SR, OR, $N(R)_2$, or carboxyl;

R represents H, alkyl, or aryl;

M represents $H_2$, O, NR, or S;

Z represents CR, O, NR, or S; and

X represents CR or N; and

Y represents CR or N.

In a further embodiment, the compound is a compound as shown as formula 2 and the attendant definitions, wherein X and Y are both CH. In a further embodiment, the compound is a compound as shown as formula 2 and the attendant definitions, wherein M is O. In a further embodiment, the compound is a compound as shown as formula 2 and the attendant definitions, wherein M is $H_2$. In a further embodiment, the compound is a compound as shown as formula 2 and the attendant definitions, wherein Z is O. In a further embodiment, the compound is a compound as shown as formula 2 and the attendant definitions, wherein R" is H. In a further embodiment, the compound is a compound as shown as formula 2 and the attendant definitions, wherein R" is OH. In a further embodiment, the compound is a compound as shown as formula 2 and the attendant definitions, wherein R" is an ester. In a further embodiment, the compound is a compound as shown as formula 2 and the attendant definitions, wherein $R_1$ is

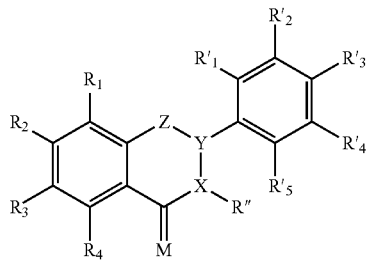

In a further embodiment, the compound is a compound as shown as formula 2 and the attendant definitions, wherein $R_1$, $R_2$, $R_3$, $R_4$, $R'_1$, $R'_3$, $R'_4$, $R'_5$ and R" are H. In a further embodiment, the compound is a compound as shown as formula 2 and the attendant definitions, wherein $R_2$, $R_4$, and $R'_3$ are OH. In a further embodiment, the compound is a compound as shown as formula 2 and the attendant definitions, wherein $R_4$, $R'_2$, $R'_3$, and R" are OH. In a further embodiment, the compound is a compound as shown as formula 2 and the attendant definitions, wherein $R_2$, $R_4$, $R'_2$, $R'_3$, and R" are OH. In a further embodiment, the compound is a compound as shown as formula 2 and the attendant definitions, wherein $R_2$, $R_4$, $R'_2$, $R'_3$, $R'_4$, and R" are OH.

In a further embodiment, the compound is a compound as shown as formula 2 and the attendant definitions, wherein X and Y are CH; M is O; Z and O; R" is H; and $R_1$, $R_2$, $R_3$, $R_4$, $R'_1$, $R'_2$, $R'_3$, $R'_4$, $R'_5$ and R" are H (flavanone). In a further embodiment, the compound is a compound as shown as formula 2 and the attendant definitions, wherein X and Y are CH; M is O; Z and O; R" is H; $R_2$, $R_4$, and $R'_3$ are OH; and $R_1$, $R_3$, $R'_1$, $R'_2$, $R'_4$, and $R'_5$ are H (naringenin). In a further embodiment, the compound is a compound as shown as formula 2 and the attendant definitions, wherein X and Y are CH; M is O; Z and O; R" is OH; $R_2$, $R_4$, $R'_2$, and $R'_3$ are OH; and $R_1$, $R_3$, $R'_1$, $R'_4$, and $R'_5$ are H (3,5,7,3',4'-pentahydroxyflavanone). In a further embodiment, the compound is a compound as shown as formula 2 and the attendant definitions, wherein X and Y are CH; M is $H_2$; Z and O; R" is OH; $R_2$, $R_4$, $R'_2$, and $R'_3$, are OH; and $R_1$, $R_3$, $R'_1$, $R'_4$ and $R'_5$ are H (epicatechin). In a further embodiment, the compound is a compound as shown as formula 2 and the attendant definitions, wherein X and Y are CH; M is $H_2$; Z and O; R″ is OH; $R_2$, $R_4$, $R'_2$, $R'_3$, and $R'_4$ are OH; and $R_1$, $R_3$, $R'_1$, and $R'_5$ are H (gallocatechin). In a further embodiment, the compound is a compound as shown as formula 2 and the attendant definitions, wherein X and Y are CH; M is $H_2$; Z and O; R″ is

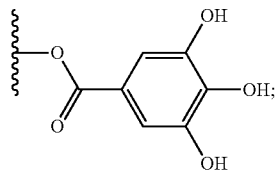 [SMILES: *OC(=O)c1cc(O)c(O)c(O)c1]

$R_2$, $R_4$, $R'_2$, $R'_3$, $R'_4$, and R″ are OH; and $R_1$, $R_3$, $R'_1$, and $R'_5$ are H (epigallocatechin gallate).

In another embodiment, a sirtuin-activating compound is an iso flavanone compound of formula 3:

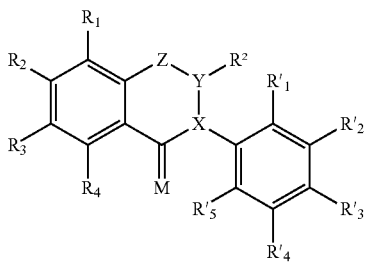

wherein, independently for each occurrence, $R_1$, $R_2$, $R_3$, $R_4$, $R_5$, $R'_1$, $R'_2$, $R'_3$, $R'_4$, $R'_5$, and R″$_1$ represent H, alkyl, aryl, heteroaryl, alkaryl, heteroaralkyl, halide, $NO_2$, SR, OR, $N(R)_2$, or carboxyl;

R represents H, alkyl, or aryl;

M represents $H_2$, O, NR, or S;

Z represents CR, O, NR, or S; and

X represents CR or N; and

Y represents CR or N.

In another embodiment, a sirtuin-activating compound is a flavone compound of formula

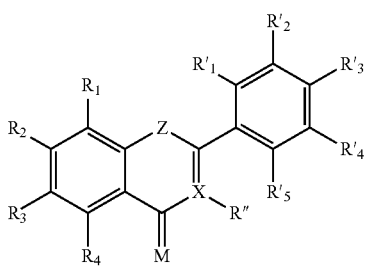

wherein, independently for each occurrence, $R_1$, $R_2$, $R_3$, $R_4$, $R_5$, $R'_1$, $R'_2$, $R'_3$, $R'_4$, and $R'_5$, represent H, alkyl, aryl, heteroaryl, alkaryl, heteroaralkyl, halide, $NO_2$, SR, OR, $N(R)_2$, or carboxyl;

R″ is absent or represents H, alkyl, aryl, heteroaryl, alkaryl, heteroaralkyl, halide, $NO_2$, SR, OR, $N(R)_2$, or carboxyl;

R represents H, alkyl, or aryl;

M represents $H_2$, O, NR, or S;

Z represents CR, O, NR, or S; and

X represents CR or N when R″ is absent or C when R″ is present.

In a further embodiment, the compound is a compound as shown as formula 4 and the attendant definitions, wherein X is C. In a further embodiment, the compound is a compound as shown as formula 4 and the attendant definitions, wherein X is CR. In a further embodiment, the compound is a compound as shown as formula 4 and the attendant definitions, wherein Z is O. In a further embodiment, the compound is a compound as shown as formula 4 and the attendant definitions, wherein M is O. In a further embodiment, the compound is a compound as shown as formula 4 and the attendant definitions, wherein R″ is H. In a further embodiment, the compound is a compound as shown as formula 4 and the attendant definitions, wherein R″ is OH. In a further embodiment, the compound is a compound as shown as formula 4 and the attendant definitions, wherein $R_1$, $R_2$, $R_3$, $R_4$, $R_5$, $R'_1$, $R'_2$, $R'_3$, $R'_4$, and $R'_5$ are H. In a further embodiment, the compound of formula 4 and the attendant definitions, wherein $R_2$, $R'_2$, and $R'_3$ are OH. In a further embodiment, the compound is a compound as shown as formula 4 and the attendant definitions, wherein $R_2$, $R_4$, $R'_2$, $R'_3$, and $R'_4$ are OH. In a further embodiment, the compound is a compound as shown as formula 4 and the attendant definitions, wherein $R_2$, $R_4$, $R'_2$, and $R'_3$ are OH. In a further embodiment, the compound is a compound as shown as formula 4 and the attendant definitions, wherein $R_3$, $R'_2$, and $R'_3$ are OH. In a further embodiment, the compound is a compound as shown as formula 4 and the attendant definitions, wherein $R_2$, $R_4$, $R'_2$, and $R'_3$ are OH. In a further embodiment, the compound is a compound as shown as formula 4 and the attendant definitions, wherein $R_2$, $R'_2$, $R'_3$, and $R'_4$ are OH. In a further embodiment, the compound is a compound as shown as formula 4 and the attendant definitions, wherein $R_2$, $R_4$, and $R'_3$ are OH. In a further embodiment, the compound is a compound as shown as formula 4 and the attendant definitions, wherein $R_2$, $R_3$, $R_4$, and $R'_3$ are OH. In a further embodiment, the compound is a compound as shown as formula 4 and the attendant definitions, wherein $R_2$, $R_4$, and $R'_3$ are OH. In a further embodiment, the compound is a compound as shown as formula 4 and the attendant definitions, wherein $R_3$, $R'_1$, and $R'_3$ are OH. In a further embodiment, the compound is a compound as shown as formula 4 and the attendant definitions, wherein $R_2$ and $R'_3$ are OH. In a further embodiment, the compound is a compound as shown as formula 4 and the attendant definitions, wherein $R_1$, $R_2$, $R'_2$, and $R'_3$ are OH. In a further embodiment, the compound is a compound as shown as formula 4 and the attendant definitions, wherein $R_3$, $R'_1$, and $R'_2$ are OH. In a further embodiment, the compound is a compound as shown as formula 4 and the attendant definitions, wherein $R'_3$ is OH. In a further embodiment, the compound is a compound as shown as formula 4 and the attendant definitions, wherein $R_4$ and $R'_3$ are OH. In a further embodiment, the compound is a compound as shown as formula 4 and the attendant definitions, wherein $R_2$ and $R_4$ are OH. In a further embodiment, the compound is a compound as shown as formula 4 and the attendant definitions, wherein $R_2$, $R_4$, $R'_1$, and $R'_3$ are OH. In a further embodiment, the compound is a compound as shown as formula 4 and the attendant definitions, wherein $R_4$ is OH. In a further embodiment, the compound is a compound as shown as formula 4 and the attendant definitions, wherein $R_2$, $R_4$, $R'_2$, $R'_3$, and $R'_4$ are OH. In a further embodiment, the compound is a compound as shown as formula 4 and the attendant definitions, wherein $R_2$, $R'_2$, $R'_3$, and $R'_4$ are OH. In a further embodiment, the compound is a compound as shown as formula 4 and the attendant definitions, wherein $R_1$, $R_2$, $R_4$, $R'_2$, and $R'_3$ are OH.

In a further embodiment, the compound is a compound as shown as formula 4 and the attendant definitions, wherein X is CH; R" is absent; Z is O; M is O; and $R_1, R_2, R_3, R_4, R_5, R'_1, R'_2, R'_3, R'_4$, and $R'_5$ are H (flavone). In a further embodiment, the compound is a compound as shown as formula 4 and the attendant definitions, wherein X is C; R" is OH; Z is O; M is O; $R_2, R'_2$, and $R'_3$ are OH; and $R_1, R_3, R_4, R'_1, R'_4$, and $R'_5$ are H (fisetin). In a further embodiment, the compound is a compound as shown as formula 4 and the attendant definitions, wherein X is CH; R" is absent; Z is O; M is O; $R_2, R_4, R'_2, R'_3$, and $R'_4$ are OH; and $R_1, R_3, R'_1$, and $R'_5$ are H (5,7,3',4',5'-pentahydroxyflavone). In a further embodiment, the compound is a compound as shown as formula 4 and the attendant definitions, wherein X is CH; R" is absent; Z is O; M is O; $R_2, R_4, R'_2$, and $R'_3$ are OH; and $R_1, R_3, R'_1, R'_4$, and $R'_5$ are H (luteolin). In a further embodiment, the compound is a compound as shown as formula 4 and the attendant definitions, wherein X is C, R" is OH; Z is O; M is O; $R_3, R'_2$, and $R'_3$ are OH; and $R_1, R_2, R_4, R'_1, R'_4$, and $R'_5$ are H (3,6,3',4'-tetrahydroxyflavone). In a further embodiment, the compound is a compound as shown as formula 4 and the attendant definitions, wherein X is C, R" is OH; Z is O; M is O; $R_2, R_4, R'_2$, and $R'_3$ are OH; and $R_1, R_3, R'_1, R'_4$, and $R'_5$ are H (quercetin). In a further embodiment, the compound is a compound as shown as formula 4 and the attendant definitions, wherein X is CH; R" is absent; Z is O; M is O; $R_2, R'_2, R'_3$, and $R'_4$ are OH; and $R_1, R_3, R_4, R'_1$, and $R'_5$ are H. In a further embodiment, the compound is a compound as shown as formula 4 and the attendant definitions, wherein X is C; R" is OH; Z is O; M is O; $R_2, R_4$, and $R'_3$ are OH; and $R_1, R_3, R'_1, R'_2, R'_4$, and $R'_5$ are H. In a further embodiment, the compound is a compound as shown as formula 4 and the attendant definitions, wherein X is CH; R" is absent; Z is O; M is O; $R_2, R_3, R_4$, and $R'_3$ are OH; and $R_1, R'_1, R'_2, R'_4$, and $R'_5$ are H. In a further embodiment, the compound is a compound as shown as formula 4 and the attendant definitions, wherein X is CH; R" is absent; Z is O; M is O; $R_2, R_4$, and $R'_3$ are OH; and $R_1, R_3, R'_1, R'_2, R'_4$, and $R'_5$ are H. In a further embodiment, the compound is a compound as shown as formula 4 and the attendant definitions, wherein X is C, R" is OH; Z is O; M is O; $R_3, R'_1$, and $R'_3$ are OH; and $R_1, R_2, R_4, R'_2, R'_4$, and $R'_5$ are H. In a further embodiment, the compound is a compound as shown as formula 4 and the attendant definitions, wherein X is CH; R" is absent; Z is O; M is O; $R_2$ and $R'_3$ are OH; and $R_1, R_3, R_4, R'_1, R'_2, R'_4$, and $R'_5$ are H. In a further embodiment, the compound is a compound as shown as formula 4 and the attendant definitions, wherein X is C, R" is OH; Z is O; M is O; $R_1, R_2, R'_2$, and $R'_3$ are OH; and $R_1, R_2, R_4, R'_3, R'_4$, and $R'_5$ are H. In a further embodiment, the compound is a compound as shown as formula 4 and the attendant definitions, wherein X is C; R" is OH; Z is O; M is O; $R_3, R'_1$, and $R'_2$ are OH; and $R_1, R_2, R_4; R'_3. R'_4$, and $R'_5$ are H. In a further embodiment, the compound is a compound as shown as formula 4 and the attendant definitions, wherein X is CH; R" is absent; Z is O; M is O; $R'_3$ is OH; and $R_1, R_2, R_3, R_4, R'_1, R'_2, R'_4$, and $R'_5$ are H. In a further embodiment, the compound is a compound as shown as formula 4 and the attendant definitions, wherein X is CH; R" is absent; Z is O; M is O; $R_4$ and $R'_3$ are OH; and $R_1, R_2, R_3, R'_1, R'_2, R'_4$, and $R'_5$ are H. In a further embodiment, the compound is a compound as shown as formula 4 and the attendant definitions, wherein X is CH; R" is absent; Z is O; M is O; $R_2$ and $R_4$ are OH; and $R_1, R_3, R'_1, R'_2, R'_3, R'_4$, and $R'_5$ are H. In a further embodiment, the compound is a compound as shown as formula 4 and the attendant definitions, wherein X is C; R" is OH; Z is O; M is O; $R_2, R_4, R'_1$, and $R'_3$ are OH; and $R_1, R_3, R'_2, R'_4$, and $R'_5$ are H. In a further embodiment, the compound is a compound as shown as formula 4 and the attendant definitions, wherein X is CH; R" is absent; Z is O; M is O; $R_4$ is OH; and $R_1, R_2, R_3, R'_1, R'_2, R'_3, R'_4$, and $R'_5$ are H. In a further embodiment, the compound is a compound as shown as formula 4 and the attendant definitions, wherein X is C; R" is OH; Z is O; M is O; $R_2, R_4, R'_2, R'_3$, and $R'_4$ are OH; and $R_1, R_3, R'_1$, and $R'_5$ are H. In a further embodiment, the compound is a compound as shown as formula 4 and the attendant definitions, wherein X is C; R" is OH; Z is O; M is O; $R_2, R'_2, R'_3$, and $R'_4$ are OH; and $R_1, R_3, R_4, R'_1$, and $R'_5$ are H. In a further embodiment, the compound is a compound as shown as formula 4 and the attendant definitions, wherein X is C; R" is OH; Z is O; M is O; $R_1, R_2, R_4, R'_2$, and $R'_3$ are OH; and $R_3, R'_1, R'_4$, and $R'_5$ are H.

In another embodiment, a sirtuin-activating compound is an iso flavone compound of formula 5:

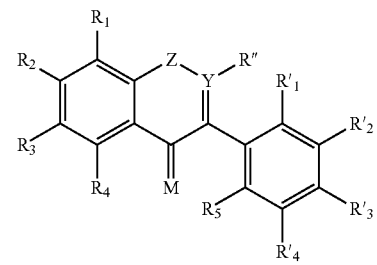

wherein, independently for each occurrence, $R_1, R_2, R_3, R_4, R_5, R'_1, R'_2, R'_3, R'_4$, and $R'_5$, represent H, alkyl, aryl, heteroaryl, alkaryl, heteroaralkyl, halide, $NO_2$, SR, OR, $N(R)_2$, or carboxyl;

R" is absent or represents H, alkyl, aryl, heteroaryl, alkaryl, heteroaralkyl, halide, $NO_2$, SR, OR, $N(R)_2$, or carboxyl;

R represents H, alkyl, or aryl;

M represents $H_2$, O, NR, or S;

Z represents CR, O, NR, or S; and

Y represents CR or N when R" is absent or C when R" is present.

In a further embodiment, the compound is a compound as shown as formula 5 and the attendant definitions, wherein Y is CR. In a further embodiment, the compound is a compound as shown as formula 5 and the attendant definitions, wherein Y is C H. In a further embodiment, the compound is a compound as shown as formula 5 and the attendant definitions, wherein Z is O. In a further embodiment, the compound is a compound as shown as formula 5 and the attendant definitions, wherein M is O. In a further embodiment, the compound is a compound as shown as formula 5 and the attendant definitions, wherein $R_2$ and $R'_3$ are OH. In a further embodiment, the compound of formula 5 and the attendant definitions, wherein $R_2, R_4$, and $R'_3$ are OH.

In a further embodiment, the compound is a compound as shown as formula 5 and the attendant definitions, wherein Y is CH; R" is absent; Z is O; M is O; $R_2$ and $R'_3$ are OH; and $R_1, R_3, R_4, R'_1, R'_2, R'_4$, and $R'_5$ are H. In a further embodiment, the compound is a compound as shown as formula 5 and the attendant definitions, wherein Y is CH; R" is absent; Z is O; M is O; $R_2, R_4$, and $R'_3$ are OH; and $R_1, R_3, R'_1, R'_2, R'_4$, and $R'_5$ are H.

In another embodiment, a sirtuin-activating compound is an anthocyanidin compound of formula 6:

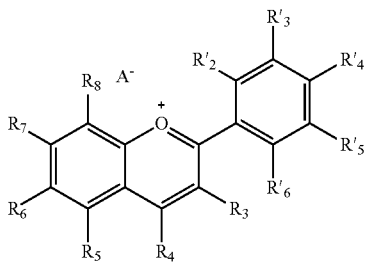

wherein, independently for each occurrence, $R_3$, $R_4$, $R_5$, $R_6$, $R_7$, $R_8$, $R'_2$, $R'_3$, $R'_4$, $R'_5$, and $R'_6$ represent H, alkyl, aryl, heteroaryl, alkaryl, heteroaralkyl, halide, $NO_2$, SR, OR, $N(R)_2$, or carboxyl;

R represents H, alkyl, or aryl; and

K represents an anion selected from the following: $Cl^-$, $Br^-$, or $I^-$.

In a further embodiment, the compound is a compound as shown as formula 6 and the attendant definitions, wherein $A^-$ is $Cl^-$. In a further embodiment, the compound is a compound as shown as formula 6 and the attendant definitions, wherein $R_3$, $R_5$, $R_7$, and $R'_4$ are OH. In a further embodiment, the compound is a compound as shown as formula 6 and the attendant definitions, wherein $R_3$, $R_5$, $R_7$, $R'_3$, and $R'_4$ are OH. In a further embodiment, the compound is a compound as shown as formula 6 and the attendant definitions, wherein $R_3$, $R_5$, $R_7$, $R'_3$, $R'_4$, and $R'_5$ are OH.

In a further embodiment, the compound is a compound as shown as formula 6 and the attendant definitions, wherein $A^-$ is $Cl^-$; $R_3$, $R_5$, $R_7$, and $R'_4$ are OH; and $R_4$, $R_6$, $R_8$, $R'_2$, $R'_3$, $R'_5$, and $R'_6$ are H. In a further embodiment, the compound is a compound as shown as formula 6 and the attendant definitions, wherein $A^-$ is $Cl^-$; $R_3$, $R_5$, $R_7$, $R'_3$, and $R'_4$ are OH; and $R_4$, $R_6$, $R_8$, $R'_2$, $R'_5$, and $R'_6$ are H. In a further embodiment, the compound is a compound as shown as formula 6 and the attendant definitions, wherein $A^-$ is $Cl^-$; $R_3$, $R_5$, $R_7$, $R'_3$, $R'_4$, and $R'_5$ are OH; and $R_4$, $R_6$, $R_8$, $R'_2$, and $R'_6$ are H.

Methods for activating a sirtuin protein family member may also comprise contacting the cell with a stilbene, chalcone, or flavone compound represented by formula 7:

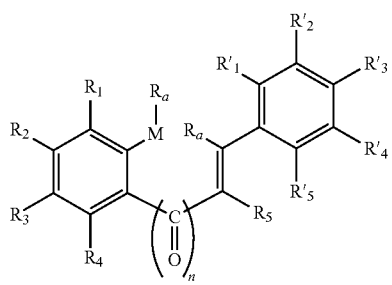

wherein, independently for each occurrence,

M is absent or O;

$R_1$, $R_2$, $R_3$, $R_4$, $R_5$, $R'_1$, $R'_2$, $R'_3$, $R'_4$, and $R'_5$ represent H, alkyl, aryl, heteroaryl, alkaryl, heteroaralkyl, halide, $NO_2$, SR, OR, $N(R)_2$, or carboxyl;

$R_a$ represents H or the two $R_a$ form a bond;

R represents H, alkyl, or aryl; and n is 0 or 1;

provided that when n is 0:

when $R_2$ and $R_4$ are OR, and $R_1$, $R_3$, $R_5$, $R'_1$, $R'_2$, $R'_4$, and $R'_5$ are H, $R'_3$ is not Cl, F, —$CH_3$, —$CH_2CH_3$, —SMe, $NO_2$, i-propyl, —OMe, or carboxyl;

when $R_3$ is OR at least one of $R'_1$, $R'_2$, $R'_3$, $R'_4$, or $R'_5$ is not H; and $R_4$ is not carboxyl.

In a further embodiment, the compound is a compound as shown as formula 7 and the attendant definitions, wherein n is 0. In a further embodiment, the compound is a compound as shown as formula 7 and the attendant definitions, wherein n is 1. In a further embodiment, the compound is a compound as shown as formula 7 and the attendant definitions, wherein M is absent. In a further embodiment, the compound is a compound as shown as formula 7 and the attendant definitions, wherein M is O. In a further embodiment, the compound is a compound as shown as formula 7 and the attendant definitions, wherein $R_a$ is H. In a further embodiment, the compound is a compound as shown as formula 7 and the attendant definitions, wherein M is O and the two $R_a$ form a bond.

In a further embodiment, the compound is a compound as shown as formula 7 and the attendant definitions, wherein $R_5$ is H. In a further embodiment, the compound is a compound as shown as formula 7 and the attendant definitions, wherein $R_5$ is OH. In a further embodiment, the compound is a compound as shown as formula 7 and the attendant definitions, wherein $R_1$, $R_3$, and $R'_3$ are OH. In a further embodiment, the compound is a compound as shown as formula 7 and the attendant definitions, wherein $R_2$, $R_4$, $R'_2$, and $R'_3$ are OH. In a further embodiment, the compound is a compound as shown as formula 7 and the attendant definitions, wherein $R_2$, $R'_2$, and $R'_3$ are OH. In a further embodiment, the compound is a compound as shown as formula 7 and the attendant definitions, wherein $R_2$ and $R_4$ are OH.

In a further embodiment, the compound is a compound as shown as formula 7 and the attendant definitions, wherein n is 0; M is absent; $R_a$ is H; $R_5$ is H; $R_1$, $R_3$, and $R'_3$ are OH; and $R_2$, $R_4$, $R'_1$, $R'_2$, $R'_4$, and $R'_5$ are H. In a further embodiment, the activating compound is a compound as shown as formula 7 and the attendant definitions, wherein n is 1; M is absent; $R_a$ is H; $R_5$ is H; $R_2$, $R_4$, $R'_2$, and $R'_3$ are OH; and $R_1$, $R_3$, $R'_1$, $R'_4$, and $R'_5$ are H. In a further embodiment, the activating compound is a compound as shown as formula 7 and the attendant definitions, wherein n is 1; M is O; the two $R_a$ form a bond; $R_5$ is OH; $R_2$, $R'_2$, and $R'_3$ are OH; and $R_1$, $R_3$, $R_4$, $R'_1$, $R'_4$, and $R'_5$ are H.

Other sirtuin-activating compounds include compounds having a formula selected from the group consisting of formulas 8-10 set forth below.

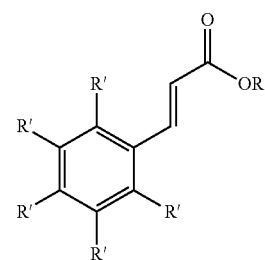

R=H, alkyl, aryl, heterocyclyl, or heteroaryl
R'=H, halogen, $NO_2$, SR, OR, $NR_2$, alkyl, aryl, or carboxy

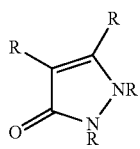

9

R=H, alkyl, aryl, heterocyclyl, or heteroaryl

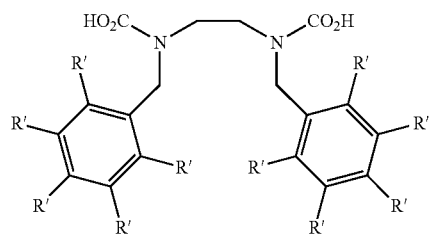

10 wherein, independently for each occurrence,
R'=H, halogen, $NO_2$, SR, OR, $NR_2$, alkyl, aryl, or carboxy
R=H, alkyl, aryl, heterocyclyl, or heteroaryl In another embodiment, exemplary sirtuin-activating compounds are isonicotinamide analogs, such as, for example, the isonicotinamide analogs described in U.S. Pat. Nos. 5,985,848; 6,066,722; 6,228,847; 6,492,347; 6,803,455; and U.S. Patent Publication Nos. 2001/0019823; 2002/0061898; 2002/0132783; 2003/0149261; 2003/0229033; 2003/0096830; 2004/0053944; 2004/0110772; and 2004/0181063, the disclosures of which are hereby incorporated by reference in their entirety. In an exemplary embodiment, sirtuin-activating compounds may be an isonicotinamide analog having any of formulas 11-14 below. In one embodiment, a sirtuin-activating compound is an isonicotinamide analog compound of formula 11:

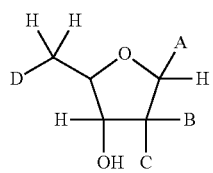

11

Wherein A is a nitrogen-, oxygen-, or sulfur-linked aryl, alkyl, cyclic, or heterocyclic group. The A moieties thus described, optionally have leaving group characteristics. In embodiments encompassed herein, A is further substituted with an electron contributing moiety. B and C are both hydrogen, or one of B or C is a halogen, amino, or thiol group and the other of B or C is hydrogen; and D is a primary alcohol, a hydrogen, or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge.

In one example, A is a substituted N-linked aryl or heterocyclic group, an O-linked aryl or heterocyclic group having the formula —O—Y, or an S-linked aryl or heterocyclic group having the formula —O—Y; both B and C are hydrogen, or one of B or C is a halogen, amino, or thiol group and the other of B or C is hydrogen; and D is a primary alcohol or hydrogen. Nonlimiting preferred examples of A are set forth below, where each R is H or an electron-contributing moiety and Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl.

Examples of A include i-xiv below:

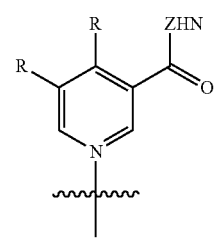

i

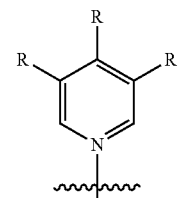

ii

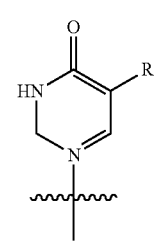

iii

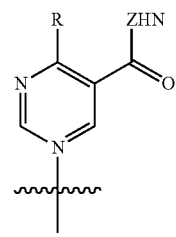

iv

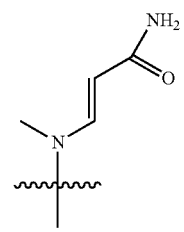

v

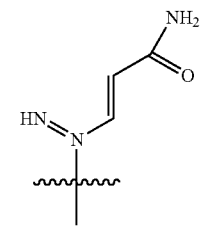

vi

-continued
vii 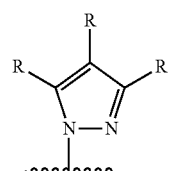
viii 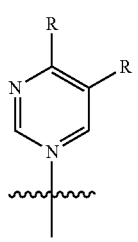
ix 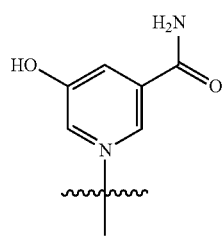
x 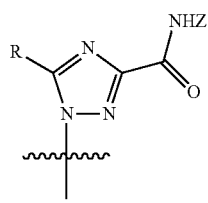
xi 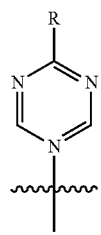
xii 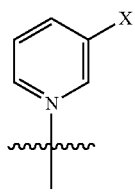
xiii 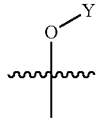
xiv 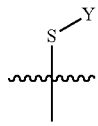
where Y=a group consistent with leaving group function.
Examples of Y include, but are not limited to, xv-xxvii below:
xv 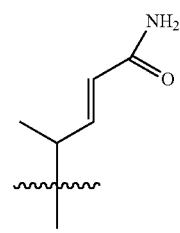
xvi 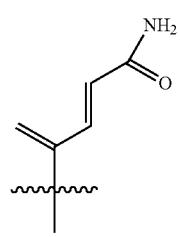
xvii 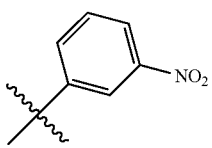
xviii 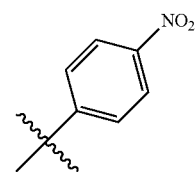
xix 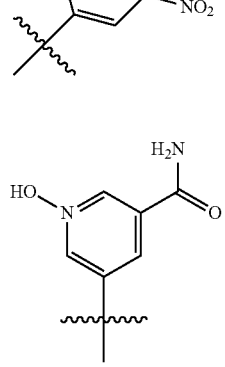
xx 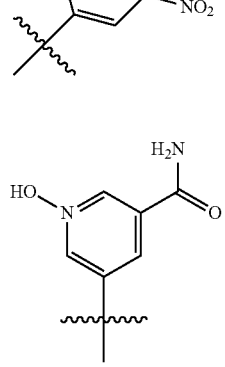
xxi 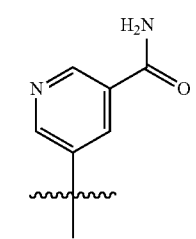

xxii 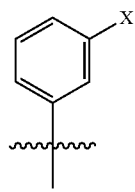

xxiii 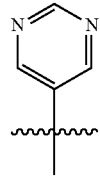

xxiv 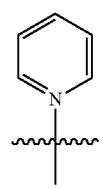

xxv 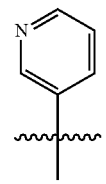

xxvi 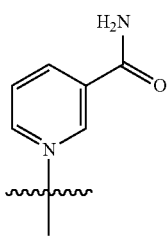

xxvii 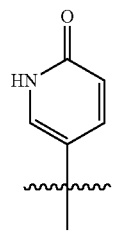

Wherein, for i-xxvii, X is halogen, thiol, or substituted thiol, amino or substituted amino, oxygen or substituted oxygen, or aryl or alkyl groups or heterocycles.

In certain embodiments, A is a substituted nicotinamide group (i above, where Z is H), a substituted pyrazolo group (vii above), or a substituted 3-carboxamid-imidazolo group (x above, where Z is H). Additionally, both B and C may be hydrogen, or one of B or C is a halogen, amino, or thiol group and the other of B or C is hydrogen; and D is a primary alcohol or hydrogen.

In other embodiments, one of B or C may be halogen, amino, or thiol group when the other of B or C is a hydrogen. Furthermore, D may be a hydrogen or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge. Analogues of adenosine monophosphate or adenosine diphosphate also can replace the adenosine monophosphate or adenosine diphosphate groups.

In some embodiments, A has two or more electron contributing moieties.

In other embodiments, a sirtuin-activating compound is an isonicotinamide analog compound of formulas 12, 13, or 14 below.

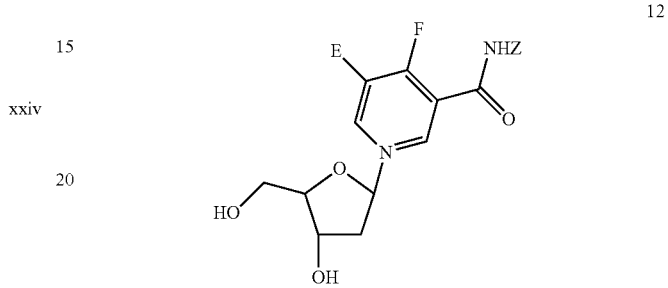

12 wherein Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl; E and F are independently H, $CH_3$, $OCH_3$, $CH_2CH_3$, $NH_2$, OH, NHCOH, $NHCOCH_3$, $N(CH_3)_2$, $C(CH_3)_2$, an aryl or a $C_3$-$C_{10}$ alkyl, preferably provided that, when one of E or F is H, the other of E or F is not H;

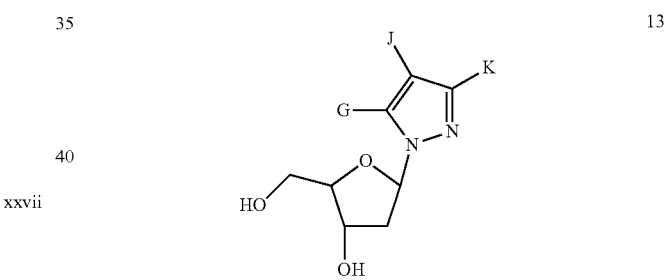

13 wherein G, J or K is CONHZ, Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl, and the other two of G, J and K is independently $CH_3$, $OCH_3$, $CH_2CH_3$, $NH_2$, OH, NHCOH, $NHCOCH_3$,

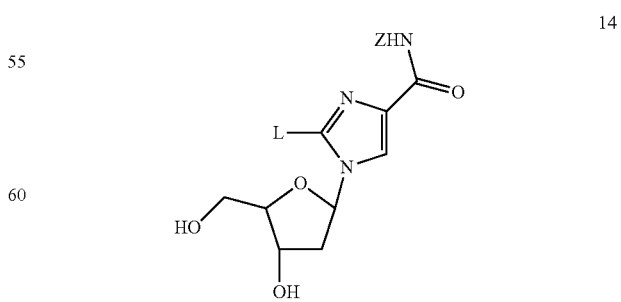

14 wherein Z is an alkyl, aryl, hydroxyl, OZ' where Z' is an alkyl or aryl, amino, NHZ' where Z' is an alkyl or aryl, or NHZ'Z"

where Z' and Z" are independently an alkyl or aryl; and L is $CH_3$, $OCH_3$, $CH_2CH_3$, $NH_2$, OH, NHCOH, $NHCOCH_3$.

In an exemplary embodiment, the compound is formula 12 above, wherein E and F are independently H, $CH_3$, $OCH_3$, or OH, preferably provided that, when one of E or F is H, the other of E or F is not H.

In another exemplary embodiment, the compound is β-1'-5-methyl-nicotinamide-2'-deoxyribose, β-D-1'-5-methyl-nico-tinamide-2'-deoxyribofuranoside, β-1'-4,5-dimethyl-nicotinamide-2'-de-oxyribose or β-D-1'-4,5-dimethyl-nicotinamide-2'-deoxyribofuranoside.

In yet another embodiment, the compound is β-1'-5-methyl-nicotinamide-2'-deoxyribose.

Without being bound to any particular mechanism, it is believed that the electron-contributing moiety on A stabilizes the compounds of the invention such that they are less susceptible to hydrolysis from the rest of the compound. This improved chemical stability improves the value of the compound, since it is available for action for longer periods of time in biological systems due to resistance to hydrolytic breakdown. The skilled artisan could envision many electron-contributing moieties that would be expected to serve this stabilizing function. Nonlimiting examples of suitable electron contributing moieties are methyl, ethyl, O-methyl, amino, $NMe_2$, hydroxyl, $CMe_3$, aryl and alkyl groups. Preferably, the electron-contributing moiety is a methyl, ethyl, O-methyl, amino group. In the most preferred embodiments, the electron-contributing moiety is a methyl group.

The compounds of formulas 11-14 are useful both in free form and in the form of salts. The term "pharmaceutically acceptable salts" is intended to apply to non-toxic salts derived from inorganic or organic acids and includes, for example, salts derived from the following acids: hydrochloric, sulfuric, phosphoric, acetic, lactic, fumaric, succinic, tartaric, gluconic, citric, methanesulfonic, and p-toluenesulfonic acids.

Also provided are compounds of formulas 11-14 that are the tautomers, pharmaceutically-acceptable salts, esters, and pro-drugs of the inhibitor compounds disclosed herein.

The biological availability of the compounds of formulas 11-14 can be enhanced by conversion into a pro-drug form. Such a pro-drug can have improved lipophilicity relative to the unconverted compound, and this can result in enhanced membrane permeability. One particularly useful form of pro-drug is an ester derivative. Its utility relies upon the action of one or more of the ubiquitous intracellular lipases to catalyse the hydrolysis of ester groups, to release the active compound at or near its site of action. In one form of pro-drug, one or more hydroxy groups in the compound can be O-acylated, to make an acylate derivative.

Pro-drug forms of a 5-phosphate ester derivative of compounds of formulas 11-14 can also be made. These may be particularly useful, since the anionic nature of the 5-phosphate may limit its ability to cross cellular membranes. Conveniently, such a 5-phosphate derivative can be converted to an uncharged-bis(acyloxymethyl) ester derivative. The utility of such a pro-drug relies upon the action of one or more of the ubiquitous intracellular lipases to catalyse the hydrolysis of ester groups, releasing a molecule of formaldehyde and a compound of the present invention at or near its site of action. Specific examples of the utility of, and general methods for making, such acyloxymethyl ester pro-drug forms of phosphorylated carbohydrate derivatives have been described (Kang et al., 1998; Jiang et al., 1998; Li et al., 1997; Kruppa et al., 1997).

In another embodiment, exemplary sirtuin-activating compounds are O-acetyl-ADP-ribose analogs, including 2'-O-acetyl-ADP-ribose and 3'-O-acetyl-ADP-ribose, and analogs thereof. Exemplary O-acetyl-ADP-ribose analogs are described, for example, in U.S. Patent Publication Nos. 2004/0053944; 2002/0061898; and 2003/0149261, the disclosures of which are hereby incorporated by reference in their entirety. In an exemplary embodiment, sirtuin-activating compounds may be an O-acetyl-ADP-ribose analog having any of formulas 15-18 below. In one embodiment, a sirtuin-activating compound is an O-acetyl-ADP-ribose analog compound of formula 15:

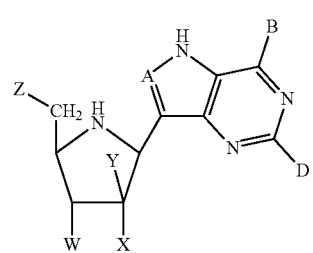

15 wherein:

A is selected from N, CH and C R, where R is selected from halogen, optionally substituted alkyl, aralkyl and aryl, OH, $NH_2$, $NHR_1$, $NR_1R_2$ and $SR_3$, where $R_1$, $R_2$ and $R_3$ are each optionally substituted alkyl, aralkyl or aryl groups;

B is selected from OH, $NH_2$, $NHR_4$, H and halogen, where $R_4$ is an optionally substituted alkyl, aralkyl or aryl group;

D is selected from OH, $NH_2$, $NHR_5$, H, halogen and $SCH_3$, where $R_5$ is an optionally substituted alkyl, aralkyl or aryl group;

X and Y are independently selected from H, OH and halogen, with the proviso that when one of X and Y is hydroxy or halogen, the other is hydrogen;

Z is OH, or, when X is hydroxy, Z is selected from hydrogen, halogen, hydroxy, SQ and OQ, where Q is an optionally substituted alkyl, aralkyl or aryl group; and W is OH or H, with the proviso that when W is OH, then A is CR where R is as defined above; or a tautomer thereof; or a pharmaceutically acceptable salt thereof; or an ester thereof; or a prodrug thereof.

In certain embodiments, when B is $NHR_4$ and/or D is $NHR_5$, then $R_4$ and/or $R_5$ are $C_1$-$C_4$ alkyl.

In other embodiments, when one or more halogens are present they are chosen from chlorine and fluorine.

In another embodiment, when Z is SQ or OQ, Q is $C_1$-$C_5$ alkyl or phenyl.

In an exemplary embodiment, D is H, or when D is other than H, B is OH.

In another embodiment, B is OH, D is H, OH or $NH_2$, X is OH or H, Y is H, most preferably with Z as OH, H, or methylthio, especially OH.

In certain embodiments W is OH, Y is H, X is OH, and A is CR where R is methyl or halogen, preferably fluorine.

In other embodiments, W is H, Y is H, X is OH and A is CH.

In other embodiments, a sirtuin-activating compound is an O-acetyl-ADP-ribose analog compound of formula 16:

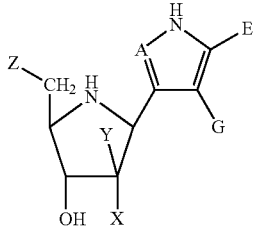

wherein A, X, Y, Z and R are defined for compounds of formula (15) where first shown above; E is chosen from $CO_2H$ or a corresponding salt form, $CO_2R$, CN, $CONH_2$, CONHR or $CONR_2$; and G is chosen from $NH_2$, NHCOR, NHCONHR or NHCSNHR; or a tautomer thereof, or a pharmaceutically acceptable salt thereof, or an ester thereof, or a prodrug thereof.

In certain embodiments, E is $CONH_2$ and G is $NH_2$.

In other embodiments, E is $CONH_2$, G is $NH_2$, X is OH or H, is H, most preferable with Z as OH, H or methylthio, especially OH.

Exemplary sirtuin-activating compounds include the following:
(1S)-1,4-dideoxy-1-C-(4-hydroxypyrrolo[3,2-d]pyrimidin-7-yl)-1,4-imino-D-ribitol
(1S)-1-C-(2-amino-4-hydroxypyrrolo[3,2-d]pyrimidin-7-yl)-1,4-dideoxy-1,4-imino-D-ribitol
(1R)-1-C-(4-hydroxypyrrolo[3,2-d]pyrimidin-7-yl)-1,4-imino-1,2,4-trideoxy-D-erythro-pentitol
(1S)-1-C-(4-hydroxypyrrolo[3,2-d]pyrimidin-7-yl)-1,4-imino-1,4,5-trideoxy-D-ribitol
(1S)-1,4-dideoxy-1-C-(4-hydroxypyrrolo[3,2-d]pyrimidin-7-yl)-1,4-imino-5-methylthio-D-ribitol
(1S)-1,4-dideoxy-1-C-(2,4-dihydroxypyrrolo[3,2-d]pyrimidin-7-yl)-1,4-imino-D-ribitol
(1R)-1-C-(2,4-dihydroxypyrrolo[3,2-d]pyrimidin-7-yl)-1,4-imino-1,2,4-trideoxy-D-erthro-pentitol
(1S)-1-C-(2,4-dihydroxypyrrolo[3,2-d]pyrimidin-7-yl)-1,4-imino-1,4,5-trideoxy-D-ribitol
(1S)-1,4-dideoxy-1-C-(2,4-dihydroxypyrrolo[3,2-d]pyrimidin-7-yl)-1,4-imino-5-ethylthio-D-ribitol
(1R)-1-C-(2-amino-4-hydroxypyrrolo[3,2-d]pyrimidin-7-yl)-1,4-imino-1,2,4-trideoxy-D-erythro-pentitol
(1S)-1-C-(2-amino-4-hydroxypyrrolo[3,2-d]pyrimidin-7-yl)-1,4-imino-1,4,5-trideoxy-D-ribitol
(1S)-1-C-(2-amino-4-hydroxypyrrolo[3,2-d]pyrimidin-7-yl)-1,4-dideoxy-1,4-imino-5-methylthio-D-ribitol
(1S)-1,4-dideoxy-1-C-(7-hydroxypyrazolo[4,3-d]pyrimidin-3-yl)-1,4-imino-D-ribitol
(1R)-1-C-(7-hydroxypyrazolo[4,3-d]pyrimidin-3-yl)-1,4-imino-1,2,4-trideoxy-D-erythro-pentitol
(1S)-1-C-(7-hydroxypyrazolo[4,3-d]pyrimidin-3-yl)-1,4-imino-1,4,5-trideoxy-D-ribitol
(1S)-1,4-dideoxy-1-C-(7-hydroxypyrazolo[4,3-d]pyrimidin-3-yl)-1,4-imino-5-ethylthio-D-ribitol
(1S)-1,4-dideoxy-1-C-(5,7-dihydroxypyrazolo[4,3-d]pyrimidin-3-yl)-1,4-imino-D-ribitol
(1R)-1-C-(5,7-dihydroxypyrazolo[4,3-d]pyrimidin-3-yl)-1,4-imino-1,2,4-trideoxy-D-erythro-pentitol
(1S)-1-C-(5,7-dihydroxypyrazolo[4,3-d]pyrimidin-3-yl)-1,4-imino-1,4,5-trideoxy-D-ribitol
(1S)-1,4-dideoxy-1-C-(5,7-dihydroxypyrazolo[4,3-d]pyrimidin-3-yl)-1,4-imino-5-methylthio-D-ribitol
(1S)-1-C-(5-amino-7-hydroxypyrazolo[4,3-d]pyrimidin-3-yl)-1,4-dideoxy-1,4-imino-D-ribitol
(1R)-1-C—(S-amino-7-hydroxypyrazolo[4,3-d]pyrimidin-3-yl)-1,4-imino-1,2,4-trideoxy-D-erythro-pentitol
(1S)-1-C-(5-amino-7-hydroxypyrazolo[4,3-d]pyrimidin-3-yl)-1,4-imino-1,4,5-trideoxy-D-ribitol
(1S)-1-C-(5-amino-7-hydroxypyrazolo[4,3-d]pyrimidin-3-yl)-1,4-dideoxy-1,4-imino-5-methylthio-D-ribitol
(1S)-1-C-(3-amino-2-carboxamido-4-pyrroly)-1,4-dideoxy-1,4-imino-D-ribitol.
(1S)-1,4-dideoxy-1-C-(4-hydroxypyrrolo[3,2-d]pyrimidin-7-yl)-1,4-imino-D-ribitol 5-phosphate
(1S)-1-C-(2-amino-4-hydroxypyrrolo[3,2-d]pyrimidin-7-yl)-1,4-imino-D-ribitol 5-phosphate
(1S)-1-C-(3-amino-2-carboxamido-4-pyrrolyl)-1,4-dideoxy-1,4-imino-D-ribitol In yet other embodiments, sirtuin-activating compounds are O-acetyl-ADP-ribose analog compounds of formula 17 and 18, their tautomers and pharmaceutically acceptable salts.

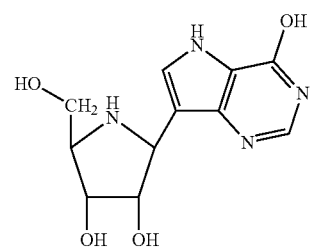

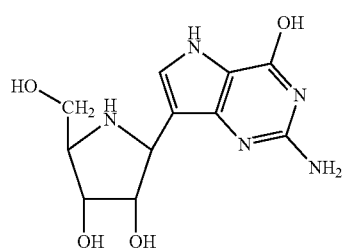

The biological availability of a compound of formula (15) or formula (16) can be enhanced by conversion into a pro-drug form. Such a pro-drug can have improved lipophilicity relative to the compound of formula (15) or formula (16), and this can result in enhanced membrane permeability. One particularly useful form of a pro-drug is an ester derivative. Its utility relies upon the action of one or more of the ubiquitous intracellular lipases to catalyse the hydrolysis of these ester group(s), to release the compound of formula (15) and formula (16) at or near its site of action.

In one form of a prodrug, one or more of the hydroxy groups in a compound of formula (15) or formula (16) can be O-acylated, to make, for example a 5-O-butyrate or a 2,3-di-O-butyrate derivative.

Prodrug forms of 5-phosphate ester derivative of a compounds of formula (15) or formula (16) can also be made and may be particularly useful, since the anionic nature of the 5-phosphate may limit its ability to cross cellular membranes. Conveniently, such a 5-phosphate derivative can be converted to an uncharged bis(acyloxymethyl) ester derivative. The utility of such a pro-drug relies upon the action of one or more of the ubiquitous intracellular lipases to catalyse the hydrolysis of these ester group(s), releasing a molecule of formaldehyde and the compound of formula (15) or formula (16) at or near its site of action.

In an exemplary embodiment, analogs of 2'-AADPR or 3'-AADPR that are designed to have increased stability from esterase action through the use of well-known substitutes for ester oxygen atoms that are subject to esterase attack. The esterase-labile oxygen atoms in 2'-AADPR and 3'-AADPR would be understood to be the ester oxygen linking the acetate group with the ribose, and the ester oxygen between the two phosphorus atoms. As is known in the art, substitution of either or both of these ester oxygen atoms with a CF2, a NH, or a S would be expected to provide a 2'-AADPR or 3'-AADPR analog that is substantially more stable due to increased resistance to esterase action.

Thus, in some embodiments, the invention is directed to analogs 2'-O-acetyl-ADP-ribose or 3'-O-acetyl-ADP-ribose exhibiting increased stability in cells. The preferred analogs comprise a C2, a NH, or a S instead of the acetyl ester oxygen or the oxygen between two phosphorus atoms. The most preferred substitute is $CF_2$. Replacement of the acetyl ester oxygen is particularly preferred. In other preferred embodiments, both the ester oxygen and the oxygen between the two phosphorus atoms are independently substituted with a $CF_1$, a NH, or a S.

Other sirtuin-activating compounds are set forth in the appended Tables (compounds for which the ratio to control rate is >1). The compounds of Tables 1-8 may be obtained from Biomol, Sigma/Aldrich or Indofine.

In one embodiment, methods for activating a sirtuin protein comprise using an activating compound that is a stilbene or chalcone compound of formula 23:

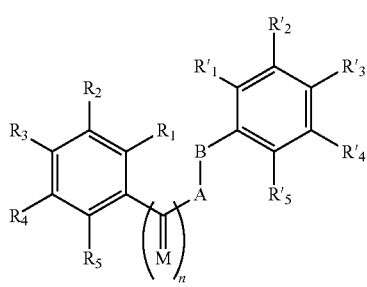

wherein, independently for each occurrence, $R_1$, $R_2$, $R_3$, $R_4$, $R_5$, $R'_1$, $R'_2$, $R'_3$, $R'_4$, and $R'_5$ represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, aralkyl, —$SO_3H$, monosaccharide, oligosaccharide, glycofuranosyl, glycopyranosyl, glucuronosyl, or glucuronide;

M represents O, NR, or S;

A-B represents a bivalent alkyl, alkenyl, alkynyl, amido, sulfonamido, diazo, ether, alkylamino, alkylsulfide, hydroxylamine, or hydrazine group; and n is 0 or 1.

In a further embodiment, the methods comprise a compound of formula 23 and the attendant definitions, wherein n is 0. In a further embodiment, the methods comprise a compound of formula 23 and the attendant definitions, wherein n is 1. In a further embodiment, the methods comprise a compound of formula 23 and the attendant definitions, wherein A-B is ethenyl. In a further embodiment, the methods comprise a compound of formula 23 and the attendant definitions, wherein A-B is —$CH_2CH(Me)CH(Me)CH_2^-$. In a further embodiment, the methods comprise a compound of formula 23 and the attendant definitions, wherein M is O. In a further embodiment, the methods comprises a compound of formula 23 and the attendant definitions, wherein $R_1$, $R_2$, $R_3$, $R_4$, $R_5$, $R'_1$, $R'_2$, $R'_3$, $R'_4$, and $R'_5$ are H. In a further embodiment, the methods comprise a compound of formula 23 and the attendant definitions, wherein $R_2$, $R_4$, and $R'_3$ are OH. In a further embodiment, the methods comprise a compound of formula 23 and the attendant definitions, wherein $R_2$, $R_4$, $R'_2$ and $R'_3$ are OH. In a further embodiment, the methods comprise a compound of formula 23 and the attendant definitions, wherein $R_3$, $R_5$, $R'_2$ and $R'_3$ are OH. In a further embodiment, the methods comprise a compound of formula 23 and the attendant definitions, wherein $R_1$, $R_3$, $R_5$, $R'_2$ and $R'_3$ are OH. In a further embodiment, the methods comprise a compound of formula 23 and the attendant definitions, wherein $R_2$ and $R'_2$ are OH; $R_4$ is O-β-D-glucoside; and $R'_3$ is $OCH_3$. In a further embodiment, the methods comprise a compound of formula 23 and the attendant definitions, wherein $R_2$ is OH; $R_4$ is O-β-D-glucoside; and $R'_3$ is $OCH_3$.

In a further embodiment, the methods comprise a compound of formula 23 and the attendant definitions, wherein n is 0; A-B is ethenyl; and $R_1$, $R_2$, $R_3$, $R_4$, $R_5$, $R'_1$, $R'_2$, $R'_3$, $R'_4$, and $R'_5$ are H (trans stilbene). In a further embodiment, the methods comprise a compound of formula 23 and the attendant definitions, wherein n is 1; A-B is ethenyl; M is O; and $R_1$, $R_2$, $R_3$, $R_4$, $R_5$, $R'_1$, $R'_2$, $R'_3$, $R'_4$, and $R'_5$ are H (chalcone). In a further embodiment, the methods comprise a compound of formula 23 and the attendant definitions, wherein n is 0; A-B is ethenyl; $R_2$, $R_4$, and $R'_3$ are OH; and $R_1$, $R_3$, $R_5$, $R'_1$, $R'_2$, $R'_4$, and $R'_5$ are H (resveratrol). In a further embodiment, the methods comprise a compound of formula 23 and the attendant definitions, wherein n is 0; A-B is ethenyl; $R_2$, $R_4$, $R'_2$ and $R'_3$ are OH; and $R_1$, $R_3$, $R_5$, $R'_1$, $R'_4$ and $R'_5$ are H (piceatannol). In a further embodiment, the methods comprise a compound of formula 23 and the attendant definitions, wherein n is 1; A-B is ethenyl; M is O; $R_3$, $R_5$, $R'_2$ and $R'_3$ are OH; and $R_1$, $R_2$, $R_4$, $R'_1$, $R'_4$, and $R'_5$ are H (butein). In a further embodiment, the methods comprise a compound of formula 23 and the attendant definitions, wherein n is 1; A-B is ethenyl; M is O; $R_1$, $R_3$, $R_5$, $R'_2$ and $R'_3$ are OH; and $R_2$, $R_4$, $R'_1$, $R'_4$, and $R'_5$ are H (3,4,2',4',6'-pentahydroxychalcone). In a further embodiment, the methods comprise a compound of formula 23 and the attendant definitions, wherein n is 0; A-B is ethenyl; $R_2$ and $R'_2$ are OH, $R_4$ is O-β-D-glucoside, $R'_3$ is $OCH_3$; and $R_1$, $R_3$, $R_5$, $R'_1$, $R'_4$, and $R'_5$ are H (rhapontin). In a further embodiment, the methods comprise a compound of formula 23 and the attendant definitions, wherein n is 0; A-B is ethenyl; $R_2$ is OH, $R_4$ is O-β-D-glucoside, $R'_3$ is $OCH_3$; and $R_1$, $R_3$, $R_5$, $R'_1$, $R'_2$, $R'_4$, and $R'_5$ are H (deoxyrhapontin). In a further embodiment, the methods comprise a compound of formula 23 and the attendant definitions, wherein n is 0; A-B is —$CH_2CH(Me)CH(Me)CH_2$—; $R_2$, $R_3$, $R'_2$, and $R'_3$ are OH; and $R_1$, $R_4$, $R_5$, $R'_1$, $R'_4$, and $R'_5$ are H(NDGA).

In another embodiment, methods for activating a sirtuin protein comprise using an activating compound that is a flavanone compound of formula 24:

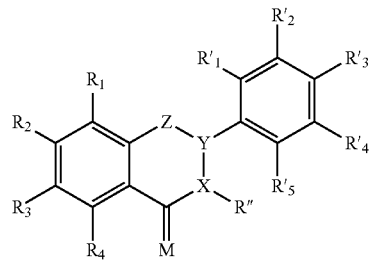

wherein, independently for each occurrence, $R_1$, $R_2$, $R_3$, $R_4$, $R'_1$, $R'_2$, $R'_3$, $R'_4$, $R'_5$, and R" represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, aralkyl, —SO₃H, monosaccharide, oligosaccharide, glycofuranosyl, glycopyranosyl, glucuronosyl, or glucuronide;

M represents H₂, O, NR, or S;
Z represents CR, O, NR, or S;
X represents CR or N; and
Y represents CR or N.

In a further embodiment, the methods comprise a compound of formula 24 and the attendant definitions, wherein X and Y are both CH. In a further embodiment, the methods comprise a compound of formula 24 and the attendant definitions, wherein M is O. In a further embodiment, the methods comprise a compound of formula 24 and the attendant definitions, wherein M is H₂. In a further embodiment, the methods comprise a compound of formula 24 and the attendant definitions, wherein Z is O. In a further embodiment, the methods comprise a compound of formula 24 and the attendant definitions, wherein R" is H. In a further embodiment, the methods comprise a compound of formula 24 and the attendant definitions, wherein R" is OH. In a further embodiment, the methods comprise a compound of formula 24 and the attendant definitions, wherein R" is an alkoxycarbonyl. In a further embodiment, the methods comprise a compound of formula 24 and the attendant definitions, wherein $R_1$ is

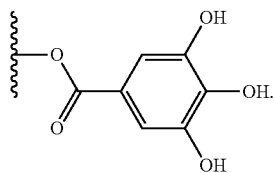 [SMILES: *OC(=O)c1cc(O)c(O)c(O)c1]

In a further embodiment, the methods comprise a compound of formula 24 and the attendant definitions, wherein $R_1$, $R_2$, $R_3$, $R_4$, $R'_1$, $R'_2$, $R'_3$, $R'_4$, $R_5$ and R" are H. In a further embodiment, the methods comprise a compound of formula 24 and the attendant definitions, wherein $R_2$, $R_4$, and $R'_3$ are OH. In a further embodiment, the methods comprise a compound of formula 24 and the attendant definitions, wherein $R_4$, $R'_2$, $R'_3$, and R" are OH. In a further embodiment, the methods comprise a compound of formula 24 and the attendant definitions, wherein $R_2$, $R_4$, $R'_2$, $R'_3$, and R" are OH. In a further embodiment, the methods comprise a compound of formula 24 and the attendant definitions, wherein $R_2$, $R_4$, $R'_2$, $R'_3$, $R'_4$, and R" are OH.

In a further embodiment, the methods comprise a compound of formula 24 and the attendant definitions, wherein X and Y are CH; M is O; Z and O; R" is H; and $R_1$, $R_2$, $R_3$, $R_4$, $R'_1$, $R'_2$, $R'_3$, $R'_4$, $R'_5$ and R" are H (flavanone). In a further embodiment, the methods comprise a compound of formula 24 and the attendant definitions, wherein X and Y are CH; M is O; Z and O; R" is H; $R_2$, $R_4$, and $R'_3$ are OH; and $R_1$, $R_3$, $R'_1$, $R'_2$, $R'_4$, and $R'_5$ are H (naringenin). In a further embodiment, the methods comprise a compound of formula 24 and the attendant definitions, wherein X and Y are CH; M is O; Z and O; R" is OH; $R_2$, $R_4$, $R'_2$, and $R'_3$ are OH; and $R_1$, $R_3$, $R'_1$, $R'_4$, and $R'_5$ are H (3,5,7,3',4'-pentahydroxyflavanone). In a further embodiment, the methods comprise a compound of formula 24 and the attendant definitions, wherein X and Y are CH; M is H₂; Z and O; R" is OH; $R_2$, $R_4$, $R'_2$, and $R'_3$, are OH; and $R_1$, $R_3$, $R'_1$, $R'_4$ and $R'_5$ are H (epicatechin). In a further embodiment, the methods comprise a compound of formula 24 and the attendant definitions, wherein X and Y are CH; M is H₂; Z and O; R" is OH; $R_2$, $R_4$, $R'_2$, $R'_3$, and $R'_4$ are OH; and $R_1$, $R_3$, $R'_1$, and $R'_5$ are H (gallocatechin). In a further embodiment, the methods comprise a compound of formula 24 and the attendant definitions, wherein X and Y are CH; M is H₂; Z and O; R" is

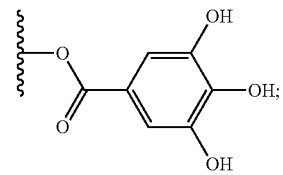 [SMILES: *OC(=O)c1cc(O)c(O)c(O)c1]

$R_2$, $R_4$, $R'_2$, $R'_3$, $R'_4$, and R" are OH; and $R_1$, $R_3$, $R'_1$, and $R'_5$ are H (epigallocatechin gallate).

In another embodiment, methods for activating a sirtuin protein comprise using an activating compound that is an isoflavanone compound of formula 25:

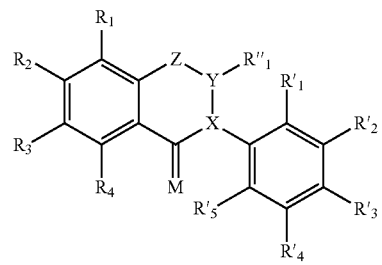

wherein, independently for each occurrence,
$R_1$, $R_2$, $R_3$, $R_4$, $R'_1$, $R'_2$, $R'_3$, $R'_4$, $R'_5$, and $R"_1$, represent H, alkyl, aryl, heteroaryl, aralkyl, alkaryl, heteroaralkyl, halide, NO₂, SR, OR, N(R)₂, or carboxyl;

R represents H, alkyl, aryl, heteroaryl, aralkyl, —SO₃H, monosaccharide, oligosaccharide, glycofuranosyl, glycopyranosyl, glucuronosyl, or glucuronide;

M represents H₂, O, NR, or S;
Z represents C(R)₂, O, NR, or S;
X represents CR or N; and
Y represents CR or N.

In another embodiment, methods for activating a sirtuin protein comprise using an activating compound that is a flavone compound of formula 26:

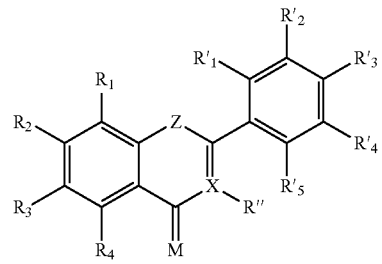

wherein, independently for each occurrence,
$R_1$, $R_2$, $R_3$, $R_4$, $R'_1$, $R'_2$, $R'_3$, $R'_4$, and $R'_5$, represent H, alkyl, aryl, heteroaryl, aralkyl, alkaryl, heteroaralkyl, halide, NO₂, SR, OR, N(R)₂, or carboxyl;

R represents H, alkyl, aryl, heteroaryl, aralkyl, —SO₃H, monosaccharide, oligosaccharide, glycofuranosyl, glycopyranosyl, glucuronosyl, or glucuronide;

M represents $H_2$, O, NR, or S;

Z represents CR, O, NR, or S; and

X represents CR" or N, wherein

R" is H, alkyl, aryl, heteroaryl, alkaryl, heteroaralkyl, halide, $NO_2$, SR, OR, $N(R)_2$, or carboxyl.

In a further embodiment, the methods comprise a compound of formula 26 and the attendant definitions, wherein X is C. In a further embodiment, the methods comprise a compound of formula 26 and the attendant definitions, wherein X is CR. In a further embodiment, the methods comprise a compound of formula 26 and the attendant definitions, wherein Z is O. In a further embodiment, the methods comprise a compound of formula 26 and the attendant definitions, wherein M is O. In a further embodiment, the methods comprise a compound of formula 26 and the attendant definitions, wherein R" is H. In a further embodiment, the methods comprise a compound of formula 26 and the attendant definitions, wherein R" is OH. In a further embodiment, the methods comprise a compound of formula 26 and the attendant definitions, wherein $R_1$, $R_2$, $R_3$, $R_4$, $R'_1$, $R'_2$, $R'_3$, $R'_4$, and $R'_5$ are H. In a further embodiment, the methods comprise a compound of formula 26 and the attendant definitions, wherein $R_2$, $R'_2$, and $R'_3$ are OH. In a further embodiment, the methods comprise a compound of formula 26 and the attendant definitions, wherein $R_2$, $R_4$, $R'_2$, $R'_3$, and $R'_4$ are OH. In a further embodiment, the methods comprise a compound of formula 26 and the attendant definitions, wherein $R_2$, $R_4$, $R'_2$, and $R'_3$ are OH. In a further embodiment, the methods comprise a compound of formula 26 and the attendant definitions, wherein $R_3$, $R'_2$, and $R'_3$ are OH. In a further embodiment, the methods comprise a compound of formula 26 and the attendant definitions, wherein $R_2$, $R_4$, $R'_2$, and $R'_3$ are OH. In a further embodiment, the methods comprise a compound of formula 26 and the attendant definitions, wherein $R_2$, $R'_2$, $R'_3$, and $R'_4$ are OH. In a further embodiment, the methods comprise a compound of formula 26 and the attendant definitions, wherein $R_2$, $R_4$, and $R'_3$ are OH. In a further embodiment, the methods comprise a compound of formula 26 and the attendant definitions, wherein $R_2$, $R_3$, $R_4$, and $R'_3$ are OH. In a further embodiment, the methods comprise a compound of formula 26 and the attendant definitions, wherein $R_2$, $R_4$, and $R'_3$ are OH. In a further embodiment, the methods comprise a compound of formula 26 and the attendant definitions, wherein $R_3$, $R'_1$, and $R'_3$ are OH. In a further embodiment, the methods comprise a compound of formula 26 and the attendant definitions, wherein $R_2$ and $R'_3$ are OH. In a further embodiment, the methods comprise a compound of formula 26 and the attendant definitions, wherein $R_1$, $R_2$, $R'_2$, and $R'_3$ are OH. In a further embodiment, the methods comprise a compound of formula 26 and the attendant definitions, wherein $R_3$, $R'_1$, and $R'_2$ are OH. In a further embodiment, the methods comprise a compound of formula 26 and the attendant definitions, wherein $R'_3$ is OH. In a further embodiment, the methods comprise a compound of formula 26 and the attendant definitions, wherein $R_4$ and $R'_3$ are OH. In a further embodiment, the methods comprise a compound of formula 26 and the attendant definitions, wherein $R_2$ and $R_4$ are OH. In a further embodiment, the methods comprise a compound of formula 26 and the attendant definitions, wherein $R_2$, $R_4$, $R'_1$, and $R'_3$ are OH. In a further embodiment, the methods comprise a compound of formula 26 and the attendant definitions, wherein $R_4$ is OH. In a further embodiment, the methods comprise a compound of formula 26 and the attendant definitions, wherein $R_2$, $R_4$, $R'_2$, $R'_3$, and $R'_4$ are OH. In a further embodiment, the methods comprise a compound of formula 26 and the attendant definitions, wherein $R_2$, $R'_2$, $R'_3$, and $R'_4$ are OH. In a further embodiment, the methods comprise a compound of formula 26 and the attendant definitions, wherein $R_1$, $R_2$, $R_4$, $R'_2$, and $R'_3$ are OH.

In a further embodiment, the methods comprise a compound of formula 26 and the attendant definitions, wherein X is CH; Z is O; M is O; and $R_1$, $R_2$, $R_3$, $R_4$, $R'_1$, $R'_2$, $R'_3$, $R'_4$, and $R'_5$ are H (flavone). In a further embodiment, the methods comprise a compound of formula 26 and the attendant definitions, wherein X is COH; Z is O; M is O; $R_2$, $R'_2$, and $R'_3$ are OH; and $R_1$, $R_3$, $R_4$, $R'_1$, $R'_4$, and $R'_5$ are H (fisetin). In a further embodiment, the methods comprise a compound of formula 26 and the attendant definitions, wherein X is CH; Z is O; M is O; $R_2$, $R_4$, $R'_2$, $R'_3$, and $R'_4$ are OH; and $R_1$, $R_3$, $R'_1$, and $R'_5$ are H (5,7,3',4',5'-pentahydroxyflavone). In a further embodiment, the methods comprise a compound of formula 26 and the attendant definitions, wherein X is CH; Z is O; M is O; $R_2$, $R_4$, $R'_2$, and $R'_3$ are OH; and $R_1$, $R_3$, $R'_1$, $R'_4$, and $R'_5$ are H (luteolin). In a further embodiment, the methods comprise a compound of formula 26 and the attendant definitions, wherein X is COH; Z is O; M is O; $R_3$, $R'_2$, and $R'_3$ are OH; and $R_1$, $R_2$, $R_4$, $R'_1$, $R'_4$, and $R'_5$ are H (3,6,3',4'-tetrahydroxyflavone). In a further embodiment, the methods comprise a compound of formula 26 and the attendant definitions, wherein X is COH; Z is O; M is O; $R_2$, $R_4$, $R'_2$, and $R'_3$ are OH; and $R_1$, $R_3$, $R'_1$, $R'_4$, and $R'_5$ are H (quercetin). In a further embodiment, the methods comprise a compound of formula 26 and the attendant definitions, wherein X is CH; Z is O; M is O; $R_2$, $R'_2$, $R'_3$, and $R'_4$ are OH; and $R_1$, $R_3$, $R_4$, $R'_1$, and $R'_5$ are H. In a further embodiment, the methods comprise a compound of formula 26 and the attendant definitions, wherein X is COH; Z is O; M is O; $R_2$, $R_4$, and $R'_3$ are OH; and $R_1$, $R_3$, $R'_1$, $R'_2$, $R'_4$, and $R'_5$ are H. In a further embodiment, the methods comprise a compound of formula 26 and the attendant definitions, wherein X is CH; Z is O; M is O; $R_2$, $R_3$, $R_4$, and $R'_3$ are OH; and $R_1$, $R'_1$, $R'_2$, $R'_4$, and $R'_5$ are H. In a further embodiment, the methods comprise a compound of formula 26 and the attendant definitions, wherein X is CH; Z is O; M is O; $R_2$, $R_4$, and $R'_3$ are OH; and $R_1$, $R_3$, $R'_1$, $R'_2$, $R'_4$, and $R'_5$ are H. In a further embodiment, the methods comprise a compound of formula 26 and the attendant definitions, wherein X is COH; Z is O; M is O; $R_3$, $R'_1$, and $R'_3$ are OH; and $R_1$, $R_2$, $R_4$, $R'_2$, $R'_4$, and $R'_5$ are H. In a further embodiment, the methods comprise a compound of formula 26 and the attendant definitions, wherein X is CH; Z is O; M is O; $R_2$ and $R'_3$ are OH; and $R_1$, $R_3$, $R_4$, $R'_1$, $R'_2$, $R'_4$, and $R'_5$ are H. In a further embodiment, the methods comprise a compound of formula 26 and the attendant definitions, wherein X is COH; Z is O; M is O; $R_1$, $R_2$, $R'_2$, and $R'_3$ are OH; and $R_1$, $R_2$, $R_4$, $R'_3$, $R'_4$, and $R'_5$ are H. In a further embodiment, the methods comprise a compound of formula 26 and the attendant definitions, wherein X is COH; Z is O; M is O; $R_3$, $R'_1$, and $R'_2$ are OH; and $R_1$, $R_2$, $R_4$; $R'_3$, $R'_4$, and $R'_5$ are H. In a further embodiment, the methods comprise a compound of formula 26 and the attendant definitions, wherein X is CH; Z is O; M is O; $R'_3$ is OH; and $R_1$, $R_2$, $R_3$, $R_4$, $R'_1$, $R'_2$, $R'_4$, and $R'_5$ are H. In a further embodiment, the methods comprise a compound of formula 26 and the attendant definitions, wherein X is CH; Z is O; M is O; $R_4$ and $R'_3$ are OH; and $R_1$, $R_2$, $R_3$, $R'_1$, $R'_2$, $R'_4$, and $R'_5$ are H. In a further embodiment, the methods comprise a compound of formula 26 and the attendant definitions, wherein X is CH; Z is O; M is O; $R_2$ and $R_4$ are OH; and $R_1$, $R_3$, $R'_1$, $R'_2$, $R'_3$, $R'_4$, and $R'_5$ are H. In a further embodiment, the methods comprise a compound of formula 26 and the attendant definitions, wherein X is COH; Z is O; M is O; $R_2$, $R_4$, $R'_1$, and $R'_3$ are OH; and $R_1$, $R_3$, $R'_2$, $R'_4$, and $R'_5$ are H. In a further embodiment, the methods comprise a compound of formula 26 and the attendant definitions, wherein X is CH; Z is O; M is O; $R_4$ is OH; and $R_1$, $R_2$, $R_3$, $R'_1$, $R'_2$, $R'_3$, $R'_4$, and R'$_5$ are H. In a further embodiment, the methods comprise a compound of formula 26 and the attendant definitions, wherein X is COH; Z is O; M is O; R$_2$, R$_4$, R'$_2$, R'$_3$, and R'$_4$ are OH; and R$_1$, R$_3$, R'$_1$, and R'$_5$ are H. In a further embodiment, the methods comprise a compound of formula 26 and the attendant definitions, wherein X is COH; Z is O; M is O; R$_2$, R'$_2$, R'$_3$, and R'$_4$ are OH; and R$_1$, R$_3$, R$_4$, R'$_1$, and R'$_5$ are H. In a further embodiment, the methods comprise a compound of formula 26 and the attendant definitions, wherein X is COH; Z is O; M is O; R, R$_2$, R$_4$, R'$_2$, and R'$_3$ are OH; and R$_3$, R'$_1$, R'$_4$, and R'$_5$ are H.

In another embodiment, methods for activating a sirtuin protein comprise using an activating compound that is an isoflavone compound of formula 27:

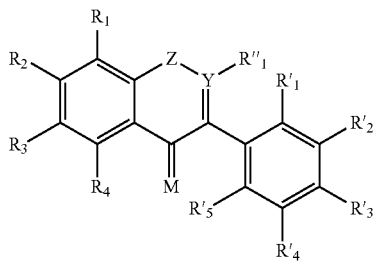

27 wherein, independently for each occurrence,

R$_1$, R$_2$, R$_3$, R$_4$, R'$_1$, R'$_2$, R'$_3$, R'$_4$, and R'$_5$, represent H, alkyl, aryl, heteroaryl, aralkyl, alkaryl, heteroaralkyl, halide, NO$_2$, SR, OR, N(R)$_2$, or carboxyl;

R represents H, alkyl, aryl, heteroaryl, aralkyl, —SO$_3$H, monosaccharide, oligosaccharide, glycofuranosyl, glycopyranosyl, glucuronosyl, or glucuronide;

M represents H$_2$, O, NR, or S;

Z represents C(R)$_2$, O, NR, or S; and

Y represents CR" or N, wherein

R" represents H, alkyl, aryl, heteroaryl, alkaryl, heteroaralkyl, halide, NO$_2$, SR, OR, N(R)$_2$, or carboxyl.

In a further embodiment, the methods comprise a compound of formula 27 and the attendant definitions, wherein Y is CR". In a further embodiment, the methods comprise a compound of formula 27 and the attendant definitions, wherein Y is CH. In a further embodiment, the methods comprise a compound of formula 27 and the attendant definitions, wherein Z is O. In a further embodiment, the methods comprise a compound of formula 27 and the attendant definitions, wherein M is O. In a further embodiment, the methods comprise a compound of formula 27 and the attendant definitions, wherein R$_2$ and R'$_3$ are OH. In a further embodiment, the methods comprise a compound of formula 27 and the attendant definitions, wherein R$_2$, R$_4$, and R'$_3$ are OH.

In a further embodiment, the methods comprise a compound of formula 27 and the attendant definitions, wherein Y is CH; Z is O; M is O; R$_2$ and R'$_3$ are OH; and R$_1$, R$_3$, R$_4$, R'$_1$, R'$_2$, R'$_4$, and R'$_5$ are H. In a further embodiment, the methods comprise a compound of formula 27 and the attendant definitions, wherein Y is CH; Z is O; M is O; R$_2$, R$_4$, and R'$_3$ are OH; and R$_1$, R$_3$, R'$_1$, R'$_2$, R'$_4$, and R'$_5$ are H.

In another embodiment, methods for activating a sirtuin protein comprise using an activating compound that is an anthocyanidin compound of formula 28:

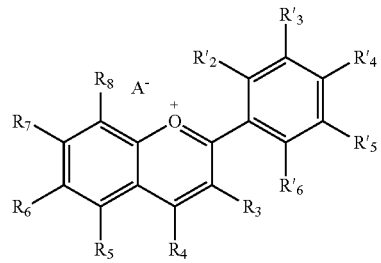

28 wherein, independently for each occurrence,

R$_3$, R$_4$, R$_5$, R$_6$, R$_7$, R$_8$, R'$_2$, R'$_3$, R'$_4$, R'$_5$, and R'$_6$ represent H, alkyl, aryl, heteroaryl, aralkyl, alkaryl, heteroaralkyl, halide, NO$_2$, SR, OR, N(R)$_2$, or carboxyl;

R represents H, alkyl, aryl, heteroaryl, aralkyl, —SO$_3$H, monosaccharide, oligosaccharide, glycofuranosyl, glycopyranosyl, glucuronosyl, or glucuronide; and A$^-$ represents an anion selected from the following: Cl$^-$, Br$^-$, or I$^-$.

In a further embodiment, the methods comprise a compound of formula 28 and the attendant definitions, wherein A$^-$ is Cl$^-$. In a further embodiment, the methods comprise a to compound of formula 28 and the attendant definitions, wherein R$_3$, R$_5$, R$_7$, and R'$_4$ are OH. In a further embodiment, the methods comprise a compound of formula 28 and the attendant definitions, wherein R$_3$, R$_5$, R$_7$, R'$_3$, and R'$_4$ are OH. In a further embodiment, the methods comprise a compound of formula 28 and the attendant definitions, wherein R$_3$, R$_5$, R$_7$, R'$_3$, R'$_4$, and R'$_5$ are OH.

In a further embodiment, the methods comprise a compound of formula 28 and the attendant definitions, wherein A$^-$ is Cl$^-$; R$_3$, R$_5$, R$_7$, and R'$_4$ are OH; and R$_4$, R$_6$, R$_8$, R'$_2$, R'$_3$, R'$_5$, and R'$_6$ are H. In a further embodiment, the methods comprise a compound of formula 28 and the attendant definitions, wherein A$^-$ is Cl$^-$; R$_3$, R$_5$, R$_7$, R'$_3$, and R'$_4$ are OH; and R$_4$, R$_6$, R$_8$, R'$_2$, R'$_5$, and R'$_6$ are H. In a further embodiment, the methods comprise a compound of formula 28 and the attendant definitions, wherein A$^-$ is Cl$^-$; R$_3$, R$_5$, R$_7$, R'$_3$, R'$_4$, and R'$_5$ are OH; and R$_4$, R$_6$, R$_8$, R'$_2$, and R'$_6$ are H.

Methods for activating a sirtuin protein may also comprise using a stilbene, chalcone, or flavone compound represented by formula 29:

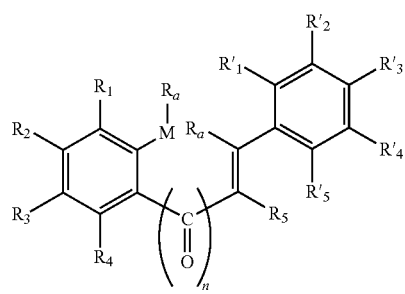

29 wherein, independently for each occurrence:

M is absent or O;

R$_1$, R$_2$, R$_3$, R$_4$, R$_5$, R'$_1$, R'$_2$, R'$_3$, R'$_4$, and R$_5$ represent H, alkyl, aryl, heteroaryl, aralkyl, alkaryl, heteroaralkyl, halide, NO$_2$, SR, OR, N(R)$_2$, or carboxyl;

$R_a$ represents H or the two instances of $R_a$ form a bond;

R represents H, alkyl, aryl, heteroaryl, aralkyl, —SO$_3$H, monosaccharide, oligosaccharide, glycofuranosyl, glycopyranosyl, glucuronosyl, or glucuronide; and n is 0 or 1.

In a further embodiment, the methods comprise an activating compound represented by formula 29 and the attendant definitions, wherein n is 0. In a further embodiment, the methods comprise an activating compound represented by formula 29 and the attendant definitions, wherein n is 1. In a further embodiment, the methods comprise an activating compound represented by formula 29 and the attendant definitions, wherein M is absent. In a further embodiment, the methods comprise an activating compound represented by formula 29 and the attendant definitions, wherein M is O. In a further embodiment, the methods comprise an activating compound represented by formula 29 and the attendant definitions, wherein $R_a$ is H. In a further embodiment, the methods comprise an activating compound represented by formula 29 and the attendant definitions, wherein M is O and the two $R_a$ form a bond.

In a further embodiment, the methods comprise an activating compound represented by formula 29 and the attendant definitions, wherein $R_5$ is H. In a further embodiment, the methods comprise an activating compound represented by formula 29 and the attendant definitions, wherein $R_5$ is OH. In a further embodiment, the methods comprise an activating compound represented by formula 29 and the attendant definitions, wherein $R_1$, $R_3$, and $R'_3$ are OH. In a further embodiment, the methods comprise an activating compound represented by formula 29 and the attendant definitions, wherein $R_2$, $R_4$, $R'_2$, and $R'_3$ are OH. In a further embodiment, the methods comprise an activating compound represented by formula 29 and the attendant definitions, wherein $R_2$, $R'_2$, and $R'_3$ are OH. In a further embodiment, the methods comprise an activating compound represented by formula 29 and the attendant definitions, wherein $R_2$ and $R_4$ are OH.

In a further embodiment, the methods include contacting a cell with an activating compound represented by formula 29 and the attendant definitions, wherein n is 0; M is absent; $R_a$ is H; $R_5$ is H; $R_1$, $R_3$, and $R'_3$ are OH; and $R_2$, $R_4$, $R'_1$, $R'_2$, $R'_4$, and $R_5$ are H. In a further embodiment, the methods comprise an activating compound represented by formula 29 and the attendant definitions, wherein n is 1; M is absent; $R_a$ is H; $R_5$ is H; $R_2$, $R_4$, $R'_2$, and $R'_3$ are OH; and $R_1$, $R_3$, $R'_1$, $R'_4$, and $R'_5$ are H. In a further embodiment, the methods comprise an activating compound represented by formula 29 and the attendant definitions, wherein n is 1; M is O; the two $R_a$ form a bond; $R_5$ is OH; $R_2$, $R'_2$, and $R'_3$ are OH; and $R_1$, $R_3$, $R_4$, $R'_1$, $R'_4$, and $R'_5$ are H.

In a further embodiment, the methods comprise a compound represented by formula 29 and the attendant definitions, wherein n is 0. In a further embodiment, the methods comprise a compound represented by formula 29 and the attendant definitions, wherein n is 1. In a further embodiment, the methods comprise a compound represented by formula 29 and the attendant definitions, wherein M is absent. In a further embodiment, the methods comprise a compound represented by formula 29 and the attendant definitions, wherein M is O. In a further embodiment, the methods comprise a compound represented by formula 29 and the attendant definitions, wherein $R_a$ is H. In a further embodiment, the methods comprise a compound represented by formula 29 and the attendant definitions, wherein M is O and the two $R_a$ form a bond. In a further embodiment, the methods comprise a compound represented by formula 29 and the attendant definitions, wherein $R_5$ is H. In a further embodiment, the methods comprise a compound represented by formula 29 and the attendant definitions, wherein $R_5$ is OH. In a further embodiment, the methods comprise a compound represented by formula 29 and the attendant definitions, wherein $R_1$, $R_3$, and $R'_3$ are OH. In a further embodiment, the methods comprise a compound represented by formula 29 and the attendant definitions, wherein $R_2$, $R_4$, $R'_2$, and $R'_3$ are OH. In a further embodiment, the methods comprise a compound represented by formula 29 and the attendant definitions, wherein $R_2$, $R'_2$, and $R'_3$ are OH.

In a further embodiment, methods for extending the lifespan of a eukaryotic cell comprise contacting the cell with a compound represented by formula 29 and the attendant definitions, wherein n is 0; M is absent; $R_a$ is H; $R_5$ is H; $R_1$, $R_3$, and $R'_3$ are OH; and $R_2$, $R_4$, $R'_1$, $R'_2$, $R'_4$, and $R'_5$ are H. In a further embodiment, the methods comprise a compound represented by formula 29 and the attendant definitions, wherein n is 1; M is absent; $R_a$ is H; $R_5$ is H; $R_2$, $R_4$, $R'_2$, and $R'_3$ are OH; and $R_1$, $R_3$, $R'_1$, $R'_4$, and $R'_5$ are H. In a further embodiment, the methods comprise a compound represented by formula 29 and the attendant definitions, wherein n is 1; M is O; the two $R_a$ form a bond; $R_5$ is OH; $R_2$, $R'_2$, and $R'_3$ are OH; and $R_1$, $R_3$, $R_4$, $R'_1$, $R'_4$, and $R'_5$ are H.

Other compounds for activating sirtuin deacetylase protein family members include compounds having a formula selected from the group consisting of formulas 30-47 and 52 set forth below:

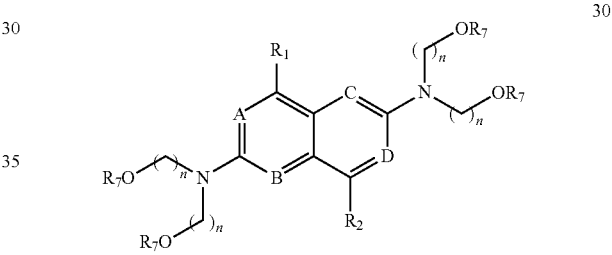

wherein, independently for each occurrence:

$R_1$ and $R_2$ represent H, aryl, heterocycle, or small alkyl;

$R_7$ represents H, alkyl, aryl, heteroaryl, aralkyl, —SO$_3$H, monosaccharide, oligosaccharide, glycofuranosyl, glycopyranosyl, glucuronosyl, or glucuronide;

A, B, C, and D represent CR$_1$ or N; and n is 0, 1, 2, or 3;

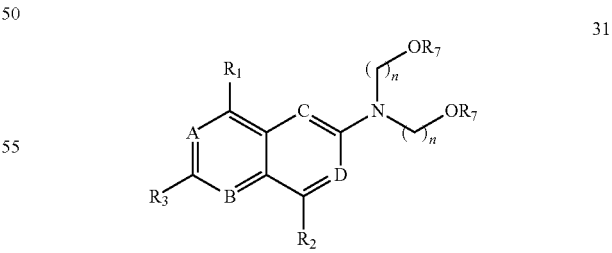

wherein, independently for each occurrence:

$R_1$ and $R_2$ represent H, aryl, heterocycle, or small alkyl;

$R_3$ represents small alkyl;

$R_7$ represents H, alkyl, aryl, heteroaryl, aralkyl, —SO$_3$H, monosaccharide, oligosaccharide, glycofuranosyl, glycopyranosyl, glucuronosyl, or glucuronide;

A, B, C, and D represent CR₁ or N; and
n is 0, 1, 2, or 3;

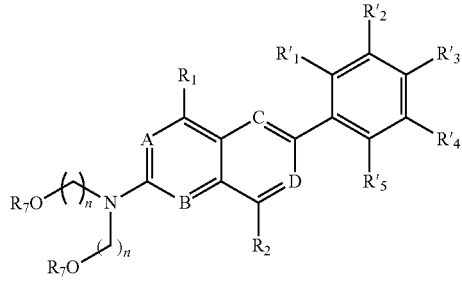

wherein, independently for each occurrence,
R₁ and R₂ represent H, aryl, heterocycle, or small alkyl;
R'₁, R'₂, R'₃, R'₄, and R'₅ represent H or OR₇;
R₇ represents H, alkyl, aryl, heteroaryl, aralkyl, —SO₃H, monosaccharide, oligosaccharide, glycofuranosyl, glycopyranosyl, glucuronosyl, or glucuronide;
A, B, C, and D represent CR₁ or N; and
n is 0, 1, 2, or 3;

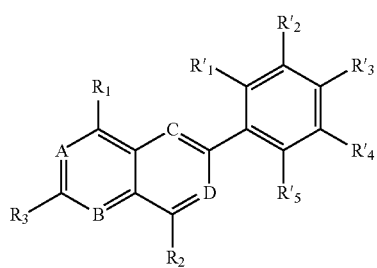

wherein, independently for each occurrence:
R₁ and R₂ represent H, aryl, heterocycle, or small alkyl;
R₃ represents small alkyl;
R'₁, R'₂, R'₃, R'₄, and R'₅ represent H or OR₇;
R₇ represents H, alkyl, aryl, heteroaryl, aralkyl, —SO₃H, monosaccharide, oligosaccharide, glycofuranosyl, glycopyranosyl, glucuronosyl, or glucuronide;
A, B, C, and D represent CR₁ or N; and
n is 0, 1, 2, or 3;

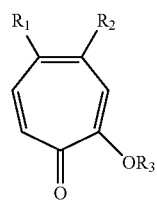

wherein, independently for each occurrence:
R₁ and R₂ represent H, aryl, or alkenyl; and
R₇ represents H, —SO₃H, monosaccharide, oligosaccharide, glycofuranosyl, glycopyranosyl, glucuronosyl, or glucuronide;

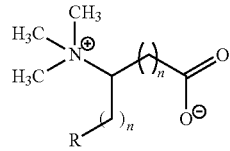

wherein, independently for each occurrence:
R represents heterocycle or aryl; and
n is 0 to 10 inclusive;

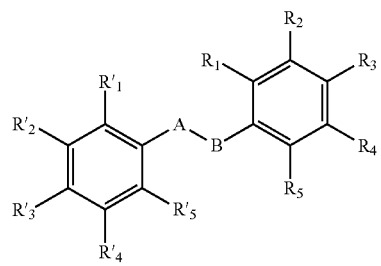

wherein, independently for each occurrence:
R₁, R₂, R₃, R₄, R₅, R'₁, R'₂, R'₃, R'₄, and R'₅ represents H, halogen, NO₂, SH, SR, OH, OR, NRR', alkyl, aryl or carboxy;
R represents H, alkyl, aryl, heteroaryl, aralkyl, —SO₃H, monosaccharide, oligosaccharide, glycofuranosyl, glycopyranosyl, glucuronosyl, or glucuronide;
R' represents H, alkyl, aryl, heteroaryl, aralkyl, —SO₃H, monosaccharide, oligosaccharide, glycofuranosyl, glycopyranosyl, glucuronosyl, or glucuronide; and
A-B represents ethene, ethyne, amide, sulfonamide, diazo, alkyl, ether, alkyl amine, alkyl sulfide, hydroxyamine, or hydrazine;

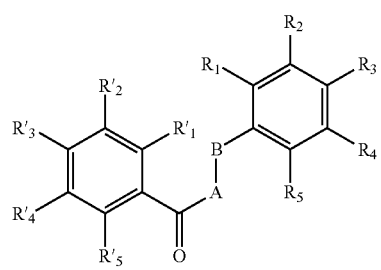

wherein, independently for each occurrence:
R₁, R₂, R₃, R₄, R₅, R'₁, R'₂, R'₃, R'₄, and R'₅ represents H, halogen, NO₂, SH, SR, OH, OR, NRR', alkyl, aryl or carboxy;
R represents H, alkyl, aryl, heteroaryl, aralkyl, —SO₃H, monosaccharide, oligosaccharide, glycofuranosyl, glycopyranosyl, glucuronosyl, or glucuronide;
R' represents H, alkyl, aryl, heteroaryl, aralkyl, —SO₃H, monosaccharide, oligosaccharide, glycofuranosyl, glycopyranosyl, glucuronosyl, or glucuronide; and A-B represents ethene, ethyne, amide, sulfonamide, diazo, alkyl, ether, alkyl amine, alkyl sulfide, hydroxyamine, or hydrazine;

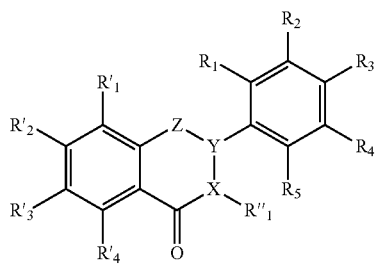

38 wherein, independently for each occurrence:

$R_1$, $R_2$, $R_3$, $R_4$, $R_5$, $R'_1$, $R'_2$, $R'_3$, $R'_4$, and $R'_5$ represents H, halogen, $NO_2$, SH, SR, OH, OR, NRR', alkyl, aryl or carboxy;

R represents H, alkyl, aryl, heteroaryl, aralkyl, —$SO_3H$, monosaccharide, oligosaccharide, glycofuranosyl, glycopyranosyl, glucuronosyl, or glucuronide;

R' represents H, alkyl, aryl, heteroaryl, aralkyl, —$SO_3H$, monosaccharide, oligosaccharide, glycofuranosyl, glycopyranosyl, glucuronosyl, or glucuronide;

X represents $CR_8$ or N;

Y represents $CR_8$ or N;

Z represents O, S, $C(R_8)_2$, or $NR_8$; and $R_8$ represents alkyl, aryl or aralkyl;

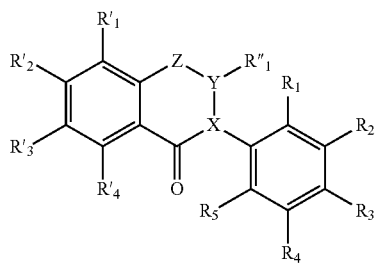

39 wherein, independently for each occurrence:

$R_1$, $R_2$, $R_3$, $R_4$, $R_5$, $R'_1$, $R'_2$, $R'_3$, $R'_4$, and $R'_5$ represents H, halogen, $NO_2$, SH, SR, OH, OR, NRR', alkyl, aryl or carboxy;

R represents H, alkyl, aryl, heteroaryl, aralkyl, —$SO_3H$, monosaccharide, oligosaccharide, glycofuranosyl, glycopyranosyl, glucuronosyl, or glucuronide;

R' represents H, alkyl, aryl, heteroaryl, aralkyl, —$SO_3H$, monosaccharide, oligosaccharide, glycofuranosyl, glycopyranosyl, glucuronosyl, or glucuronide;

X represents $CR_8$ or N;

Y represents $CR_8$ or N;

Z represents O, S, $C(R_8)_2$, or $NR_8$; and $R_8$ represents alkyl, aryl or aralkyl;

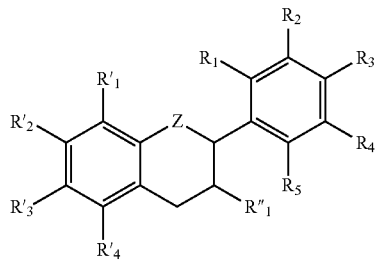

40 wherein, independently for each occurrence:

$R_1$, $R_2$, $R_3$, $R_4$, $R_5$, $R'_1$, $R'_2$, $R'_3$, $R'_4$, and $R'_5$ represents H, halogen, $NO_2$, SH, SR, OH, OR, NRR', alkyl, aryl or carboxy;

R represents H, alkyl, aryl, heteroaryl, aralkyl, —$SO_3H$, monosaccharide, oligosaccharide, glycofuranosyl, glycopyranosyl, glucuronosyl, or glucuronide;

R' represents H, alkyl, aryl, heteroaryl, aralkyl, —$SO_3H$, monosaccharide, oligosaccharide, glycofuranosyl, glycopyranosyl, glucuronosyl, or glucuronide;

Z represents O, S, $C(R_8)_2$, or $NR_8$; and $R_8$ represents alkyl, aryl or aralkyl;

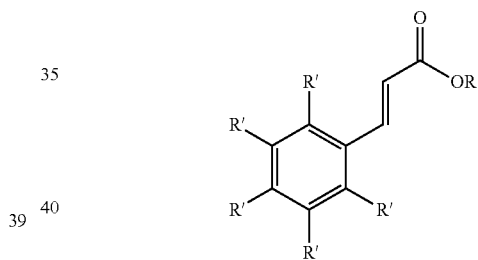

41 wherein, independently for each occurrence:

R is H, alkyl, aryl, heterocycyl, heteroaryl, aralkyl, —$SO_3H$, monosaccharide, oligosaccharide, glycofuranosyl, glycopyranosyl, glucuronosyl, or glucuronide; and R' is H, halogen, $NO_2$, SR, OR, $NR_2$, alkyl, aryl, or carboxy;

42 wherein, independently for each occurrence:

R is H, alkyl, aryl, heterocycyl, heteroaryl, aralkyl, —$SO_3H$, monosaccharide, oligosaccharide, glycofuranosyl, glycopyranosyl, glucuronosyl, or glucuronide;

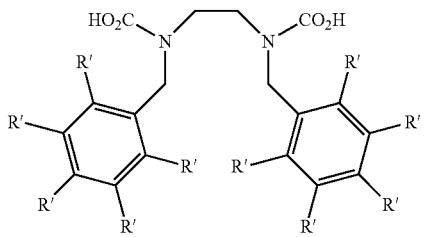

43

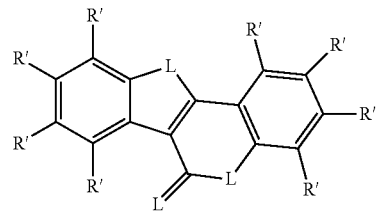

46 wherein, independently for each occurrence:

R' is H, halogen, $NO_2$, SR, OR, $NR_2$, alkyl, aryl, aralkyl, or carboxy; and

R is H, alkyl, aryl, heterocycyl, heteroaryl, aralkyl, —$SO_3$1-1, monosaccharide, oligosaccharide, glycofuranosyl, glycopyranosyl, glucuronosyl, or glucuronide;

wherein, independently for each occurrence:

L represents $CR_2$, O, NR, or S;

R represents H, alkyl, aryl, aralkyl, heteroaralkyl, —$SO_3H$, monosaccharide, oligosaccharide, glycofuranosyl, glycopyranosyl, glucuronosyl, or glucuronide; and R' represents H, halogen, $NO_2$, SR, OR, $NR_2$, alkyl, aryl, aralkyl, or carboxy;

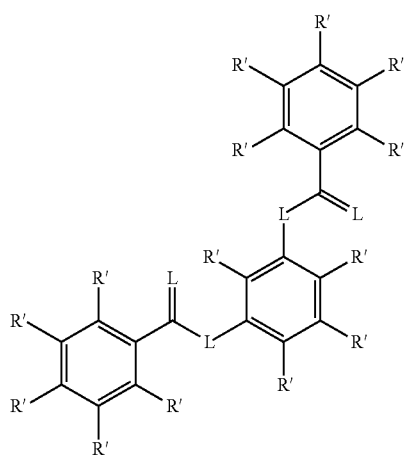

44

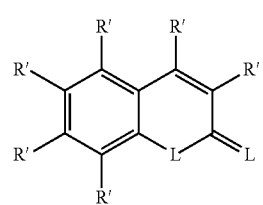

47 wherein, independently for each occurrence:

L represents $CR_2$, O, NR, or S;

R represents H, alkyl, aryl, aralkyl, heteroaralkyl, —$SO_3$1-1, monosaccharide, oligosaccharide, glycofuranosyl, glycopyranosyl, glucuronosyl, or glucuronide; and R' represents H, halogen, $NO_2$, SR, OR, $NR_2$, alkyl, aryl, aralkyl, or carboxy;

wherein, independently for each occurrence:

L represents $CR_2$, O, NR, or S;

R represents H, alkyl, aryl, aralkyl, heteroaralkyl, —$SO_3H$, monosaccharide, oligosaccharide, glycofuranosyl, glycopyranosyl, glucuronosyl, or glucuronide; and R' represents H, halogen, $NO_2$, SR, OR, $NR_2$, alkyl, aryl, aralkyl, or carboxy.

Methods for activating a sirtuin protein may also comprise using a stilbene, chalcone, or flavone compound represented by formula 52:

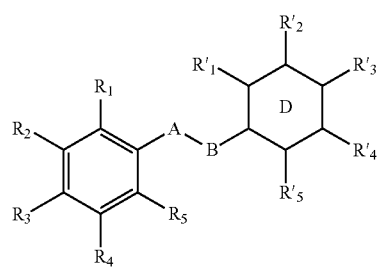

52

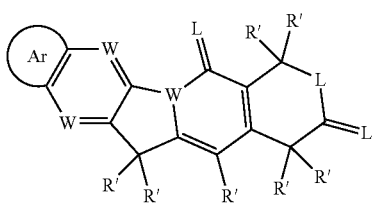

45 wherein, independently for each occurrence:

L represents $CR_2$, O, NR, or S;

W represents CR or N;

R represents H, alkyl, aryl, aralkyl, heteroaralkyl, —$SO_3H$ monosaccharide, oligosaccharide, glycofuranosyl, glycopyranosyl, glucuronosyl, or glucuronide; and Ar represents a fused aryl or heteroaryl ring; and R' represents H, halogen, $NO_2$, SR, OR, $NR_2$, alkyl, aryl, aralkyl, or carboxy;

wherein, independently for each occurrence:

D is a phenyl or cyclohexyl group;

$R_1$, $R_2$, $R_3$, $R_4$, $R_5$, $R'_1$, $R'_2$, $R'_3$, $R'_4$, and $R'_5$ represent H, alkyl, aryl, heteroaryl, alkaryl, heteroaralkyl, halide, $NO_2$, SR, OR, $N(R)_2$, carboxyl, azide, ether; or any two adjacent $R_1$, $R_2$, $R_3$, $R_4$, $R_5$, $R'_1$, $R'_2$, $R'_3$, $R'_4$, or $R'_5$ groups taken together form a fused benzene or cyclohexyl group;

R represents H, alkyl, aryl, aralkyl, —$SO_3H$, monosaccharide, oligosaccharide, glycofuranosyl, glycopyranosyl, glucuronosyl, or glucuronide; and A-B represents an ethylene, ethenylene, or imine group;

provided that when A-B is ethenylene, D is phenyl, and $R'_3$ is H; $R_3$ is not OH when $R_1$, $R_2$, $R_4$, and $R_5$ are H; and $R_2$ and $R_4$ are not OMe when $R_1$, $R_3$, and $R_5$ are H; and $R_3$ is not OMe when $R_1$, $R_2$, $R_4$, and $R_5$ are H.

In a further embodiment, the methods include contacting a cell with an activating compound represented by formula 52 and the attendant definitions, wherein D is a phenyl group.

In a further embodiment, the methods include contacting a cell with an activating compound represented by formula 52 and the attendant definitions, wherein A-B is an ethenylene or imine group.

In a further embodiment, the methods include contacting a cell with an activating compound represented by formula 52 and the attendant definitions, wherein A-B is an ethenylene group.

In a further embodiment, the methods include contacting a cell with an activating compound represented by formula 52 and the attendant definitions, wherein $R_2$ is OH.

In a further embodiment, the methods include contacting a cell with an activating compound represented by formula 52 and the attendant definitions, wherein $R_4$ is OH In a further embodiment, the methods include contacting a cell with an activating compound represented by formula 52 and the attendant definitions, wherein $R_2$ and $R_4$ are OH.

In a further embodiment, the methods include contacting a cell with an activating compound represented by formula 52 and the attendant definitions, wherein D is a phenyl group; and A-B is an ethenylene group.

In a further embodiment, the methods include contacting a cell with an activating compound represented by formula 52 and the attendant definitions, wherein D is a phenyl group; A-B is an ethenylene group; and $R_2$ and $R_4$ are OH.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is Cl.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is OH.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is H.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is $CH_2CH_3$.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is F.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is Me.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is an azide.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is SMe.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is $NO_2$.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is $CH(CH_3)_2$.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is OMe.

In a further embodiment, the methods include contacting a cell with an activating compound represented by formula 52 and the attendant definitions, wherein A-B is ethenylene; D is a phenyl ring; $R_2$ and $R_4$ are OH; $R'_2$ is OH; and $R'_3$ is OMe.

In a further embodiment, the methods include contacting a cell with an activating compound represented by formula 52 and the attendant definitions, wherein A-B is ethenylene; D is a phenyl ring; $R_2$ is OH; $R_4$ is carboxyl; and $R'_3$ is OH.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is carboxyl.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ and $R'_4$ taken together form a fused benzene ring.

In a further embodiment, the methods include contacting a cell with an activating compound represented by formula 52 and the attendant definitions, wherein A-B is ethenylene; D is a phenyl ring; and $R_4$ is OH.

In a further embodiment, the methods include contacting a cell with an activating compound represented by formula 52 and the attendant definitions, wherein A-B is ethenylene; D is a phenyl ring; $R_2$ and $R_4$ are $OCH_2OCH_3$; and $R'_3$ is SMe.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is carboxyl.

In a further embodiment, the methods include contacting a cell with an activating compound represented by formula 52 and the attendant definitions, wherein A-B is ethenylene; D is a cyclohexyl ring; and $R_2$ and $R_4$ are OH.

In a further embodiment, the methods include contacting a cell with an activating compound represented by formula 52 and the attendant definitions, wherein A-B is ethenylene; D is a phenyl ring; and $R_3$ and $R_4$ are OMe.

In a further embodiment, the methods include contacting a cell with an activating compound represented by formula 52 and the attendant definitions, wherein A-B is ethenylene; D is a phenyl ring; $R_2$ and $R_4$ are OH; and $R'_3$ is OH.

In another embodiment, methods for activating a sirtuin protein comprise using an activating compound of formula 54:

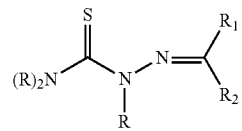

54 wherein, independently for each occurrence,

R is H, or a substituted or unsubstituted alkyl, aryl, aralkyl, heterocyclyl, heterocyclylalkyl, heteroaryl, or heteroaralkyl; and R₁ and R₂ are a substituted or unsubstituted alkyl, aryl, aralkyl, heterocyclyl, heterocyclylalkyl, heteroaryl, or heteroaralkyl.

In a further embodiment, the methods comprise a compound of formula 54 and the attendant definitions wherein R is H.

In a further embodiment, the methods comprise a compound of formula 54 and the attendant definitions wherein R₁ is 3-hydroxyphenyl.

In a further embodiment, the methods comprise a compound of formula 54 and the attendant definitions wherein R₂ is methyl.

In a further embodiment, the methods comprise a compound of formula 54 and the attendant definitions wherein R is H and R₁ is 3-hydroxyphenyl.

In a further embodiment, the methods comprise a compound of formula 54 and the attendant definitions wherein R is H, R₁ is 3-hydroxyphenyl, and R₂ is methyl.

In another embodiment, methods for activating a sirtuin protein comprise using an activating compound of formula 55:

wherein, independently for each occurrence:

R is H, or a substituted or unsubstituted alkyl, alkenyl, or alkynyl;

R₁ and R₂ are a substituted or unsubstituted alkyl, aryl, aralkyl, heterocyclyl, heterocyclylalkyl, heteroaryl, or heteroaralkyl; and L is O, S, or NR.

In a further embodiment, the methods comprise a compound of formula 55 and the attendant definitions wherein R is alkynyl.

In a further embodiment, the methods comprise a compound of formula 55 and the attendant definitions wherein R₁ is 2,6-dichlorophenyl.

In a further embodiment, the methods comprise a compound of formula 55 and the attendant definitions wherein R₂ is methyl.

In a further embodiment, the methods comprise a compound of formula 55 and the attendant definitions wherein L is O.

In a further embodiment, the methods comprise a compound of formula 55 and the attendant definitions wherein R is alkynyl and R₁ is 2,6-dichlorophenyl.

In a further embodiment, the methods comprise a compound of formula 55 and the attendant definitions wherein R is alkynyl, R₁ is 2,6-dichlorophenyl, and R₂ is methyl.

In a further embodiment, the methods comprise a compound of formula 55 and the attendant definitions wherein R is alkynyl, R₁ is 2,6-dichlorophenyl, R₂ is methyl, and L is O.

In another embodiment, methods for activating a sirtuin protein comprise using an activating compound of formula 56:

wherein, independently for each occurrence:

R, R₁, and R₂ are H, or a substituted or unsubstituted alkyl, aryl, aralkyl, heterocyclyl, heterocyclylalkyl, heteroaryl, or heteroaralkyl; and n is an integer from 0 to 5 inclusive.

In a further embodiment, the methods comprise a compound of formula 56 and the attendant definitions wherein R is 3,5-dichloro-2-hydroxyphenyl.

In a further embodiment, the methods comprise a compound of formula 56 and the attendant definitions wherein R₁ is H.

In a further embodiment, the methods comprise a compound of formula 56 and the attendant definitions wherein R₂ is H.

In a further embodiment, the methods comprise a compound of formula 56 and the attendant definitions wherein n is 1.

In a further embodiment, the methods comprise a compound of formula 56 and the attendant definitions wherein R is 3,5-dichloro-2-hydroxyphenyl and R₁ is H.

In a further embodiment, the methods comprise a compound of formula 56 and the attendant definitions wherein R is 3,5-dichloro-2-hydroxyphenyl, R₁ is H, and R₂ is H.

In a further embodiment, the methods comprise a compound of formula 56 and the attendant definitions wherein R is 3,5-dichloro-2-hydroxyphenyl, R₁ is H, R₂ is H, and n is 1.

In another embodiment, methods for activating a sirtuin protein comprise using an activating compound of formula 59:

wherein, independently for each occurrence:

R is H or a substituted or unsubstituted alkyl, aryl, aralkyl, heterocyclyl, heterocyclylalkyl, heteroaryl, or heteroaralkyl;

R₁ is a substituted or unsubstituted alkyl, aryl, aralkyl, heterocyclyl, heterocyclylalkyl, heteroaryl, or heteroaralkyl;

R₂ is hydroxy, amino, cyano, halide, OR₃, ether, ester, amido, ketone, carboxylic acid, nitro, or a substituted or unsubstituted alkyl, aryl, aralkyl, heterocyclyl, heterocyclylalkyl, heteroaryl, heteroaralkyl;

R₃ is alkyl, —SO₃H, monosaccharide, oligosaccharide, glycofuranosyl, glycopyranosyl, glucuronosyl, or glucuronide;

L is O, NR, or S;

m is an integer from 0 to 3 inclusive;

n is an integer from 0 to 5 inclusive; and o is an integer from 0 to 2 inclusive.

In a further embodiment, the methods comprise a compound of formula 57 and the attendant definitions wherein R is phenyl.

In a further embodiment, the methods comprise a compound of formula 57 and the attendant definitions wherein $R_1$ is pyridine.

In a further embodiment, the methods comprise a compound of formula 57 and the attendant definitions wherein L is S.

In a further embodiment, the methods comprise a compound of formula 57 and the attendant definitions wherein m is 0.

In a further embodiment, the methods comprise a compound of formula 57 and the attendant definitions wherein n is 1.

In a further embodiment, the methods comprise a compound of formula 57 and the attendant definitions wherein o is 0.

In a further embodiment, the methods comprise a compound of formula 57 and the attendant definitions wherein R is phenyl and $R_1$ is pyridine.

In a further embodiment, the methods comprise a compound of formula 57 and the attendant definitions wherein R is phenyl, $R_1$ is pyridine, and L is S.

In a further embodiment, the methods comprise a compound of formula 57 and the attendant definitions wherein R is phenyl, $R_1$ is pyridine, L is S, and m is 0.

In a further embodiment, the methods comprise a compound of formula 57 and the attendant definitions wherein R is phenyl, $R_1$ is pyridine, L is S, m is 0, and n is 1.

In a further embodiment, the methods comprise a compound of formula 57 and the attendant definitions wherein R is phenyl, $R_1$ is pyridine, L is S, m is 0, n is 1, and o is 0.

In another embodiment, methods for activating a sirtuin protein comprise using an activating compound of formula 58:

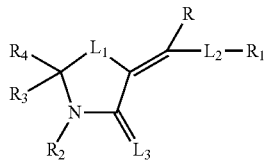

58 wherein, independently for each occurrence:

R, $R_3$, and $R_4$ are H, hydroxy, amino, cyano, halide, $OR_5$, ether, ester, amido, ketone, carboxylic acid, nitro, or a substituted or unsubstituted alkyl, aryl, aralkyl, heterocyclyl, heterocyclylalkyl, heteroaryl, heteroaralkyl;

$R_5$ is alkyl, —$SO_3H$, monosaccharide, oligosaccharide, glycofuranosyl, glycopyranosyl, glucuronosyl, or glucuronide;

$R_1$ and $R_2$ are H or a substituted or unsubstituted alkyl, aryl, aralkyl, heterocyclyl, heterocyclylalkyl, heteroaryl, heteroaralkyl;

$L_1$ is O, $NR_1$, S, $C(R)_2$, or $SO_2$; and $L_2$ and $L_3$ are O, $NR_1$, S, or $C(R)_2$.

In a further embodiment, the methods comprise a compound of formula 58 and the attendant definitions wherein R is H.

In a further embodiment, the methods comprise a compound of formula 58 and the attendant definitions wherein $R_1$ is 4-chlorophenyl.

In a further embodiment, the methods comprise a compound of formula 58 and the attendant definitions wherein $R_2$ is 4-chlorophenyl.

In a further embodiment, the methods comprise a compound of formula 58 and the attendant definitions wherein $R_3$ is H.

In a further embodiment, the methods comprise a compound of formula 58 and the attendant definitions wherein $R_4$ is H.

In a further embodiment, the methods comprise a compound of formula 58 and the attendant definitions wherein $L_1$ is $SO_2$.

In a further embodiment, the methods comprise a compound of formula 58 and the attendant definitions wherein $L_2$ is NH.

In a further embodiment, the methods comprise a compound of formula 58 and the attendant definitions wherein $L_3$ is O.

In a further embodiment, the methods comprise a compound of formula 58 and the attendant definitions wherein R is H and $R_1$ is 4-chlorophenyl.

In a further embodiment, the methods comprise a compound of formula 58 and the attendant definitions wherein R is H, $R_1$ is 4-chlorophenyl, and $R_2$ is 4-chlorophenyl.

In a further embodiment, the methods comprise a compound of formula 58 and the attendant definitions wherein R is H, $R_1$ is 4-chlorophenyl, $R_2$ is 4-chlorophenyl, and $R_3$ is H.

In a further embodiment, the methods comprise a compound of formula 58 and the attendant definitions wherein R is H, $R_1$ is 4-chlorophenyl, $R_2$ is 4-chlorophenyl, $R_3$ is H, and $R_4$ is H.

In a further embodiment, the methods comprise a compound of formula 58 and the attendant definitions wherein R is H, $R_1$ is 4-chlorophenyl, $R_2$ is 4-chlorophenyl, $R_3$ is H, $R_4$ is H, and $L_1$ is $SO_2$.

In a further embodiment, the methods comprise a compound of formula 58 and the attendant definitions wherein R is H, $R_1$ is 4-chlorophenyl, $R_2$ is 4-chlorophenyl, $R_3$ is H, $R_4$ is H, $L_1$ is $SO_2$, and $L_2$ is NH.

In a further embodiment, the methods comprise a compound of formula 58 and the attendant definitions wherein R is H, $R_1$ is 4-chlorophenyl, $R_2$ is 4-chlorophenyl, $R_3$ is H, $R_4$ is H, $L_1$ is $SO_2$, $L_2$ is NH, and $L_3$ is O.

In another embodiment, methods for activating a sirtuin protein comprise using an activating compound of formula 59:

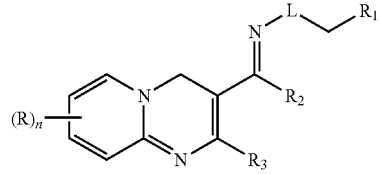

59 wherein, independently for each occurrence:

R is hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, heteroaralkyl;

$R_1$ is H or a substituted or unsubstituted alkyl, aryl, aralkyl, heterocyclyl, heterocyclylalkyl, heteroaryl, heteroaralkyl;

$R_2$ and $R_3$ are H or a substituted or unsubstituted alkyl, aryl, aralkyl, heterocyclyl, heterocyclylalkyl, heteroaryl, heteroaralkyl;

R$_4$ is alkyl, —SO$_3$H, monosaccharide, oligosaccharide, glycofuranosyl, glycopyranosyl, glucuronosyl, or glucuronide;

L is O, NR$_1$, or S; and n is an integer from 0 to 4 inclusive.

In a further embodiment, the methods comprise a compound of formula 59 and the attendant definitions wherein R is methyl.

In a further embodiment, the methods comprise a compound of formula 59 and the attendant definitions wherein n is 1.

In a further embodiment, the methods comprise a compound of formula 59 and the attendant definitions wherein R$_1$ is 3-fluorophenyl.

In a further embodiment, the methods comprise a compound of formula 59 and the attendant definitions wherein R$_2$ is H.

In a further embodiment, the methods comprise a compound of formula 59 and the attendant definitions wherein R$_3$ is 4-chlorophenyl.

In a further embodiment, the methods comprise a compound of formula 59 and the attendant definitions wherein L is O.

In a further embodiment, the methods comprise a compound of formula 59 and the attendant definitions wherein R is methyl and n is 1.

In a further embodiment, the methods comprise a compound of formula 59 and the attendant definitions wherein R is methyl, n is 1, and R$_1$ is 3-fluorophenyl.

In a further embodiment, the methods comprise a compound of formula 59 and the attendant definitions wherein R is methyl, n is 1, R$_1$ is 3-fluorophenyl, and R$_2$ is H.

In a further embodiment, the methods comprise a compound of formula 59 and the attendant definitions wherein R is methyl, n is 1, R$_1$ is 3-fluorophenyl, R$_2$ is H, and R$_3$ is 4-chlorophenyl.

In another embodiment, methods for activating a sirtuin protein comprise using an activating compound of formula 60:

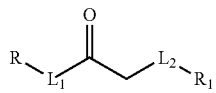

60 wherein, independently for each occurrence:

R and R$_1$ are H or a substituted or unsubstituted alkyl, aryl, aralkyl, heterocyclyl, heterocyclylalkyl, heteroaryl, or heteroaralkyl; and L$_1$ and L$_2$ are O, NR, or S.

In a further embodiment, the methods comprise a compound of formula 60 and the attendant definitions wherein R is 3-methoxyphenyl.

In a further embodiment, the methods comprise a compound of formula 60 and the attendant definitions wherein R$_1$ is 4-t-butylphenyl.

In a further embodiment, the methods comprise a compound of formula 60 and the attendant definitions wherein L$_1$ is NH.

In a further embodiment, the methods comprise a compound of formula 60 and the attendant definitions wherein L$_2$ is O.

In a further embodiment, the methods comprise a compound of formula 60 and the attendant definitions wherein R is 3-methoxyphenyl and R$_1$ is 4-t-butylphenyl.

In a further embodiment, the methods comprise a compound of formula 60 and the attendant definitions wherein R is 3-methoxyphenyl, R$_1$ is 4-t-butylphenyl, and L$_1$ is NH.

In a further embodiment, the methods comprise a compound of formula 60 and the attendant definitions wherein R is 3-methoxyphenyl, R$_1$ is 4-t-butylphenyl, L$_1$ is NH, and L$_2$ is O.

In another embodiment, methods for activating a sirtuin protein comprise using an activating compound of formula 61:

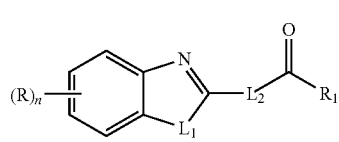

61 wherein, independently for each occurrence:

R is H, hydroxy, amino, cyano, halide, OR$_2$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

R$_1$ is H or a substituted or unsubstituted alkyl, aryl, alkaryl, heterocyclyl, heterocyclylalkyl, heteroaryl, or heteroaralkyl;

R$_2$ is alkyl, —SO$_3$H, monosaccharide, oligosaccharide, glycofuranosyl, glycopyranosyl, glucuronosyl, or glucuronide;

L$_1$ and L$_2$ are O, NR, or S; and n is an integer from 0 to 4 inclusive.

In a further embodiment, the methods comprise a compound of formula 61 and the attendant definitions wherein R is methyl.

In a further embodiment, the methods comprise a compound of formula 61 and the attendant definitions wherein n is 1.

In a further embodiment, the methods comprise a compound of formula 61 and the attendant definitions wherein R$_1$ is 3,4,5-trimethoxyphenyl.

In a further embodiment, the methods comprise a compound of formula 61 and the attendant definitions wherein L$_1$ is S.

In a further embodiment, the methods comprise a compound of formula 61 and the attendant definitions wherein L$_2$ is NH.

In a further embodiment, the methods comprise a compound of formula 61 and the attendant definitions wherein R is methyl and n is 1.

In a further embodiment, the methods comprise a compound of formula 61 and the attendant definitions wherein R is methyl, n is 1, and R$_1$ is 3,4,5-trimethoxyphenyl.

In a further embodiment, the methods comprise a compound of formula 61 and the attendant definitions wherein R is methyl, n is 1, R$_1$ is 3,4,5-trimethoxyphenyl, and L$_1$ is S.

In a further embodiment, the methods comprise a compound of formula 61 and the attendant definitions wherein R is methyl, n is 1, R$_1$ is 3,4,5-trimethoxyphenyl, L$_1$ is S, and L$_2$ is NH.

In another embodiment, methods for activating a sirtuin protein comprise using an activating compound of formula 62:

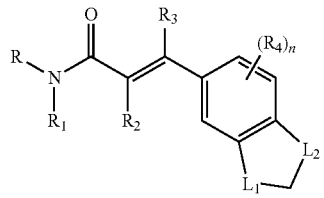

wherein, independently for each occurrence:

$R$, $R_1$, $R_2$, $R_3$ are H or a substituted or unsubstituted alkyl, aryl, alkaryl, heterocyclyl, heterocyclylalkyl, heteroaryl, or heteroaralkyl;

$R_4$ is hydroxy, amino, cyano, halide, $OR_S$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_5$ is alkyl, —$SO_3H$, monosaccharide, oligosaccharide, glycofuranosyl, glycopyranosyl, glucuronosyl, or glucuronide;

$L_1$ and $L_2$ are O, NR, or S; and n is an integer from 0 to 3 inclusive.

In a further embodiment, the methods comprise a compound of formula 62 and the attendant definitions wherein R is H.

In a further embodiment, the methods comprise a compound of formula 62 and the attendant definitions wherein $R_1$ is perfluorophenyl.

In a further embodiment, the methods comprise a compound of formula 62 and the attendant definitions wherein $R_2$ is H.

In a further embodiment, the methods comprise a compound of formula 62 and the attendant definitions wherein $R_3$ is H.

In a further embodiment, the methods comprise a compound of formula 62 and the attendant definitions wherein $L_1$ is O.

In a further embodiment, the methods comprise a compound of formula 62 and the attendant definitions wherein $L_2$ is O.

In a further embodiment, the methods comprise a compound of formula 62 and the attendant definitions wherein n is 0.

In a further embodiment, the methods comprise a compound of formula 62 and the attendant definitions wherein R is H and $R_1$ is perfluorophenyl.

In a further embodiment, the methods comprise a compound of formula 62 and the attendant definitions wherein R is H, $R_1$ is perfluorophenyl, and $R_2$ is H.

In a further embodiment, the methods comprise a compound of formula 62 and the attendant definitions R is H, $R_1$ is perfluorophenyl, $R_2$ is H, and $R_3$ is H.

In a further embodiment, the methods comprise a compound of formula 62 and the attendant definitions wherein R is H, $R_1$ is perfluorophenyl, $R_2$ is H, $R_3$ is H, and $L_1$ is O.

In a further embodiment, the methods comprise a compound of formula 62 and the attendant definitions wherein R is H, $R_1$ is perfluorophenyl, $R_2$ is H, $R_3$ is H, $L_1$ is O, and $L_2$ is O.

In a further embodiment, the methods comprise a compound of formula 62 and the attendant definitions wherein R is H, $R_1$ is perfluorophenyl, $R_2$ is H, $R_3$ is H, $L_1$ is O, $L_2$ is O, and n is 0.

In another embodiment, methods for activating a sirtuin protein comprise using an activating compound of formula 63:

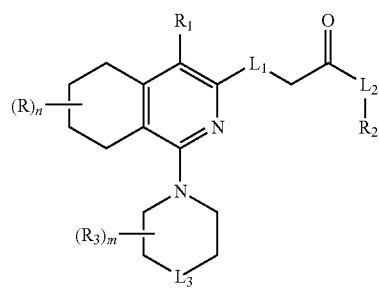

wherein, independently for each occurrence:

$R$, $R_1$, and $R_3$ are hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ is H or a substituted or unsubstituted alkyl, aryl, aralkyl, heterocyclyl, heterocyclylalkyl, heteroaryl, or heteroaralkyl;

$R_4$ is alkyl, —$SO_3H$, monosaccharide, oligosaccharide, glycofuranosyl, glycopyranosyl, glucuronosyl, or glucuronide;

$L_1$, $L_2$, and $L_3$ are O, $NR_2$, or S; and m and n are integers from 0 to 8 inclusive.

In a further embodiment, the methods comprise a compound of formula 63 and the attendant definitions wherein n is 0.

In a further embodiment, the methods comprise a compound of formula 63 and the attendant definitions wherein $R_1$ is cyano.

In a further embodiment, the methods comprise a compound of formula 63 and the attendant definitions wherein $R_2$ is ethyl.

In a further embodiment, the methods comprise a compound of formula 63 and the attendant definitions wherein m is 0.

In a further embodiment, the methods comprise a compound of formula 63 and the attendant definitions wherein $L_1$ is S.

In a further embodiment, the methods comprise a compound of formula 63 and the attendant definitions wherein $L_2$ is O.

In a further embodiment, the methods comprise a compound of formula 63 and the attendant definitions wherein $L_3$ is O.

In a further embodiment, the methods comprise a compound of formula 63 and the attendant definitions wherein n is 0 and $R_1$ is cyano.

In a further embodiment, the methods comprise a compound of formula 63 and the attendant definitions wherein n is 0, $R_1$ is cyano, and $R_2$ is ethyl.

In a further embodiment, the methods comprise a compound of formula 63 and the attendant definitions wherein n is 0, $R_1$ is cyano, $R_2$ is ethyl, and m is 0.

In a further embodiment, the methods comprise a compound of formula 63 and the attendant definitions wherein n is 0, $R_1$ is cyano, $R_2$ is ethyl, m is 0, and $L_1$ is S.

In a further embodiment, the methods comprise a compound of formula 63 and the attendant definitions wherein n is 0, $R_1$ is cyano, $R_2$ is ethyl, m is 0, $L_1$ is S, and $L_2$ is O.

In a further embodiment, the methods comprise a compound of formula 63 and the attendant definitions wherein n is 0, $R_1$ is cyano, $R_2$ is ethyl, m is 0, $L_1$ is S, $L_2$ is O, and $L_3$ is O.

In another embodiment, methods for activating a sirtuin protein comprise using an activating compound of formula 64:

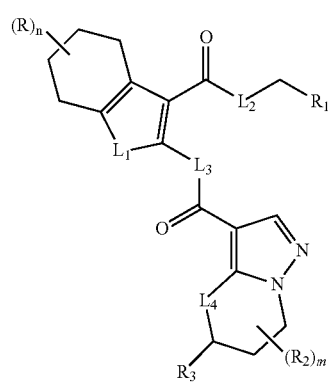

(64)

wherein, independently for each occurrence:

R and $R_2$ are H, hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ and $R_3$ are H or a substituted or unsubstituted alkyl, aryl, aralkyl, heterocyclyl, heterocyclylalkyl, heteroaryl, or heteroaralkyl;

$R_4$ is alkyl, —$SO_3H$, monosaccharide, oligosaccharide, glycofuranosyl, glycopyranosyl, glucuronosyl, or glucuronide;

$L_1$, $L_2$, $L_3$, and $L_4$ are O, $NR_1$, or S;

m is an integer from 0 to 6 inclusive; and n is an integer from 0 to 8 inclusive.

In a further embodiment, the methods comprise a compound of formula 64 and the attendant definitions wherein n is 0.

In a further embodiment, the methods comprise a compound of formula 64 and the attendant definitions wherein $R_1$ is methyl.

In a further embodiment, the methods comprise a compound of formula 64 and the attendant definitions wherein $R_2$ is $CF_3$ and m is 1.

In a further embodiment, the methods comprise a compound of formula 64 and the attendant definitions wherein $R_3$ is 4-methylphenyl.

In a further embodiment, the methods comprise a compound of formula 64 and the attendant definitions wherein $L_1$ is S.

In a further embodiment, the methods comprise a compound of formula 64 and the attendant definitions wherein $L_2$ is O.

In a further embodiment, the methods comprise a compound of formula 64 and the attendant definitions wherein $L_3$ is $NR_1$.

In a further embodiment, the methods comprise a compound of formula 64 and the attendant definitions wherein $L_4$ is $NR_1$.

In a further embodiment, the methods comprise a compound of formula 64 and the attendant definitions wherein n is 0 and $R_1$ is methyl.

In a further embodiment, the methods comprise a compound of formula 64 and the attendant definitions wherein n is 0, $R_1$ is methyl, $R_2$ is $CF_3$, and m is 1.

In a further embodiment, the methods comprise a compound of formula 64 and the attendant definitions wherein n is 0, $R_1$ is methyl, $R_2$ is $CF_3$, m is 1; and $R_3$ is 4-methylphenyl.

In a further embodiment, the methods comprise a compound of formula 64 and the attendant definitions wherein n is 0, $R_1$ is methyl, $R_2$ is $CF_3$, m is 1; $R_3$ is 4-methylphenyl; and $L_1$ is S.

In a further embodiment, the methods comprise a compound of formula 64 and the attendant definitions wherein n is 0, $R_1$ is methyl, $R_2$ is $CF_3$, m is 1; $R_3$ is 4-methylphenyl; $L_1$ is S, and $L_2$ is O.

In a further embodiment, the methods comprise a compound of formula 64 and the attendant definitions wherein n is 0, $R_1$ is methyl, $R_2$ is $CF_3$, m is 1; $R_3$ is 4-methylphenyl; $L_1$ is S, $L_2$ is O; and $L_3$ is $NR_1$.

In a further embodiment, the methods comprise a compound of formula 64 and the attendant definitions wherein n is 0, $R_1$ is methyl, $R_2$ is $CF_3$, m is 1; $R_3$ is 4-methylphenyl; $L_1$ is S, $L_2$ is O; $L_3$ is $NR_1$, and $L_4$ is $NR_1$.

In another embodiment, methods for activating a sirtuin protein comprise using an activating compound of formula 65:

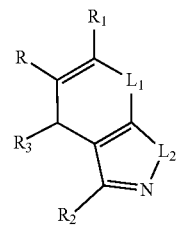

(65)

wherein, independently for each occurrence:

R and $R_1$ are hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ and $R_3$ are H or a substituted or unsubstituted alkyl, aryl, aralkyl, heterocyclyl, heterocyclylalkyl, heteroaryl, or heteroaralkyl;

$R_4$ is alkyl, —$SO_3H$, monosaccharide, oligosaccharide, glycofuranosyl, glycopyranosyl, glucuronosyl, or glucuronide; and $L_1$ and $L_2$ are O, $NR_2$, or S.

In a further embodiment, the methods comprise a compound of formula 65 and the attendant definitions wherein R is cyano.

In a further embodiment, the methods comprise a compound of formula 65 and the attendant definitions wherein $R_1$ is $NH_2$.

In a further embodiment, the methods comprise a compound of formula 65 and the attendant definitions wherein $R_2$ is 4-bromophenyl.

In a further embodiment, the methods comprise a compound of formula 65 and the attendant definitions wherein $R_3$ is 3-hydroxy-4-methoxyphenyl.

In a further embodiment, the methods comprise a compound of formula 65 and the attendant definitions wherein $L_1$ is O.

In a further embodiment, the methods comprise a compound of formula 65 and the attendant definitions wherein $L_2$ is $NR_2$.

In a further embodiment, the methods comprise a compound of formula 65 and the attendant definitions wherein R is cyano and $R_1$ is $NH_2$.

In a further embodiment, the methods comprise a compound of formula 65 and the attendant definitions wherein R is cyano, $R_1$ is $NH_2$, and $R_2$ is 4-bromophenyl.

In a further embodiment, the methods comprise a compound of formula 65 and the attendant definitions wherein R is cyano, $R_1$ is $NH_2$, $R_2$ is 4-bromophenyl, and $R_3$ is 3-hydroxy-4-methoxyphenyl.

In a further embodiment, the methods comprise a compound of formula 65 and the attendant definitions wherein R is cyano, $R_1$ is $NH_2$, $R_2$ is 4-bromophenyl, $R_3$ is 3-hydroxy-4-methoxyphenyl, and $L_1$ is O.

In a further embodiment, the methods comprise a compound of formula 65 and the attendant definitions wherein R is cyano, $R_1$ is $NH_2$, $R_2$ is 4-bromophenyl, $R_3$ is 3-hydroxy-4-methoxyphenyl, $L_1$ is O, and $L_2$ is $NR_2$.

In another embodiment, methods for activating a sirtuin protein comprise using an activating compound of formula 66:

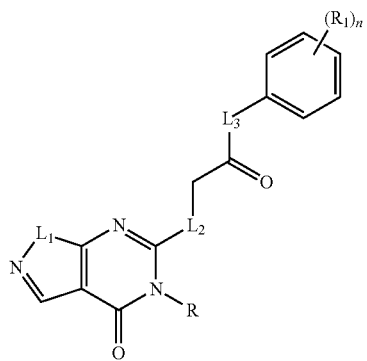

wherein, independently for each occurrence:

R is H or a substituted or unsubstituted alkyl, aryl, aralkyl, heterocyclyl, heterocyclylalkyl, heteroaryl, or heteroaralkyl;

$R_1$ is hydroxy, amino, cyano, halide, $OR_2$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ is alkyl, —$SO_3H$, monosaccharide, oligosaccharide, glycofuranosyl, glycopyranosyl, glucuronosyl, or glucuronide;

$L_1$, $L_2$, and $L_3$ are O, NR, or S; and n is an integer from 0 to 5 inclusive.

In a further embodiment, the methods comprise a compound of formula 66 and the attendant definitions wherein R is 3-trifluoromethylphenyl.

In a further embodiment, the methods comprise a compound of formula 66 and the attendant definitions wherein $R_1$ is $C(O)OCH_3$.

In a further embodiment, the methods comprise a compound of formula 66 and the attendant definitions wherein $L_1$ is NR.

In a further embodiment, the methods comprise a compound of formula 66 and the attendant definitions wherein $L_2$ is S.

In a further embodiment, the methods comprise a compound of formula 66 and the attendant definitions wherein $L_3$ is NR.

In a further embodiment, the methods comprise a compound of formula 66 and the attendant definitions wherein n is 2.

In a further embodiment, the methods comprise a compound of formula 66 and the attendant definitions wherein R is 3-trifluoromethylphenyl and $R_1$ is $C(O)OCH_3$.

In a further embodiment, the methods comprise a compound of formula 66 and the attendant definitions wherein R is 3-trifluoromethylphenyl, $R_1$ is $C(O)OCH_3$, and $L_1$ is NR.

In a further embodiment, the methods comprise a compound of formula 66 and the attendant definitions wherein R is 3-trifluoromethylphenyl, $R_1$ is $C(O)OCH_3$, $L_1$ is NR, and $L_2$ is S.

In a further embodiment, the methods comprise a compound of formula 66 and the attendant definitions wherein R is 3-trifluoromethylphenyl, $R_1$ is $C(O)OCH_3$, $L_1$ is NR, $L_2$ is S, and $L_3$ is NR.

In a further embodiment, the methods comprise a compound of formula 66 and the attendant definitions wherein R is 3-trifluoromethylphenyl, $R_1$ is $C(O)OCH_3$, $L_1$ is NR, $L_2$ is S, $L_3$ is NR, and n is 2.

In another embodiment, methods for activating a sirtuin protein comprise using an activating compound of formula 67:

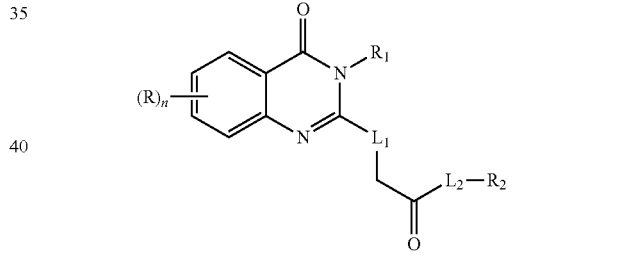

wherein, independently for each occurrence:

R is hydroxy, amino, cyano, halide, $OR_3$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ and $R_2$ are H or a substituted or unsubstituted alkyl, aryl, aralkyl, heterocyclyl, heterocyclylalkyl, heteroaryl, or heteroaralkyl;

$R_3$ is alkyl, —$SO_3H$, monosaccharide, oligosaccharide, glycofuranosyl, glycopyranosyl, glucuronosyl, or glucuronide;

$L_1$ and $L_2$ are O, $NR_1$, or S; and n is an integer from 0 to 4 inclusive.

In a further embodiment, the methods comprise a compound of formula 67 and the attendant definitions wherein n is 0.

In a further embodiment, the methods comprise a compound of formula 67 and the attendant definitions wherein $R_1$ is 2-tetrahydrofuranylmethyl.

In a further embodiment, the methods comprise a compound of formula 67 and the attendant definitions wherein $R_2$ is —$CH_2CH_2C_6H_4SO_2NH_2$.

In a further embodiment, the methods comprise a compound of formula 67 and the attendant definitions wherein $L_1$ is S.

In a further embodiment, the methods comprise a compound of formula 67 and the attendant definitions wherein $L_2$ is $NR_1$.

In a further embodiment, the methods comprise a compound of formula 67 and the attendant definitions wherein n is 0 and $R_1$ is 2-tetrahydrofuranylmethyl.

In a further embodiment, the methods comprise a compound of formula 67 and the to attendant definitions wherein n is 0, $R_1$ is 2-tetrahydrofuranylmethyl, and $R_2$ is —$CH_2CH_2C_6H_4SO_2NH_2$.

In a further embodiment, the methods comprise a compound of formula 67 and the attendant definitions wherein n is 0, $R_1$ is 2-tetrahydrofuranylmethyl, $R_2$ is —$CH_2CH_2C_6H_4SO_2NH_2$, and $L_1$ is S.

In a further embodiment, the methods comprise a compound of formula 67 and the attendant definitions wherein n is 0, $R_1$ is 2-tetrahydrofuranylmethyl, $R_2$ is —$CH_2CH_2C_6H_4SO_2NH_2$, $L_1$ is S, and $L_2$ is $NR_1$.

In another embodiment, methods for activating a sirtuin protein comprise using an activating compound of formula 68:

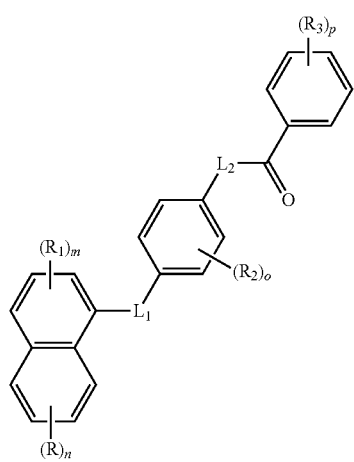

wherein, independently for each occurrence:

R, $R_1$, $R_2$, and $R_3$ are hydroxy, amino, cyano, halide, $OR_S$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_5$ is alkyl, —$SO_3H$, monosaccharide, oligosaccharide, glycofuranosyl, glycopyranosyl, glucuronosyl, or glucuronide;

$L_1$ and $L_2$ are O, $NR_4$, or S;

$R_4$ is H or a substituted or unsubstituted alkyl, aryl, aralkyl, heterocyclyl, heterocyclylalkyl, heteroaryl, or heteroaralkyl;

n is an integer from 0 to 4 inclusive;

m is an integer from 0 to 3 inclusive;

o is an integer from 0 to 4 inclusive; and p is an integer from 0 to 5 inclusive.

In a further embodiment, the methods comprise a compound of formula 68 and the attendant definitions wherein n is 0.

In a further embodiment, the methods comprise a compound of formula 68 and the attendant definitions wherein m is 1.

In a further embodiment, the methods comprise a compound of formula 68 and the attendant definitions wherein $R_1$ is Cl.

In a further embodiment, the methods comprise a compound of formula 68 and the attendant definitions wherein o is 1.

In a further embodiment, the methods comprise a compound of formula 68 and the attendant definitions wherein $R_2$ is Cl.

In a further embodiment, the methods comprise a compound of formula 68 and the attendant definitions wherein p is 3.

In a further embodiment, the methods comprise a compound of formula 68 and the attendant definitions wherein $R_3$ is OH or I.

In a further embodiment, the methods comprise a compound of formula 68 and the attendant definitions wherein n is 0 and m is 1.

In a further embodiment, the methods comprise a compound of formula 68 and the attendant definitions wherein n is 0, m is 1, and o is 1.

In a further embodiment, the methods comprise a compound of formula 68 and the attendant definitions wherein n is 0, m is 1, o is 1, and $R_1$ is Cl.

In a further embodiment, the methods comprise a compound of formula 68 and the attendant definitions wherein n is 0, m is 1, o is 1, $R_1$ is Cl, and p is 3.

In a further embodiment, the methods comprise a compound of formula 68 and the attendant definitions wherein n is 0, m is 1, o is 1, $R_1$ is Cl, p is 3, and $R_2$ is OH or I.

In another embodiment, methods for activating a sirtuin protein comprise using an activating compound of formula 69:

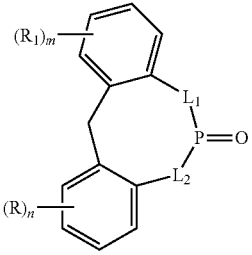

wherein, independently for each occurrence:

R and $R_1$ are hydroxy, amino, cyano, halide, $OR_S$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$ and $L_2$ are O, $NR_4$, or S;

$R_4$ is H or a substituted or unsubstituted alkyl, aryl, aralkyl, heterocyclyl, heterocyclylalkyl, heteroaryl, or heteroaralkyl;

$R_5$ is alkyl, —$SO_3H$, monosaccharide, oligosaccharide, glycofuranosyl, glycopyranosyl, glucuronosyl, or glucuronide; and m and n are integers from 0 to 4 inclusive.

In a further embodiment, the methods comprise a compound of formula 69 and the attendant definitions wherein n is 2.

In a further embodiment, the methods comprise a compound of formula 69 and the attendant definitions wherein R is methyl or t-butyl.

In a further embodiment, the methods comprise a compound of formula 69 and the attendant definitions wherein m is 2.

In a further embodiment, the methods comprise a compound of formula 69 and the attendant definitions wherein $R_1$ is methyl or t-butyl.

In a further embodiment, the methods comprise a compound of formula 69 and the attendant definitions wherein $L_1$ is O.

In a further embodiment, the methods comprise a compound of formula 69 and the attendant definitions wherein $L_2$ is O.

In a further embodiment, the methods comprise a compound of formula 69 and the attendant definitions wherein n is 2 and R is methyl or t-butyl.

In a further embodiment, the methods comprise a compound of formula 69 and the attendant definitions wherein n is 2, R is methyl or t-butyl, and m is 2.

In a further embodiment, the methods comprise a compound of formula 69 and the attendant definitions wherein n is 2, R is methyl or t-butyl, m is 2, and $R_1$ is methyl or t-butyl.

In a further embodiment, the methods comprise a compound of formula 69 and the attendant definitions wherein n is 2, R is methyl or t-butyl, m is 2, $R_1$ is methyl or t-butyl, and $L_1$ is O.

In a further embodiment, the methods comprise a compound of formula 69 and the attendant definitions wherein n is 2, R is methyl or t-butyl, m is 2, $R_1$ is methyl or t-butyl, $L_1$ is O, and $L_2$ is O.

In another embodiment, methods for activating a sirtuin protein comprise using an activating compound of formula 70:

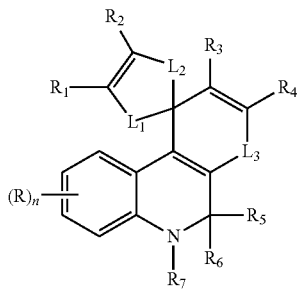

wherein, independently for each occurrence:

R, $R_1$, $R_2$, $R_3$, $R_4$, $R_5$, and $R_6$ are hydroxy, amino, cyano, halide, $OR_8$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_7$ is H or a substituted or unsubstituted alkyl, acyl, aryl, aralkyl, heterocyclyl, heterocyclylalkyl, heteroaryl, or heteroaralkyl;

$R_8$ is alkyl, —$SO_3H$, monosaccharide, oligosaccharide, glycofuranosyl, glycopyranosyl, glucuronosyl, or glucuronide;

$L_1$, $L_2$, and $L_3$ are O, $NR_7$, or S and n is an integer from 0 to 4 inclusive.

In a further embodiment, the methods comprise a compound of formula 70 and the attendant definitions wherein n is 1.

In a further embodiment, the methods comprise a compound of formula 70 and the attendant definitions wherein R is methyl.

In a further embodiment, the methods comprise a compound of formula 70 and the attendant definitions wherein $R_1$ is $C(O)OCH_3$.

In a further embodiment, the methods comprise a compound of formula 70 and the attendant definitions wherein $R_2$ is $C(O)OCH_3$.

In a further embodiment, the methods comprise a compound of formula 70 and the attendant definitions wherein $R_3$ is $C(O)OCH_3$.

In a further embodiment, the methods comprise a compound of formula 70 and the attendant definitions wherein $R_4$ is $C(O)OCH_3$.

In a further embodiment, the methods comprise a compound of formula 70 and the attendant definitions wherein $R_5$ is methyl.

In a further embodiment, the methods comprise a compound of formula 70 and the attendant definitions wherein $R_6$ is methyl.

In a further embodiment, the methods comprise a compound of formula 70 and the attendant definitions wherein $R_7$ is $C(O)CF_3$.

In a further embodiment, the methods comprise a compound of formula 70 and the attendant definitions wherein $L_1$ is S.

In a further embodiment, the methods comprise a compound of formula 70 and the attendant definitions wherein $L_2$ is S.

In a further embodiment, the methods comprise a compound of formula 70 and the attendant definitions wherein $L_3$ is S.

In a further embodiment, the methods comprise a compound of formula 70 and the attendant definitions wherein n is 1 and R is methyl.

In a further embodiment, the methods comprise a compound of formula 70 and the attendant definitions wherein n is 1, R is methyl, and $R_1$ is $C(O)OCH_3$.

In a further embodiment, the methods comprise a compound of formula 70 and the attendant definitions wherein n is 1, R is methyl, $R_1$ is $C(O)OCH_3$, and $R_2$ is $C(O)OCH_3$.

In a further embodiment, the methods comprise a compound of formula 70 and the attendant definitions wherein n is 1, R is methyl, $R_1$ is $C(O)OCH_3$, $R_2$ is $C(O)OCH_3$, and $R_3$ is $C(O)OCH_3$.

In a further embodiment, the methods comprise a compound of formula 70 and the attendant definitions wherein n is 1, R is methyl, $R_1$ is $C(O)OCH_3$, $R_2$ is $C(O)OCH_3$, $R_3$ is $C(O)OCH_3$, and $R_4$ is $C(O)OCH_3$.

In a further embodiment, the methods comprise a compound of formula 70 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, and $R_5$ is methyl.

In a further embodiment, the methods comprise a compound of formula 70 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, and $R_6$ is methyl.

In a further embodiment, the methods comprise a compound of formula 70 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, $R_6$ is methyl, and $R_7$ is $C(O)CF_3$.

In a further embodiment, the methods comprise a compound of formula 70 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, $R_6$ is methyl, $R_7$ is $C(O)CF_3$, and $L_1$ is S.

In a further embodiment, the methods comprise a compound of formula 70 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, $R_6$ is methyl, $R_7$ is $C(O)CF_3$, $L_1$ is S, and $L_2$ is S.

In a further embodiment, the methods comprise a compound of formula 70 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, $R_6$ is methyl, $R_7$ is $C(O)CF_3$, $L_1$ is S, $L_2$ is S, and $L_3$ is S.

In another embodiment, methods for activating a sirtuin protein comprise using an activating compound of formula 71:

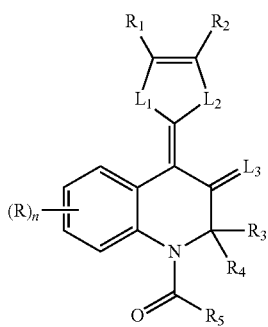

wherein, independently for each occurrence:

R, $R_1$, $R_2$, $R_3$, $R_4$, and $R_5$ are hydroxy, amino, cyano, halide, $OR_7$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$, $L_2$, and $L_3$ are O, $NR_6$, or S;

$R_6$ is H or a substituted or unsubstituted alkyl, aryl, aralkyl, heterocyclyl, heterocyclylalkyl, heteroaryl, or heteroaralkyl;

$R_7$ is alkyl, $-SO_3H$, monosaccharide, oligosaccharide, glycofuranosyl, glycopyranosyl, glucuronosyl, or glucuronide; and n is an integer from 0 to 4 inclusive.

In a further embodiment, the methods comprise a compound of formula 71 and the attendant definitions wherein n is 1.

In a further embodiment, the methods comprise a compound of formula 71 and the attendant definitions wherein R is methyl.

In a further embodiment, the methods comprise a compound of formula 71 and the attendant definitions wherein $R_1$ is $C(O)OCH_3$.

In a further embodiment, the methods comprise a compound of formula 71 and the attendant definitions wherein $R_2$ is $C(O)OCH_3$.

In a further embodiment, the methods comprise a compound of formula 71 and the attendant definitions wherein $R_3$ is methyl.

In a further embodiment, the methods comprise a compound of formula 71 and the attendant definitions wherein $R_4$ is methyl.

In a further embodiment, the methods comprise a compound of formula 71 and the attendant definitions wherein $R_5$ is $CH_2CH(CH_3)_2$.

In a further embodiment, the methods comprise a compound of formula 71 and the attendant definitions wherein $L_1$ is S.

In a further embodiment, the methods comprise a compound of formula 71 and the attendant definitions wherein $L_2$ is S.

In a further embodiment, the methods comprise a compound of formula 71 and the attendant definitions wherein $L_3$ is S.

In a further embodiment, the methods comprise a compound of formula 71 and the attendant definitions wherein n is 1 and R is methyl.

In a further embodiment, the methods comprise a compound of formula 71 and the attendant definitions wherein n is 1, R is methyl, and $R_1$ is $C(O)OCH_3$.

In a further embodiment, the methods comprise a compound of formula 71 and the attendant definitions wherein n is 1, R is methyl, $R_1$ is $C(O)OCH_3$, and $R_2$ is $C(O)OCH_3$.

In a further embodiment, the methods comprise a compound of formula 71 and the attendant definitions wherein n is 1, R is methyl, $R_1$ is $C(O)OCH_3$, $R_2$ is $C(O)OCH_3$, and $R_3$ is methyl.

In a further embodiment, the methods comprise a compound of formula 71 and the attendant definitions wherein n is 1, R is methyl, $R_1$ is $C(O)OCH_3$, $R_2$ is $C(O)OCH_3$, $R_3$ is methyl, and $R_4$ is methyl.

In a further embodiment, the methods comprise a compound of formula 71 and the attendant definitions wherein n is 1, R is methyl, $R_1$ is $C(O)OCH_3$, $R_2$ is $C(O)OCH_3$, $R_3$ is methyl, $R_4$ is methyl, and $R_5$ is $CH_2CH(CH_3)_2$.

In a further embodiment, the methods comprise a compound of formula 71 and the attendant definitions wherein n is 1, R is methyl, $R_1$ is $C(O)OCH_3$, $R_2$ is $C(O)OCH_3$, $R_3$ is methyl, $R_4$ is methyl, $R_5$ is $CH_2CH(CH_3)_2$, and $L_1$ is S.

In a further embodiment, the methods comprise a compound of formula 71 and the attendant definitions wherein n is 1, R is methyl, $R_1$ is $C(O)OCH_3$, $R_2$ is $C(O)OCH_3$, $R_3$ is methyl, $R_4$ is methyl, $R_5$ is $CH_2CH(CH_3)_2$, and $L_1$ is S.

In a further embodiment, the methods comprise a compound of formula 71 and the attendant definitions wherein n is 1, R is methyl, $R_1$ is $C(O)OCH_3$, $R_2$ is $C(O)OCH_3$, $R_3$ is methyl, $R_4$ is methyl, $R_5$ is $CH_2CH(CH_3)_2$, $L_1$ is S, and $L_2$ is S.

In a further embodiment, the methods comprise a compound of formula 71 and the attendant definitions wherein n is 1, R is methyl, $R_1$ is $C(O)OCH_3$, $R_2$ is $C(O)OCH_3$, $R_3$ is methyl, $R_4$ is methyl, $R_5$ is $CH_2CH(CH_3)_2$, $L_1$ is S, and $L_2$ is S.

In a further embodiment, the methods comprise a compound of formula 71 and the attendant definitions wherein n is 1, R is methyl, $R_1$ is $C(O)OCH_3$, $R_2$ is $C(O)OCH_3$, $R_3$ is methyl, $R_4$ is methyl, $R_5$ is $CH_2CH(CH_3)_2$, $L_1$ is S, $L_2$ is S, and $L_3$ is S.

In another embodiment, methods for activating a sirtuin protein comprise using an activating compound of formula 72:

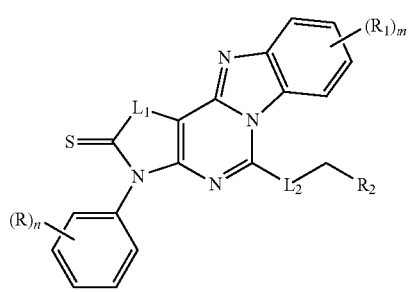

wherein, independently for each occurrence:

R and $R_1$ are hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ is H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_4$ is alkyl, —$SO_3H$, monosaccharide, oligosaccharide, glycofuranosyl, glycopyranosyl, glucuronosyl, or glucuronide;

$L_1$ and $L_2$ are O, $NR_3$, or S;

$R_3$ is H or a substituted or unsubstituted alkyl, aryl, aralkyl, heterocyclyl, heterocyclylalkyl, heteroaryl, or heteroaralkyl;

n is an integer from 0 to 5 inclusive; and m is an integer from 0 to 4 inclusive.

In a further embodiment, the methods comprise a compound of formula 72 and the attendant definitions wherein n is 1.

In a further embodiment, the methods comprise a compound of formula 72 and the attendant definitions wherein R is $CO_2Et$.

In a further embodiment, the methods comprise a compound of formula 72 and the attendant definitions wherein m is 0.

In a further embodiment, the methods comprise a compound of formula 72 and the attendant definitions wherein $R_2$ is cyano.

In a further embodiment, the methods comprise a compound of formula 72 and the attendant definitions wherein $L_1$ is S.

In a further embodiment, the methods comprise a compound of formula 72 and the attendant definitions wherein $L_2$ is S.

In a further embodiment, the methods comprise a compound of formula 72 and the attendant definitions wherein n is 1 and R is $CO_2Et$.

In a further embodiment, the methods comprise a compound of formula 72 and the attendant definitions wherein n is 1, R is $CO_2Et$, and m is 0.

In a further embodiment, the methods comprise a compound of formula 72 and the attendant definitions wherein n is 1, R is $CO_2Et$, m is 0, and $R_2$ is cyano.

In a further embodiment, the methods comprise a compound of formula 72 and the attendant definitions wherein n is 1, R is $CO_2Et$, m is 0, $R_2$ is cyano, and $L_1$ is S.

In a further embodiment, the methods comprise a compound of formula 72 and the attendant definitions wherein n is 1, R is $CO_2Et$, m is 0, $R_2$ is cyano, $L_1$ is S, and $L_2$ is S.

In another embodiment, methods for activating a sirtuin protein comprise using an activating compound of formula 73:

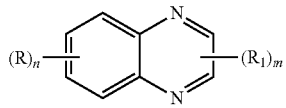

73 wherein, independently for each occurrence:

R and $R_1$ are hydroxy, amino, cyano, halide, $OR_2$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ is alkyl, —$SO_3H$, monosaccharide, oligosaccharide, glycofuranosyl, glycopyranosyl, glucuronosyl, or glucuronide;

n is an integer from 0 to 4 inclusive; and m is an integer from 0 to 2 inclusive.

In a further embodiment, the methods comprise a compound of formula 73 and the attendant definitions wherein n is 2.

In a further embodiment, the methods comprise a compound of formula 73 and the attendant definitions wherein R is Cl or trifluoromethyl.

In a further embodiment, the methods comprise a compound of formula 73 and the attendant definitions wherein m is 2.

In a further embodiment, the methods comprise a compound of formula 73 and the attendant definitions wherein $R_1$ is phenyl.

In a further embodiment, the methods comprise a compound of formula 73 and the attendant definitions wherein n is 2 and R is Cl or trifluoromethyl.

In a further embodiment, the methods comprise a compound of formula 73 and the attendant definitions wherein n is 2, R is Cl or trifluoromethyl, and m is 2.

In a further embodiment, the methods comprise a compound of formula 73 and the attendant definitions wherein n is 2, R is Cl or trifluoromethyl, m is 2, and $R_1$ is phenyl.

In a further embodiment, the methods comprise a compound of formula 73 and the attendant definitions wherein n is 1.

In a further embodiment, the methods comprise a compound of formula 73 and the attendant definitions wherein R is F.

In a further embodiment, the methods comprise a compound of formula 73 and the attendant definitions wherein $R_1$ is 4-methylphenyl.

In a further embodiment, the methods comprise a compound of formula 73 and the attendant definitions wherein n is 1 and R is F.

In a further embodiment, the methods comprise a compound of formula 73 and the attendant definitions wherein n is 1, R is F, and m is 2.

In a further embodiment, the methods comprise a compound of formula 73 and the attendant definitions wherein n is 1, R is F, m is 2, and $R_1$ is 4-methylphenyl.

In another embodiment, methods for activating a sirtuin protein comprise using an activating compound of formula 74:

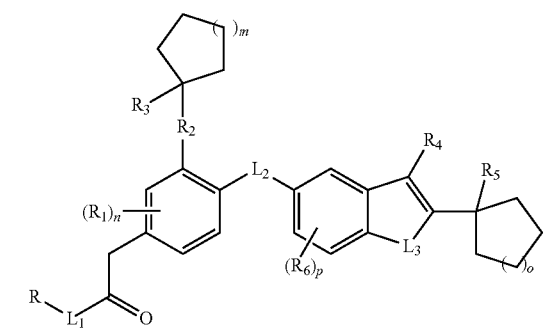

74 wherein, independently for each occurrence:

R is H or a substituted or unsubstituted alkyl, aryl, aralkyl, heterocyclyl, heterocyclylalkyl, heteroaryl, or heteroaralkyl;

$R_1$ and $R_6$ are hydroxy, amino, cyano, halide, $OR_7$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ is alkylene, alkenylene, or alkynylene;

$R_3$, $R_4$, and $R_5$ are H, hydroxy, amino, cyano, halide, $OR_7$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_7$ is alkyl, —$SO_3H$, monosaccharide, oligosaccharide, glycofuranosyl, glycopyranosyl, glucuronosyl, or glucuronide;

$L_1$, $L_2$, and $L_3$ are O, NR, or S;

n and p are integers from 0 to 3 inclusive; and m and o are integers from 0 to 2 inclusive.

In a further embodiment, the methods comprise a compound of formula 74 and the attendant definitions wherein R is $CH_2CH_2OH$.

In a further embodiment, the methods comprise a compound of formula 74 and the attendant definitions wherein n is 1.

In a further embodiment, the methods comprise a compound of formula 74 and the attendant definitions wherein $R_1$ is I.

In a further embodiment, the methods comprise a compound of formula 74 and the attendant definitions wherein $R_2$ is alkynylene.

In a further embodiment, the methods comprise a compound of formula 74 and the attendant definitions wherein m is 1.

In a further embodiment, the methods comprise a compound of formula 74 and the attendant definitions wherein $R_3$ is OH.

In a further embodiment, the methods comprise a compound of formula 74 and the attendant definitions wherein $R_4$ is C(O)OEt.

In a further embodiment, the methods comprise a compound of formula 74 and the attendant definitions wherein o is 1.

In a further embodiment, the methods comprise a compound of formula 74 and the attendant definitions wherein $R_5$ is OH.

In a further embodiment, the methods comprise a compound of formula 74 and the attendant definitions wherein p is 0.

In a further embodiment, the methods comprise a compound of formula 74 and the attendant definitions wherein $L_1$ is NH.

In a further embodiment, the methods comprise a compound of formula 74 and the attendant definitions wherein $L_2$ is O.

In a further embodiment, the methods comprise a compound of formula 74 and the attendant definitions wherein $L_3$ is O.

In a further embodiment, the methods comprise a compound of formula 74 and the attendant definitions wherein R is $CH_2CH_2OH$ and n is 1.

In a further embodiment, the methods comprise a compound of formula 74 and the attendant definitions wherein R is $CH_2CH_2OH$, n is 1, and $R_1$ is I.

In a further embodiment, the methods comprise a compound of formula 74 and the attendant definitions wherein R is $CH_2CH_2OH$, n is 1, $R_1$ is I, and $R_2$ is alkynylene.

In a further embodiment, the methods comprise a compound of formula 74 and the attendant definitions wherein R is $CH_2CH_2OH$, n is 1, $R_1$ is I, $R_2$ is alkynylene, and m is 1.

In a further embodiment, the methods comprise a compound of formula 74 and the attendant definitions wherein R is $CH_2CH_2OH$, n is 1, $R_1$ is I, $R_2$ is alkynylene, m is 1, and $R_3$ is OH.

In a further embodiment, the methods comprise a compound of formula 74 and the attendant definitions wherein R is $CH_2CH_2OH$, n is 1, $R_1$ is I, $R_2$ is alkynylene, m is 1, $R_3$ is OH, and $R_4$ is C(O)OEt.

In a further embodiment, the methods comprise a compound of formula 74 and the attendant definitions wherein R is $CH_2CH_2OH$, n is 1, $R_1$ is I, $R_2$ is alkynylene, m is 1, $R_3$ is OH, $R_4$ is C(O)OEt, and o is 1.

In a further embodiment, the methods comprise a compound of formula 74 and the attendant definitions wherein R is $CH_2CH_2OH$, n is 1, $R_1$ is I, $R_2$ is alkynylene, m is 1, $R_3$ is OH, $R_4$ is C(O)OEt, o is 1, and $R_5$ is OH.

In a further embodiment, the methods comprise a compound of formula 74 and the attendant definitions wherein R is $CH_2CH_2OH$, n is 1, $R_1$ is I, $R_2$ is alkynylene, m is 1, $R_3$ is OH, $R_4$ is C(O)OEt, o is 1, $R_5$ is OH, and p is 0.

In a further embodiment, the methods comprise a compound of formula 74 and the attendant definitions wherein R is $CH_2CH_2OH$, n is 1, $R_1$ is I, $R_2$ is alkynylene, m is 1, $R_3$ is OH, $R_4$ is C(O)OEt, o is 1, $R_5$ is OH, p is 0, and $L_1$ is NH.

In a further embodiment, the methods comprise a compound of formula 74 and the attendant definitions wherein R is $CH_2CH_2OH$, n is 1, $R_1$ is I, $R_2$ is alkynylene, m is 1, $R_3$ is OH, $R_4$ is C(O)OEt, o is 1, $R_5$ is OH, p is 0, $L_1$ is NH, and $L_2$ is O.

In a further embodiment, the methods comprise a compound of formula 74 and the attendant definitions wherein R is $CH_2CH_2OH$, n is 1, $R_1$ is I, $R_2$ is alkynylene, m is 1, $R_3$ is OH, $R_4$ is C(O)OEt, o is 1, $R_5$ is OH, p is 0, $L_1$ is NH, $L_2$ is O, and $L_3$ is O.

In another embodiment, methods for activating a sirtuin protein comprise using an activating compound of formula 75:

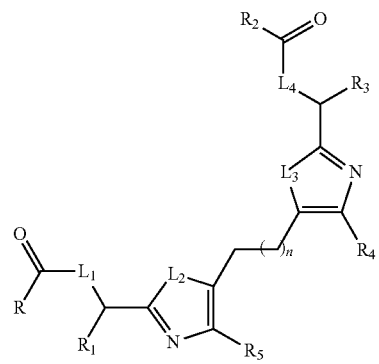

75 wherein, independently for each occurrence:

R, $R_1$, $R_2$, $R_3$, $R_4$, and $R_5$ are H, hydroxy, amino, cyano, halide, $OR_7$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$, $L_2$, $L_3$, and $L_4$ are O, $NR_6$, or S;

$R_6$ is and H, or a substituted or unsubstituted alkyl, aryl, aralkyl, heterocyclyl, heterocyclylalkyl, heteroaryl, or heteroaralkyl;

$R_7$ is alkyl, —$SO_3H$, monosaccharide, oligosaccharide, glycofuranosyl, glycopyranosyl, glucuronosyl, or glucuronide; and n is an integer from 0 to 5 inclusive.

In a further embodiment, the methods comprise a compound of formula 75 and the attendant definitions wherein R is O-t-butyl.

In a further embodiment, the methods comprise a compound of formula 75 and the attendant definitions wherein $R_1$ is t-butyl.

In a further embodiment, the methods comprise a compound of formula 75 and the attendant definitions wherein $R_2$ is O-t-butyl.

In a further embodiment, the methods comprise a compound of formula 75 and the attendant definitions wherein $R_3$ is t-butyl.

In a further embodiment, the methods comprise a compound of formula 75 and the attendant definitions wherein $R_4$ is C(O)OMe.

In a further embodiment, the methods comprise a compound of formula 75 and the attendant definitions wherein $R_5$ is C(O)OMe.

In a further embodiment, the methods comprise a compound of formula 75 and the attendant definitions wherein $L_1$ is NH.

In a further embodiment, the methods comprise a compound of formula 75 and the attendant definitions wherein $L_2$ is O.

In a further embodiment, the methods comprise a compound of formula 75 and the attendant definitions wherein $L_3$ is O.

In a further embodiment, the methods comprise a compound of formula 75 and the attendant definitions wherein $L_4$ is NH.

In a further embodiment, the methods comprise a compound of formula 75 and the attendant definitions wherein n is 1.

In a further embodiment, the methods comprise a compound of formula 75 and the attendant definitions wherein R is O-t-butyl and $R_1$ is t-butyl.

In a further embodiment, the methods comprise a compound of formula 75 and the attendant definitions wherein R is O-t-butyl, $R_1$ is t-butyl, and $R_2$ is O-t-butyl.

In a further embodiment, the methods comprise a compound of formula 75 and the attendant definitions wherein R is O-t-butyl, $R_1$ is t-butyl, $R_2$ is O-t-butyl, and $R_3$ is t-butyl.

In a further embodiment, the methods comprise a compound of formula 75 and the attendant definitions wherein R is O-t-butyl, $R_1$ is t-butyl, $R_2$ is O-t-butyl, $R_3$ is t-butyl, and $R_4$ is C(O)OMe.

In a further embodiment, the methods comprise a compound of formula 75 and the attendant definitions wherein R is O-t-butyl, $R_1$ is t-butyl, $R_2$ is O-t-butyl, $R_3$ is t-butyl, $R_4$ is C(O)OMe, and $R_5$ is C(O)OMe.

In a further embodiment, the methods comprise a compound of formula 75 and the attendant definitions wherein R is O-t-butyl, $R_1$ is t-butyl, $R_2$ is O-t-butyl, $R_3$ is t-butyl, $R_4$ is C(O)OMe, $R_5$ is C(O)OMe, and $L_1$ is NH.

In a further embodiment, the methods comprise a compound of formula 75 and the attendant definitions wherein R is O-t-butyl, $R_1$ is t-butyl, $R_2$ is O-t-butyl, $R_3$ is t-butyl, $R_4$ is C(O)OMe, $R_5$ is C(O)OMe, $L_1$ is NH, and $L_2$ is O.

In a further embodiment, the methods comprise a compound of formula 75 and the attendant definitions wherein R is O-t-butyl, $R_1$ is t-butyl, $R_2$ is O-t-butyl, $R_3$ is t-butyl, $R_4$ is C(O)OMe, $R_5$ is C(O)OMe, $L_1$ is NH, $L_2$ is O, and $L_3$ is O.

In a further embodiment, the methods comprise a compound of formula 75 and the attendant definitions wherein R is O-t-butyl, $R_1$ is t-butyl, $R_2$ is O-t-butyl, $R_3$ is t-butyl, $R_4$ is C(O)OMe, $R_5$ is C(O)OMe, $L_1$ is NH, $L_2$ is O, $L_3$ is O, and $L_4$ is NH.

In a further embodiment, the methods comprise a compound of formula 75 and the attendant definitions wherein R is O-t-butyl, $R_1$ is t-butyl, $R_2$ is O-t-butyl, $R_3$ is t-butyl, $R_4$ is C(O)OMe, $R_5$ is C(O)OMe, $L_1$ is NH, $L_2$ is O, $L_3$ is O, and $L_4$ is NH, and n is 1.

In another embodiment, methods for activating a sirtuin protein comprise using an activating compound of formula 76:

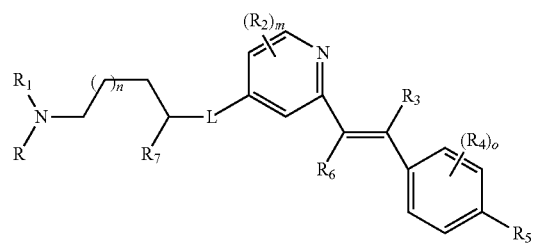

wherein, independently for each occurrence:

R and $R_1$ are H or a substituted or unsubstituted alkyl, aryl, aralkyl, heterocyclyl, heterocyclylalkyl, heteroaryl, or heteroaralkyl;

$R_2$, $R_4$, and $R_5$ are hydroxy, amino, cyano, halide, $OR_8$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_3$, $R_6$, and $R_7$ are H, hydroxy, amino, cyano, halide, $OR_8$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_8$ is alkyl, —$SO_3H$, monosaccharide, oligosaccharide, glycofuranosyl, glycopyranosyl, glucuronosyl, or glucuronide;

L is O, NR, or S;

n and o are integers from 0 to 4 inclusive; and m is an integer from 0 to 3 inclusive.

In a further embodiment, the methods comprise a compound of formula 76 and the attendant definitions wherein R is ethyl.

In a further embodiment, the methods comprise a compound of formula 76 and the attendant definitions wherein $R_1$ is ethyl.

In a further embodiment, the methods comprise a compound of formula 76 and the attendant definitions wherein m is 0.

In a further embodiment, the methods comprise a compound of formula 76 and the attendant definitions wherein $R_3$ is H.

In a further embodiment, the methods comprise a compound of formula 76 and the attendant definitions wherein o is 0.

In a further embodiment, the methods comprise a compound of formula 76 and the attendant definitions wherein $R_5$ is Cl.

In a further embodiment, the methods comprise a compound of formula 76 and the attendant definitions wherein $R_6$ is H.

In a further embodiment, the methods comprise a compound of formula 76 and the attendant definitions wherein $R_7$ is methyl.

In a further embodiment, the methods comprise a compound of formula 76 and the attendant definitions wherein L is NH.

In a further embodiment, the methods comprise a compound of formula 76 and the attendant definitions wherein n is 1.

In a further embodiment, the methods comprise a compound of formula 76 and the attendant definitions wherein R is ethyl and $R_1$ is ethyl.

In a further embodiment, the methods comprise a compound of formula 76 and the attendant definitions wherein R is ethyl, $R_1$ is ethyl, and m is 0.

In a further embodiment, the methods comprise a compound of formula 76 and the attendant definitions wherein R is ethyl, $R_1$ is ethyl, m is 0, and $R_3$ is H.

In a further embodiment, the methods comprise a compound of formula 76 and the attendant definitions wherein R is ethyl, $R_1$ is ethyl, m is 0, $R_3$ is H, and o is 0.

In a further embodiment, the methods comprise a compound of formula 76 and the attendant definitions wherein R is ethyl, $R_1$ is ethyl, m is 0, $R_3$ is H, o is 0, and $R_5$ is Cl.

In a further embodiment, the methods comprise a compound of formula 76 and the attendant definitions wherein R is ethyl, $R_1$ is ethyl, m is 0, $R_3$ is H, o is 0, $R_5$ is Cl, and $R_6$ is H.

In a further embodiment, the methods comprise a compound of formula 76 and the attendant definitions wherein R is ethyl, $R_1$ is ethyl, m is 0, $R_3$ is H, o is 0, $R_5$ is Cl, $R_6$ is H, and $R_7$ is methyl.

In a further embodiment, the methods comprise a compound of formula 76 and the attendant definitions wherein R is ethyl, $R_1$ is ethyl, m is 0, $R_3$ is H, o is 0, $R_5$ is Cl, $R_6$ is H, $R_7$ is methyl, and L is NH.

In a further embodiment, the methods comprise a compound of formula 76 and the attendant definitions wherein R is ethyl, $R_1$ is ethyl, m is 0, $R_3$ is H, o is 0, $R_5$ is Cl, $R_6$ is H, $R_7$ is methyl, L is NH, and n is 1.

In another embodiment, methods for activating a sirtuin protein comprise using an activating compound of formula 77:

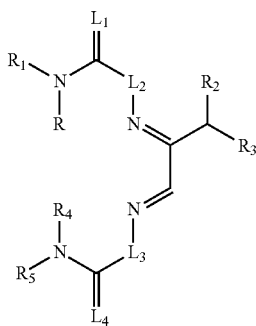

77 wherein, independently for each occurrence:

R, $R_1$, $R_4$, and $R_5$ are H or a substituted or unsubstituted alkyl, aryl, aralkyl, heterocyclyl, heterocyclylalkyl, heteroaryl, or heteroaralkyl;

$R_2$ and $R_3$ are H, hydroxy, amino, cyano, halide, $OR_6$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_6$ is alkyl, —$SO_3H$, monosaccharide, oligosaccharide, glycofuranosyl, glycopyranosyl, glucuronosyl, or glucuronide; and $L_1$, $L_2$, $L_3$, and $L_4$ are O, NR, or S.

In a further embodiment, the methods comprise a compound of formula 77 and the attendant definitions wherein R is H.

In a further embodiment, the methods comprise a compound of formula 77 and the attendant definitions wherein $R_1$ is H.

In a further embodiment, the methods comprise a compound of formula 77 and the attendant definitions wherein $R_2$ is OEt.

In a further embodiment, the methods comprise a compound of formula 77 and the attendant definitions wherein $R_3$ is methyl.

In a further embodiment, the methods comprise a compound of formula 77 and the attendant definitions wherein $R_4$ is H.

In a further embodiment, the methods comprise a compound of formula 77 and the attendant definitions wherein $R_5$ is H.

In a further embodiment, the methods comprise a compound of formula 77 and the attendant definitions wherein $L_1$ is S.

In a further embodiment, the methods comprise a compound of formula 77 and the attendant definitions wherein $L_2$ is NH.

In a further embodiment, the methods comprise a compound of formula 77 and the attendant definitions wherein $L_3$ is NH.

In a further embodiment, the methods comprise a compound of formula 77 and the attendant definitions wherein $L_4$ is S.

In a further embodiment, the methods comprise a compound of formula 77 and the attendant definitions wherein R is H and $R_1$ is H.

In a further embodiment, the methods comprise a compound of formula 77 and the attendant definitions wherein R is H, $R_1$ is H, and $R_2$ is OEt.

In a further embodiment, the methods comprise a compound of formula 77 and the attendant definitions wherein R is H, $R_1$ is H, $R_2$ is OEt, and $R_3$ is methyl.

In a further embodiment, the methods comprise a compound of formula 77 and the attendant definitions wherein R is H, $R_1$ is H, $R_2$ is OEt, $R_3$ is methyl, and $R_4$ is H.

In a further embodiment, the methods comprise a compound of formula 77 and the attendant definitions wherein R is H, $R_1$ is H, $R_2$ is OEt, $R_3$ is methyl, $R_4$ is H, and $R_5$ is H.

In a further embodiment, the methods comprise a compound of formula 77 and the attendant definitions wherein R is H, $R_1$ is H, $R_2$ is OEt, $R_3$ is methyl, $R_4$ is H, $R_5$ is H, and $L_1$ is S.

In a further embodiment, the methods comprise a compound of formula 77 and the attendant definitions wherein R is H, $R_1$ is H, $R_2$ is OEt, $R_3$ is methyl, $R_4$ is H, $R_5$ is H, $L_1$ is S, and $L_2$ is NH.

In a further embodiment, the methods comprise a compound of formula 77 and the attendant definitions wherein R is H, $R_1$ is H, $R_2$ is OEt, $R_3$ is methyl, $R_4$ is H, $R_5$ is H, $L_1$ is S, $L_2$ is NH, and $L_3$ is NH.

In a further embodiment, the methods comprise a compound of formula 77 and the attendant definitions wherein R is H, $R_1$ is H, $R_2$ is OEt, $R_3$ is methyl, $R_4$ is H, $R_5$ is H, $L_1$ is S, $L_2$ is NH, $L_3$ is NH, and $L_4$ is S.

In another embodiment, methods for activating a sirtuin protein comprise using an activating compound of formula 78:

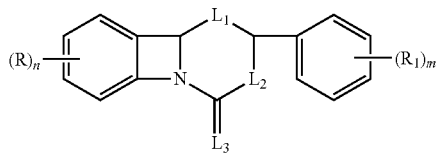

wherein, independently for each occurrence:

R and $R_1$ are hydroxy, amino, cyano, halide, $OR_3$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_3$ is alkyl, $-SO_3H$, monosaccharide, oligosaccharide, glycofuranosyl, glycopyranosyl, glucuronosyl, or glucuronide;

$L_1$, $L_2$, and $L_3$ are O, $NR_2$, or S;

$R_2$ is H or a substituted or unsubstituted alkyl, aryl, aralkyl, heterocyclyl, heterocyclylalkyl, heteroaryl, or heteroaralkyl;

n is an integer from 0 to 4 inclusive; and m is an integer from 0 to 5 inclusive.

In a further embodiment, the methods comprise a compound of formula 78 and the attendant definitions wherein n is 0.

In a further embodiment, the methods comprise a compound of formula 78 and the attendant definitions wherein m is 0.

In a further embodiment, the methods comprise a compound of formula 78 and the attendant definitions wherein $L_1$ is NH.

In a further embodiment, the methods comprise a compound of formula 78 and the attendant definitions wherein $L_2$ is S.

In a further embodiment, the methods comprise a compound of formula 78 and the attendant definitions wherein $L_3$ is S.

In a further embodiment, the methods comprise a compound of formula 78 and the attendant definitions wherein m is 0 and n is 0.

In a further embodiment, the methods comprise a compound of formula 78 and the attendant definitions wherein m is 0, n is 0, and $L_1$ is NH.

In a further embodiment, the methods comprise a compound of formula 78 and the attendant definitions wherein m is 0, n is 0, $L_1$ is NH, and $L_2$ is S.

In a further embodiment, the methods comprise a compound of formula 78 and the attendant definitions wherein m is 0, n is 0, $L_1$ is NH, $L_2$ is S, and $L_3$ is S.

In another embodiment, methods for activating a sirtuin protein comprise using an activating compound of formula 79:

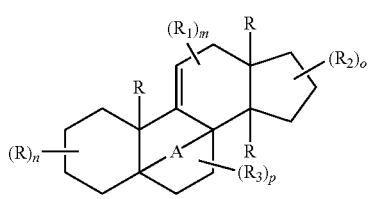

wherein, independently for each occurrence:

R, $R_1$, $R_2$, and $R_3$ are hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_3$ is alkyl, $-SO_3H$, monosaccharide, oligosaccharide, glycofuranosyl, glycopyranosyl, glucuronosyl, or glucuronide;

A is alkylene, alkenylene, or alkynylene;

n is an integer from 0 to 8 inclusive;

m is an integer from 0 to 3 inclusive;

o is an integer from 0 to 6 inclusive; and p is an integer from 0 to 4 inclusive.

In a further embodiment, the methods comprise a compound of formula 79 and the attendant definitions wherein n is 2.

In a further embodiment, the methods comprise a compound of formula 79 and the attendant definitions wherein R is OH or methyl.

In a further embodiment, the methods comprise a compound of formula 79 and the attendant definitions wherein m is 1.

In a further embodiment, the methods comprise a compound of formula 79 and the attendant definitions wherein $R_1$ is methyl.

In a further embodiment, the methods comprise a compound of formula 79 and the attendant definitions wherein o is 1.

In a further embodiment, the methods comprise a compound of formula 79 and the attendant definitions wherein $R_2$ is $C(O)CH_3$.

In a further embodiment, the methods comprise a compound of formula 79 and the attendant definitions wherein p is 2.

In a further embodiment, the methods comprise a compound of formula 79 and the attendant definitions wherein $R_3$ is $CO_2H$.

In a further embodiment, the methods comprise a compound of formula 79 and the attendant definitions wherein A is alkenylene.

In a further embodiment, the methods comprise a compound of formula 79 and the attendant definitions wherein n is 2 and R is OH or methyl.

In a further embodiment, the methods comprise a compound of formula 79 and the attendant definitions wherein n is 2, R is OH or methyl, and m is 1.

In a further embodiment, the methods comprise a compound of formula 79 and the attendant definitions wherein n is 2, R is OH or methyl, m is 1, and $R_1$ is methyl.

In a further embodiment, the methods comprise a compound of formula 79 and the attendant definitions wherein n is 2, R is OH or methyl, m is 1, $R_1$ is methyl, and o is 1.

In a further embodiment, the methods comprise a compound of formula 79 and the attendant definitions wherein n is 2, R is OH or methyl, m is 1, $R_1$ is methyl, o is 1, and $R_2$ is $C(O)CH_3$.

In a further embodiment, the methods comprise a compound of formula 79 and the attendant definitions wherein n is 2, R is OH or methyl, m is 1, $R_1$ is methyl, o is 1, $R_2$ is $C(O)CH_3$, and p is 2.

In a further embodiment, the methods comprise a compound of formula 79 and the attendant definitions wherein n is 2, R is OH or methyl, m is 1, $R_1$ is methyl, o is 1, $R_2$ is $C(O)CH_3$, p is 2, and $R_3$ is $CO_2H$.

In a further embodiment, the methods comprise a compound of formula 79 and the attendant definitions wherein n is 2, R is OH or methyl, m is 1, $R_1$ is methyl, o is 1, $R_2$ is $C(O)CH_3$, p is 2, $R_3$ is $CO_2H$, and A is alkenylene.

In another embodiment, methods for activating a sirtuin protein comprise using an activating compound of formula 80:

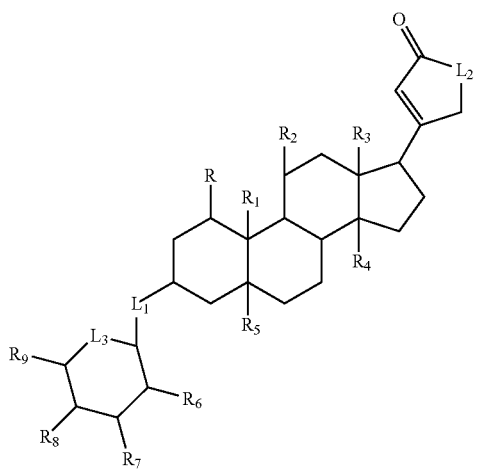

wherein, independently for each occurrence:

R, $R_1$, $R_2$, $R_3$, $R_4$, $R_5$, $R_6$, $R_7$, $R_8$, and $R_9$ are hydroxy, amino, cyano, halide, $OR_{11}$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_{11}$ is alkyl, —$SO_3H$, monosaccharide, oligosaccharide, glycofuranosyl, glycopyranosyl, glucuronosyl, or glucuronide;

$L_1$, $L_2$, and $L_3$ are O, $NR_{10}$, or S; and $R_{10}$ is H or a substituted or unsubstituted alkyl, aryl, aralkyl, heterocyclyl, heterocyclylalkyl, heteroaryl, or heteroaralkyl.

In a further embodiment, the methods comprise a compound of formula 80 and the attendant definitions wherein R is OH.

In a further embodiment, the methods comprise a compound of formula 80 and the attendant definitions wherein $R_1$ is $CH_2OH$.

In a further embodiment, the methods comprise a compound of formula 80 and the attendant definitions wherein $R_2$ is OH.

In a further embodiment, the methods comprise a compound of formula 80 and the attendant definitions wherein $R_3$ is methyl.

In a further embodiment, the methods comprise a compound of formula 80 and the attendant definitions wherein $R_4$ is OH.

In a further embodiment, the methods comprise a compound of formula 80 and the attendant definitions wherein $R_5$ is OH.

In a further embodiment, the methods comprise a compound of formula 80 and the attendant definitions wherein $R_6$ is OH.

In a further embodiment, the methods comprise a compound of formula 80 and the attendant definitions wherein $R_7$ is OH.

In a further embodiment, the methods comprise a compound of formula 80 and the attendant definitions wherein $R_8$ is OH.

In a further embodiment, the methods comprise a compound of formula 80 and the attendant definitions wherein $R_9$ is methyl.

In a further embodiment, the methods comprise a compound of formula 80 and the attendant definitions wherein $L_1$ is O.

In a further embodiment, the methods comprise a compound of formula 80 and the attendant definitions wherein $L_2$ is O.

In a further embodiment, the methods comprise a compound of formula 80 and the attendant definitions wherein $L_3$ is O.

In a further embodiment, the methods comprise a compound of formula 80 and the attendant definitions wherein R is OH and $R_1$ is $CH_2OH$.

In a further embodiment, the methods comprise a compound of formula 80 and the attendant definitions wherein R is OH, $R_1$ is $CH_2OH$, and $R_2$ is OH.

In a further embodiment, the methods comprise a compound of formula 80 and the attendant definitions wherein R is OH, $R_1$ is $CH_2OH$, $R_2$ is OH, and $R_3$ is methyl.

In a further embodiment, the methods comprise a compound of formula 80 and the attendant definitions wherein R is OH, $R_1$ is $CH_2OH$, $R_2$ is OH, $R_3$ is methyl, and $R_4$ is OH.

In a further embodiment, the methods comprise a compound of formula 80 and the attendant definitions wherein R is OH, $R_1$ is $CH_2OH$, $R_2$ is OH, $R_3$ is methyl, $R_4$ is OH, and $R_5$ is OH.

In a further embodiment, the methods comprise a compound of formula 80 and the attendant definitions wherein R is OH, $R_1$ is $CH_2OH$, $R_2$ is OH, $R_3$ is methyl, $R_4$ is OH, $R_5$ is OH, and $R_6$ is OH.

In a further embodiment, the methods comprise a compound of formula 80 and the attendant definitions wherein R is OH, $R_1$ is $CH_2OH$, $R_2$ is OH, $R_3$ is methyl, $R_4$ is OH, $R_5$ is OH, $R_6$ is OH, and $R_7$ is OH.

In a further embodiment, the methods comprise a compound of formula 80 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, and $R_8$ is OH.

In a further embodiment, the methods comprise a compound of formula 80 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, $R_8$ is OH, and $R_9$ is methyl.

In a further embodiment, the methods comprise a compound of formula 80 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, $R_8$ is OH, $R_9$ is methyl, and $L_1$ is O.

In a further embodiment, the methods comprise a compound of formula 80 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, $R_8$ is OH, $R_9$ is methyl, $L_1$ is O, and $L_2$ is O.

In a further embodiment, the methods comprise a compound of formula 80 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, $R_8$ is OH, R is methyl, $L_1$ is O, $L_2$ is O, and $L_3$ is O.

In another embodiment, methods for activating a sirtuin protein comprise using an activating compound of formula 81:

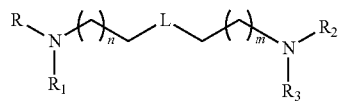

wherein, independently for each occurrence:

R, $R_1$, $R_2$, and $R_3$ are H or a substituted or unsubstituted alkyl, aryl, aralkyl, heterocyclyl, heterocyclylalkyl, heteroaryl, or heteroaralkyl;

L is O, NR, S, or Se; and n and m are integers from 0 to 5 inclusive.

In a further embodiment, the methods comprise a compound of formula 81 and the attendant definitions wherein R is H.

In a further embodiment, the methods comprise a compound of formula 81 and the attendant definitions wherein $R_1$ is H.

In a further embodiment, the methods comprise a compound of formula 81 and the attendant definitions wherein $R_2$ is H.

In a further embodiment, the methods comprise a compound of formula 81 and the attendant definitions wherein $R_3$ is H.

In a further embodiment, the methods comprise a compound of formula 81 and the attendant definitions wherein L is Se.

In a further embodiment, the methods comprise a compound of formula 81 and the attendant definitions wherein n is 1.

In a further embodiment, the methods comprise a compound of formula 81 and the attendant definitions wherein m is 1.

In a further embodiment, the methods comprise a compound of formula 81 and the attendant definitions wherein R is H and $R_1$ is H.

In a further embodiment, the methods comprise a compound of formula 81 and the attendant definitions wherein R is H, $R_1$ is H, and $R_2$ is H.

In a further embodiment, the methods comprise a compound of formula 81 and the attendant definitions wherein R is H, $R_1$ is H, $R_2$ is H, and $R_3$ is H.

In a further embodiment, the methods comprise a compound of formula 81 and the attendant definitions wherein R is H, $R_1$ is H, $R_2$ is H, $R_3$ is H, and L is Se.

In a further embodiment, the methods comprise a compound of formula 81 and the attendant definitions wherein R is H, $R_1$ is H, $R_2$ is H, $R_3$ is H, L is Se, and n is 1.

In a further embodiment, the methods comprise a compound of formula 81 and the attendant definitions wherein R is H, $R_1$ is H, $R_2$ is H, $R_3$ is H, L is Se, n is 1, and m is 1.

In another embodiment, methods for activating a sirtuin protein comprise using an activating compound of formula 82:

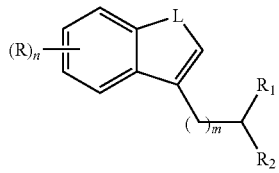

wherein, independently for each occurrence:

R is hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ and $R_2$ are H, hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_4$ is alkyl, $-SO_3H$, monosaccharide, oligosaccharide, glycofuranosyl, glycopyranosyl, glucuronosyl, or glucuronide;

L is O, $NR_3$, S, or $SO_2$, $R_3$ is H or a substituted or unsubstituted alkyl, aryl, aralkyl, heterocyclyl, heterocyclylalkyl, heteroaryl, or heteroaralkyl;

n is an integer from 0 to 4 inclusive; and m is an integer from 1 to 5 inclusive.

In a further embodiment, the methods comprise a compound of formula 82 and the attendant definitions wherein n is 1.

In a further embodiment, the methods comprise a compound of formula 82 and the attendant definitions wherein R is Cl.

In a further embodiment, the methods comprise a compound of formula 82 and the attendant definitions wherein $R_1$ is $NH_2$.

In a further embodiment, the methods comprise a compound of formula 82 and the attendant definitions wherein $R_2$ is $CO_2H$.

In a further embodiment, the methods comprise a compound of formula 82 and the attendant definitions wherein L is $SO_2$.

In a further embodiment, the methods comprise a compound of formula 82 and the attendant definitions wherein m is 1.

In a further embodiment, the methods comprise a compound of formula 82 and the attendant definitions wherein n is 1 and R is Cl.

In a further embodiment, the methods comprise a compound of formula 82 and the attendant definitions wherein n is 1, R is Cl, and $R_1$ is $NH_2$.

In a further embodiment, the methods comprise a compound of formula 82 and the attendant definitions wherein n is 1, R is Cl, $R_1$ is $NH_2$, and $R_2$ is $CO_2H$.

In a further embodiment, the methods comprise a compound of formula 82 and the attendant definitions wherein n is 1, R is Cl, $R_1$ is $NH_2$, $R_2$ is $CO_2H$, and L is $SO_2$.

In a further embodiment, the methods comprise a compound of formula 82 and the attendant definitions wherein n is 1, R is Cl, $R_1$ is $NH_2$, $R_2$ is $CO_2H$, L is $SO_2$, and m is 1.

In another embodiment, methods for activating a sirtuin protein comprise using an activating compound of formula 83:

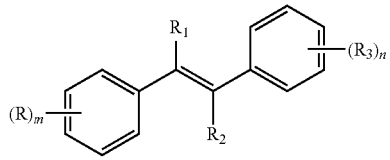

wherein, independently for each occurrence:

R, $R_1$, $R_2$, and $R_3$ are H, hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_4$ is alkyl, —SO$_3$H, monosaccharide, oligosaccharide, glycofuranosyl, glycopyranosyl, glucuronosyl, or glucuronide; and n and m are integers from 0 to 5 inclusive.

In a further embodiment, the methods comprise a compound of formula 83 and the attendant definitions wherein n is 2.

In a further embodiment, the methods comprise a compound of formula 83 and the attendant definitions wherein R is 3-hydroxy and 5-hydroxy.

In a further embodiment, the methods comprise a compound of formula 83 and the attendant definitions wherein $R_1$ is H.

In a further embodiment, the methods comprise a compound of formula 83 and the attendant definitions wherein $R_2$ is H.

In a further embodiment, the methods comprise a compound of formula 83 and the attendant definitions wherein m is 0.

In a further embodiment, the methods comprise a compound of formula 83 and the attendant definitions wherein m is 1.

In a further embodiment, the methods comprise a compound of formula 83 and the attendant definitions wherein $R_3$ is 4-hydroxy.

In a further embodiment, the methods comprise a compound of formula 83 and the attendant definitions wherein $R_3$ is 4-methoxy.

In a further embodiment, the methods comprise a compound of formula 83 and the attendant definitions wherein n is 2 and R is 3-hydroxy and 5-hydroxy.

In a further embodiment, the methods comprise a compound of formula 83 and the attendant definitions wherein n is 2, R is 3-hydroxy and 5-hydroxy, and $R_1$ is H.

In a further embodiment, the methods comprise a compound of formula 83 and the attendant definitions wherein n is 2, R is 3-hydroxy and 5-hydroxy, $R_1$ is H, and $R_2$ is H.

In a further embodiment, the methods comprise a compound of formula 83 and the attendant definitions wherein n is 2, R is 3-hydroxy and 5-hydroxy, $R_1$ is H, $R_2$ is H, and m is 0.

In a further embodiment, the methods comprise a compound of formula 83 and the attendant definitions wherein n is 2, R is 3-hydroxy and 5-hydroxy, $R_1$ is H, $R_2$ is H, and m is 1.

In a further embodiment, the methods comprise a compound of formula 83 and the attendant definitions wherein n is 2, R is 3-hydroxy and 5-hydroxy, $R_1$ is H, $R_2$ is H, m is 1, and $R_3$ is 4-hydroxy.

In a further embodiment, the methods comprise a compound of formula 83 and the attendant definitions wherein n is 2, R is 3-hydroxy and 5-hydroxy, $R_1$ is H, $R_2$ is H, m is 1, and $R_3$ is 4-methoxy.

In another embodiment, methods for activating a sirtuin protein comprise using an activating compound of formula 84:

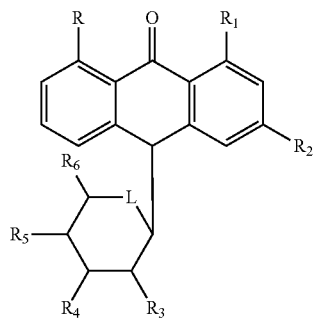

wherein, independently for each occurrence:

R, $R_1$, $R_3$, $R_4$, $R_5$, and $R_6$ are H, hydroxy, amino, cyano, OR$_8$, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

R8 is alkyl, —SO$_3$H, monosaccharide, oligosaccharide, glycofuranosyl, glycopyranosyl, glucuronosyl, or glucuronide;

L is O, NR$_S$, or S; and $R_7$ is H or a substituted or unsubstituted alkyl, aryl, aralkyl, heterocyclyl, heterocyclylalkyl, heteroaryl, or heteroaralkyl.

In a further embodiment, the methods comprise a compound of formula 84 and the attendant definitions wherein R is OH.

In a further embodiment, the methods comprise a compound of formula 84 and the attendant definitions wherein $R_1$ is OH.

In a further embodiment, the methods comprise a compound of formula 84 and the attendant definitions wherein $R_2$ is CH$_2$OH.

In a further embodiment, the methods comprise a compound of formula 84 and the attendant definitions wherein $R_3$ is OH.

In a further embodiment, the methods comprise a compound of formula 84 and the attendant definitions wherein $R_4$ is OH.

In a further embodiment, the methods comprise a compound of formula 84 and the attendant definitions wherein $R_5$ is OH.

In a further embodiment, the methods comprise a compound of formula 84 and the attendant definitions wherein $R_6$ is CH$_2$OH.

In a further embodiment, the methods comprise a compound of formula 84 and the attendant definitions wherein L is O.

In a further embodiment, the methods comprise a compound of formula 84 and the attendant definitions wherein R is OH and $R_1$ is OH.

In a further embodiment, the methods comprise a compound of formula 84 and the attendant definitions wherein R is OH, $R_1$ is OH, and $R_2$ is CH$_2$OH.

In a further embodiment, the methods comprise a compound of formula 84 and the attendant definitions wherein R is OH, $R_1$ is OH, $R_2$ is CH$_2$OH, and $R_3$ is OH.

In a further embodiment, the methods comprise a compound of formula 84 and the attendant definitions wherein R is OH, $R_1$ is OH, $R_2$ is CH$_2$OH, $R_3$ is OH, and $R_4$ is OH.

In a further embodiment, the methods comprise a compound of formula 84 and the attendant definitions wherein R is OH, $R_1$ is OH, $R_2$ is CH$_2$OH, $R_3$ is OH, $R_4$ is OH, and $R_5$ is OH.

In a further embodiment, the methods comprise a compound of formula 84 and the attendant definitions wherein R is OH, $R_1$ is OH, $R_2$ is $CH_2OH$, $R_3$ is OH, $R_4$ is OH, $R_5$ is OH, and $R_6$ is $CH_2OH$.

In a further embodiment, the methods comprise a compound of formula 84 and the attendant definitions wherein R is OH, $R_1$ is OH, $R_2$ is $CH_2OH$, $R_3$ is OH, $R_4$ is OH, $R_5$ is OH, $R_6$ is $CH_2OH$, and L is O.

In another embodiment, methods for activating a sirtuin protein comprise using an activating compound of formula 85:

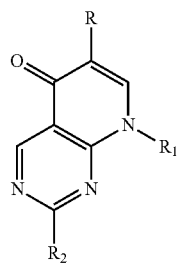

85 wherein, independently for each occurrence:

R, $R_1$, and $R_2$ are H, hydroxy, amino, cyano, halide, $OR_3$, ether, ester, amido, ketone, carboxylic acid, nitro, or a substituted or unsubstituted alkyl, aryl, aralkyl, heterocyclyl, heterocyclylalkyl, heteroaryl, or heteroaralkyl; and $R_3$ is alkyl, —$SO_3H$, monosaccharide, oligosaccharide, glycofuranosyl, glycopyranosyl, glucuronosyl, or glucuronide.

In a further embodiment, the methods comprise a compound of formula 85 and the attendant definitions wherein R is $CO_2H$.

In a further embodiment, the methods comprise a compound of formula 85 and the attendant definitions wherein $R_1$ is ethyl.

In a further embodiment, the methods comprise a compound of formula 85 and the attendant definitions wherein $R_2$ is N-1-pyrrolidine.

In a further embodiment, the methods comprise a compound of formula 85 and the attendant definitions wherein R is $CO_2H$ and $R_1$ is ethyl.

In a further embodiment, the methods comprise a compound of formula 85 and the attendant definitions wherein R is $CO_2H$ and $R_2$ is N-1-pyrrolidine.

In a further embodiment, the methods comprise a compound of formula 85 and the attendant definitions wherein $R_1$ is ethyl and $R_2$ is N-1-pyrrolidine.

In a further embodiment, the methods comprise a compound of formula 85 and the attendant definitions wherein R is $CO_2H$, $R_1$ is ethyl, and $R_2$ is N-1-pyrrolidine.

In another embodiment, methods for activating a sirtuin protein comprise using an activating compound of formula 86:

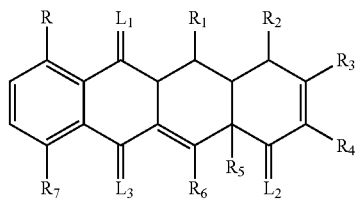

86 wherein, independently for each occurrence:

R, $R_1$, $R_2$, $R_3$, $R_4$, $R_5$, $R_6$, and $R_7$ are H, hydroxy, amino, cyano, halide, $OR_9$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_9$ is alkyl, —$SO_3H$, monosaccharide, oligosaccharide, glycofuranosyl, glycopyranosyl, glucuronosyl, or glucuronide;

$L_1$, $L_2$, and $L_3$ are $CH_2$, O, $NR_8$, or S; and $R_8$ is H or a substituted or unsubstituted alkyl, aryl, aralkyl, heterocyclyl, heterocyclylalkyl, heteroaryl, or heteroaralkyl.

In a further embodiment, the methods comprise a compound of formula 86 and the attendant definitions wherein R is Cl.

In a further embodiment, the methods comprise a compound of formula 86 and the attendant definitions wherein R is H.

In a further embodiment, the methods comprise a compound of formula 86 and the attendant definitions wherein $R_1$ is OH.

In a further embodiment, the methods comprise a compound of formula 86 and the attendant definitions wherein $R_2$ is $N(Me)_2$.

In a further embodiment, the methods comprise a compound of formula 86 and the attendant definitions wherein $R_3$ is OH.

In a further embodiment, the methods comprise a compound of formula 86 and the attendant definitions wherein $R_4$ is $C(O)NH_2$.

In a further embodiment, the methods comprise a compound of formula 86 and the attendant definitions wherein $R_5$ is OH.

In a further embodiment, the methods comprise a compound of formula 86 and the attendant definitions wherein $R_6$ is OH.

In a further embodiment, the methods comprise a compound of formula 86 and the attendant definitions wherein $R_7$ is OH.

In a further embodiment, the methods comprise a compound of formula 86 and the attendant definitions wherein $L_1$ is $CH_2$.

In a further embodiment, the methods comprise a compound of formula 86 and the attendant definitions wherein $L_2$ is O.

In a further embodiment, the methods comprise a compound of formula 86 and the attendant definitions wherein $L_3$ is O.

In a further embodiment, the methods comprise a compound of formula 86 and the attendant definitions wherein R is Cl and $R_1$ is OH.

In a further embodiment, the methods comprise a compound of formula 86 and the attendant definitions wherein R is Cl, $R_1$ is OH, and $R_2$ is $N(Me)_2$.

In a further embodiment, the methods comprise a compound of formula 86 and the attendant definitions wherein R is Cl, $R_1$ is OH, $R_2$ is $N(Me)_2$, and $R_3$ is OH.

In a further embodiment, the methods comprise a compound of formula 86 and the attendant definitions wherein R is Cl, $R_1$ is OH, $R_2$ is $N(Me)_2$, $R_3$ is OH, and $R_4$ is $C(O)NH_2$.

In a further embodiment, the methods comprise a compound of formula 86 and the attendant definitions wherein R is Cl, $R_1$ is OH, $R_2$ is $N(Me)_2$, $R_3$ is OH, $R_4$ is $C(O)NH_2$, and $R_5$ is OH.

In a further embodiment, the methods comprise a compound of formula 86 and the attendant definitions wherein R is Cl, $R_1$ is OH, $R_2$ is $N(Me)_2$, $R_3$ is OH, $R_4$ is $C(O)NH_2$, $R_5$ is OH, and $R_6$ is OH.

In a further embodiment, the methods comprise a compound of formula 86 and the attendant definitions wherein R is Cl, $R_1$ is OH, $R_2$ is $N(Me)_2$, $R_3$ is OH, $R_4$ is $C(O)NH_2$, $R_5$ is OH, $R_6$ is OH, and $R_7$ is OH.

In a further embodiment, the methods comprise a compound of formula 86 and the attendant definitions wherein R is Cl, $R_1$ is OH, $R_2$ is $N(Me)_2$, $R_3$ is OH, $R_4$ is $C(O)NH_2$, $R_5$ is OH, $R_6$ is OH, $R_7$ is OH, and $L_1$ is $CH_2$.

In a further embodiment, the methods comprise a compound of formula 86 and the attendant definitions wherein R is Cl, $R_1$ is OH, $R_2$ is $N(Me)_2$, $R_3$ is OH, $R_4$ is $C(O)NH_2$, $R_5$ is OH, $R_6$ is OH, $R_7$ is OH, $L_1$ is $CH_2$, and $L_2$ is O.

In a further embodiment, the methods comprise a compound of formula 86 and the attendant definitions wherein R is Cl, $R_1$ is OH, $R_2$ is $N(Me)_2$, $R_3$ is OH, $R_4$ is $C(O)NH_2$, $R_5$ is OH, $R_6$ is OH, $R_7$ is OH, $L_1$ is $CH_2$, $L_2$ is O, and $L_3$ is O.

In a further embodiment, the methods comprise a compound of formula 86 and the attendant definitions wherein R is H and $R_1$ is OH.

In a further embodiment, the methods comprise a compound of formula 86 and the attendant definitions wherein R is H, $R_1$ is OH, and $R_2$ is $N(Me)_2$.

In a further embodiment, the methods comprise a compound of formula 86 and the attendant definitions wherein R is H, $R_1$ is OH, $R_2$ is $N(Me)_2$, and $R_3$ is OH.

In a further embodiment, the methods comprise a compound of formula 86 and the attendant definitions wherein R is H, $R_1$ is OH, $R_2$ is $N(Me)_2$, $R_3$ is OH, and $R_4$ is $C(O)NH_2$.

In a further embodiment, the methods comprise a compound of formula 86 and the attendant definitions wherein R is H, $R_1$ is OH, $R_2$ is $N(Me)_2$, $R_3$ is OH, $R_4$ is $C(O)NH_2$, and $R_5$ is OH.

In a further embodiment, the methods comprise a compound of formula 86 and the attendant definitions wherein R is H, $R_1$ is OH, $R_2$ is $N(Me)_2$, $R_3$ is OH, $R_4$ is $C(O)NH_2$, $R_5$ is OH, and $R_6$ is OH.

In a further embodiment, the methods comprise a compound of formula 86 and the attendant definitions wherein R is H, $R_1$ is OH, $R_2$ is $N(Me)_2$, $R_3$ is OH, $R_4$ is $C(O)NH_2$, $R_5$ is OH, $R_6$ is OH, and $R_7$ is OH.

In a further embodiment, the methods comprise a compound of formula 86 and the attendant definitions wherein R is H, $R_1$ is OH, $R_2$ is $N(Me)_2$, $R_3$ is OH, $R_4$ is $C(O)NH_2$, $R_5$ is OH, $R_6$ is OH, $R_7$ is OH, and $L_1$ is $CH_2$.

In a further embodiment, the methods comprise a compound of formula 86 and the attendant definitions wherein R is H, $R_1$ is OH, $R_2$ is $N(Me)_2$, $R_3$ is OH, $R_4$ is $C(O)NH_2$, $R_5$ is OH, $R_6$ is OH, $R_7$ is OH, $L_1$ is $CH_2$, and $L_2$ is O.

In a further embodiment, the methods comprise a compound of formula 86 and the attendant definitions wherein R is H, $R_1$ is OH, $R_2$ is $N(Me)_2$, $R_3$ is OH, $R_4$ is $C(O)NH_2$, $R_5$ is OH, $R_6$ is OH, $R_7$ is OH, $L_1$ is $CH_2$, $L_2$ is O, and $L_3$ is O.

In another embodiment, methods for activating a sirtuin protein comprise using an activating compound of formula 87:

wherein, independently for each occurrence:

R is H or a substituted or unsubstituted alkyl, aryl, aralkyl, heterocyclyl, heterocyclylalkyl, heteroaryl, or heteroaralkyl;

$R_1$, $R_2$, and $R_3$ are hydroxy, amino, cyano, halide, $OR_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_4$ is alkyl, —$SO_3H$, monosaccharide, oligosaccharide, glycofuranosyl, glycopyranosyl, glucuronosyl, or glucuronide; and $L_1$ and $L_2$ are O, NR, or S.

In a further embodiment, the methods comprise a compound of formula 87 and the attendant definitions wherein R is methyl.

In a further embodiment, the methods comprise a compound of formula 87 and the attendant definitions wherein $R_1$ is methyl.

In a further embodiment, the methods comprise a compound of formula 87 and the attendant definitions wherein $R_2$ is $CO_2H$.

In a further embodiment, the methods comprise a compound of formula 87 and the attendant definitions wherein $R_3$ is F.

In a further embodiment, the methods comprise a compound of formula 87 and the attendant definitions wherein $L_1$ is O.

In a further embodiment, the methods comprise a compound of formula 87 and the attendant definitions wherein $L_2$ is O.

In a further embodiment, the methods comprise a compound of formula 87 and the attendant definitions wherein R is methyl and $R_1$ is methyl.

In a further embodiment, the methods comprise a compound of formula 87 and the attendant definitions wherein R is methyl, $R_1$ is methyl, and $R_2$ is $CO_2H$.

In a further embodiment, the methods comprise a compound of formula 87 and the attendant definitions wherein R is methyl, $R_1$ is methyl, $R_2$ is $CO_2H$, and $R_3$ is F.

In a further embodiment, the methods comprise a compound of formula 87 and the attendant definitions wherein R is methyl, $R_1$ is methyl, $R_2$ is $CO_2H$, $R_3$ is F, and $L_1$ is O.

In a further embodiment, the methods comprise a compound of formula 87 and the attendant definitions wherein R is methyl, $R_1$ is methyl, $R_2$ is $CO_2H$, $R_3$ is F, $L_1$ is O, and $L_2$ is O.

A preferred compound of formula 74 is Dipyridamole; a preferred compound of formula 12 is Hinokitiol; a preferred compound of formula 13 is L-(+)-Ergothioneine; a preferred compound of formula 19 is Caffeic Acid Phenol Ester; a preferred compound of formula 20 is MCI-186 and a preferred compound of formula 21 is HBED (Supplementary Table 6). Activating compounds may also be oxidized forms of the compounds of Table 21.

Also included are pharmaceutically acceptable addition salts and complexes of the sirtuin-activating compounds described herein. In cases wherein the compounds may have one or more chiral centers, unless specified, the compounds contemplated herein may be a single stereoisomer or racemic mixtures of stereoisomers.

In cases in which the sirtuin-activating compounds have unsaturated carbon-carbon double bonds, both the cis (Z) and trans (E) isomers are contemplated herein. In cases wherein the compounds may exist in tautomeric forms, such as keto-enol tautomers, such as

each tautomeric form is contemplated as being included within the methods presented herein, whether existing in equilibrium or locked in one form by appropriate substitution with R'. The meaning of any substituent at any one occurrence is independent of its meaning, or any other substituent's meaning, at any other occurrence.

Also included in the methods presented herein are prodrugs of the sirtuin-activating compounds described herein. Prodrugs are considered to be any covalently bonded carriers that release the active parent drug in vivo. Metabolites, such as in vivo degradation products, of the compounds described herein are also included.

Analogs and derivatives of the above sirtuin-activating compounds described herein can also be used for activating a member of the sirtuin protein family. For example, derivatives or analogs may make the compounds more stable or improve their ability to traverse cell membranes or being phagocytosed or pinocytosed. Exemplary derivatives include glycosylated derivatives, as described, e.g., in U.S. Pat. No. 6,361,815 for resveratrol. Other derivatives of resveratrol include cis- and trans-resveratrol and conjugates thereof with a saccharide, such as to form a glucoside (see, e.g., U.S. Pat. No. 6,414,037). Glucoside polydatin, referred to as piceid or resveratrol 3-O-beta-D-glucopyranoside, can also be used. Saccharides to which compounds may be conjugated include glucose, galactose, maltose, lactose and sucrose. Glycosylated stilbenes are further described in Regev-Shoshani et al. Biochemical J. (published on Apr. 16, 2003 as BJ20030141). Other derivatives of compounds described herein are esters, amides and prodrugs. Esters of resveratrol are described, e.g., in U.S. Pat. No. 6,572,882. Resveratrol and derivatives thereof can be prepared as described in the art, e.g., in U.S. Pat. Nos. 6,414,037; 6,361,815; 6,270,780; 6,572,882; and Brandolini et al. (2002) J. Agric. Food. Chem. 50:7407. Derivatives of hydroxyflavones are described, e.g., in U.S. Pat. No. 4,591,600. Resveratrol and other activating compounds can also be obtained commercially, e.g., from Sigma.

In certain embodiments, if a sirtuin-activating compound occurs naturally, it may be at least partially isolated from its natural environment prior to use. For example, a plant polyphenol may be isolated from a plant and partially or significantly purified prior to use in the methods described herein. An activating compound may also be prepared synthetically, in which case it would be free of other compounds with which it is naturally associated. In an illustrative embodiment, an activating composition comprises, or an activating compound is associated with, less than about 50%, 10%, 1%, 0.1%, $10^{-2}$% or $10^{-3}$% of a compound with which it is naturally associated.

In certain embodiments, a certain biological function, e.g., reducing body weight, is modulated by any one of a sirtuin-activating compound of a genus of compounds (e.g., having formula I), with the proviso that the genus does not include one or more specific compounds. For example, in certain embodiments, a sirtuin activator-activating compound may be any compound that is capable of increasing the level of expression and/or activity of a sirtuin protein with the proviso that the compound is not resveratrol, a flavone, or any other compound specifically cited herein or any other compound that has been shown to have an activating effect on a sirtuin protein prior to the priority date of this application. In an exemplary embodiment, a sirtuin-activating compound may be a compound of any one of formulas 1-18, 23-47, 52 and 54-87 with the proviso that the compound is not resveratrol, a flavone or, or any of the other compounds specifically cited herein, or any other compound which has been shown to have an activating effect on a sirtuin protein prior to the priority date of this application. In an exemplary embodiment, a sirtuin-activating compound does not include any of the compounds cited in U.S. Pat. Nos. 6,410,596 or 6,552,085, the disclosures of which are hereby incorporated by reference in their entirety. For example, in one embodiment, a sirtuin-activating compound does not include a compound having formula 22 as set forth below:

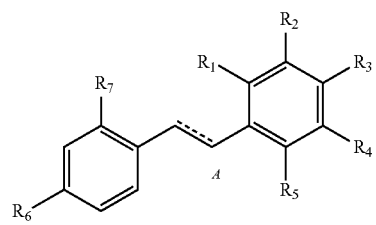

22 wherein,

A is selected from the group consisting of a single bond and a double bond in trans conformation;

$R_1$ is selected from the group consisting of H, OH, $C_{1-6}$ alkoxy, COOH, and $COOC_{1-6}$ alkyl;

$R_2$ is selected from the group consisting of H, OH, and $C_{1-10}$ alkoxy;

$R_3$ is selected from the group consisting of H, $C_{1-10}$ alkyl, $C_{2-10}$ alkenyl, $C_{2-10}$ alkynyl, and $C_{1-8}$ cycloalkyl;

$R_4$ is selected from the group consisting of H, OH, and $C_{1-10}$ alkoxy;

$R_5$ are selected from the group consisting of H, $C_{1-10}$ alkyl, $C_{2-10}$ alkenyl, $C_{2-10}$ alkynyl, and $C_{1-8}$ cycloalkyl;

$R_6$ is selected from the group consisting of H, OH, $C_{1-6}$ alkoxy, COOH, and $COOC_{1-6}$ alkyl;

$R_7$ is selected from the group consisting of H, OH, $C_{1-6}$ alkoxy, COOH, and $COOC_{1-6}$ alkyl; and wherein at least one of $R_3$ and $R_5$ is selected from the group consisting of $C_{1-10}$ alkyl, $C_{2-10}$ alkenyl, $C_{2-10}$ alkynyl; and $C_{1-8}$ cycloalkyl;

In certain embodiments, the subject sirtuin activators, such as SIRT1 activators, do not have any substantial ability to inhibit PI3-kinase, inhibit aldoreductase and/or inhibit tyrosine protein kinases at concentrations (e.g., in vivo) effective for activating the deacetylase activity of the sirtuin, e.g., SIRT1. For instance, in preferred embodiments the sirtuin activator is chosen to have an EC50 for activating sirtuin deacetylase activity that is at least 5 fold less than the EC50 for inhibition of one or more of aldoreductase and/or tyrosine protein kinases, and even more preferably at least 10 fold, 100 fold or even 1000 fold less. Methods for assaying PI3-Kinase activity, aldose reductase activity, and tyrosine kinase activity are well known in the art and kits to perform such assays may be purchased commercially. See e.g., U.S. Patent Publication No. 2003/0158212 for PI3-kinase assays; U.S. Patent Publication No. 2002/20143017 for aldose reductase assays; tyrosine kinase assay kits may be purchased commercially, for example, from Promega (Madison, Wis.; world wide web at promega.com), Invitrogen (Carlsbad, Calif.; world wide web at invitrogen.com) or Molecular Devices (Sunnyvale, Calif.; world wide web at moleculardevices.com).

In certain embodiments, the subject sirtuin activators do not have any substantial ability to transactivate EGFR tyrosine kinase activity at concentrations (e.g., in vivo) effective for activating the deacetylase activity of the sirtuin. For instance, in preferred embodiments the sirtuin activator is chosen to have an EC50 for activating sirtuin deacetylase activity that is at least 5 fold less than the EC50 for transactivating EGFR tyrosine kinase activity, and even more preferably at least 10 fold, 100 fold or even 1000 fold less. Methods for assaying transactivation of EGFR tyrosine kinase activity are well known in the art, see e.g., Pai et al. Nat. Med. 8: 289-93 (2002) and Vacca et al. Cancer Research 60: 5310-5317 (2000).

In certain embodiments, the subject sirtuin activators do not have any substantial ability to cause coronary dilation at concentrations (e.g., in vivo) effective for activating the deacetylase activity of the sirtuin. For instance, in preferred embodiments the sirtuin activator is chosen to have an EC50 for activating sirtuin deacetylase activity that is at least 5 fold less than the EC50 for coronary dilation, and even more preferably at least 10 fold, 100 fold or even 1000 fold less. Methods for assaying vasodilation are well known in the art, see e.g., U.S. Patent Publication No. 2004/0236153.

In certain embodiments, the subject sirtuin activators do not have any substantial spasmolytic activity at concentrations (e.g., in vivo) effective for activating the deacetylase activity of the sirtuin. For instance, in preferred embodiments the sirtuin activator is chosen to have an EC50 for activating sirtuin deacetylase activity that is at least 5 fold less than the EC50 for spasmolytic effects (such as on gastrointestinal muscle), and even more preferably at least 10 fold, 100 fold or even 1000 fold less. Methods for assaying spasmolytic activity are well known in the art, see e.g., U.S. Patent Publication No. 2004/0248987.

In certain embodiments, the subject sirtuin activators do not have any substantial ability to inhibit hepatic cytochrome P450 1B1 (CYP) at concentrations (e.g., in vivo) effective for activating the deacetylase activity of the sirtuin. For instance, in preferred embodiments the sirtuin activator is chosen to have an EC50 for activating sirtuin deacetylase activity that is at least 5 fold less than the EC50 for inhibition of P450 1B1, and even more preferably at least 10 fold, 100 fold or even 1000 fold less. Methods for assaying cytochrome P450 activity are well known in the art and kits to perform such assays may be purchased commercially. See e.g., U.S. Pat. Nos. 6,420,131 and 6,335,428 and Promega (Madison, Wis.; world wide web at promega.com).

In certain embodiments, the subject sirtuin activators do not have any substantial ability to inhibit nuclear factor-kappaB (NF-κB) at concentrations (e.g., in vivo) effective for activating the deacetylase activity of the sirtuin. For instance, in preferred embodiments the sirtuin activator is chosen to have an EC50 for activating sirtuin deacetylase activity that is at least 5 fold less than the EC50 for inhibition of NF-κB, and even more preferably at least 10 fold, 100 fold or even 1000 fold less. Methods for assaying NF-κB activity are well known in the art and kits to perform such assays may be purchased commercially (e.g., from Oxford Biomedical Research (Ann Arbor, Mich.; world wide web at oxfordbiomed.com)).

In certain embodiments, the subject sirtuin activators do not have any substantial ability to inhibit a histone deacetylase (HDACs) class I, a HDAC class II, or HDACs I and II, at concentrations (e.g., in vivo) effective for activating the deacetylase activity of the sirtuin. For instance, in preferred embodiments the sirtuin activator is chosen to have an EC50 for activating sirtuin deacetylase activity that is at least 5 fold less than the EC50 for inhibition of an HDAC I and/or HDAC II, and even more preferably at least 10 fold, 100 fold or even 1000 fold less. Methods for assaying HDAC I and/or HDAC II activity are well known in the art and kits to perform such assays may be purchased commercially. See e.g., BioVision, Inc. (Mountain View, Calif.; world wide web at biovision.com) and Thomas Scientific (Swedesboro, N.J.; world wide web at tomassci.com).

In certain embodiments, the subject SIRT1 activators do not have any substantial ability to activate SIRT1 orthologs in lower eukaryotes, particularly yeast or human pathogens, at concentrations (e.g., in vivo) effective for activating the deacetylase activity of human SIRT1. For instance, in preferred embodiments the SIRT1 activator is chosen to have an EC50 for activating human SIRT1 deacetylase activity that is at least 5 fold less than the EC50 for activating yeast Sir2 (such as *Candida, S. cerevisiae*, etc), and even more preferably at least 10 fold, 100 fold or even 1000 fold less.

In certain embodiments, the sirtuin activating compounds may have the ability to activate one or more sirtuin protein homologs, such as, for example, one or more of human SIRT1, SIRT2, SIRT3, SIRT4, SIRT5, SIRT6, or SIRT7. In other embodiments, a SIRT1 activator does not have any substantial ability to activate other sirtuin protein homologs, such as, for example, one or more of human SIRT2, SIRT3, SIRT4, SIRT5, SIRT6, or SIRT7, at concentrations (e.g., in vivo) effective for activating the deacetylase activity of human SIRT1. For instance, the SIRT1 activator may be chosen to have an EC50 for activating human SIRT1 deacetylase activity that is at least 5 fold less than the EC50 for activating one or more of human SIRT2, SIRT3, SIRT4, SIRT5, SIRT6, or SIRT7, and even more preferably at least 10 fold, 100 fold or even 1000 fold less.

In certain embodiments, SIRT3 and SIRT4 modulators may be used to modulate fat mobilization. For example, SIRT3 and/or SIRT4 activators may be used to induce fat mobilization and may be used to treat, e.g., obesity and insulin resistance disorders.

In other embodiments, the subject sirtuin activators do not have any substantial ability to inhibit protein kinases; to phosphorylate mitogen activated protein (MAP) kinases; to inhibit the catalytic or transcriptional activity of cyclo-oxygenases, such as COX-2; to inhibit nitric oxide synthase (iNOS); or to inhibit platelet adhesion to type I collagen at concentrations (e.g., in vivo) effective for activating the deacetylase activity of the sirtuin. For instance, in preferred embodiments, the sirtuin activator is chosen to have an EC50 for activating sirtuin deacetylase activity that is at least 5 fold less than the EC50 for performing any of these activities, and even more preferably at least 10 fold, 100 fold or even 1000 fold less. Methods for assaying protein kinase activity, cyclo-oxygenase activity, nitric oxide synthase activity, and platelet adhesion activity are well known in the art and kits to perform such assays may be purchased commercially. See e.g., Promega (Madison, Wis.; world wide web at promega.com), Invitrogen (Carlsbad, Calif.; world wide web at invitrogen.com); Molecular Devices (Sunnyvale, Calif.; world wide web at moleculardevices.com) or Assay Designs (Ann Arbor, Mich.; world wide web at assaydesigns.com) for protein kinase assay kits; Amersham Biosciences (Piscataway, N.J.; world wide web at amershambiosciences.com) for cyclo-oxygenase assay kits; Amersham Biosciences (Piscataway, N.J.; world wide web at amershambiosciences.com) and R&D Systems (Minneapolis, Minn.; world wide web at mdsystems.com) for nitric oxide synthase assay kits; and U.S. Pat. Nos. 5,321,010; 6,849,290; and 6,774,107 for platelet adhesion assays.

The sirtuin-activitating compounds described herein may be taken alone or in combination with other compounds. The other compounds may be other sirtuin and/or AMPK activators. For example, Longevinex™, which is a red wine extract, and contains, in addition to resveratrol, other sirtuin activators, such as quercetin, is a particularly potent agent for mobilizing fat. Longevinex™ can be obtained on the world wide web at www.longevinex.com.

A combination drug regimen may also include drugs or compounds for the treatment or prevention of obesity and/or diabetes.

In an exemplary embodiment, sirtuin-activating compounds may be administered as a combination therapy. For example, for reducing weight, preventing weight gain, or treatment or prevention of obesity, one or more sirtuin-activating compounds may be used in combination with the following "anti-obesity agents": phenylpropanolamine, ephedrine, pseudoephedrine, phentermine, a cholecystokinin-A agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (leptin), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Alternatively, one or more sirtuin-activating compounds may be used in combination with the following "anti-diabetic agents": an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a peroxisome proliferator-activated receptor-γ (PPAR-γ) ligand such as troglitazone, rosaglitazone, pioglitazone or GW-1929, a sulfonylurea, glipazide, glyburide, or chlorpropamide wherein the amounts of the first and second compounds result in a therapeutic effect. Other anti-diabetic agents include a glucosidase inhibitor, a glucagon-like peptide-1 (GLP-1), insulin, a PPAR α/γ dual agonist, a meglitimide and an αP2 inhibitor. In an exemplary embodiment, an anti-diabetic agent may be a dipeptidyl peptidase IV (DP-IV or DPP-IV) inhibitor, such as, for example LAF237 from Novartis (NVP DPP728; 1-[[[2-[(5-cyanopyridin-2-yl)amino]ethyl]amino] acetyl]-2-cyano-(S)-pyrrolidine) or MK-04301 from Merck (see e.g., Hughes et al., Biochemistry 38: 11597-603 (1999)).

In certain embodiments, one or more sirtuin-activating compounds may be directed specifically to a certain tissue (e.g., liver) rather than the whole body. Tissue specific treatments may be used to treat, e.g., obesity and insulin resistance disorder.

In certain embodiments the methods are useful for preventing fat accumulation in cells with lipogenic capacity, e.g. liver, pancreas and muscle cells.

Methods for reducing or preventing fat accumulation in a cell may also comprise increasing the protein level of a sirtuin, such as SIRT1 in a human cell, Sir2 in a yeast cell, Sir2.1 in C. elegans or a homologue of any of these sirtuins in other organisms. Increasing protein levels can be achieved by introducing into a cell one or more copies of a nucleic acid that encodes a sirtuin. For example, the level of SIRT1 can be increased in a mammalian cell by introducing into the mammalian cell a nucleic acid encoding SIRT1, e.g., having the amino acid sequence set forth in SEQ ID NO: 2. The nucleic acid may be under the control of a promoter that regulates the expression of the SIRT1 nucleic acid. Alternatively, the nucleic acid may be introduced into the cell at a location in the genome that is downstream of a promoter. Methods for increasing the level of a protein using these methods are well known in the art. Exemplary methods are described in the Examples.

A nucleic acid that is introduced into a cell to increase the protein level of a sirtuin may encode a protein that is at least about 80%, 85%, 90%, 95%, 98%, or 99% identical to the sequence of a sirtuin, e.g., SEQ ID NO: 2. For example, the nucleic acid encoding the protein may be at least about 80%, 85%, 90%, 95%, 98%, or 99% identical to SEQ ID NO: 1. The nucleic acid may also be a nucleic acid that hybridizes, preferably under stringent hybridization conditions, to a nucleic acid encoding a wild-type sirtuin, e.g., SEQ ID NO: 1. Stringent hybridization conditions may include hybridization and a wash in 0.2×SSC at 65° C. When using a nucleic acid that encodes a protein that is different from a wild-type sirtuin protein, such as a protein that is a fragment of a wild-type sirtuin, the protein is preferably biologically active, e.g., is capable of deacetylation. It is only necessary to express in a cell a portion of the sirtuin that is biologically active. For example, a protein that differs from wild-type SIRT1 having SEQ ID NO: 2, preferably contains the core structure thereof. The core structure sometimes refers to amino acids 62-293 of SEQ ID NO: 2, which are encoded by nucleotides 237 to 932 of SEQ ID NO: 1, which encompasses the NAD binding as well as the substrate binding domains. The core domain of SIRT1 may also refer to about amino acids 261 to 447 of SEQ ID NO: 2, which are encoded by nucleotides 834 to 1394 of SEQ ID NO: 1; to about amino acids 242 to 493 of SEQ ID NO: 2, which are encoded by nucleotides 777 to 1532 of SEQ ID NO: 1; or to about amino acids 254 to 495 of SEQ ID NO: 2, which are encoded by nucleotides 813 to 1538 of SEQ ID NO: 1. Whether a protein retains a biological function, e.g., deacetylation capabilities, can be determined according to methods known in the art.

Nucleotide and amino acid sequences of human sirtuins and exemplary conserved domains are set forth below:

| Sirt | | nucleotide sequence | amino acid sequence | conserved domains (amino acids) |
|---|---|---|---|---|
| SIRT1 | | NM_012238 | NP_036370 | 431-536; 254-489 |
| SIRT2 | i1 | NM_012237 | NP_036369 | 77-331 |
| | i2 | NM_030593 | NP_085096 | 40-294 |
| SIRT3 | ia | NM_012239 | NP_036371 | 138-373 |
| | ib | NM_001017524 | NP_001017524 | 1-231 |
| SIRT4 | | NM_012240 | NP_036372 | 47-308 |
| SIRT5 | i1 | NM_012241 | NP_036373 | 51-301 |
| | i2 | NM_031244 | NP_112534 | 51-287 |
| SIRT6 | | NM_016539 | NP_057623 | 45-257 |
| SIRT7 | | NM_016538 | NP_057622 | 100-314 |

Methods for increasing sirtuin protein levels also include methods for stimulating the transcription of genes encoding sirtuins, methods for stabilizing the corresponding mRNAs, methods, and other methods known in the art.

In other embodiments, methods of activating sirtuins include increasing the flux through the NAD+ salvage pathway or reducing nicotinamide levels, such as described in WO 2004/01676. The activity or protein level of an enzyme of the NAD+ salvage pathway, such as PNC1, NPT1 (or human homologues thereof) or nicotinamide phosphoribosyltransferase (NAMPRT) may be increased. The human gene for NAMPRT is also referred to as pre-B-cell colony enhancing factor 1 (PBEF1) and visfatin and exists as two isoforms (see, e.g., Samal et al. (1994) Mol. Cell. Biol. 14:1431, Rongwaux et al. (2002) Euro. J. Immunol. 32:3225 and Fukuhara et al. Science 307:426-30 (2005); U.S. Pat. Nos. 5,874,399 and 6,844,163). The sequence of isoform a is available under GenBank Accession numbers NM_005746, NP_005737 and U02020 and the sequence of isoform b is available under GenBank Accession numbers NM_182790, NP_877591 and BC020691.

In yet other embodiments, nicotinamide riboside or analogs thereof are administered. Nicotinamide riboside can be prepared by treating NMN (from, e.g., Sigma) with a phosphatase, as described, e.g., in Bieganowski et al. (2004) Cell 117:495. Nicotinamide riboside can be in the oxidized or reduced form, the latter of which appears to be more stable (Friedlos et al. (1992) Biochem Pharmacol. 44:631. Nicotinamide riboside (91) is depicted below.

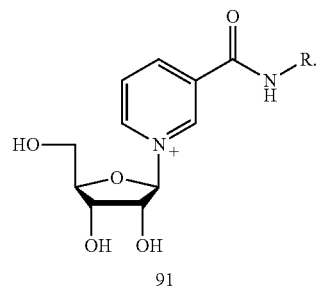

91

Nicotinamide riboside and some of its analogs are represented by formula A:

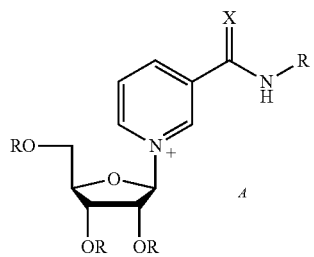

A wherein

R represents independently for each occurrence H, acetyl, benzoyl, acyl, phosphate, sulfate, (alkyoxy)methyl, triarylmethyl, (trialkyl)silyl, (dialkyl)(aryl)silyl, (alkyl)(diaryl)silyl, or (triaryl)silyl; and X represents O or S.

Nicotinamide riboside can be contacted with the cell at a concentration of about 1 nM to 10 µM. A cell may be optionally contacted with an agent that increases protein or activity levels of a nicotinamide riboside kinase (Nrk) enzyme, that phosphorylates nicotinamide riboside to form nicotinamide mononucleotide (NMN). Nrk exits in one form in yeast, Nrk1, and in two forms in humans, Nrk1 (GenBank Accession No. NM_017881.1; NP_060351) and Nrk2 (GenBank Accession Nos. NM_170678, NP_733778).

Exemplary Sirtuin Inhibitory Compounds and Methods of Use

The Examples show that sirtuin inhibitory agents, such as nicotinamide, increase fat accumulation in C. elegans (See example 2).

Sirtuin inhibitory compounds include compounds that inhibit the activity of a class III histone deacetylase, such as a sirtuin, and include for example, nicotinamide (NAM), suranim; NF023 (a G-protein antagonist); NF279 (a purinergic receptor antagonist); Trolox (6-hydroxy-2,5,7,8,tetramethylchroman-2-carboxylic acid); (−)-epigallocatechin (hydroxy on sites 3,5,7,3',4',5'); (−)-epigallocatechin (hydroxy on sites 3,5,7,3',4',5'); (−)-epigallocatechin gallate (Hydroxy sites 5,7,3',4',5' and gallate ester on 3); cyanidin choloride (3,5,7,3',4'-pentahydroxyflavylium chloride); delphinidin chloride (3,5,7,3',4',5'-hexahydroxyflavylium chloride); myricetin (cannabiscetin; 3,5,7,3',4',5'-hexahydroxyflavone); 3,7,3',4',5'-pentahydroxyflavone; and gossypetin (3,5,7,8,3',4'-hexahydroxyflavone), all of which are further described in Howitz et al. (2003) Nature 425:191. Other inhibitors, such as sirtinol and splitomicin, are described in Grozinger et al. (2001) J. Biol. Chem. 276:38837, Dedalov et al. (2001) PNAS 98:15113 and Hirao et al. (2003) J. Biol. Chem. 278:52773. Analogs and derivatives of these compounds can also be used.

Yet other sirtuin inhibitory compounds may have any one of the following formulas:

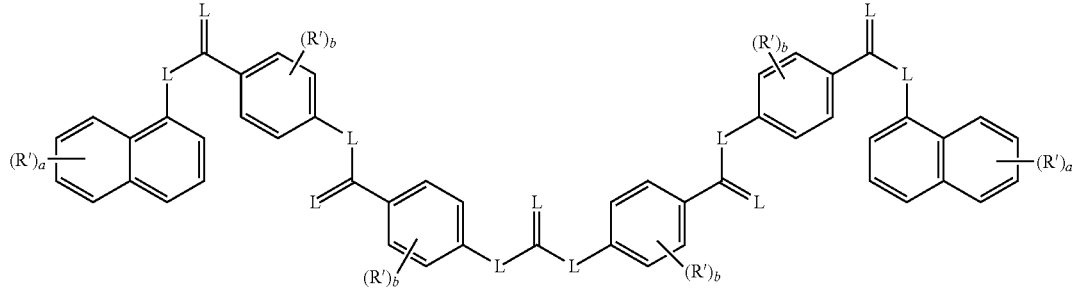

19 wherein, independently for each occurrence,
L represents O, NR, or S;
R represents H, alkyl, aryl, aralkyl, or heteroaralkyl;
R' represents H, halogen, $NO_2$, SR, $SO_3$, OR, $NR_2$, alkyl, aryl, or carboxy;
a represents an integer from 1 to 7 inclusively; and
b represents an integer from 1 to 4 inclusively.

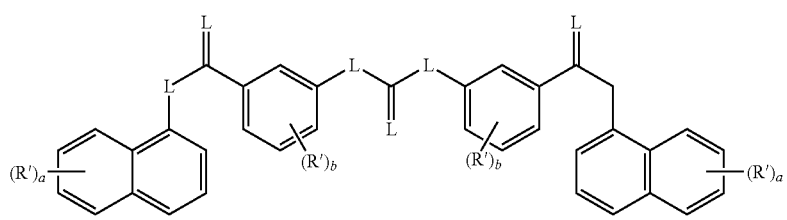

20 wherein, independently for each occurrence,
L represents O, NR, or S;
R represents H, alkyl, aryl, aralkyl, or heteroaralkyl;
R' represents H, halogen, $NO_2$, SR, $SO_3$, OR, $NR_2$, alkyl, aryl, or carboxy;
a represents an integer from 1 to 7 inclusively; and
b represents an integer from 1 to 4 inclusively.

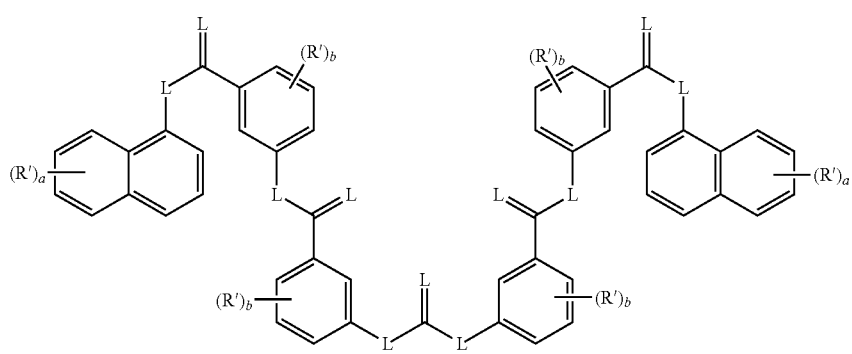

21 wherein, independently for each occurrence,
L represents O, NR, or S;
R represents H, alkyl, aryl, aralkyl, or heteroaralkyl;
R' represents H, halogen, $NO_2$, SR, $SO_3$, OR, $NR_2$, alkyl, aryl, or carboxy;

a represents an integer from 1 to 7 inclusively; and
b represents an integer from 1 to 4 inclusively.

Exemplary inhibiting compounds are set forth in the appended Tables (compounds for which the ratio to control rate is <1). Another compound is Mercury, (2-hydroxy-5-nitrophenyl)(6-thioguanosinato-N7,S6).

A sirtuin inhibitory compound may also have a formula selected from the group of formulas 48-51, 53, and 88-90:

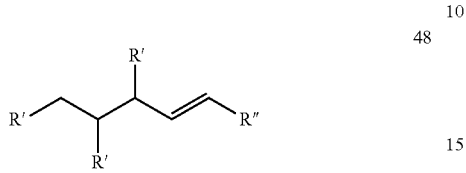

48 wherein, independently for each occurrence,
R' represents H, halogen, $NO_2$, SR, OR, $NR_2$, alkyl, aryl, aralkyl, or carboxy;
R represents H, alkyl, aryl, aralkyl, heteroaralkyl, —$SO_3H$, monosaccharide, oligosaccharide, glycofuranosyl, glycopyranosyl, glucuronosyl, or glucuronide; and
R" represents alkyl, alkenyl, or alkynyl;

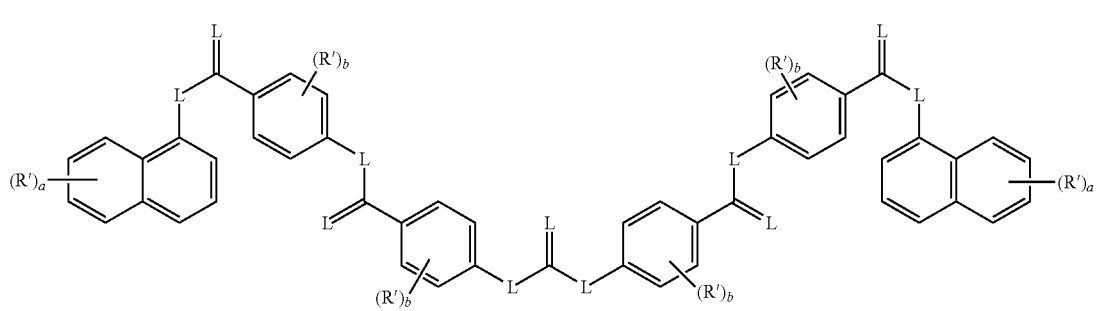

49 wherein, independently for each occurrence,
L represents O, NR, or S;
R represents H, alkyl, aryl, aralkyl, heteroaralkyl, —$SO_3H$, monosaccharide, oligosaccharide, glycofuranosyl, glycopyranosyl, glucuronosyl, or glucuronide; and
R' represents H, halogen, $NO_2$, SR, $SO_3$, OR, $NR_2$, alkyl, aryl, aralkyl, or carboxy;
a represents an integer from 1 to 7 inclusive; and
b represents an integer from 1 to 4 inclusive;

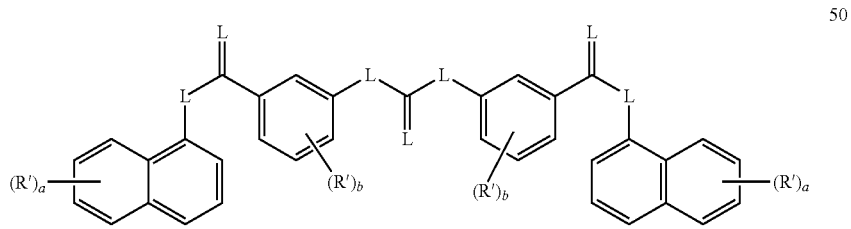

50 wherein, independently for each occurrence,
L represents O, NR, or S;
R represents H, alkyl, aryl, aralkyl, heteroaralkyl, —$SO_3H$, monosaccharide, oligosaccharide, glycofuranosyl, glycopyranosyl, glucuronosyl, or glucuronide; and R' represents H, halogen, NO$_2$, SR, SO$_3$, OR, NR$_2$, alkyl, aryl, or carboxy;
a represents an integer from 1 to 7 inclusive; and
b represents an integer from 1 to 4 inclusive;

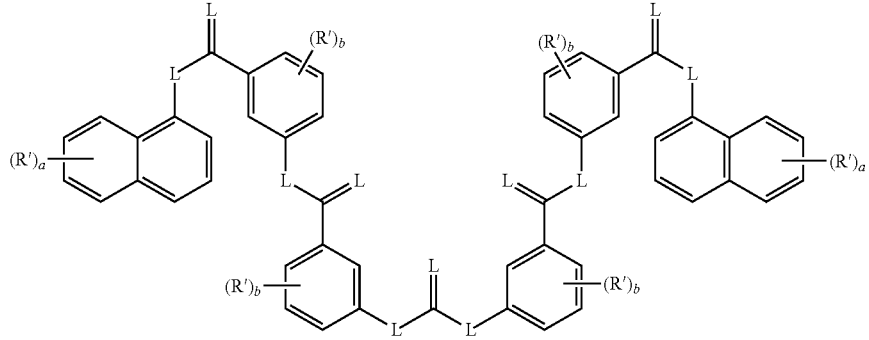

51 wherein, independently for each occurrence,
L represents O, NR, or S;
R represents H, alkyl, aryl, aralkyl, heteroaralkyl, —SO$_3$H, monosaccharide, oligosaccharide, glycofuranosyl, glycopyranosyl, glucuronosyl, or glucuronide; and
R' represents H, halogen, NO$_2$, SR, SO$_3$, OR, NR$_2$, alkyl, aryl, aralkyl, or carboxy;
a represents an integer from 1 to 7 inclusive; and
b represents an integer from 1 to 4 inclusive;

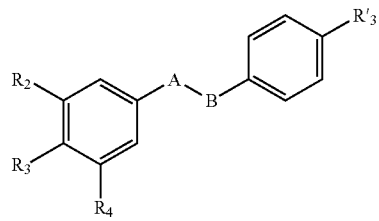

wherein, independently for each occurrence,
R$_2$, R$_3$, and R$_4$ are H, OR, or O-alkyl;
R represents H, —SO$_3$H, monosaccharide, oligosaccharide, glycofuranosyl, glycopyranosyl, glucuronosyl, or glucuronide; and
R'$_3$ is H or NO$_2$; and
A-B is an ethenylene or amido group.

In a further embodiment, the inhibiting compound is represented by formula 53 and the attendant definitions, wherein R$_3$ is OH, A-B is ethenylene, and R'$_3$ is H.

In a further embodiment, the inhibiting compound is represented by formula 53 and the attendant definitions, wherein R$_2$ and R$_4$ are OH, A-B is an amido group, and R'$_3$ is H.

In a further embodiment, the inhibiting compound is represented by formula 53 and the attendant definitions, wherein R$_2$ and R$_4$ are OMe, A-B is ethenylene, and R'$_3$ is NO$_2$.

In a further embodiment, the inhibiting compound is represented by formula 53 and the attendant definitions, wherein R$_3$ is OMe, A-B is ethenylene, and R'$_3$ is H.

In another embodiment, methods for inhibiting a sirtuin protein comprise using an inhibiting compound of formula 88:

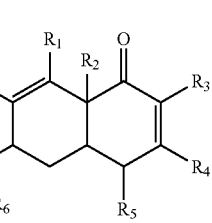

88 wherein, independently for each occurrence:
R, R$_1$, R$_2$, R$_3$, R$_4$, R$_5$, R$_6$, R$_7$, and R$_8$ are H, hydroxy, amino, cyano, halide, OR$_9$, ether, ester, amido, ketone, carboxylic acid, nitro, or a substituted or unsubstituted alkyl, aryl, aralkyl, heterocyclyl, heterocyclylalkyl, heteroaryl, or heteroaralkyl; and
R$_9$ represents alkyl, —SO$_3$H, monosaccharide, oligosaccharide, glycofuranosyl, glycopyranosyl, glucuronosyl, or glucuronide.

In a further embodiment, the methods comprise a compound of formula 88 and the attendant definitions wherein R is OH.

In a further embodiment, the methods comprise a compound of formula 88 and the attendant definitions wherein R$_1$ is OH.

In a further embodiment, the methods comprise a compound of formula 88 and the attendant definitions wherein R$_2$ is OH.

In a further embodiment, the methods comprise a compound of formula 88 and the attendant definitions wherein R$_3$ is C(O)NH$_2$.

In a further embodiment, the methods comprise a compound of formula 88 and the attendant definitions wherein R$_4$ is OH.

In a further embodiment, the methods comprise a compound of formula 88 and the attendant definitions wherein R$_5$ is NMe$_2$.

In a further embodiment, the methods comprise a compound of formula 88 and the attendant definitions wherein R$_6$ is methyl.

In a further embodiment, the methods comprise a compound of formula 88 and the attendant definitions wherein R$_7$ is OH.

In a further embodiment, the methods comprise a compound of formula 88 and the attendant definitions wherein R$_8$ is Cl.

In a further embodiment, the methods comprise a compound of formula 88 and the attendant definitions wherein R is OH and $R_1$ is OH.

In a further embodiment, the methods comprise a compound of formula 88 and the attendant definitions wherein R is OH, $R_1$ is OH, and $R_2$ is OH.

In a further embodiment, the methods comprise a compound of formula 88 and the attendant definitions wherein R is OH, $R_1$ is OH, $R_2$ is OH, and $R_3$ is C(O)NH$_2$.

In a further embodiment, the methods comprise a compound of formula 88 and the attendant definitions wherein R is OH, $R_1$ is OH, $R_2$ is OH, $R_3$ is C(O)NH$_2$, and $R_4$ is OH.

In a further embodiment, the methods comprise a compound of formula 88 and the attendant definitions wherein R is OH, $R_1$ is OH, $R_2$ is OH, $R_3$ is C(O)NH$_2$, $R_4$ is OH, and $R_5$ is NMe$_2$.

In a further embodiment, the methods comprise a compound of formula 88 and the attendant definitions wherein R is OH, $R_1$ is OH, $R_2$ is OH, $R_3$ is C(O)NH$_2$, $R_4$ is OH, $R_5$ is NMe$_2$, and $R_6$ is methyl.

In a further embodiment, the methods comprise a compound of formula 88 and the attendant definitions wherein R is OH, $R_1$ is OH, $R_2$ is OH, $R_3$ is C(O)NH$_2$, $R_4$ is OH, $R_5$ is NMe$_2$, $R_6$ is methyl, and $R_7$ is OH.

In a further embodiment, the methods comprise a compound of formula 88 and the attendant definitions wherein R is OH, $R_1$ is OH, $R_2$ is OH, $R_3$ is C(O)NH$_2$, $R_4$ is OH, $R_5$ is NMe$_2$, $R_6$ is methyl, $R_7$ is OH, and $R_8$ is Cl.

In another embodiment, methods for inhibiting a sirtuin protein comprise using an inhibiting compound of formula 89:

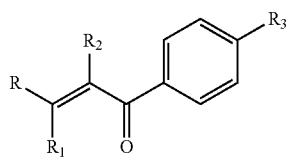

89 wherein, independently for each occurrence:

R, $R_1$, $R_2$, and $R_3$ are H, hydroxy, amino, cyano, halide, OR$_4$, ether, ester, amido, ketone, carboxylic acid, nitro, or a substituted or unsubstituted alkyl, aryl, aralkyl, heterocyclyl, heterocyclylalkyl, heteroaryl, or heteroaralkyl; and $R_4$ represents alkyl, —SO$_3$H, monosaccharide, oligosaccharide, glycofuranosyl, glycopyranosyl, glucuronosyl, or glucuronide.

In a further embodiment, the methods comprise a compound of formula 89 and the attendant definitions wherein R is Cl.

In a further embodiment, the methods comprise a compound of formula 89 and the attendant definitions wherein $R_1$ is H.

In a further embodiment, the methods comprise a compound of formula 89 and the attendant definitions wherein $R_2$ is H.

In a further embodiment, the methods comprise a compound of formula 89 and the attendant definitions wherein $R_3$ is Br.

In a further embodiment, the methods comprise a compound of formula 89 and the attendant definitions wherein R is Cl and $R_1$ is H.

In a further embodiment, the methods comprise a compound of formula 89 and the attendant definitions wherein R is Cl, $R_1$ is H, and $R_2$ is H.

In a further embodiment, the methods comprise a compound of formula 89 and the attendant definitions wherein R is Cl, $R_1$ is H, $R_2$ is H, and $R_3$ is Br.

In another embodiment, methods for inhibiting a sirtuin protein comprise using an inhibiting compound of formula 90:

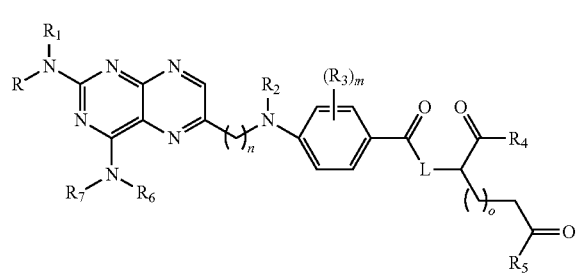

90 wherein, independently for each occurrence:

R, $R_1$, $R_2$, $R_6$, and $R_7$ are H or a substituted or unsubstituted alkyl, aryl, aralkyl, heterocyclyl, heterocyclylalkyl, heteroaryl, or heteroaralkyl;

$R_3$, $R_4$, and $R_5$ are H, hydroxy, amino, cyano, halide, OR$_6$, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_6$ represents alkyl, —SO$_3$H, monosaccharide, oligosaccharide, glycofuranosyl, glycopyranosyl, glucuronosyl, or glucuronide.

L is O, NR, or S;

m is an integer from 0 to 4 inclusive; and n and o are integers from 0 to 6 inclusive.

In a further embodiment, the methods comprise a compound of formula 90 and the attendant definitions wherein R is H.

In a further embodiment, the methods comprise a compound of formula 90 and the attendant definitions wherein $R_1$ is H.

In a further embodiment, the methods comprise a compound of formula 90 and the attendant definitions wherein $R_2$ is methyl.

In a further embodiment, the methods comprise a compound of formula 90 and the attendant definitions wherein m is 0.

In a further embodiment, the methods comprise a compound of formula 90 and the attendant definitions wherein $R_4$ is OH.

In a further embodiment, the methods comprise a compound of formula 90 and the attendant definitions wherein $R_5$ is OH.

In a further embodiment, the methods comprise a compound of formula 90 and the attendant definitions wherein $R_6$ is H.

In a further embodiment, the methods comprise a compound of formula 90 and the attendant definitions wherein $R_7$ is H.

In a further embodiment, the methods comprise a compound of formula 90 and the attendant definitions wherein L is NH.

In a further embodiment, the methods comprise a compound of formula 90 and the attendant definitions wherein n is 1.

In a further embodiment, the methods comprise a compound of formula 90 and the attendant definitions wherein o is 1.

In a further embodiment, the methods comprise a compound of formula 90 and the attendant definitions wherein R is H and $R_1$ is H.

In a further embodiment, the methods comprise a compound of formula 90 and the attendant definitions wherein R is H, $R_1$ is H, and $R_2$ is methyl.

In a further embodiment, the methods comprise a compound of formula 90 and the attendant definitions wherein R is H, $R_1$ is H, $R_2$ is methyl, and m is 0.

In a further embodiment, the methods comprise a compound of formula 90 and the attendant definitions wherein R is H, $R_1$ is H, $R_2$ is methyl, m is 0, and $R_4$ is OH.

In a further embodiment, the methods comprise a compound of formula 90 and the attendant definitions wherein R is H, $R_1$ is H, $R_2$ is methyl, m is 0, $R_4$ is OH, and $R_5$ is OH.

In a further embodiment, the methods comprise a compound of formula 90 and the attendant definitions wherein R is H, $R_1$ is H, $R_2$ is methyl, m is 0, $R_4$ is OH, $R_5$ is OH, and $R_6$ is H.

In a further embodiment, the methods comprise a compound of formula 90 and the attendant definitions wherein R is H, $R_1$ is H, $R_2$ is methyl, m is 0, $R_4$ is OH, $R_5$ is OH, $R_6$ is H, and $R_7$ is H.

In a further embodiment, the methods comprise a compound of formula 90 and the attendant definitions wherein R is H, $R_1$ is H, $R_2$ is methyl, m is 0, $R_4$ is OH, $R_5$ is OH, $R_6$ is H, $R_7$ is H, and L is NH.

In a further embodiment, the methods comprise a compound of formula 90 and the attendant definitions wherein R is H, $R_1$ is H, $R_2$ is methyl, m is 0, $R_4$ is OH, $R_5$ is OH, $R_6$ is H, $R_7$ is H, L is NH, and n is 1.

In a further embodiment, the methods comprise a compound of formula 90 and the attendant definitions wherein R is H, $R_1$ is H, $R_2$ is methyl, m is 0, $R_4$ is OH, $R_5$ is OH, $R_6$ is H, $R_7$ is H, L is NH, n is 1, and o is 1.

Inhibitory compounds may also be oxidized forms of the compounds of Table 22. An oxidized form of chlortetracyclin may be an activator.

Also included are pharmaceutically acceptable addition salts and complexes of the sirtuin inhibitory compounds described herein. In cases wherein the compounds may have one or more chiral centers, unless specified, the compounds contemplated herein may be a single stereoisomer or racemic mixtures of stereoisomers.

In cases in which the sirtuin inhibitory compounds have unsaturated carbon-carbon double bonds, both the cis (Z) and trans (E) isomers are contemplated herein. In cases wherein the compounds may exist in tautomeric forms, such as keto-enol tautomers, such as

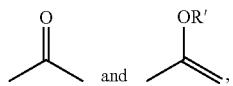

each tautomeric form is contemplated as being included within the methods presented herein, whether existing in equilibrium or locked in one form by appropriate substitution with R'. The meaning of any substituent at any one occurrence is independent of its meaning, or any other substituent's meaning, at any other occurrence.

Also included in the methods presented herein are prodrugs of the sirtuin inhibitory compounds described herein. Prodrugs are considered to be any covalently bonded carriers that release the active parent drug in vivo. Metabolites, such as in vivo degradation products, of the compounds described herein are also included.

Whether in vitro or in vivo, a sirtuin inhibitory compound may also be contacted with a cell or administered either alone or in combination with other therapeutic agents. In one embodiment, more than one sirtuin inhibitory compound may be contacted with a cell or administered. For example, at least 2, 3, 5, or 10 different sirtuin inhibitory compounds may be contacted with a cell or administered. In another embodiment, a sirtuin inhibitory compound may be administered as part of a combination therapy with another therapeutic agent. Such combination therapies may be administered simultaneously (e.g., more than one therapeutic agent administered at the same time) or sequentially with e.g., different compounds or therapeutic agents administered at different times during a treatment regimen.

To promote weight gain, one or more sirtuin inhibitory compounds of formulas 19-21, 48-51, 53 and 88-90 may be used in combination with the following "weight gain promoting agents": beta blockers (such as propranolo), alpha blockers (such as clonidine, prazosin and terazosin); insulin, sulfonylureas (such as glipizide and glyburide), thiazolidinediones (such as pioglitazone and rosiglitazone), meglitinides, nateglinide, repaglinide, lithium carbonate, valproic acid, carbamazepine, antidepressants, including, for example, tricyclics (such as amitriptyline and imipramine), monoamine-oxidase inhibitors, selective serotonin reuptake inhibitors (SSRIs), bupropion, paroxetine and mirtazapine, chlorpromazine, thiothixene, steroids (such as prednisone), oral contraceptives (birth control pills) or other contraceptives containing estrogen and/or progesterone (Depo-Provera, Norplant, Ortho), testosterone or Megestrol.

In another embodiment, one or more sirtuin inhibitory compounds may be directed specifically to a certain tissue (e.g., liver) rather than the whole body. Tissue specific treatments may be used to treat, e.g., hypoglycemia.

Methods for stimulating fat accumulation in a cell may also comprise decreasing the protein level of a sirtuin in the cell. Decreasing a protein level can be achieved according to methods known in the art. For example, an siRNA, an antisense or ribozyme targeted to the sirtuin can be expressed in the cell. A dominant negative sirtuin mutant, e.g., a mutant that is not capable of deacetylating, may be used. For example, mutant H363Y of SIRT1, described, e.g., in Luo et al. (2001) Cell 107:137 can be used. Alternatively, agents that inhibit transcription can be used.

Other Potential Characteristics of Sirtuin-activators and Inhibitors

In other embodiments, a compound described herein, e.g., a sirtuin activator or inhibitor, does not have significant or detectable anti-oxidant activities, as determined by any of the standard assays known in the art. For example, a compound does not significantly scavenge free-radicals, such as $O_2$ radicals. A compound may have less than about 2, 3, 5, 10, 30 or 100 fold anti-oxidant activity relative to another compound, e.g., resveratrol.

A compound may also have a binding affinity for a sirtuin of about $10^{-9}$M, $10^{-10}$M, $10^{-11}$M, $10^{-12}$M or less. A compound may reduce the Km of a sirtuin for its substrate or NAD+ by a factor of at least about 2, 3, 4, 5, 10, 20, 30, 50 or 100. A compound may increase the Vmax of a sirtuin by a factor of at least about 2, 3, 4, 5, 10, 20, 30, 50 or 100. Exemplary compounds that may increase the Vmax of a sirtuin include, for example, analogs of isonicotinamide, such as, for example, compounds of formulas 11-14, and/or analogs of O-acetyl-ADP-ribose, such as, for example, compounds of formulas 15-18. A compound may have an EC50 for activating the deacetylase activity of a sirtuin of less than about 1 nM, less than about 10 nM, less than about 100 nM, less than about 1 µM, less than about 10 µM, less than about 100 µM, or from about 1-10 nM, from about 10-100 nM, from about 0.1-1 µM, from about 1-10 µM or from about 10-100 µM. A compound may activate the deacetylase activity of a sirtuin by a factor of at least about 5, 10, 20, 30, 50, or 100, as measured in an acellular assay or in a cell based assay as described in the Examples. A compound may cause at least a 10%, 30%, 50%, 80%, 2 fold, 5 fold, 10 fold, 50 fold or 100 fold greater induction of the deacetylase activity of SIRT1 relative to the same concentration of resveratrol or other compound described herein. A compound may also have an EC50 for activating SIRT5 that is at least about 10 fold, 20 fold, 30 fold, 50 fold greater than that for activating SIRT1.

In an exemplary embodiment, the methods and compositions described herein may include a combination therapy comprising (i) at least one sirtuin-activating compound that reduce the Km of a sirtuin for its substrate or NAD+ by a factor of at least about 2, 3, 4, 5, 10, 20, 30, 50 or 100, and (ii) at least one sirtuin-activating compound that increases the Vmax of a sirtuin by a factor of at least about 2, 3, 4, 5, 10, 20, 30, 50 or 100. In one embodiment, a combination therapy may comprise (i) at least one sirtuin-activating compound of formula 1-10, and (ii) at least one sirtuin-activating compound of formula 11-18.

A compound may traverse the cytoplasmic membrane of a cell. For example, a compound may have a cell-permeability of at least about 20%, 50%, 75%, 80%, 90% or 95%.

Compounds described herein may also have one or more of the following characteristics: the compound may be essentially non-toxic to a cell or subject; the compound may be an organic molecule or a small molecule of 2000 amu or less, 1000 amu or less; a compound may have a half-life under normal atmospheric conditions of at least about 30 days, 60 days, 120 days, 6 months or 1 year; the compound may have a half-life in solution of at least about 30 days, 60 days, 120 days, 6 months or 1 year; a compound may be more stable in solution than resveratrol by at least a factor of about 50%, 2 fold, 5 fold, 10 fold, 30 fold, 50 fold or 100 fold; a compound may promote deacetylation of the DNA repair factor Ku70; a compound may promote deacetylation of RelA/p65; a compound may increase general turnover rates and enhance the sensitivity of cells to TNF-induced apoptosis.

The effect of a compound on the activity of a sirtuin, such as SIRT1, may be determined as described, e.g., in Howitz et al., supra or as follows. For instance, sirtuin proteins may be contacted with a compound in vitro, e.g., in a solution or in a cell. In one embodiment, a sirtuin protein is contacted with a compound in a solution and an activity of the sirtuin, e.g., its ability to deacetylate a protein, such as a histone or, p53, or portions thereof, is determined. Generally, a sirtuin is activated or inhibited by a compound when at least one of its biological activities, e.g., deacetylation activity, is higher or lower, respectively, in the presence of the compound than in its absence. Activation or inhibition may be by a factor of at least about 10%, 30%, 50%, 100% (i.e., a factor of two), 3, 10, 30, or 100.

Whether a sirtuin is activated or inhibited can be determined, e.g., by contacting the sirtuin or a cell or cell extract containing the sirtuin with a deacetylation target, such as a histone or, p53 protein, or portions thereof, and determining the level of acetylation of the deacetylation target. A higher level of acetylation of the target incubated with the sirtuin that is being tested relative to the level of acetylation of a control sirtuin indicates that the sirtuin that is being tested is activated. Conversely, a lower level of acetylation of the target incubated with the sirtuin that is being tested relative to the level of acetylation of a control sirtuin indicates that the sirtuin that is being tested is inhibited. The control sirtuin may be a recombinantly produced sirtuin that has not been contacted with a sirtuin-activating or -inhibiting compound.

Additional Exemplary Methods

Described herein are methods for treating or preventing obesity or generally weight gain, in a subject, such as to reduce the weight of the subject or reduce weight gain. A method may comprise administering to a subject, such as a subject in need thereof, a pharmaceutically effective amount of an agent that increases the activity or protein level of a sirtuin, such as SIRT1 or Sir2. A subject in need of such a treatment may be a subject who is obese, or likely to become obese, or who has, or is, likely to gain excess weight, as predicted, e.g., from family history. Exemplary agents are those described herein. A combination of agents may also be administered. A method may further comprise monitoring the weight of the subject and/or the level of activation of sirtuins, for example, in adipose tissue.

Also described herein are methods for treating or preventing a metabolic disorder, such as insulin-resistance or other precursor symptom of type II diabetes, type II diabetes or complications thereof. Methods may increase insulin sensitivity or decrease insulin levels in a subject. A method may comprise administering to a subject, such as a subject in need thereof, a pharmaceutically effective amount of an agent that increases the activity or protein level of a sirtuin, such as SIRT1 or Sir2. A subject in need of such a treatment may be a subject who has insulin resistance or other precusor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy. Exemplary agents are those described herein.

A combination of agents may also be administered. A method may further comprise monitoring in the subject the state of any of these conditions and/or the level of activation of sirtuins, for example, in adipose tissue.

Other methods include administering to a subject of a combination of an agent that increases the activity or protein level of a sirtuin and an agent that increases the activity or protein level of an AMPK, e.g., other than an agent that activates a sirtuin. Activators of AMPK include AICAR or Metformin. Alternatively, the protein level of AMPK may be increased by introducing into the cell a nucleic acid encoding AMPK. The nucleotide sequence of the catalytic domain (α1) of human AMPK has the nucleotide sequence set forth in GenBank Accession No. NM_206907 and encodes a protein having the amino acid sequence set forth in GenBank Accession No. NP_996790. The nucleotide sequence of the non-catalytic domain (β1) of human AMPK has the nucleotide sequence set forth in GenBank Accession No. NM_006253 and encodes a protein having the amino acid sequence set forth in GenBank Accession No. NP_006244. The nucleotide sequence of the non-catalytic domain (γ1) of human AMPK has the nucleotide sequence set forth in GenBank Accession No. NM_212461 and encodes a protein having the amino acid sequence sets forth in GenBank Accession No. NP_997626. To increase the protein level of human AMPK in a cell, it may be necessary to introduce nucleic acids encoding each of the subunits of the protein. Nucleic acid sequences encoding the different subunits may be contained on the same or separate nucleic acid molecules.

Other diseases that may be treated by administering an agent that increases the activity or protein level of a sirtuin and/or AMPK include certain renal diseases including glomerulonephritis, glomerulosclerosis, nephrotic syndrome, hypertensive nephrosclerosis. These compounds may also be useful for improving cognitive functions in dementia, treating diabetic complications, psoriasis, polycystic ovarian syndrome (PCOS) and prevention and treatment of bone loss, e.g. osteoporosis.

Additional diseases and conditions that will benefit from weight loss and can be treated as described herein include: high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholescystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self esteem). Stunkard A J, Wadden T A. (Editors) Obesity: theory and therapy, Second Edition. New York: Raven Press, 1993. Finally, patients with AIDS can develop lipodystrophy or insulin resistance in response to combination therapies for AIDS. Accordingly, any of these conditions can be treated or prevented by the methods described herein for reducing or preventing weight gain.

Also provided herein are methods for stimulating weight gain. A method may comprise administering to a subject, such as a subject in need thereof, a pharmaceutically effective amount of an agent that decreases the activity or protein level of a sirtuin, such as SIRT1 or Sir2. A subject in need of such a treatment may be a subject who has cachexia or likely to develop cachexia. Exemplary agents are those described herein. A combination of agents may also be administered. A method may further comprise monitoring in the subject the state of the disease or of activation of sirtuins, for example, in adipose tissue.

Methods for stimulating fat accumulation in cells may be used in vitro, to establish cell models of weight gain, which may be used, e.g., for identifying other drugs that prevent weight gain.

A method for stimulating weight gain or fat accumulation in a cell or subject may further comprise decreasing the activity or protein level of an AMPK. This can be achieved, e.g., by inhibiting the expression, transcription, translation or post-tanslational modification of at least one of the three subunits of AMPK, such as the catalytic subunit. Techniques known in the art, such as RNAi, antisense and ribozyme can be used. In addition, dominant negative mutants may be expressed in the cell. Dominant negative mutants, such as having a mutated AMPK alpha subunit are described, e.g., in Minokoshi et al. (2004) Nature 428:569; Xing et al. (2003) J. Biol. Chem. 278:28372 and Woods et al. (2000) Mol. Cell. Biol. 20:6704. Compounds that inhibit AMPK expression or activity may also be used. An exemplary compound is described in Zhou et al. (2001) J. Clin. Invest. 108:1167.

Also provided herein are methods for modulating adipogenesis or fat cell differentiation, whether in vitro or in vivo. In particular, high circulating levels of insulin and/or insulin like growth factor (IGF) 1 will be prevented from recruiting preadipocytes to differentiate into adipocytes. Such methods may be used to modulate obesity. A method for inhibiting adipogenesis may comprise contacting a cell with an agent that increases the activity or protein level of a sirtuin, such as a sirtuin activating compound, e.g., a compound described herein. A method for stimulating adipogenesis may comprise contacting a cell with an agent that decreases the activity or protein level of a sirtuin, such as a sirtuin inhibiting compound, e.g., a compound described herein.

Based at least on the fact that resveratrol has been shown herein to activate AMPK, resveratrol and other sirtuin activating compounds may be used for treating or preventing conditions that can benefit from AMPK modulation, e.g., which are associated with and/or regulated by AMPK, in addition to those described above. Exemplary conditions include clinical symptoms associated with hypoxia or ischemia (myocardial infarction, stroke), and disorders of nutrition (see U.S. Pat. No. 6,124,125).

Similarly, any compound that activates AMPK may be used for the same purposes as sirtuin activating compounds may be used, e.g., to extend lifespan, to make cells more resistant to stress and to protect cells against apoptosis.

Other methods provided herein are methods for reducing appetite, or increasing satiety, thereby causing weight loss or avoidance of weight gain. Methods may include administrating to a subject, e.g., a subject in need thereof, an amount of a sirtuin activator or an agent that increases the protein level of a sirtuin in the subject. A subject in need of such a treatment may be a subject who is overweight, obese or a subject likely to become overweight or obese. The method may comprise administering daily, every other day, or once a week, a dose, e.g., in the form of a pill, to a subject. The dose may be an "appetite reducing dose." Such a dose may be, e.g., one pill of Longevinex™ daily.

Assays for determining the likelihood that a subject has or will develop weight gain, obesity, insulin resistance, diabetes or precursor symptoms or conditions resulting therefrom, are also provided. Such assays may comprise determining the level activity or expression (e.g., mRNA, pre-mRNA or protein) of a sirtuin, such as SIRT1, or AMPK in a subject. A low level of sirtuin activity or expression in a subject is likely to indicate that the subject has or is likely to develop weight gain, obesity, insulin resistance, diabetes, precursor symptoms thereof or secondary conditions thereof. Alternatively, a higher level of sirtuin activity or expression in a subject is likely to indicate that the subject has or is likely to develop weight loss and be protected from developing high weight associated diseases, such as insulin resistance and diabetes. Other assays include determining the activity or level of expression of a sirtuin and AMPK.

Also provided herein are methods for identifying compounds that modulate weight gain and/or treat or prevent insulin resistance (or sensitivity) or diabetes. A method may comprise identifying an agent that modulates the activity or protein level of a sirtuin and testing whether the test agent modulates weight gain and/or can be used for treating or preventing insulin resistance or diabetes. The first step of the method may comprise contacting a sirtuin with a test agent and determining the effect of the test agent on the activity of the sirtuin, e.g., SIRT1, as described, e.g., in Howitz et al., supra. The first step of the method may also comprise contacting a cell comprising a sirtuin with a test agent and determining the effect of the test agent on the activity of or expression level of the sirtuin. Expression levels of a sirtuin may be determined by measuring the mRNA, pre-mRNA or protein level of the sirtuin. The second step of the method may comprise testing the agent in an animal model for obesity, insulin resistance and/or diabetes. Such animal models are well known in the art. Screening methods may further comprise a step to determine the toxicity or adverse effects of the agents.

Other screening assays comprise identifying agents that modulate AMPK activity or protein levels. There is a need for compounds that activate AMPK but do not have the toxicities or adverse effects of known AMPK activators, such as metformin/phenformin.

Pharmaceutical Formulations and Administration Modes

Pharmaceutical compositions for use in accordance with the present methods may be formulated in conventional manner using one or more physiologically acceptable carriers or excipients. Thus, sirtuin-activating or -inhibiting compounds and their physiologically acceptable salts and solvates may be formulated for administration by, for example, injection, inhalation or insufflation (either through the mouth or the nose) or oral, buccal, parenteral or rectal administration. In one embodiment, the compound is administered locally, at the site where the target cells, e.g., fat cells, are present, i.e., in the adipose tissue.

Compounds can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozanges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

Polyphenols such as resveratrol can oxidize and lose sirtuin-stimulatory activity, especially in a liquid or semi-solid form. To prevent oxidation and preserve the sirtuin-stimulatory activity of polyphenol-containing compounds, the compounds may be stored in a nitrogen atmosphere or sealed in a type of capsule and/or foil package that excludes oxygen (e.g. Capsugel™).

For administration by inhalation, the compounds may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Controlled release formula also include patches.

Pharmaceutical compositions (including cosmetic preparations) may comprise from about 0.00001 to 100% such as from 0.001 to 10% or from 0.1% to 5% by weight of one or more compounds described herein.

In one embodiment, a compound described herein, is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions and gels.

Compounds may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's, cited in the preceding section, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols (PEGs) of varying molecular weight; again, reference may be had to Remington's, supra, for further information.

Compounds may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum such as that which may be obtained under the trademark Aquaphor R™ from Beiersdorf, Inc. (Norwalk, Conn.).

Compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Compounds may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifer") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono-di- and triglycerides, mono- and di-esters of PEG (e.g., oleoyl macrogol glycerides), etc.

Compounds may be incorporated into gel formulations, which generally are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in formulations, e.g., topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation.

A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide ($C_{10}$MSO) and tetradecylmethyl sulfboxide; pyrrolidones such as 2-pyrrolidone, N-methyl-2-pyrrolidone and N-(-hydroxyethyl)pyrrolidone; urea; N,N-diethyl-m-toluamide; $C_2$-$C_6$ alkanediols; miscellaneous solvents such as dimethyl formamide (DMF), N,N-dimethylacetamide (DMA) and tetrahydrofurfuryl alcohol; and the 1-substituted azacycloheptan-2-ones, particularly 1-n-dodecylcyclazacycloheptan-2-one (laurocapram; available under the trademark AzoneR™ from Whitby Research Incorporated, Richmond, Va.).

Examples of solubilizers include, but are not limited to, the following: hydrophilic ethers such as diethylene glycol monoethyl ether (ethoxydiglycol, available commercially as TranscutoleR™ and diethylene glycol monoethyl ether oleate (available commercially as SoftcutolR™); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as LabrasolR™); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in formulations, e.g., anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Topical skin treatment compositions can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507. Accordingly, also provided are closed containers containing a cosmetically acceptable composition as herein defined.

In an alternative embodiment, a pharmaceutical formulation is provided for oral or parenteral administration, in which case the formulation may comprise an activating compound-containing microemulsion as described above, and may contain alternative pharmaceutically acceptable carriers, vehicles, additives, etc. particularly suited to oral or parenteral drug administration. Alternatively, an activating compound-containing microemulsion may be administered orally or parenterally substantially as described above, without modification.

Administration of a sirtuin activator or inhibitor may be followed by measuring a factor in the subject, such as measuring the activity of the sirtuin. In an illustrative embodiment, a cell is obtained from a subject following administration of an activating or inhibiting compound to the subject, such as by obtaining a biopsy, and the activity of the sirtuin or sirtuin expression level is determined in the biopsy. Alternatively, biomarkers, such as plasma biomarkers may be followed. Biomarkers may be adipose cell derived secretory proteins, such as leptin, adiponectin, and resistin. The cell may be any cell of the subject, but in cases in which an activating compound is administered locally, the cell is preferably a cell that is located in the vicinity of the site of administration. The cell may be an adipocyte.

Other factors that may be monitored include weight, body mass, blood glucose sugar levels, blood lipid levels and any other factor that may be measured for monitoring diseases or conditions described herein.

Introduction and expression of a nucleic acid encoding a sirtuin, an AMPK or molecules that will reduced the protein level of a sirtuin or AMPK in a cell, e.g., an siRNA, may be accomplished using an expression vector. Exemplary expression vectors include adenoviral vectors or adenoviral-associated viruses (AAV). These vectors, as well as others and methods for infecting target cells are well known in the art. Alternatively, nucleic acids may also be introduced into cells using liposomes or similar technologies.

Kits

Also provided herein are kits, e.g., kits for therapeutic purposes, including kits for modulating fat accumulation. A kit may comprise one or more agent that modulates sirtuin or AMPK protein activity or level, e.g., sirtuin activating or inhibitory compounds, such as those described herein, and optionally devices for contacting cells with the agents. Devices include syringes, stents and other devices for introducing a compound into a subject or applying it to the skin of a subject.

Further, a kit may also contain components for measuring a factor, e.g., described above, such as the activity of sirtuin proteins, e.g., in tissue samples.

Other kits include kits for diagnosing the likelihood of having or developing weight gain, obesity, insulin-resistance, diabetes, precursors thereof or secondary conditions thereof. A kit may comprise an agent for measuring the activity and or expression level of a sirtuin or AMPK.

Kits for screening assays are also provided. Exemplary kits comprise one or more agents for conducting a screening assay, such as a sirtuin, an AMPK or a biologically active portion thereof, or a cell or cell extract comprising such. Any of the kits may also comprise instructions for use.

The present description is further illustrated by the following examples, which should not be construed as limiting in any way. The contents of all cited references (including literature references, issued patents, published patent applications and GenBank Accession numbers as cited throughout this application) are hereby expressly incorporated by reference.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1

Resveratrol Promotes Fat Mobilization

This example shows that a compound that activates sirtuins, resveratrol, stimulates fat metabolism by reducing fat accumulation in *C. elegans*.

Wild-type N2 *C. elegans* worms were grown on OP50 bacteria and exposed overnight to vehicle (0.1% ethanol) alone or with 10, 50 or 100 μM of resveratrol (in ethanol). Fat accumulation was visualized with Nile Red staining, as described further below and in Ashrafi K, et al. Nature 421: 268-27 (2003).

The results, which are shown in FIG. 1, indicate that resveratrol treatment with 100 μM resulted in a 90% reduction of fat accumulation. Similarly, incubation of the worms in the presence of 10 μM or 50 μM of resveratrol showed a marked decrease in fat accumulation. The decrease in fat accumulation is as or more striking than treatments with AICAR, a know activator of AMPK and fatty acid oxidation.

Figure 2:
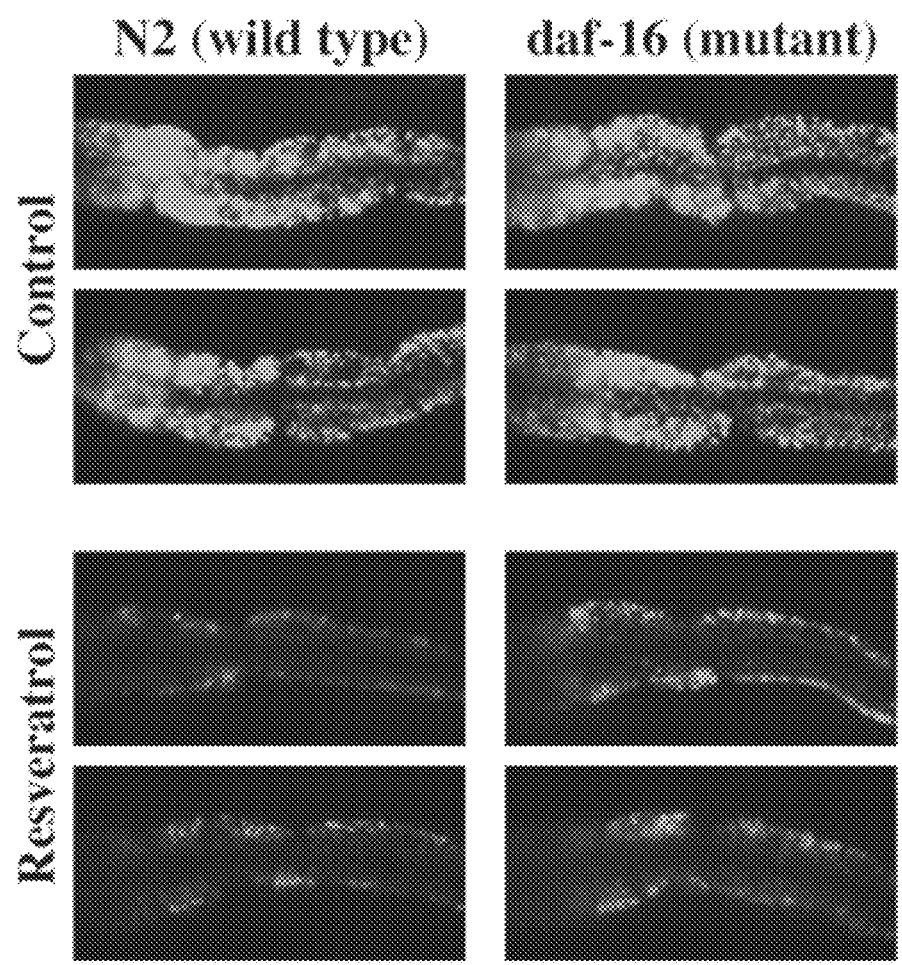
FIG. 2 is a series of photomicrographs that depict the effect of resveratrol to induce fat mobilization in a mutant worm with disrupted insulin signaling.

Sir2.1, which is activated by resveratrol, acts via the transcription factor DAF-16 to prolong lifespan in yeast (Tissenbaum and Guarente (2001) Nature 410:227). Similarly to the wild-type *C. elegans*, in DAF-16 mutant worms (mgDf47), which are defective in insulin-signaling (Wolkow, et al. Science 290:147, 2000), resveratrol stimulates fat mobilization and a decrease in fat accumulation (FIG. 2). This indicates that resveratrol signaling to fat metabolism in adult worms occurs via a pathway that is independent of DAF-16.

Accordingly, compounds in the resveratrol class that stimulate sirtuin proteins can promote fat mobilization in both wild-type and mutant *C. elegans*.

Example 2

Nicotinamide Promotes Fat Accumulation

If stimulators of sirtuin proteins decrease fat accumulation, inhibitors of sirtuin proteins, such as nicotinamide, should increase fat accumulation.

Figure 3:
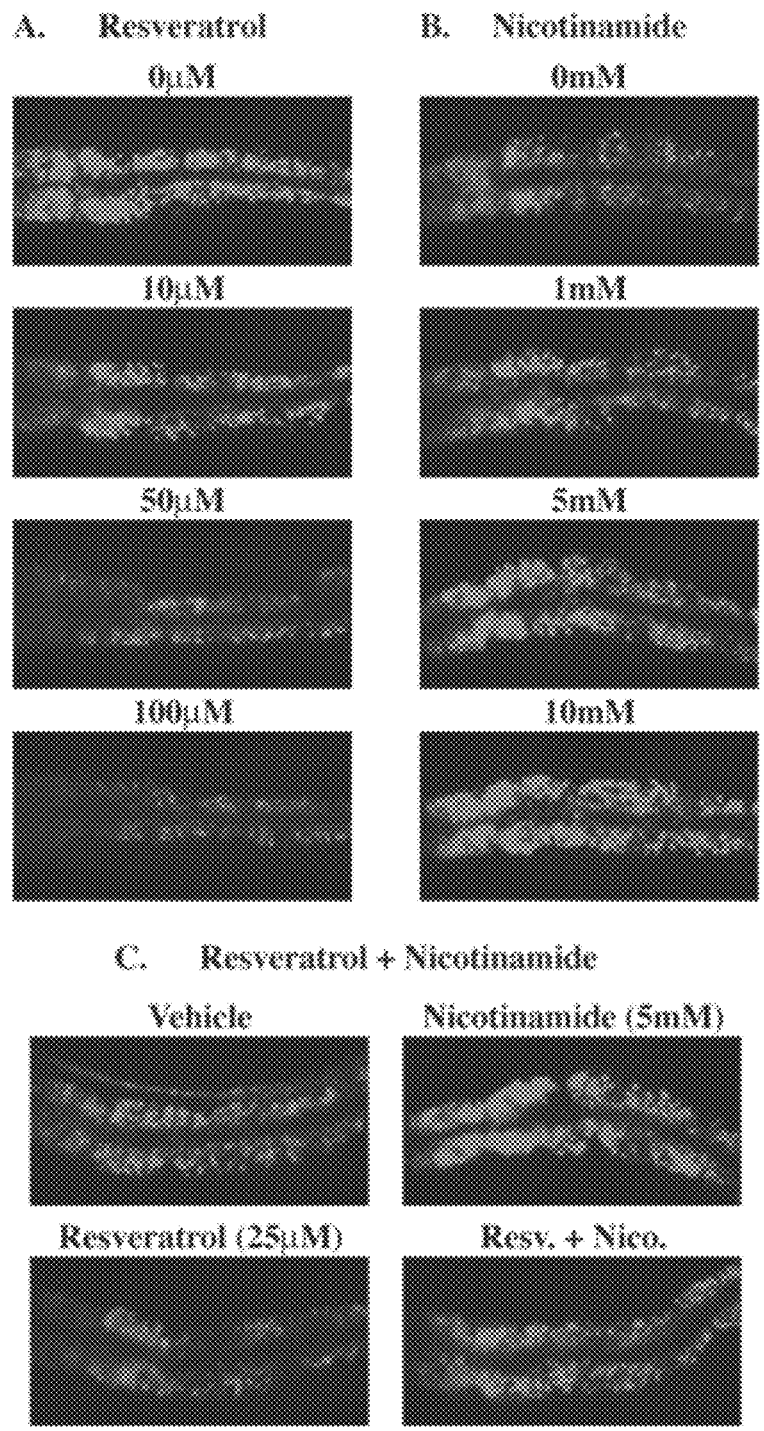
FIG. 3 is a series of photomicrographs that depict the effect of the sirtuin-inhibiting compound nicotinamide on fat accumulation. A. Resveratrol stimulates fat mobilization in wild type animals. Worms grown in the presence of vehicle alone, or 10 µM, 50 µM, and 100 µM resveratrol in vehicle were stained with Nile Red. B. Nicotinamide promotes fat accumulation in wild type animals. Nile Red staining in the presence of PBS alone, 1 mM, 5 mM and 10 mM nicotinamide is shown. C. Lower panel, Resveratrol and Nicotinamide have opposing effects on fat content. Effect of vehicle alone, resveratrol (25 µM), Nicotinamide (5 mM) or resveratrol 25 µM and Nicotinamide 5 mM in combination, on fat accumulation as assessed by Nile Red staining.

*C. elegans* worms were incubated overnight in the presence of 0, 1 or 10 mM nicotinamide, and stained with Nile-Red as described above. The results, which are shown in FIG. 3, indicate that the worms displayed a nicotinamide-concentration dependent increase in fat accumulation.

Example 3

Sir2 is Necessary for Resveratrol Mediated Fat Mobilization

Figure 4:
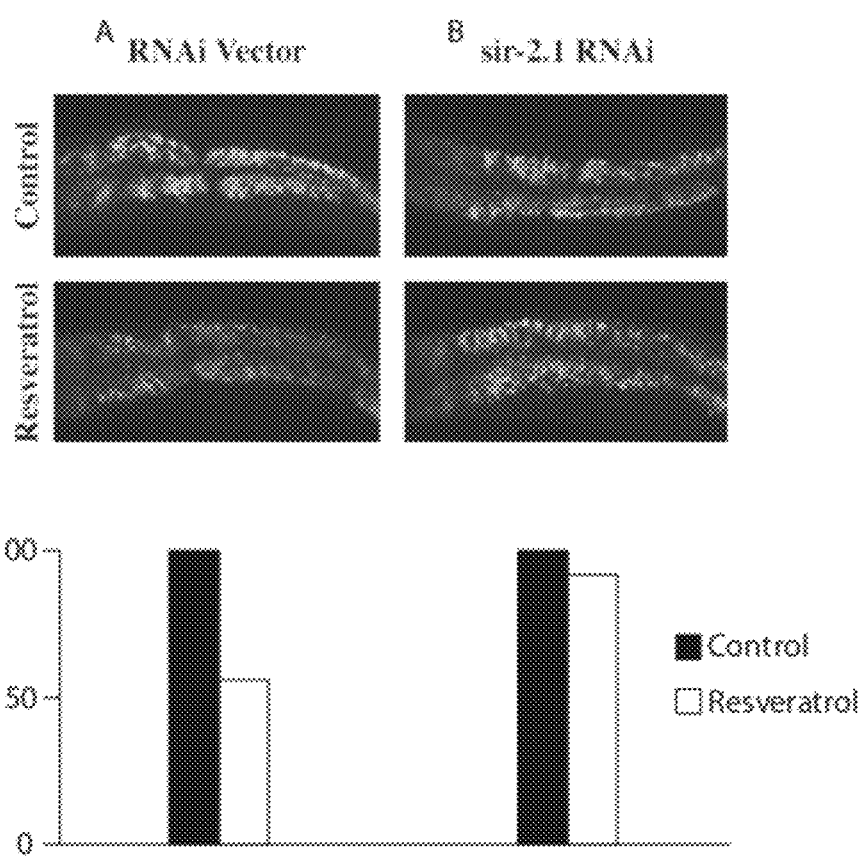
FIG. 4a-b is a series of photomicrographs that demonstrate fat content of C. elegans wild-type treated or not with Sir2.1 RNAi and incubated in the presence or absence of resveratrol.

The role of Sir2.1 in fat metabolism was shown in *C. elegans* worms in which Sir2.1 was RNA inactivated. Young adult worms were grown to adulthood in the presence of bacteria that carry RNAi vector alone or vector encoding Sir2.1 RNAi (R11A8.4), as described below. These worms were grown in the presence or absence of resveratrol, and stained with Nile-Red as described below. The results, which are shown in FIG. 4, indicate that the worms cultured in the presence of bacteria that carry Sir2.1 RNAi did not show resveratrol induced fat mobilization. These results further confirm that Sir2 is necessary for mediating the fat mobilization effect of resveratrol.

Example 4

AMPK is Necessary for Resveratrol Mediated Fat Mobilization

It was shown above that Sir2 is necessary for mediating the effect of resveratrol on fat mobilization. It is shown in this Example that AMPK is also necessary for mediating this effect. AMPK regulates diverse aspects of cell metabolism, glucose uptake and fatty acid oxidation. Many therapeutic agents and hormones that improve insulin sensitivity, e.g., 5-aminoimidazole-4-carboxamide-1-beta-D-ribofuranoside (AICAR) and Metformin, (decrease circulating insulin levels) are known to activate AMPK signaling to glucose uptake and fatty acid oxidation. In mammals, AMPK regulates fat metabolism by stimulating fatty acid oxidation via a series of complex steps that involve phosphorylation/inactivation of acetyl coA carboxylase, release of carnitine-palmitoyl transferase-1 (CPT-1) and carnitine octanoyl transferase (COT) from end product inhibition by malonyl coA, and transport of fatty acids into the mitochondria to be oxidized.

We have examined the *C. elegans* database and found two gene products that are highly related to mammalian AMPK, TOC1.8 and Par2.3; five genes encoding homologs of CPT-1 and one gene encoding a homolog of COT. *C. elegans* worms were incubated with bacteria carrying RNAi vector alone, or interfering RNA against TOC1.8 or F41E7.3, a *C. elegans* homologue of COT in the presence or absence of AICAR. Fat accumulation was visualized with Nile-Red, as described below. The results indicate that RNA inactivation of TOC1.8 or COT inhibits AICAR-stimulated fat mobilization. Thus, AICAR/AMPK signaling to fatty acid oxidation is conserved in worms and mammalian cells.

The effect of TOC1.8 and COT inactivation was then investigated in *C. elegans* incubated with resveratrol. *C. elegans* worms were incubated with bacteria carrying RNAi vector alone, or a vector encoding TOC1.8 or COT interfering RNA in the presence or absence of resveratrol. Fat accumulation was visualized with Nile-Red, as described below.

Figure 5A:
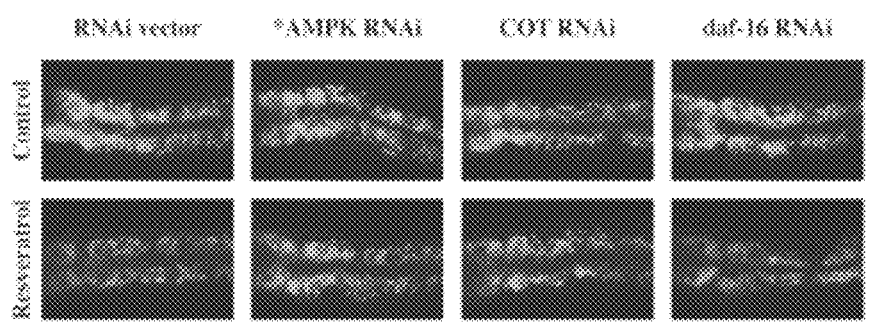
FIG. 5A a-d represents a series of photomicrographs of C. elegans incubated with empty RNAi vector (panel a); AMPK RNAi (panel b); COT RNAi (panel c) and DAF-16 RNAi (panel d) in the presence or absence of resveratrol.
Figure 5B:
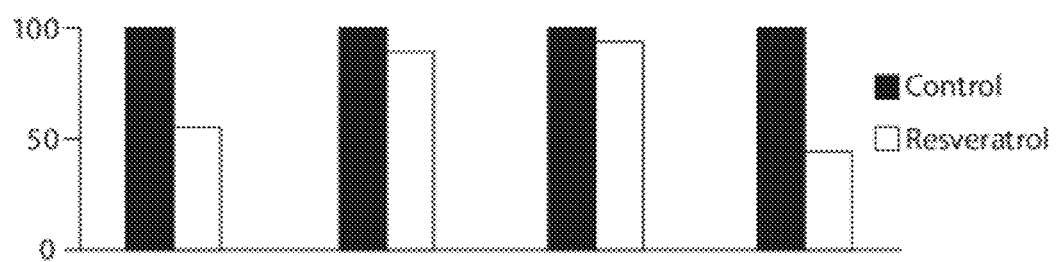
FIG. 5B represents the amount of Nile-Red staining in C. elegans shown in FIG. 5A.

The results are shown in FIG. 5. In the presence of the RNAi vector alone, resveratrol reduces fat content in normal worms by 75% (FIG. 5, panel a). However, RNA inactivation of TOC1.8, a homolog of mammalian AMPK or F41E7.3, a homolog of mammalian COT, blocks resveratrol-stimulated fat mobilization (see panels b and c of FIG. 5). Thus, AMPK is necessary for resveratrol-induced fat mobilization. Thus, we conclude that resveratrol, analogous to the direct AMPK activator AICAR, stimulates the AMPK signaling cascade to fat metabolism in worms. In contrast, RNA inactivation of DAF-16, the transcription factor downstream of insulin signaling to longevity, or inactivation of DAF-16 by mutation, had no effect on resveratrol-stimulated fat mobilization (see panel d of FIG. 5).

Thus, inhibition of the resveratrol effect by RNA inactivation of AMPK and COT suggests that mobilization of fat requires activation of the AMPK signaling cascade to fatty acid oxidation.

Example 5

AICAR and Resveratrol Stimulate AMPK and ACC Phosphorylation

RNA inactivation of AMPK and COT suggested that the effect of resveratrol and AICAR to mobilize fat in worms is dependent on activation of the AMPK signaling cascade to fatty acid oxidation. To obtain direct evidence of AMPK activation, we examined whether resveratrol-stimulated cells show increased phosphorylation of threonine residue 172 in AMPK or increased phosphorylation of acetyl coA carboxylase (ACC) at serine 79, modifications that correlate with activation of AMPK and inactivation of ACC, respectively.

CHO—HIR mammalian cells were washed in PBS and incubated overnight in serum-free DMEM before treatment with 500 μM AICAR (positive control) or 12.5 μM, 25 μM or 50 μM resveratrol. Cells were harvested after 30 minutes and lysates were immediately boiled in SDS and subjected to Western analysis with site-specific antibodies. Phosphorylation of AMPK at Thr172 indicates activation of the kinase. Active AMPK phosphorylates and inactivates ACC at serine 79.

Figure 6:
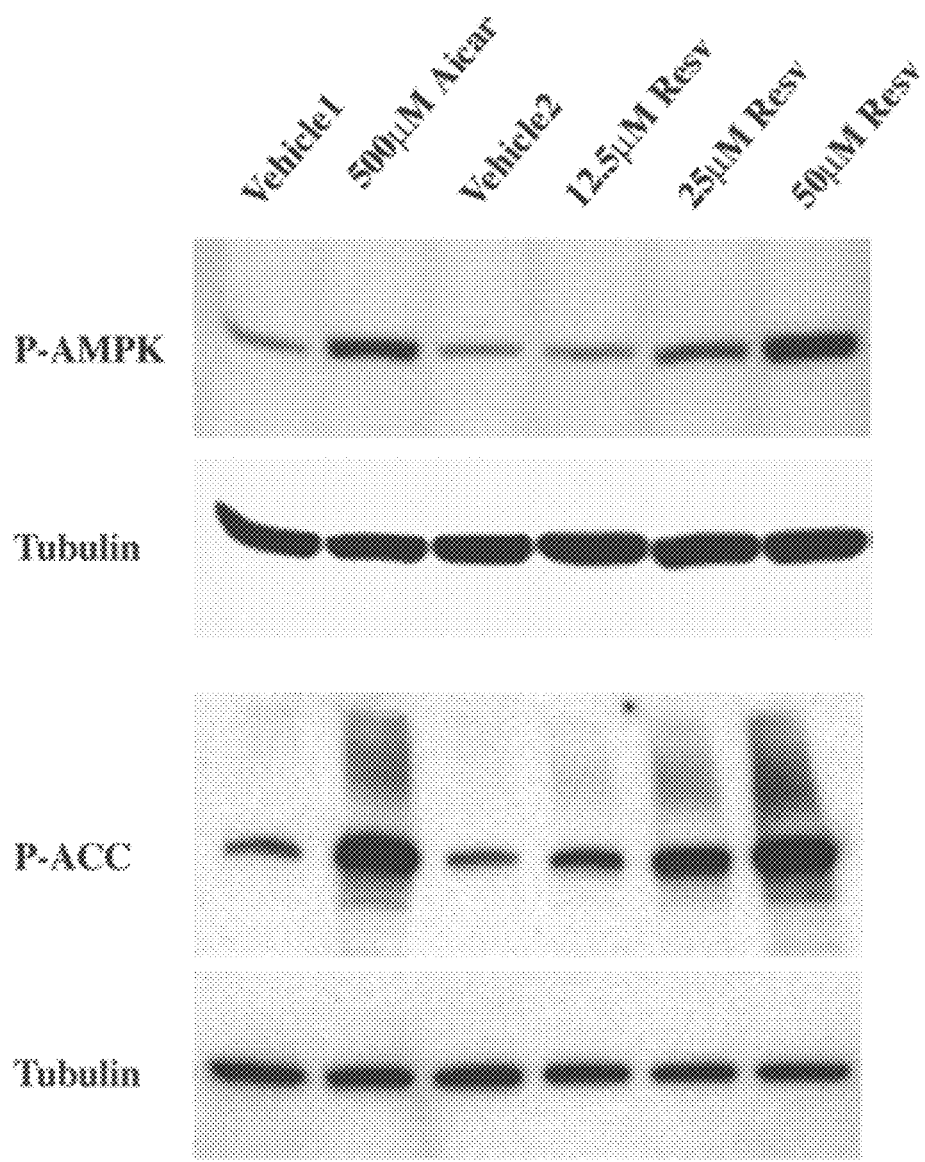
FIG. 6 shows a Western Blot of proteins from C. elegans incubated in the presence or absence (control) of 500 µM AICAR, vehicle 2 (DMSO), 12.5 µm, 25 µM or 50 µM resveratrol and stained for the presence of AMPK, ACC, or tubulin.

The results, which are shown in FIG. 6, indicate phosphorylation of AMPK on threonine 172 and phosphorylation of ACC on serine 79. Thus, like AICAR, resveratrol stimulates phosphorylation of AMPK and ACC. Accordingly, the ability of resveratrol to mobilize fat from lipogenic tissues is due, at least in part, to activation of AMPK signaling to fatty acid oxidation.

Figure 7:
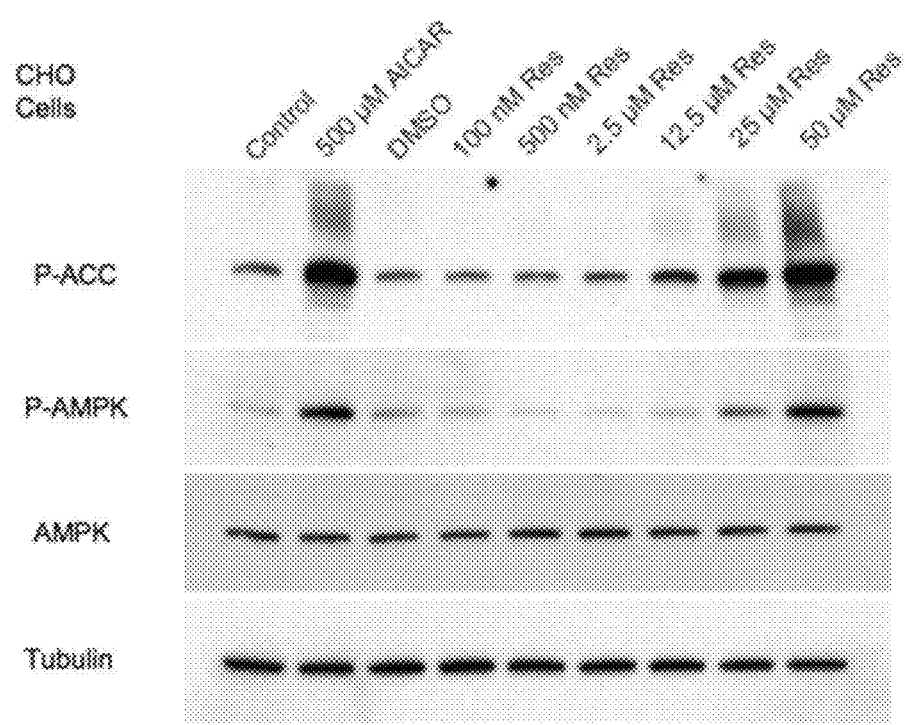
FIG. 7 shows a Western Blot of proteins incubated in the presence or absence (control) of 500 µM AICAR, DMSO, 100 nM, 500 nM, 2.5 µM, 12.5 µM, 25 µM or 50 µM resveratrol and stained for the presence of P-ACC, P-AMPK, AMPK, or tubulin.

CHO cells were also treated with 500 µM AICAR (positive control), DMSO, 100 nM, 500 nM, 2.5 µM, 12.5 µM, 25 µM, or 50 µM resveratrol and subject to Western Blot analysis as described above. Western blots were stripped and re-probed for phosphorylated (active) AMPK, total AMPK, phosphorylated acetyl CoA carboxylase (ACC), which is the downstream target of AMPK, and tubulin, which served as a loading control. FIG. 7 shows activation of AMPK in CHO cells with increasing concentrations of resveratrol.

Figure 8:
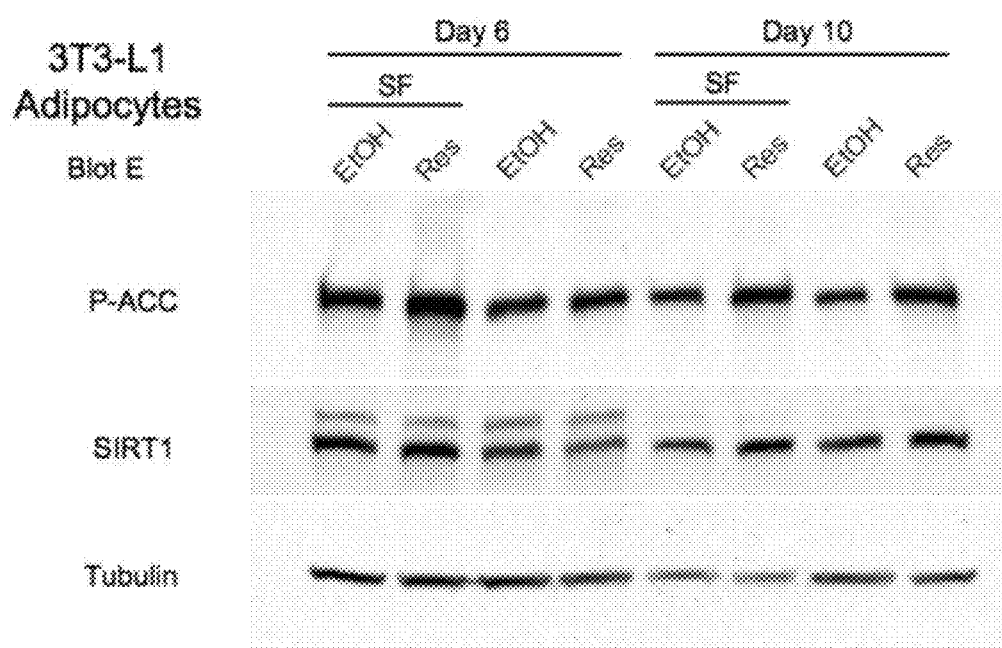
FIG. 8 is a Western Blot showing the phosphorylation of ACC in 3T3-L1 adipocytes treated either with ethanol or resveratrol and stained for the presence of P-ACC, SIRT1, or tubulin. In the lanes marked "SF", cells were left in serum free media overnight before harvesting.

Phosphorylation of ACC, which reflects AMPK activity, was also observed in 3T3-L1 adipocytes treated with either ethanol or resveratrol. 3T3-L1 cells were incubated with either ethanol or resveratrol and then harvested either 6 or 10 days after they were induced to differentiate into adipocytes from the parent 3T3 fibroblast cell line. FIG. 8 shows that resveratrol stimulated the phosphorylation of ACC at both day 6 and day 10. ACC was also phosphorylated when the cells were incubated in serum free media overnight before harvesting (lanes marked "SF"). The reason for the extra band in the SIRT1 blot at day 6 is unknown, but we hypothesize that it may be a modified form of SIRT1. Tubulin served as a loading control.

Figure 9:
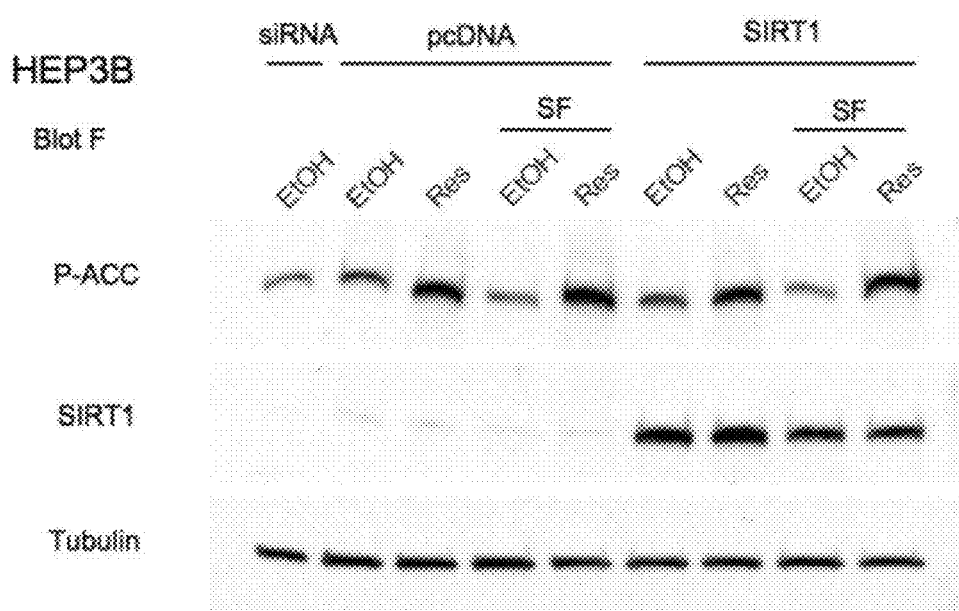
FIG. 9 is a Western Blot showing the phosphorylation of ACC in HEP3B human heptoma cells treated with either ethanol or resveratrol and stained for the presence of P-ACC, SIRT1, or tubulin. In the left lane, SIRT1 was knocked down. In the right four lanes, SIRT1 has been overexpressed.

Similar results were also observed for HEP3B human hepatoma cells. In this case phosphorylation of ACC was measured in cells were SIRT1 was overexpressed (see FIG. 9, 4 right lanes) and in cells were SIRT1 was knocked down (FIG. 9, left lane). Phosphorylation of ACC was not affected indicating that resveratrol may not be working through SIRT1 in this case. Tubulin served as a loading control.

Figure 10:
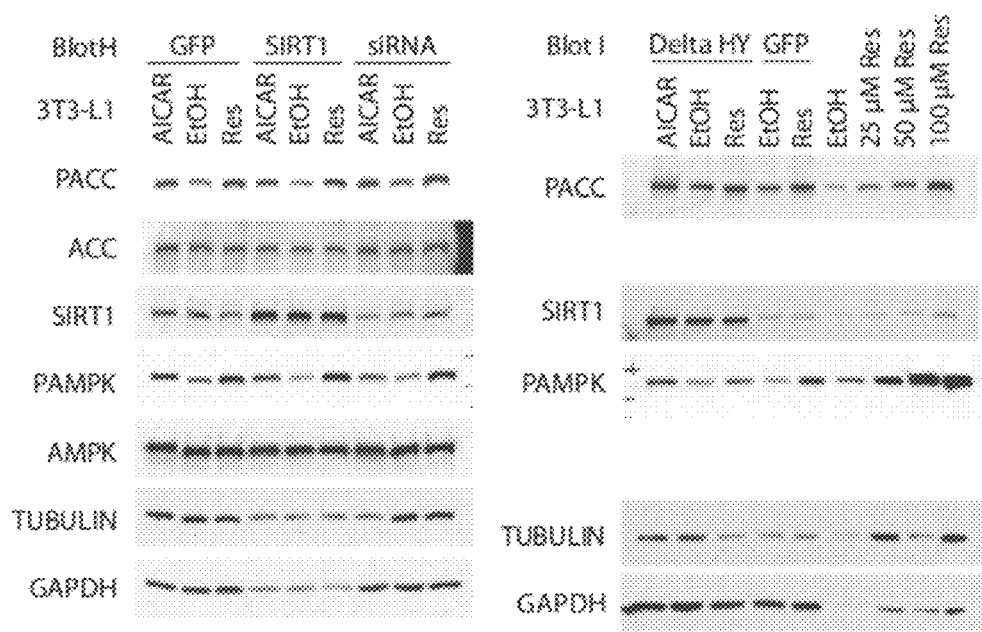
FIG. 10 is a Western Blot of proteins from 3T3-L1 adipocytes infected with either a control (GFP) retrovirus, SIRT1, SIRT1 siRNA, or SIRT1 dominant negative (delta HY). Cells were incubated in the presence of AICAR, ethanol, or resveratrol and stained for the presence of P-ACC, ACC, SIRT1, P-AMPK, AMPK, tubulin, or GAPDH. A dose response curve is shown on the far right of the blot.

To further investigate whether resveratrol is working through SIRT1, 3T3-L1 apidocytes were infected with a control (GFP) retrovirus, SIRT1, SIRT1 siRNA, or SIRT1 dominant negative (delta HY). Cells were treated with AICAR, ethanol, or resveratrol. As described above, cells were harvested and lysates were prepared for Western blot analysis with site-specific antibodies. FIG. 10 shows phosphorylation of ACC and AMPK, which reflects AMPK activity. Total protein for each is also shown. It is also noted that the loading controls, GAPDH and tubulin, are expressed but at extremely low levels in these cells and may only reflect the presence of undifferentiated 3T3 cells. FIG. 10 also shows a separate dose-response curve on the far right.

Figure 11:
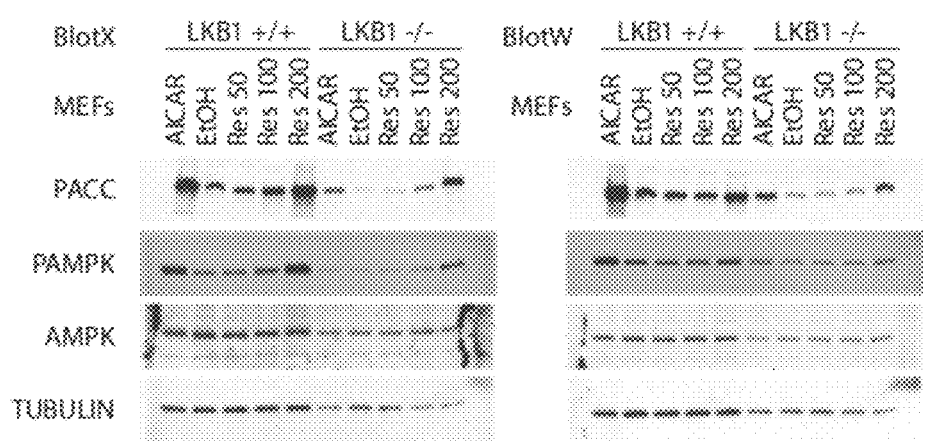
FIG. 11 is a Western Blot showing the effects of resveratrol in the presence or absence of AMPK kinase, LKB1. Mouse embryonic fibroblasts were incubated in the presence of AICAR, ethanol, 50, 100, 200 µM of resveratrol. Blots were stained for the presence of P-ACC, P-AMPK, AMPK, or tubulin as indicated on the left.

Similar results were also observed in mouse embryonic fibroblast (MEFs). FIG. 11 shows that resveratrol still has effects in the absence of the known AMPK kinase, LKB 1. Cells in the left panel were incubated overnight without serum before harvesting; the cells on the right were not incubated under serum free conditions. While loading is lower for the LKB 1 −/− cells, resveratrol still causes an upregulation of both AMPK and ACC phosphorylation. Tubulin served as a loading control.

Example 6

Resveratrol Stimulates Fat Mobilization and Inhibits Adipogenesis in Mammalian Cells To obtain evidence that resveratrol affects fat metabolism in a physiologically relevant cell, we examined the effect of increasing concentrations of resveratrol on 3T3-L1 and NIH3T3 cell differentiation and fat content. 3T3-L1 or NIH3T3 cells were grown to confluence and allowed to pack in for 2 days at which point differentiation was initiated by addition of isobutylmethylxanthine, dexamethasone and insulin in the presence of vehicle (ethanol alone) or resveratrol at concentrations of 0, 12.5 and 25 µM. After 10 days of differentiation, fat content was assessed by Oil Red O staining, as described below. The results, which are shown in FIG. 12, indicate that concentrations of 25 µM or higher resveratrol decreased the quantity of cellular fat in 3T3-L1 and NIH3T3 cells. The results in NIH3T3 cells confirm the results obtained in *C. elegans*. The results indicate that resveratrol inhibits adipogenesis (or adipocyte differentiation).

AICAR stimulates AMPK signaling and inhibits adipogenesis in 3T3 cells. To distinguish whether the effect of resveratrol was to inhibit differentiation or mobilize fat from 3T3 cells, we examined whether resveratrol inhibited the expression of adipogenic transcription regulators such as PPAR-γ. We found that cells exposed to resveratrol did not show an increase in PPAR-γ RNA, which typically accompany differentiation of the cells into adipocytes. This suggests that resveratrol inhibits differentiation of cells into adipocytes. This may also suggest that resveratrol inhibits PPAR-γ activity or expression.

Figure 13:
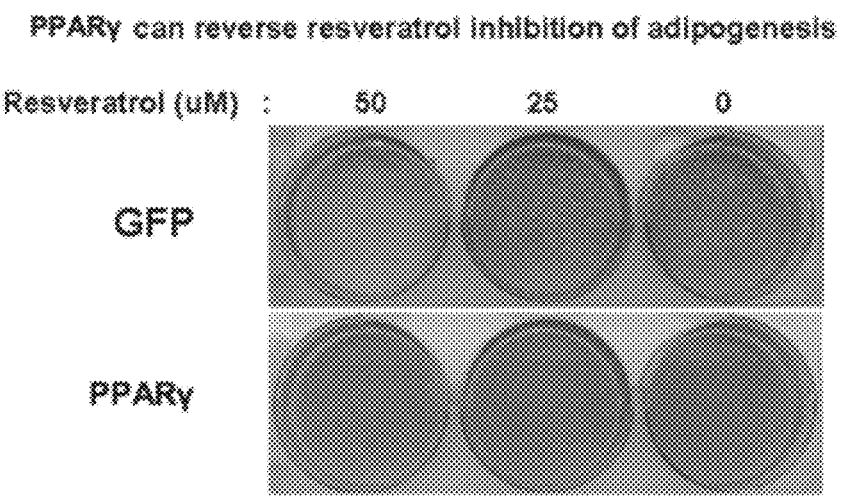
FIG. 13 shows that resveratrol inhibits adipogenesis, and that this is rescued by PPARγ. A marked decrease in PPARγ expression was detected in resveratrol-treated 3T3-L1 cells. In a separate experiment, 3T3-L1 cells were grown in the presence of virus encoding gfp or PPAR-gamma and 25 µM, 12.5 µM or 0 µM resveratrol in vehicle (ethanol). After 8 days of differentiation, cells were fixed and stained with Oil red O.

We then infected 3T3 preadipoctyes/adipocytes with pMX alone or pMX encoding PPAR-γ and examined the effect of resveratrol on 3T3 cell differentiation. 3T3-L1 and NIH3T3 cells were infected with a plasmid expressing GFP or PPAR-γ and grown to confluence. Cells were differentiated into adipocytes as described below in the presence of 0 µM, 25 µM or 50 µM resveratrol in vehicle (ethanol). After eight days of differentiation, cells were fixed and stained with Oil red O. As expected, overexpression of PPAR-γ partially negated inhibition of 3T3 preadipocyte differentiation by resveratrol (FIG. 13). This observation suggests that resveratrol inhibits PPAR-γ activated fat cell differentiation.

Figure 14:
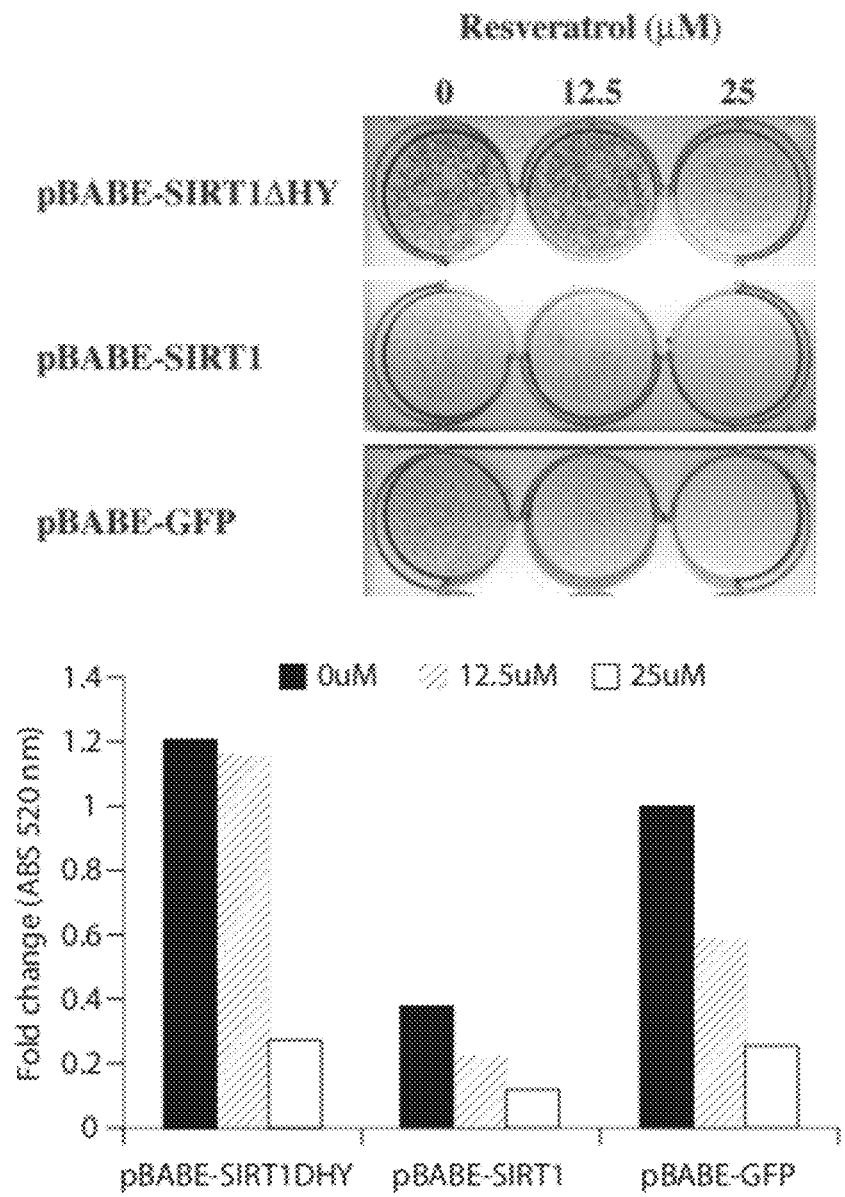
FIG. 14 shows that resveratrol inhibits lipid accumulation and the partial rescue by deacetylase deficient SIRT1. NIH3T3 cells were grown in the presence of virus encoding gfp, SIRT1 or deaceytlase deficient SIRT1. Cells were differentiated into adipocytes in the presence of 25 µM, 12.5 µM or 0 µM resveratrol in vehicle (ethanol). After 8 days of differentiation, cells were fixed and stained with Oil red O. Oil red O was extracted from stained cells and quantified.

To further examine whether resveratrol activation of sir2 could promote fat mobilization or inhibition of differentiation in mammalian cells, we infected growing cells with wild-type SIRT1 or a deacetylase deficient form of SIRT1. NIH3T3 cells were grown in the presence of virus encoding GFP, SIRT1 or the deacetylase deficient form of SIRT1 (SIRT1ΔHY) (described in Vaziri et al. (2001) Cell 107:149). Cells were differentiated into adipocytes in the presence of 0 µM, 12.5 µM or 25 µM resveratrol in vehicle (ethanol). After eight days of differentiation, cells were fixed and stained with Oil red O. The results, which are shown in FIG. 14, indicate that 3T3 cells that overexpress wild-type SIRT 1 show decreased fat content as compared to cells infected with virus encoding GFP (a negative control), while 3T3 cells that overexpress the deacetylase deficient form of SIRT1 show an increase in fat content. These results confirm the effect seen in worms, i.e., that SIRT activation by resveratrol appears to decrease fat content and SIRT1 inactivation by nicotinamide appears to increase fat content. Thus we conclude that sirtuins play a direct role in regulating fat cell differentiation and content.

The decrease in Oil Red O staining seen with SIRT1 overexpression approaches the level seen when cells are stimulated with resveratrol. This observation raised the question whether the SIRT1 deacetylase deficient mutant would reverse the effect of resveratrol. We found that in the SIRT1 deacetylase deficient mutant, the decrease in fat content normally induced by resveratrol was indeed partially reduced.

Thus, these results indicate that, in addition to reducing fat accumulation, resveratrol inhibits adipogenesis, and that this inhibition is also mediated at least in part by Sir2.

Example 7

Materials and Methods for Examples 3-6

Strains

*C. elegans* strains were maintained as described at 25° C., except when noted (Brenner (1974) Genetics 77:71). The wild type reference strain was N2 Bristol; the mutant strains were: sir-2.1 (ok434), T01C8.1 (ok524), and daf-16 (mgDf47). Daf-16 (mgDf47) was obtained from the Ruvkun laboratory, MGH; all other strains were obtained from the *Caenorhabditis* Genetics Center (from *C. Elegans* Gene Knockout Consortium).

Growth Conditions and Resveratrol Exposure

Synchronized starved L1 worms were grown in the presence of Nile Red. Strains were grown on NGM plates at 25° C. for approximately 48 hours until the young adult stage was reached. 20-30 young adult worms were then washed 2× with M9 buffer and transferred to new NGM/Nile red experimental plates that contained either OP50 or HTT5 *E. coli* carrying the L4440 RNAi control vector. For experiments comparing the effect of nicotinamide and resveratrol on fat mobilization, OP50 plates were coated with vehicle alone or Nicotinamide (in PBS), or vehicle alone and Resveratrol (in Ethanol or DMSO).

RNAi plates were seeded with HTT5 *E. coli* carrying either the L4440 RNAi vector control or the specific RNAi clones T01C8.1, AMPK; R11A8.4, sir-2.1; or F41E7.6 COT in the presence or absence of 100 µM resveratrol. Young adults were transferred to plates containing the appropriate vector, Nile Red stain and drug then maintained at 25° C. Nile Red staining was assessed 24 hours after resveratrol treatment by UV microscopy.

Resveratrol/Nicotinamide Dilutions

Resveratrol (Indofine #024964) was dissolved in Ethanol or DMSO to a 10 mM stock solution. Resveratrol was added to 60 mm NGM agar dishes containing either OP50 or RNAi expressing bacteria (HT115) to a final concentration of 10 µm, 50 µm, and 100 µM. Nile Red was also added to plates to a final concentration of 0.05 µg/ml. Nicotinamide (Supelco #47865-U) was diluted in PBS including Nile Red and added to 60 mM dishes containing OP50 to a final concentration of 1 mM, 10 mM, or 100 mM.

Fat Staining

Nile Red: Nile Red Powder (Sigma #N-3013) was dissolved in acetone at 500 µg/ml, diluted in 1× Phosphate Buffered Saline (PBS) including appropriate drug and applied to surface of Nematode Growth Media (NGM) plates previously seeded with OP50 or RNAi bacteria, at a final concentration of 0.05 µg/ml. Fat content was monitored and recorded by fluorescence microscopy.

Fluorescence Microscopy and Image Acquisition

Nile Red Staining was visualized by using a Nikon TE2000S microscope equipped with a CY3 filter (emission 535-685 nm). Images were captured using a SPOT RT monochrome digital camera attached to the Nikon Microscope with SPOT RT software v3.5. All Nile red images were acquired using identical settings and exposure times and then changed to red palette.

Feeding RNAi

HT115 *E. Coli* carrying the RNAi vector, L4440, were used for maintenance feeding. Bacteria containing experimental RNAi clones were cultured in 10 ml Luria Broth media containing 50 µg/ml ampicillin for 18 hours. 350 µl of each culture was spotted to a 60 mm dish containing NGM agar, 6 mM IPTG and 25 µg/ml carbenicillin. After overnight incubation (at room temp), Nile Red was added on top of each dish to a final concentration of 0.05 µg/ml along with the experimental compounds indicated in the figure legends. Nile Red staining was assessed after 24 hrs by UV microscopy. For each batch of RNAi clones tested, L4440 (vector alone) was included. A phenotype was assigned only if a majority of the animals displayed the phenotype. All phenotypes were confirmed by at least three additional rounds of testing.

Cell Culture and Oil Red O Staining

3T3-L1 and NIH3T3 cells were maintained in DMEM plus 10% calf serum. Adipocyte differentiation of 3T3-L1 cells was performed as described previously (MacDougald, O. A. and Lane, M. D. (1995). Transcriptional regulation of gene expression during adipocyte differentiation. Annu. Rev. Biochem. 64, 345-373). NIH3T3 cells were induced to form adipocytes under the same conditions as 3T3-L1 cells, but with 6 days of treatment with insulin, dexamethasone, and isobutylmethylxanthine in 10% fetal calf serum after cells reach confluence. The staining of adipocytes with Oil Red-0 and quantitation was performed as described previously (Ramirez-Zacarias J L, Castro-Munozledo F, Kuri-Harcuch W. Histochemistry. 1992 July; 97(6):493-7).

Retrovirus Production and Infection

The mammalian retrovirus expression vector pMX (described in Tontonoz et al. (1994) Genes Dev. 8:1224, and provided by Gary Nolan) was used to construct and express full-length murine PPARγ2 (Tontonoz et al., supra), human SIRT1, human SIRT1ΔHY (Vaziri et al., supra) and eGFP. Recombinant retroviruses were generated by calcium phosphate transfection of the retroviral constructs into Phoenix ecotropic packaging cells (described in Tontonoz et al., supra, and provided by Gary Nolan), which were maintained in DMEM plus 10% fetal calf serum. Media was changed the next day and viral supernatant was harvested twice at 48 and 72 hr post-transfection of packaging cells. Viral supernatant was passed through a 0.2 µM syringe filter and applied to pre-confluent 3T3-L1 and NIH3T3 cells after addition of polybrene to a final concentration of 6 µg/ml. Media was changed the next day and cells were allowed to grow to confluence before differentiation to adipocytes.

Example 8

Additional Sirtuin Activators Stimulate Fat Mobilization

Figure 15:
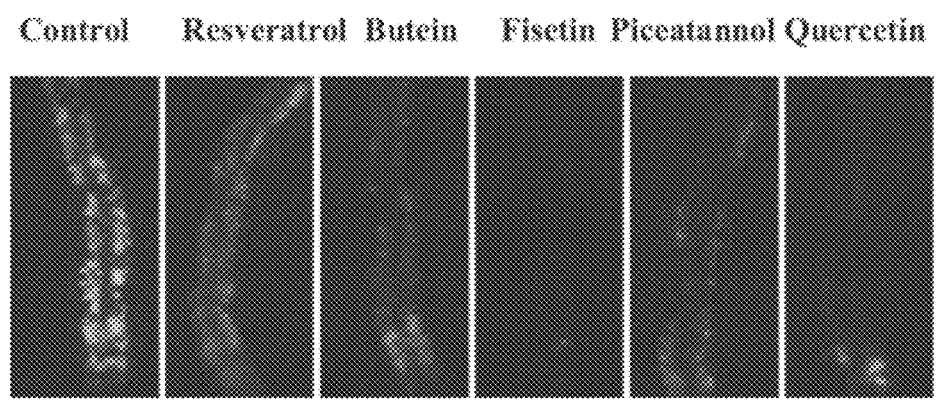
FIG. 15 shows the effect of polyphenols on C. elegans fat stores. C. elegans in L1 were exposed to Nile Red stain and vehicle (A, 20% v/v DMSO in PBS buffer) or 100 µM resveratrol, butein, fisetin, piceatannol, or quercetin for 48 hours. In each image, the head is positioned towards the bottom.
Figure 16:
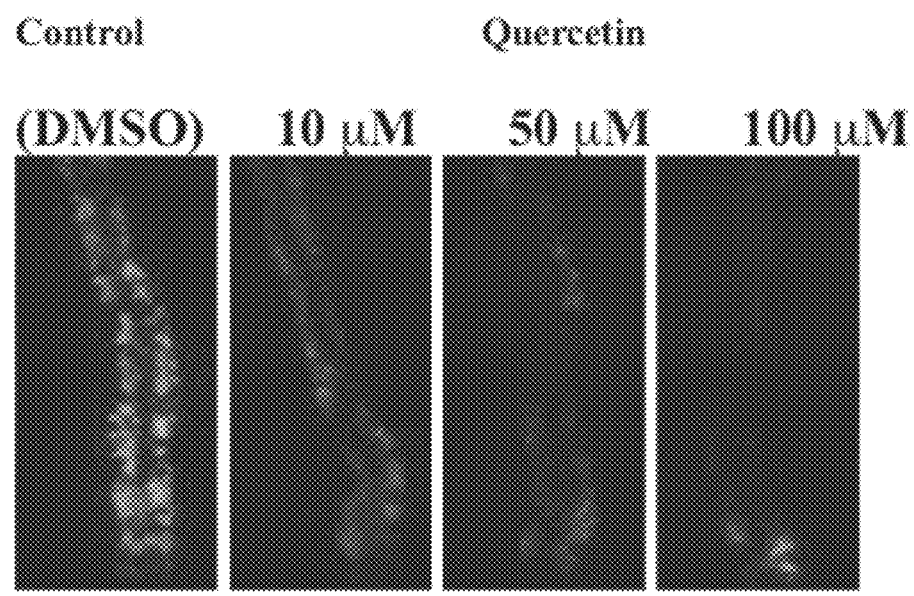
FIG. 16 shows the effect of quercetin on C. elegans fat stores. C. elegans in L1 were exposed to Nile Red and vehicle (20% v/v DMSO) or quercetin at 10 µM, 50 µM and 100 µM for 48 hours. In each image, the head is positioned towards the bottom.
Figure 17:
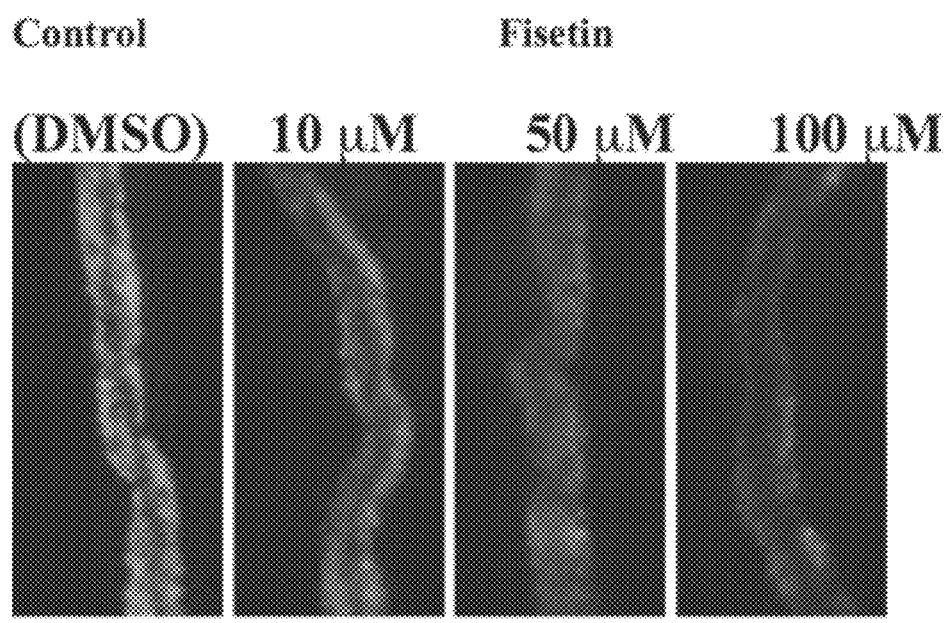
FIG. 17 shows the effect of fisetin on C. elegans fat stores. C. elegans in L1 stage were exposed to Nile Red and vehicle (A, 20% v/v DMSO) or fisetin at 10 µM, 50 µM and 100 µM for 48 hours. In each image, the head is positioned towards the bottom.

*C. elegans* worms were incubated in the presence or absence of 100 µM of the SIRT1 activators butein, fisetin, piceatannol and quercetin, and the fat content of the worms measured as described above. The results, which are shown in FIG. 15, indicated that these SIRT1 activators have a similar effect as resveratrol, i.e., they stimulate fat mobilization. Furthermore, as shown in FIGS. 16 and 17, quercetin and fisetin reduce fat accumulation at concentrations as low as 10 µM.

Example 9

Effects of Resveratrol Analogues on Fat Accumulation in C. elegans

Figure 18:
FIG. 18 shows the effect of 3,5-dihydroxy-4'-thiomethyl-trans-stilbene on C. elegans fat stores. Animals in L1 were treated with Nile Red stain and (A) 1% v/v DMSO or (B) 100 µM 3,5-dihydroxy-4'-thiomethyl-trans-stilbene for 24 hours. In each image, the head is positioned towards the bottom.
Figure 19:
FIG. 19 compares the effect of resveratrol and cis-stilbene (a resveratrol analogue) on C. elegans fat stores. Animals in L1 were exposed to Nile Red stain and (A) 2.5% v/v DMSO, (B) 100 µM resveratrol or (C) cis-stilbene for 48 hours. In each image, the head is positioned towards the bottom.

*C. elegans* worms were incubated in the absence (1% v/v DMSO) or presence of 100 µM 3,5-dihydroxy-4'-thiomethyl-trans-stilbene for 24 hours. Significant reduction of fat staining by 3,5-dihydroxy-4'-thiomethyl-trans-stilbene was observed (FIG. 18). Animals in L1 were also incubated in the absence (2.5% v/v DMSO) or presence of 100 µM resveratrol or 100 µM cis-stilbene for 48 hours. Significant reduction of fat staining by resveratrol is observed. No significant effect on worm fat staining is observed with cis-stilbene compared to the control (FIG. 19). Fat accumulation was visualized with Nile Red, a lipophilic stain, as described in Ashrafi et al., Nature 421:268-27 (2003).

Example 10

Figure 20:
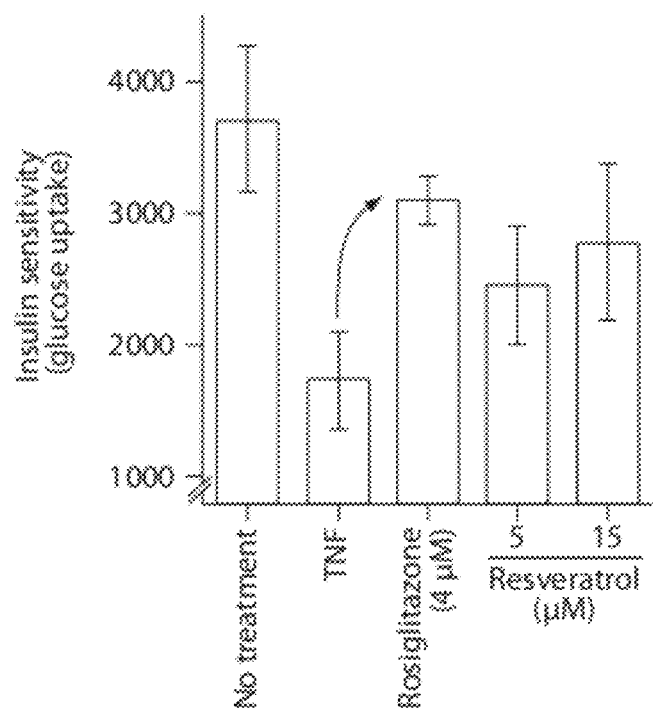
FIG. 20 shows the effect of resveratrol on TNF-alpha treated adipocytes that are insulin resistant. Lane 1, no treatment; lane 2, TNF-alpha treated; lane 3, TNF-alpha plus 4 µM roziglitazone (positive control); lane 4, TNF-alpha plus 5 µM resveratrol; and Lane 5, TNF-alpha plus 15 µM resveratrol.

Effects of Resveratrol on TNF-Alpha Treated Adipocytes that are Insulin Resistant This example shows that resveratrol boosts insulin sensitivity of adipocytes. Adipocytes were treated with TNF-alpha to induce insulin resistance as described in Kabayama et al., Glycobiology 15:21-29 (2005) and Wu et al., Mol. Cell. 3:151-8 (1999). Treatment with roziglitazone, a positive control, increases the uptake of radioactive glucose indicating increased insulin sensitivity of the TNF-alpha treated adipocytes. As shown in FIG. 20, treatment with 5 µM or 15 µM resveratrol partially rescued the TNF-alpha treated adipocytes restoring insulin sensitivity in the treated cells. The arrow in FIG. 20, shows the desired effect of increased radioactive-glucose uptake.

Example 11

Resveratrol, Like Other AMPK Activators, can Stimulate Fatty Acid Oxidation in Lipogenic Cells Insulin is the major hormone charged with promoting storage of excess energy as fat. In cells with lipogenic capacity, insulin signaling promotes fat deposition. When fat stores become excessive this process is referred to as dyslipogenesis. Dyslipogenesis, is associated with insulin resistance and the progressive increase in circulating insulin and triglycerides levels, propensity to hypertension, and atherosclerosis that is characteristic of metabolic syndrome [Muller-Wieland, D. and J. Kotzka, SREBP-1: gene regulatory key to syndrome X? Ann NY Acad Sci, 2002. 967: p. 19-27]. Insulin sensitizers, such as AICAR (5-aminoimidazole-4-carboxamide-1-beta-D-ribofuranoside) and metformin, activate AMP kinase and mobilize fat from non-adipose cells thereby reducing insulin resistance and serum lipid levels [Lin, H. Z., et al., Metformin reverses fatty liver disease in obese, leptin-deficient mice. Nat Med, 2000. 6 (9): p. 998-1003; Bergeron, R., et al., Effect of 5-aminoimidazole-4-carboxamide-1-beta-D-ribofuranoside infusion on in vivo glucose and lipid metabolism in lean and obese Zucker rats. Diabetes, 2001. 50 (5): p. 1076-82]. Ample evidence exists that polyphenolic compounds derived from wine reduce serum lipid levels and atherosclerotic plaque [Waddington, E., I. B. Puddey, and K. D. Croft, Red wine polyphenolic compounds inhibit atherosclerosis in apolipoprotein E-deficient mice independently of effects on lipid peroxidation. Am J Clin Nutr, 2004. 79 (1): p. 54-61]. Our observation that resveratrol activates AMP kinase suggested that this drug, analogous to AICAR and metformin, might be effective in reducing dyslipogenesis and increasing insulin sensitivity.

A plethora of reports indicate that AICAR and metformin activate AMPK, which in turn phosphorylates and inhibits acetyl coA carboxylase (ACC) (reviews by Kemp, B. E., et al., Dealing with energy demand: the AMP-activated protein kinase. Trends Biochem Sci, 1999. 24 (1): p. 22-5; Kemp, B. E., et al., AMP-activated protein kinase, super metabolic regulator. Biochem Soc Trans, 2003. 31 (Pt 1): p. 162-8; Viollet, B., et al., The AMP-activated protein kinase alpha2 catalytic subunit controls whole-body insulin sensitivity. J Clin Invest, 2003. 111 (1): p. 91-8; Viollet, B., et al., Physiological role of AMP-activated protein kinase (AMPK): insights from knockout mouse models. Biochem Soc Trans, 2003. 31 (Pt 1): p. 216-9; Ruderman, N. B., et al., Malonyl-CoA, fuel sensing, and insulin resistance. Am J Physiol, 1999. 276 (1 Pt 1): p. E1-E18; Mu, J., E. R. Barton, and M. J. Birnbaum, Selective suppression of AMP-activated protein kinase in skeletal muscle: update on 'lazy mice'. Biochem Soc Trans, 2003. 31 (Pt 1): p. 236-41; and Zhou, G., et al., Role of AMP-activated protein kinase in mechanism of metformin action. J Clin Invest, 2001. 108 (8): p. 1167-74). Inactivating ACC has the dual effect of inhibiting de novo fat biosynthesis and releasing fatty acid transferases carnitine-palmatoyl transferase-1 (CPT-1) and carnitine octanloyl transferase (COT) from end product inhibition by malonyl coA [Morillas, M., et al., Identification of the two histidine residues responsible for the inhibition by malonyl-CoA in peroxisomal carnitine octanoyltransferase from rat liver. FEBS Lett, 2000. 466 (1): p. 183-6]. The result is decreased de novo fat biosynthesis and increased fatty acid oxidation FAO with a consequent decrease in cellular fat content.

Having shown that resveratrol increases phosphorylation of AMP kinase and ACC, see FIG. 7, we confirmed that resveratrol stimulates $CO_2$ production from palmitate in two hepatoma cell lines (Table 1). The 3- to 6-fold increase in $CO_2$ production mirrors the stimulation achieved with AICAR. In sum, our data suggests that resveratrol can stimulate fat mobilization by activating AMPK signaling to the lipogenic enzyme ACC, reducing production of malonyl coA. The latter event inhibits the flow of substrate into de novo fat biosynthesis and stimulates fatty acid oxidation.

TABLE 23

Resveratrol, like other AMPK activators, can stimulate fatty acid oxidation. Oxidation of $^{14}C$-palmitate in hepatoma cells stimulated with vehicle control (1% DMSO or H2O as appropriate), resveratrol (10 µM in 1% DMSO), AICAR (500 µM in $H_2O$), or metformin (1 mM in $H_2O$) for 4 hours as described in Methods. The fold effect of resveratrol on $CO_2$ production is shown.
14C-$CO_2$ production (nmol/hr/106 cells)
(Fold Effect)

| Compound | Vehicle | Resveratrol | AICAR | Metformin |
|---|---|---|---|---|
| H4IIEC3 cells | 1 | 2.3 | 2.3 | 2 |
| HepG2 cells | 1 | 6 | 5 | 3.5 |

Method:

Oxidation of 14C-palmitate to acid-soluble products (modified from H4IIEC3 cells [Witters, L. A. and B. E. Kemp, Insulin activation of acetyl-CoA carboxylase accompanied by inhibition of the 5'-AMP-activated protein kinase. J Biol Chem, 1992. 267 (5): p. 2864-7] and HepG2 cells were maintained as described above. Cells (106 cells/T25) were seeded in a T25 flask one day prior to the experiment. On the day of the experiment cells were washed with assay buffer (114 mM NaCl, 4.7 mM KCL, 1.2 mM $KH_2PO_4$, 1.2 mM $MgSO_4$, 11 mM glucose) before labeling with 14C-palmitate (0.4 µCi/ml) in presence of vehicle, or resveratrol (10 µM), or AICAR (500 µM) for 4 hours.

At the end of incubation, the cap of each T25 flask was replaced with a stopper and a 1"×1.5" Whatman filter paper soaked with 250 μl 2N NaOH. Each flask was injected with 2 ml of 6N HCL, placed in a horizontal position for 10 minutes and left standing overnight. The next morning, 1 ml H$_2$O and 61 μl NaOH were added to a glass scintillation vial and the filter papers from each T25 flask were transferred to their respective vial. 10 ml Aquasol was added to each vial and allowed to stand for 2 hours, after which the vials were vortexed to dissolve the NaH$^{14}$CO$_2$ and counted in the scintillation counter. The results were expressed as nmols/h/10$^6$ cells and shown as the fold effect. $^{14}$CO$_2$ production ranged from 0.3 to 1.8 nmols/h/10$^6$ cells. The experiment was repeated three times.

Equivalents

Those skilled in the art will recognize, or be able to ascertain using no more than routine experimentation, many equivalents of the specific embodiments described herein. Such equivalents are intended to be encompassed by the following claims.

---

The invention claimed is:

1. A method of treating an insulin resistance disorder in a subject in need thereof, comprising administering to a subject in need thereof a therapeutically effective amount of a sirtuin-activating compound, or salt thereof, wherein the sirtuin-activating compound, or salt thereof, has at least about 2-fold less antioxidant activity than resveratrol, and wherein the sirtuin-activating compound, or salt thereof, is not a compound selected from the group consisting of a flavone, myricetin, quercetin, fisetin, kaempferol, a catechin, nordihydroguaiaretic acid (NDGA) and caffeic acid phenethyl ester.

2. The method of claim 1, wherein the sirtuin-activating compound, or salt thereof is a non-naturally occurring compound.

3. The method of claim 1, further comprising administering to the subject a second agent that: (i) increases the activity or protein level of a sirtuin in a cell; increases the activity or protein level of 5'-AMP-activated protein kinase (AMPK) in a cell; or is an anti-diabetic agent.

4. The method of claim 3, wherein the second agent is an anti-diabetic agent.

5. The method of claim 1, wherein the insulin resistance disorder is diabetes.

6. The method of claim 1, wherein the insulin resistance disorder is obesity.

7. The method of claim 1, wherein the insulin resistance disorder is metabolic syndrome.

8. The method of claim 2, wherein the non-naturally occurring compound activates the deacetylase activity of SIRT1 by a factor of at least about 5.

9. The method of claim 8, wherein the non-naturally occurring compound activates the deacetylase activity of SIRT1 by a factor of at least about 10.

10. The method of claim 9, wherein the non-naturally occurring compound activates the deacetylase activity of SIRT1 by a factor of at least about 20.

11. The method of claim 2, wherein the non-naturally occurring compound has an $EC_{50}$ for activating SIRT1 that is less than about 100 μM.

12. The method of claim 11, wherein the non-naturally occurring compound has an $EC_{50}$ for activating SIRT1 that is less than about 10 μM.

13. The method of claim 12, wherein the non-naturally occurring compound has an $EC_{50}$ for activating SIRT1 that is less than about 1 μM.

14. The method of claim 2, wherein the non-naturally occurring compound does not substantially inhibit the catalytic activity of cyclooxygenase.

15. The method of claim 2, wherein the non-naturally occurring compound does not substantially inhibit PI3-kinase.

16. The method of claim 2, wherein the non-naturally occurring compound does not substantially inhibit tyrosine protein kinase.

17. The method of claim 3, wherein the second agent is an anti-obesity agent.

18. The method of claim 1 for the treatment of a human subject.

19. The method of claim 1, wherein the sirtuin-activating compound has at least about 3-fold less antioxidant activity than resveratrol.

20. The method of claim 1, wherein the sirtuin-activating compound has at least about 5-fold less antioxidant activity than resveratrol.

21. The method of claim 1, wherein the sirtuin-activating compound has at least about 10-fold less antioxidant activity than resveratrol.

* * * * *

SEQUENCE LISTING

```
<160> NUMBER OF SEQ ID NOS: 20

<210> SEQ ID NO 1
<211> LENGTH: 4107
<212> TYPE: DNA
<213> ORGANISM: Homo sapiens
<220> FEATURE:
<221> NAME/KEY: CDS
<222> LOCATION: (54)..(2297)

<400> SEQUENCE: 1
gtcgagcggg agcagaggag gcgagggagg agggccagag aggcagttgg aag atg         56
                                                              Met
                                                              1 gcg gac gag gcg gcc ctc gcc ctt cag ccc ggc ggc tcc ccc tcg gcg       104
Ala Asp Glu Ala Ala Leu Ala Leu Gln Pro Gly Gly Ser Pro Ser Ala
            5                   10                  15 gcg ggg gcc gac agg gag gcc gcg tcg tcc ccc gcc ggg gag ccg ctc       152
Ala Gly Ala Asp Arg Glu Ala Ala Ser Ser Pro Ala Gly Glu Pro Leu
        20                  25                  30 cgc aag agg ccg cgg aga gat ggt ccc ggc ctc gag cgg agc ccg ggc       200
Arg Lys Arg Pro Arg Arg Asp Gly Pro Gly Leu Glu Arg Ser Pro Gly
    35                  40                  45 gag ccc ggt ggg gcg gcc cca gag cgt gag gtg ccg gcg gcg gcc agg       248
Glu Pro Gly Gly Ala Ala Pro Glu Arg Glu Val Pro Ala Ala Ala Arg
50                  55                  60                  65 ggc tgc ccg ggt gcg gcg gcg gcg gcg ctg tgg cgg gag gcg gag gca       296
Gly Cys Pro Gly Ala Ala Ala Ala Ala Leu Trp Arg Glu Ala Glu Ala
                70                  75                  80 gag gcg gcg gcg gca ggg ggg gag caa gag gcc cag gcg act gcg gcg       344
Glu Ala Ala Ala Gly Gly Glu Gln Glu Ala Gln Ala Thr Ala Ala
            85                  90                  95 gct ggg gaa gga gac aat ggg ccg ggc ctg cag ggc cca tct cgg gag       392
Ala Gly Glu Gly Asp Asn Gly Pro Gly Leu Gln Gly Pro Ser Arg Glu
        100                 105                 110 cca ccg ctg gcc gac aac ttg tac gac gaa gac gac gac gag ggc           440
Pro Pro Leu Ala Asp Asn Leu Tyr Asp Glu Asp Asp Asp Glu Gly
    115                 120                 125 gag gag gag gaa gag gcg gcg gcg gcg gcg att ggg tac cga gat aac       488
Glu Glu Glu Glu Glu Ala Ala Ala Ala Ala Ile Gly Tyr Arg Asp Asn
130                 135                 140                 145 ctt ctg ttc ggt gat gaa att atc act aat ggt ttt cat tcc tgt gaa       536
Leu Leu Phe Gly Asp Glu Ile Ile Thr Asn Gly Phe His Ser Cys Glu
                150                 155                 160 agt gat gag gag gat aga gcc tca cat gca agc tct agt gac tgg act       584
Ser Asp Glu Glu Asp Arg Ala Ser His Ala Ser Ser Ser Asp Trp Thr
            165                 170                 175 cca agg cca cgg ata ggt cca tat act ttt gtt cag caa cat ctt atg       632
Pro Arg Pro Arg Ile Gly Pro Tyr Thr Phe Val Gln Gln His Leu Met
        180                 185                 190 att ggc aca gat cct cga aca att ctt aaa gat tta ttg ccg gaa aca       680
Ile Gly Thr Asp Pro Arg Thr Ile Leu Lys Asp Leu Leu Pro Glu Thr
```

```
                  195                 200                 205
ata cct cca cct gag ttg gat gat atg aca ctg tgg cag att gtt att        728
Ile Pro Pro Pro Glu Leu Asp Asp Met Thr Leu Trp Gln Ile Val Ile
210                 215                 220                 225 aat atc ctt tca gaa cca cca aaa agg aaa aaa aga aaa gat att aat        776
Asn Ile Leu Ser Glu Pro Pro Lys Arg Lys Lys Arg Lys Asp Ile Asn
                    230                 235                 240 aca att gaa gat gct gtg aaa tta ctg caa gag tgc aaa aaa att ata        824
Thr Ile Glu Asp Ala Val Lys Leu Leu Gln Glu Cys Lys Lys Ile Ile
                245                 250                 255 gtt cta act gga gct ggg gtg tct gtt tca tgt gga ata cct gac ttc        872
Val Leu Thr Gly Ala Gly Val Ser Val Ser Cys Gly Ile Pro Asp Phe
            260                 265                 270 agg tca agg gat ggt att tat gct cgc ctt gct gta gac ttc cca gat        920
Arg Ser Arg Asp Gly Ile Tyr Ala Arg Leu Ala Val Asp Phe Pro Asp
275                 280                 285 ctt cca gat cct caa gcg atg ttt gat att gaa tat ttc aga aaa gat        968
Leu Pro Asp Pro Gln Ala Met Phe Asp Ile Glu Tyr Phe Arg Lys Asp
290                 295                 300                 305 cca aga cca ttc ttc aag ttt gca aag gaa ata tat cct gga caa ttc       1016
Pro Arg Pro Phe Phe Lys Phe Ala Lys Glu Ile Tyr Pro Gly Gln Phe
                    310                 315                 320 cag cca tct ctc tgt cac aaa ttc ata gcc ttg tca gat aag gaa gga       1064
Gln Pro Ser Leu Cys His Lys Phe Ile Ala Leu Ser Asp Lys Glu Gly
                325                 330                 335 aaa cta ctt cgc aac tat acc cag aac ata gac acg ctg gaa cag gtt       1112
Lys Leu Leu Arg Asn Tyr Thr Gln Asn Ile Asp Thr Leu Glu Gln Val
            340                 345                 350 gcg gga atc caa agg ata att cag tgt cat ggt tcc ttt gca aca gca       1160
Ala Gly Ile Gln Arg Ile Ile Gln Cys His Gly Ser Phe Ala Thr Ala
355                 360                 365 tct tgc ctg att tgt aaa tac aaa gtt gac tgt gaa gct gta cga gga       1208
Ser Cys Leu Ile Cys Lys Tyr Lys Val Asp Cys Glu Ala Val Arg Gly
370                 375                 380                 385 gat att ttt aat cag gta gtt cct cga tgt cct agg tgc cca gct gat       1256
Asp Ile Phe Asn Gln Val Val Pro Arg Cys Pro Arg Cys Pro Ala Asp
                    390                 395                 400 gaa ccg ctt gct atc atg aaa cca gag att gtg ttt ttt ggt gaa aat       1304
Glu Pro Leu Ala Ile Met Lys Pro Glu Ile Val Phe Phe Gly Glu Asn
                405                 410                 415 tta cca gaa cag ttt cat aga gcc atg aag tat gac aaa gat gaa gtt       1352
Leu Pro Glu Gln Phe His Arg Ala Met Lys Tyr Asp Lys Asp Glu Val
            420                 425                 430 gac ctc ctc att gtt att ggg tct tcc ctc aaa gta aga cca gta gca       1400
Asp Leu Leu Ile Val Ile Gly Ser Ser Leu Lys Val Arg Pro Val Ala
435                 440                 445 cta att cca agt tcc ata ccc cat gaa gtg cct cag ata tta att aat       1448
Leu Ile Pro Ser Ser Ile Pro His Glu Val Pro Gln Ile Leu Ile Asn
450                 455                 460                 465 aga gaa cct ttg cct cat ctg cat ttt gat gta gag ctt ctt gga gac       1496
Arg Glu Pro Leu Pro His Leu His Phe Asp Val Glu Leu Leu Gly Asp
                    470                 475                 480 tgt gat gtc ata att aat gaa ttg tgt cat agg tta ggt ggt gaa tat       1544
Cys Asp Val Ile Ile Asn Glu Leu Cys His Arg Leu Gly Gly Glu Tyr
                485                 490                 495 gcc aaa ctt tgc tgt aac cct gta aag ctt tca gaa att act gaa aaa       1592
Ala Lys Leu Cys Cys Asn Pro Val Lys Leu Ser Glu Ile Thr Glu Lys
            500                 505                 510 cct cca cga aca caa aaa gaa ttg gct tat ttg tca gag ttg cca ccc       1640
```

```
            Pro Pro Arg Thr Gln Lys Glu Leu Ala Tyr Leu Ser Glu Leu Pro Pro
                515             520                 525 aca cct ctt cat gtt tca gaa gac tca agt tca cca gaa aga act tca      1688
Thr Pro Leu His Val Ser Glu Asp Ser Ser Ser Pro Glu Arg Thr Ser
530                 535                 540                 545 cca cca gat tct tca gtg att gtc aca ctt tta gac caa gca gct aag      1736
Pro Pro Asp Ser Ser Val Ile Val Thr Leu Leu Asp Gln Ala Ala Lys
                550                 555                 560 agt aat gat gat tta gat gtg tct gaa tca aaa ggt tgt atg gaa gaa      1784
Ser Asn Asp Asp Leu Asp Val Ser Glu Ser Lys Gly Cys Met Glu Glu
            565                 570                 575 aaa cca cag gaa gta caa act tct agg aat gtt gaa agt att gct gaa      1832
Lys Pro Gln Glu Val Gln Thr Ser Arg Asn Val Glu Ser Ile Ala Glu
        580                 585                 590 cag atg gaa aat ccg gat ttg aag aat gtt ggt tct agt act ggg gag      1880
Gln Met Glu Asn Pro Asp Leu Lys Asn Val Gly Ser Ser Thr Gly Glu
    595                 600                 605 aaa aat gaa aga act tca gtg gct gga aca gtg aga aaa tgc tgg cct      1928
Lys Asn Glu Arg Thr Ser Val Ala Gly Thr Val Arg Lys Cys Trp Pro
610                 615                 620                 625 aat aga gtg gca aag gag cag att agt agg cgg ctt gat ggt aat cag      1976
Asn Arg Val Ala Lys Glu Gln Ile Ser Arg Arg Leu Asp Gly Asn Gln
                630                 635                 640 tat ctg ttt ttg cca cca aat cgt tac att ttc cat ggc gct gag gta      2024
Tyr Leu Phe Leu Pro Pro Asn Arg Tyr Ile Phe His Gly Ala Glu Val
            645                 650                 655 tat tca gac tct gaa gat gac gtc tta tcc tct agt tct tgt ggc agt      2072
Tyr Ser Asp Ser Glu Asp Asp Val Leu Ser Ser Ser Cys Gly Ser
        660                 665                 670 aac agt gat agt ggg aca tgc cag agt cca agt tta gaa gaa ccc atg      2120
Asn Ser Asp Ser Gly Thr Cys Gln Ser Pro Ser Leu Glu Glu Pro Met
    675                 680                 685 gag gat gaa agt gaa att gaa gaa ttc tac aat ggc tta gaa gat gag      2168
Glu Asp Glu Ser Glu Ile Glu Glu Phe Tyr Asn Gly Leu Glu Asp Glu
690                 695                 700                 705 cct gat gtt cca gag aga gct gga gga gct gga ttt ggg act gat gga      2216
Pro Asp Val Pro Glu Arg Ala Gly Gly Ala Gly Phe Gly Thr Asp Gly
                710                 715                 720 gat gat caa gag gca att aat gaa gct ata tct gtg aaa cag gaa gta      2264
Asp Asp Gln Glu Ala Ile Asn Glu Ala Ile Ser Val Lys Gln Glu Val
            725                 730                 735 aca gac atg aac tat cca tca aac aaa tca tag tgtaataatt gtgcaggtac    2317
Thr Asp Met Asn Tyr Pro Ser Asn Lys Ser
        740                 745 aggaattgtt ccaccagcat taggaacttt agcatgtcaa aatgaatgtt tacttgtgaa    2377
ctcgatagag caaggaaacc agaaaggtgt aatatttata ggttggtaaa atagattgtt    2437
tttcatggat aattttttaac ttcattattt ctgtacttgt acaaactcaa cactaacttt   2497
ttttttttta aaaaaaaaaa ggtactaagt atcttcaatc agctgttggt caagactaac    2557
tttcttttaa aggttcattt gtatgataaa ttcatatgtg tatatataat ttttttttgtt  2617 ttgtctagtg agtttcaaca ttttttaaagt tttcaaaaag ccatcggaat gttaaattaa   2677
tgtaaaggga cagctaatct agaccaaaga atggtatttt cacttttctt tgtaacattg    2737
aatggtttga agtactcaaa atctgttacg ctaaacttt gattctttaa cacaattatt    2797
tttaaacact ggcattttcc aaaactgtgg cagctaactt tttaaaatct caaatgacat   2857
gcagtgtgag tagaaggaag tcaacaatat gtggggagag cactcggttg tctttacttt   2917
```

```
taaaagtaat acttggtgct aagaatttca ggattattgt atttacgttc aaatgaagat   2977
ggcttttgta cttcctgtgg acatgtagta atgtctatat tggctcataa aactaacctg   3037
aaaaacaaat aaatgctttg gaaatgtttc agttgcttta gaaacattag tgcctgcctg   3097
gatccccta gttttgaaat atttgccatt gttgtttaaa tacctatcac tgtggtagag    3157
cttgcattga tcttttccac aagtattaaa ctgccaaaat gtgaatatgc aaagcctttc   3217
tgaatctata ataatggtac ttctactggg gagagtgtaa tattttggac tgctgttttc   3277
cattaatgag gagagcaaca ggcccctgat tatacagttc caaagtaata agatgttaat   3337
tgtaattcag ccagaaagta catgtctccc attgggagga tttggtgtta aataccaaac   3397
tgctagccct agtattatgg agatgaacat gatgatgtaa cttgtaatag cagaatagtt   3457
aatgaatgaa actagttctt ataatttatc tttatttaaa agcttagcct gccttaaaac   3517
tagagatcaa ctttctcagc tgcaaaagct tctagtcttt caagaagttc atactttatg   3577
aaattgcaca gtaagcattt attttcaga ccattttga acatcactcc taaattaata    3637
aagtattcct ctgttgcttt agtatttatt acaataaaaa gggtttgaaa tatagctgtt   3697
ctttatgcat aaaacaccca gctaggacca ttactgccag agaaaaaaat cgtattgaat   3757
ggccatttcc ctacttataa gatgtctcaa tctgaattta tttggctaca ctaaagaatg   3817
cagtatattt agttttccat ttgcatgatg tttgtgtgct atagatgata ttttaaattg   3877
aaaagtttgt tttaaattat ttttacagtg aagactgttt tcagctcttt ttatattgta   3937
catagtcttt tatgtaattt actggcatat gttttgtaga ctgtttaatg actggatatc   3997
ttccttcaac ttttgaaata caaaccagt gttttttact tgtacactgt tttaaagtct    4057
attaaaattg tcatttgact tttttctgtt aaaaaaaaaa aaaaaaaaa                4107
```

<210> SEQ ID NO 2  
<211> LENGTH: 747  
<212> TYPE: PRT  
<213> ORGANISM: Homo sapiens

<400> SEQUENCE: 2

```
Met Ala Asp Glu Ala Ala Leu Ala Leu Gln Pro Gly Gly Ser Pro Ser
 1               5                  10                  15

Ala Ala Gly Ala Asp Arg Glu Ala Ala Ser Ser Pro Ala Gly Glu Pro
            20                  25                  30

Leu Arg Lys Arg Pro Arg Arg Asp Gly Pro Gly Leu Glu Arg Ser Pro
        35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Ala Leu Trp Arg Glu Ala Glu
65                  70                  75                  80

Ala Glu Ala Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
        115                 120                 125

Gly Glu Glu Glu Glu Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
```

```
              165                 170                 175
Thr Pro Arg Pro Arg Ile Gly Pro Tyr Thr Phe Val Gln Gln His Leu
            180                 185                 190
Met Ile Gly Thr Asp Pro Arg Thr Ile Leu Lys Asp Leu Leu Pro Glu
            195                 200                 205
Thr Ile Pro Pro Glu Leu Asp Asp Met Thr Leu Trp Gln Ile Val
        210                 215                 220
Ile Asn Ile Leu Ser Glu Pro Pro Lys Arg Lys Arg Lys Asp Ile
225                 230                 235                 240
Asn Thr Ile Glu Asp Ala Val Lys Leu Leu Gln Glu Cys Lys Lys Ile
                245                 250                 255
Ile Val Leu Thr Gly Ala Gly Val Ser Val Ser Cys Gly Ile Pro Asp
            260                 265                 270
Phe Arg Ser Arg Asp Gly Ile Tyr Ala Arg Leu Ala Val Asp Phe Pro
            275                 280                 285
Asp Leu Pro Asp Pro Gln Ala Met Phe Asp Ile Glu Tyr Phe Arg Lys
        290                 295                 300
Asp Pro Arg Pro Phe Phe Lys Phe Ala Lys Glu Ile Tyr Pro Gly Gln
305                 310                 315                 320
Phe Gln Pro Ser Leu Cys His Lys Phe Ile Ala Leu Ser Asp Lys Glu
                325                 330                 335
Gly Lys Leu Leu Arg Asn Tyr Thr Gln Asn Ile Asp Thr Leu Glu Gln
            340                 345                 350
Val Ala Gly Ile Gln Arg Ile Ile Gln Cys His Gly Ser Phe Ala Thr
            355                 360                 365
Ala Ser Cys Leu Ile Cys Lys Tyr Lys Val Asp Cys Glu Ala Val Arg
        370                 375                 380
Gly Asp Ile Phe Asn Gln Val Val Pro Arg Cys Pro Arg Cys Pro Ala
385                 390                 395                 400
Asp Glu Pro Leu Ala Ile Met Lys Pro Glu Ile Val Phe Phe Gly Glu
                405                 410                 415
Asn Leu Pro Glu Gln Phe His Arg Ala Met Lys Tyr Asp Lys Asp Glu
            420                 425                 430
Val Asp Leu Leu Ile Val Ile Gly Ser Ser Leu Lys Val Arg Pro Val
            435                 440                 445
Ala Leu Ile Pro Ser Ser Ile Pro His Glu Val Pro Gln Ile Leu Ile
        450                 455                 460
Asn Arg Glu Pro Leu Pro His Leu His Phe Asp Val Glu Leu Leu Gly
465                 470                 475                 480
Asp Cys Asp Val Ile Ile Asn Glu Leu Cys His Arg Leu Gly Gly Glu
                485                 490                 495
Tyr Ala Lys Leu Cys Cys Asn Pro Val Lys Leu Ser Glu Ile Thr Glu
            500                 505                 510
Lys Pro Pro Arg Thr Gln Lys Glu Leu Ala Tyr Leu Ser Glu Leu Pro
            515                 520                 525
Pro Thr Pro Leu His Val Ser Glu Asp Ser Ser Ser Pro Glu Arg Thr
        530                 535                 540
Ser Pro Pro Asp Ser Ser Val Ile Val Thr Leu Leu Asp Gln Ala Ala
545                 550                 555                 560
Lys Ser Asn Asp Asp Leu Asp Val Ser Glu Ser Lys Gly Cys Met Glu
                565                 570                 575
Glu Lys Pro Gln Glu Val Gln Thr Ser Arg Asn Val Glu Ser Ile Ala
            580                 585                 590
```

```
Glu Gln Met Glu Asn Pro Asp Leu Lys Asn Val Gly Ser Ser Thr Gly
            595                 600                 605
Glu Lys Asn Glu Arg Thr Ser Val Ala Gly Thr Val Arg Lys Cys Trp
    610                 615                 620
Pro Asn Arg Val Ala Lys Glu Gln Ile Ser Arg Arg Leu Asp Gly Asn
625                 630                 635                 640
Gln Tyr Leu Phe Leu Pro Pro Asn Arg Tyr Ile Phe His Gly Ala Glu
                645                 650                 655
Val Tyr Ser Asp Ser Glu Asp Val Leu Ser Ser Ser Cys Gly
            660                 665                 670
Ser Asn Ser Asp Ser Gly Thr Cys Gln Ser Pro Ser Leu Glu Glu Pro
            675                 680                 685
Met Glu Asp Glu Ser Glu Ile Glu Glu Phe Tyr Asn Gly Leu Glu Asp
            690                 695                 700
Glu Pro Asp Val Pro Glu Arg Ala Gly Gly Ala Gly Phe Gly Thr Asp
705                 710                 715                 720
Gly Asp Asp Gln Glu Ala Ile Asn Glu Ala Ile Ser Val Lys Gln Glu
                725                 730                 735
Val Thr Asp Met Asn Tyr Pro Ser Asn Lys Ser
            740                 745

<210> SEQ ID NO 3
<211> LENGTH: 1963
<212> TYPE: DNA
<213> ORGANISM: Homo sapiens
<220> FEATURE:
<221> NAME/KEY: CDS
<222> LOCATION: (201)..(1370)

<400> SEQUENCE: 3
gtgttgtacg aaagcgcgtc tgcggccgca atgtctgctg agagttgtag ttctgtgccc      60
tatcacggcc actcccattt ctggtgccgt cacgggacag agcagtcggt gacaggacag     120
agcagtcggt gacgggacac agtggttggt gacgggacag agcggtcggt gacagcctca     180
agggcttcag caccgcgccc atg gca gag cca gac ccc tct cac cct ctg gag     233
                         Met Ala Glu Pro Asp Pro Ser His Pro Leu Glu
                         1               5                   10 acc cag gca ggg aag gtg cag gag gct cag gac tca gat tca gac tct        281
Thr Gln Ala Gly Lys Val Gln Glu Ala Gln Asp Ser Asp Ser Asp Ser
        15                  20                  25 gag gga gga gcc gct ggt gga gaa gca gac atg gac ttc ctg cgg aac        329
Glu Gly Gly Ala Ala Gly Gly Glu Ala Asp Met Asp Phe Leu Arg Asn
        30                  35                  40 tta ttc tcc cag acg ctc agc ctg ggc agc cag aag gag cgt ctg ctg        377
Leu Phe Ser Gln Thr Leu Ser Leu Gly Ser Gln Lys Glu Arg Leu Leu
    45                  50                  55 gac gag ctg acc ttg gaa ggg gtg gcc cgg tac atg cag agc gaa cgc        425
Asp Glu Leu Thr Leu Glu Gly Val Ala Arg Tyr Met Gln Ser Glu Arg
60                  65                  70                  75 tgt cgc aga gtc atc tgt ttg gtg gga gct gga atc tcc aca tcc gca        473
Cys Arg Arg Val Ile Cys Leu Val Gly Ala Gly Ile Ser Thr Ser Ala
                80                  85                  90 ggc atc ccc gac ttt cgc tct cca tcc acc ggc ctc tat gac aac cta        521
Gly Ile Pro Asp Phe Arg Ser Pro Ser Thr Gly Leu Tyr Asp Asn Leu
                95                 100                 105 gag aag tac cat ctt ccc tac cca gag gcc att ttt gag atc agc tat        569
Glu Lys Tyr His Leu Pro Tyr Pro Glu Ala Ile Phe Glu Ile Ser Tyr
            110                 115                 120
```

```
ttc aag aaa cat ccg gaa ccc ttc ttc gcc ctc gcc aag gaa ctc tat     617
Phe Lys Lys His Pro Glu Pro Phe Phe Ala Leu Ala Lys Glu Leu Tyr
    125                 130                 135 cct ggg cag ttc aag cca acc atc tgt cac tac ttc atg cgc ctg ctg     665
Pro Gly Gln Phe Lys Pro Thr Ile Cys His Tyr Phe Met Arg Leu Leu
140                 145                 150                 155 aag gac aag ggg cta ctc ctg cgc tgc tac acg cag aac ata gat acc     713
Lys Asp Lys Gly Leu Leu Leu Arg Cys Tyr Thr Gln Asn Ile Asp Thr
                160                 165                 170 ctg gag cga ata gcc ggg ctg gaa cag gag gac ttg gtg gag gcg cac     761
Leu Glu Arg Ile Ala Gly Leu Glu Gln Glu Asp Leu Val Glu Ala His
            175                 180                 185 ggc acc ttc tac aca tca cac tgc gtc agc gcc agc tgc cgg cac gaa     809
Gly Thr Phe Tyr Thr Ser His Cys Val Ser Ala Ser Cys Arg His Glu
        190                 195                 200 tac ccg cta agc tgg atg aaa gag aag atc ttc tct gag gtg acg ccc     857
Tyr Pro Leu Ser Trp Met Lys Glu Lys Ile Phe Ser Glu Val Thr Pro
    205                 210                 215 aag tgt gaa gac tgt cag agc ctg gtg aag cct gat atc gtc ttt ttt     905
Lys Cys Glu Asp Cys Gln Ser Leu Val Lys Pro Asp Ile Val Phe Phe
220                 225                 230                 235 ggt gag agc ctc cca gcg cgt ttc ttc tcc tgt atg cag tca gac ttc     953
Gly Glu Ser Leu Pro Ala Arg Phe Phe Ser Cys Met Gln Ser Asp Phe
                240                 245                 250 ctg aag gtg gac ctc ctc ctg gtc atg ggt acc tcc ttg cag gtg cag    1001
Leu Lys Val Asp Leu Leu Leu Val Met Gly Thr Ser Leu Gln Val Gln
            255                 260                 265 ccc ttt gcc tcc ctc atc agc aag gca ccc ctc tcc acc cct cgc ctg    1049
Pro Phe Ala Ser Leu Ile Ser Lys Ala Pro Leu Ser Thr Pro Arg Leu
        270                 275                 280 ctc atc aac aag gag aaa gct ggc cag tcg gac cct ttc ctg ggg atg    1097
Leu Ile Asn Lys Glu Lys Ala Gly Gln Ser Asp Pro Phe Leu Gly Met
    285                 290                 295 att atg ggc ctc gga gga ggc atg gac ttt gac tcc aag aag gcc tac    1145
Ile Met Gly Leu Gly Gly Gly Met Asp Phe Asp Ser Lys Lys Ala Tyr
300                 305                 310                 315 agg gac gtg gcc tgg ctg ggt gaa tgc gac cag ggc tgc ctg gcc ctt    1193
Arg Asp Val Ala Trp Leu Gly Glu Cys Asp Gln Gly Cys Leu Ala Leu
                320                 325                 330 gct gag ctc ctt gga tgg aag aag gag ctg gag gac ctt gtc cgg agg    1241
Ala Glu Leu Leu Gly Trp Lys Lys Glu Leu Glu Asp Leu Val Arg Arg
            335                 340                 345 gag cac gcc agc ata gat gcc cag tcg ggg gcg ggg gtc ccc aac ccc    1289
Glu His Ala Ser Ile Asp Ala Gln Ser Gly Ala Gly Val Pro Asn Pro
        350                 355                 360 agc act tca gct tcc ccc aag aag tcc ccg cca cct gcc aag gac gag    1337
Ser Thr Ser Ala Ser Pro Lys Lys Ser Pro Pro Pro Ala Lys Asp Glu
    365                 370                 375 gcc agg aca aca gag agg gag aaa ccc cag tga cagctgcatc tcccaggcgg   1390
Ala Arg Thr Thr Glu Arg Glu Lys Pro Gln
380                 385 gatgccgagc tcctcaggga cagctgagcc ccaaccgggc ctggcccct cttaaccagc   1450 agttcttgtc tggggagctc agaacatccc ccaatctctt acagtccct ccccaaaact   1510 ggggtcccag caaccctggc ccccaacccc agcaaatctc taacacctcc tagaggccaa   1570
ggcttaaaca ggcatctcta ccagccccac tgtctctaac cactcctggg ctaaggagta   1630
acctccctca tctctaactg cccccacggg gccagggcta cccagaaact tttaactctt   1690
```

```
ccaggacagg gagcttcggg cccccactct gtctcctgcc cccggggggcc tgtggctaag    1750 taaaccatac ctaacctacc ccagtgtggg tgtgggcctc tgaatataac ccacacccag    1810
cgtaggggga gtctgagccg ggagggctcc cgagtctctg ccttcagctc ccaaagtggg    1870
tggtgggccc ccttcacgtg ggacccactt cccatgctgg atgggcagaa gacattgctt    1930
attggagaca aattaaaaac aaaaacaact aac                                 1963
```

<210> SEQ ID NO 4
<211> LENGTH: 389
<212> TYPE: PRT
<213> ORGANISM: Homo sapiens

<400> SEQUENCE: 4

```
Met Ala Glu Pro Asp Pro Ser His Pro Leu Glu Thr Gln Ala Gly Lys
  1               5                  10                  15

Val Gln Glu Ala Gln Asp Ser Asp Ser Asp Ser Glu Gly Gly Ala Ala
                 20                  25                  30

Gly Gly Glu Ala Asp Met Asp Phe Leu Arg Asn Leu Phe Ser Gln Thr
             35                  40                  45

Leu Ser Leu Gly Ser Gln Lys Glu Arg Leu Leu Asp Glu Leu Thr Leu
 50                  55                  60

Glu Gly Val Ala Arg Tyr Met Gln Ser Glu Arg Cys Arg Arg Val Ile
 65                  70                  75                  80

Cys Leu Val Gly Ala Gly Ile Ser Thr Ser Ala Gly Ile Pro Asp Phe
                 85                  90                  95

Arg Ser Pro Ser Thr Gly Leu Tyr Asp Asn Leu Glu Lys Tyr His Leu
            100                 105                 110

Pro Tyr Pro Glu Ala Ile Phe Glu Ile Ser Tyr Phe Lys Lys His Pro
        115                 120                 125

Glu Pro Phe Phe Ala Leu Ala Lys Glu Leu Tyr Pro Gly Gln Phe Lys
130                 135                 140

Pro Thr Ile Cys His Tyr Phe Met Arg Leu Leu Lys Asp Lys Gly Leu
145                 150                 155                 160

Leu Leu Arg Cys Tyr Thr Gln Asn Ile Asp Thr Leu Glu Arg Ile Ala
                165                 170                 175

Gly Leu Glu Gln Glu Asp Leu Val Glu Ala His Gly Thr Phe Tyr Thr
            180                 185                 190

Ser His Cys Val Ser Ala Ser Cys Arg His Glu Tyr Pro Leu Ser Trp
        195                 200                 205

Met Lys Glu Lys Ile Phe Ser Glu Val Thr Pro Lys Cys Glu Asp Cys
    210                 215                 220

Gln Ser Leu Val Lys Pro Asp Ile Val Phe Phe Gly Glu Ser Leu Pro
225                 230                 235                 240

Ala Arg Phe Phe Ser Cys Met Gln Ser Asp Phe Leu Lys Val Asp Leu
                245                 250                 255

Leu Leu Val Met Gly Thr Ser Leu Gln Val Gln Pro Phe Ala Ser Leu
            260                 265                 270

Ile Ser Lys Ala Pro Leu Ser Thr Pro Arg Leu Leu Ile Asn Lys Glu
        275                 280                 285

Lys Ala Gly Gln Ser Asp Pro Phe Leu Gly Met Ile Met Gly Leu Gly
    290                 295                 300

Gly Gly Met Asp Phe Asp Ser Lys Lys Ala Tyr Arg Asp Val Ala Trp
305                 310                 315                 320

Leu Gly Glu Cys Asp Gln Gly Cys Leu Ala Leu Ala Glu Leu Leu Gly
```

```
                           325                 330                 335
Trp Lys Lys Glu Leu Glu Asp Leu Val Arg Arg Glu His Ala Ser Ile
            340                 345                 350

Asp Ala Gln Ser Gly Ala Gly Val Pro Asn Pro Ser Thr Ser Ala Ser
            355                 360                 365

Pro Lys Lys Ser Pro Pro Ala Lys Asp Glu Ala Arg Thr Thr Glu
            370                 375                 380

Arg Glu Lys Pro Gln
385

<210> SEQ ID NO 5
<211> LENGTH: 1931
<212> TYPE: DNA
<213> ORGANISM: Homo sapiens
<220> FEATURE:
<221> NAME/KEY: CDS
<222> LOCATION: (257)..(1315)

<400> SEQUENCE: 5
cgaaagcgcg tctgcggccg caatgtctgc tgagagttgt agttctgtgc cctatcacgg      60
ccactcccat ttctggtgcc gtcacgggac agagcagtcg gtgacaggac agagcagtcg     120
gtgacgggac acagtggttg gtgacgggac agagcggtcg gtgacagcct caagggcttc     180
agcaccgcgc ccatggcaga gccagaccga ctcagattca gactctgagg gaggagccgc     240
tggtggagaa gcagac atg gac ttc ctg cgg aac tta ttc tcc cag acg ctc    292
                  Met Asp Phe Leu Arg Asn Leu Phe Ser Gln Thr Leu
                    1               5                  10 agc ctg ggc agc cag aag gag cgt ctg ctg gac gag ctg acc ttg gaa      340
Ser Leu Gly Ser Gln Lys Glu Arg Leu Leu Asp Glu Leu Thr Leu Glu
         15                  20                  25 ggg gtg gcc cgg tac atg cag agc gaa cgc tgt cgc aga gtc atc tgt      388
Gly Val Ala Arg Tyr Met Gln Ser Glu Arg Cys Arg Arg Val Ile Cys
     30                  35                  40 ttg gtg gga gct gga atc tcc aca tcc gca ggc atc ccc gac ttt cgc      436
Leu Val Gly Ala Gly Ile Ser Thr Ser Ala Gly Ile Pro Asp Phe Arg
 45                  50                  55                  60 tct cca tcc acc ggc ctc tat gac aac cta gag aag tac cat ctt ccc      484
Ser Pro Ser Thr Gly Leu Tyr Asp Asn Leu Glu Lys Tyr His Leu Pro
                 65                  70                  75 tac cca gag gcc atc ttt gag atc agc tat ttc aag aaa cat ccg gaa      532
Tyr Pro Glu Ala Ile Phe Glu Ile Ser Tyr Phe Lys Lys His Pro Glu
             80                  85                  90 ccc ttc ttc gcc ctc gcc aag gaa ctc tat cct ggg cag ttc aag cca      580
Pro Phe Phe Ala Leu Ala Lys Glu Leu Tyr Pro Gly Gln Phe Lys Pro
         95                 100                 105 acc atc tgt cac tac ttc atg cgc ctg ctg aag gac aag ggg cta ctc      628
Thr Ile Cys His Tyr Phe Met Arg Leu Leu Lys Asp Lys Gly Leu Leu
    110                 115                 120 ctg cgc tgc tac acg cag aac ata gat acc ctg gag cga ata gcc ggg      676
Leu Arg Cys Tyr Thr Gln Asn Ile Asp Thr Leu Glu Arg Ile Ala Gly
125                 130                 135                 140 ctg gaa cag gag gac ttg gtg gag gcg cac ggc acc ttc tac aca tca      724
Leu Glu Gln Glu Asp Leu Val Glu Ala His Gly Thr Phe Tyr Thr Ser
                145                 150                 155 cac tgc gtc agc gcc agc tgc cgg cac gaa tac ccg cta agc tgg atg      772
His Cys Val Ser Ala Ser Cys Arg His Glu Tyr Pro Leu Ser Trp Met
            160                 165                 170 aaa gag aag atc ttc tct gag gtg acg ccc aag tgt gaa gac tgt cag      820
Lys Glu Lys Ile Phe Ser Glu Val Thr Pro Lys Cys Glu Asp Cys Gln
```

```
                 175                 180                 185
agc ctg gtg aag cct gat atc gtc ttt ttt ggt gag agc ctc cca gcg      868
Ser Leu Val Lys Pro Asp Ile Val Phe Phe Gly Glu Ser Leu Pro Ala
    190                 195                 200 cgt ttc ttc tcc tgt atg cag tca gac ttc ctg aag gtg gac ctc ctc      916
Arg Phe Phe Ser Cys Met Gln Ser Asp Phe Leu Lys Val Asp Leu Leu
205                 210                 215                 220 ctg gtc atg ggt acc tcc ttg cag gtg cag ccc ttt gcc tcc ctc atc      964
Leu Val Met Gly Thr Ser Leu Gln Val Gln Pro Phe Ala Ser Leu Ile
                225                 230                 235 agc aag gca ccc ctc tcc acc cct cgc ctg ctc atc aac aag gag aaa     1012
Ser Lys Ala Pro Leu Ser Thr Pro Arg Leu Leu Ile Asn Lys Glu Lys
            240                 245                 250 gct ggc cag tcg gac cct ttc ctg ggg atg att atg ggc ctc gga gga     1060
Ala Gly Gln Ser Asp Pro Phe Leu Gly Met Ile Met Gly Leu Gly Gly
        255                 260                 265 ggc atg gac ttt gac tcc aag aag gcc tac agg gac gtg gcc tgg ctg     1108
Gly Met Asp Phe Asp Ser Lys Lys Ala Tyr Arg Asp Val Ala Trp Leu
    270                 275                 280 ggt gaa tgc gac cag ggc tgc ctg gcc ctt gct gag ctc ctt gga tgg     1156
Gly Glu Cys Asp Gln Gly Cys Leu Ala Leu Ala Glu Leu Leu Gly Trp
285                 290                 295                 300 aag aag gag ctg gag gac ctt gtc cgg agg gag cac gcc agc ata gat     1204
Lys Lys Glu Leu Glu Asp Leu Val Arg Arg Glu His Ala Ser Ile Asp
                305                 310                 315 gcc cag tcg ggg gcg ggg gtc ccc aac ccc agc act tca gct tcc ccc     1252
Ala Gln Ser Gly Ala Gly Val Pro Asn Pro Ser Thr Ser Ala Ser Pro
            320                 325                 330 aag aag tcc ccg cca cct gcc aag gac gag gcc agg aca aca gag agg     1300
Lys Lys Ser Pro Pro Pro Ala Lys Asp Glu Ala Arg Thr Thr Glu Arg
        335                 340                 345 gag aaa ccc cag tga cagctgcatc tcccaggcgg gatgccgagc tcctcaggga     1355
Glu Lys Pro Gln
    350 cagctgagcc caaccgggc ctggccccct cttaaccagc agttcttgtc tggggagctc    1415 agaacatccc ccaatctctt acagctccct cccaaaaact ggggtcccag caaccctggc   1475 ccccaacccc agcaaatctc taacacctcc tagaggccaa ggcttaaaca ggcatctcta   1535 ccagccccac tgtctctaac cactcctggg ctaaggagta acctccctca tctctaactg   1595 cccccacggg gccagggcta ccccagaact tttaactctt ccaggacagg gagcttcggg   1655 cccccactct gtctcctgcc cccgggggcc tgtggctaag taaaccatac ctaacctacc   1715 ccagtgtggg tgtgggcctc tgaatataac ccacacccag cgtaggggga gtctgagccg   1775 ggagggctcc cgagtctctg ccttcagctc ccaaagtggg tggtgggccc ccttcacgtg   1835 ggacccactt cccatgctgg atgggcagaa gacattgctt attggagaca aattaaaaac   1895 aaaaacaact aacaaaaaaa aaaaaaaaa aaaaaa                              1931

<210> SEQ ID NO 6
<211> LENGTH: 352
<212> TYPE: PRT
<213> ORGANISM: Homo sapiens

<400> SEQUENCE: 6

Met Asp Phe Leu Arg Asn Leu Phe Ser Gln Thr Leu Ser Leu Gly Ser
1               5                   10                  15

Gln Lys Glu Arg Leu Leu Asp Glu Leu Thr Leu Glu Gly Val Ala Arg
            20                  25                  30
```

```
Tyr Met Gln Ser Glu Arg Cys Arg Arg Val Ile Cys Leu Val Gly Ala
         35                  40                  45

Gly Ile Ser Thr Ser Ala Gly Ile Pro Asp Phe Arg Ser Pro Ser Thr
 50                  55                  60

Gly Leu Tyr Asp Asn Leu Glu Lys Tyr His Leu Pro Tyr Pro Glu Ala
 65                  70                  75                  80

Ile Phe Glu Ile Ser Tyr Phe Lys Lys His Pro Glu Pro Phe Phe Ala
                 85                  90                  95

Leu Ala Lys Glu Leu Tyr Pro Gly Gln Phe Lys Pro Thr Ile Cys His
             100                 105                 110

Tyr Phe Met Arg Leu Leu Lys Asp Lys Gly Leu Leu Arg Cys Tyr
             115                 120                 125

Thr Gln Asn Ile Asp Thr Leu Glu Arg Ile Ala Gly Leu Glu Gln Glu
         130                 135                 140

Asp Leu Val Glu Ala His Gly Thr Phe Tyr Thr Ser His Cys Val Ser
145                 150                 155                 160

Ala Ser Cys Arg His Glu Tyr Pro Leu Ser Trp Met Lys Glu Lys Ile
                 165                 170                 175

Phe Ser Glu Val Thr Pro Lys Cys Glu Asp Cys Gln Ser Leu Val Lys
             180                 185                 190

Pro Asp Ile Val Phe Phe Gly Glu Ser Leu Pro Ala Arg Phe Phe Ser
             195                 200                 205

Cys Met Gln Ser Asp Phe Leu Lys Val Asp Leu Leu Leu Val Met Gly
         210                 215                 220

Thr Ser Leu Gln Val Gln Pro Phe Ala Ser Leu Ile Ser Lys Ala Pro
225                 230                 235                 240

Leu Ser Thr Pro Arg Leu Leu Ile Asn Lys Glu Lys Ala Gly Gln Ser
                 245                 250                 255

Asp Pro Phe Leu Gly Met Ile Met Gly Leu Gly Gly Gly Met Asp Phe
             260                 265                 270

Asp Ser Lys Lys Ala Tyr Arg Asp Val Ala Trp Leu Gly Glu Cys Asp
             275                 280                 285

Gln Gly Cys Leu Ala Leu Ala Glu Leu Leu Gly Trp Lys Lys Glu Leu
         290                 295                 300

Glu Asp Leu Val Arg Arg Glu His Ala Ser Ile Asp Ala Gln Ser Gly
305                 310                 315                 320

Ala Gly Val Pro Asn Pro Ser Thr Ser Ala Ser Pro Lys Lys Ser Pro
                 325                 330                 335

Pro Pro Ala Lys Asp Glu Ala Arg Thr Thr Glu Arg Glu Lys Pro Gln
             340                 345                 350

<210> SEQ ID NO 7
<211> LENGTH: 2900
<212> TYPE: DNA
<213> ORGANISM: Homo sapiens
<220> FEATURE:
<221> NAME/KEY: CDS
<222> LOCATION: (34)..(1233)

<400> SEQUENCE: 7
cgagtccgga ggactcctcg gactgcgcgg aac atg gcg ttc tgg ggt tgg cgc      54
                                    Met Ala Phe Trp Gly Trp Arg
                                     1               5 gcc gcg gca gcc ctc cgg ctg tgg ggc cgg gta gtt gaa cgg gtc gag     102
Ala Ala Ala Ala Leu Arg Leu Trp Gly Arg Val Val Glu Arg Val Glu
        10                  15                  20
```

| | | |
|---|---|---|
| gcc ggg gga ggc gtg ggg ccg ttt cag gcc tgc ggc tgt cgg ctg gtg<br>Ala Gly Gly Gly Val Gly Pro Phe Gln Ala Cys Gly Cys Arg Leu Val<br>    25                        30                      35 | | 150 |
| ctt ggc ggc agg gac gat gtg agt gcg ggg ctg aga ggc agc cat ggg<br>Leu Gly Gly Arg Asp Asp Val Ser Ala Gly Leu Arg Gly Ser His Gly<br>  40                      45                    50                    55 | | 198 |
| gcc cgc ggt gag ccc ttg gac ccg gcg cgc ccc ttg cag agg cct ccc<br>Ala Arg Gly Glu Pro Leu Asp Pro Ala Arg Pro Leu Gln Arg Pro Pro<br>                    60                    65                    70 | | 246 |
| aga ccc gag gtg ccc agg gca ttc cgg agg cag ccg agg gca gca gct<br>Arg Pro Glu Val Pro Arg Ala Phe Arg Arg Gln Pro Arg Ala Ala Ala<br>            75                    80                    85 | | 294 |
| ccc agt ttc ttc ttt tcg agt att aaa ggt gga aga agg tcc ata tct<br>Pro Ser Phe Phe Phe Ser Ser Ile Lys Gly Gly Arg Arg Ser Ile Ser<br>        90                    95                        100 | | 342 |
| ttt tct gtg ggt gct tca agt gtt gtt gga agt gga ggc agc agt gac<br>Phe Ser Val Gly Ala Ser Ser Val Val Gly Ser Gly Gly Ser Ser Asp<br>    105                    110                    115 | | 390 |
| aag ggg aag ctt tcc ctg cag gat gta gct gag ctg att cgg gcc aga<br>Lys Gly Lys Leu Ser Leu Gln Asp Val Ala Glu Leu Ile Arg Ala Arg<br>120                    125                    130                    135 | | 438 |
| gcc tgc cag agg gtg gtg gtc atg gtg ggg gcc ggc atc agc aca ccc<br>Ala Cys Gln Arg Val Val Val Met Val Gly Ala Gly Ile Ser Thr Pro<br>            140                    145                    150 | | 486 |
| agt ggc att cca gac ttc aga tcg ccg ggg agt ggc ctg tac agc aac<br>Ser Gly Ile Pro Asp Phe Arg Ser Pro Gly Ser Gly Leu Tyr Ser Asn<br>                155                    160                    165 | | 534 |
| ctc cag cag tac gat ctc ccg tac ccc gag gcc att ttt gaa ctc cca<br>Leu Gln Gln Tyr Asp Leu Pro Tyr Pro Glu Ala Ile Phe Glu Leu Pro<br>        170                    175                    180 | | 582 |
| ttc ttc ttt cac aac ccc aag ccc ttt ttc act ttg gcc aag gag ctg<br>Phe Phe Phe His Asn Pro Lys Pro Phe Phe Thr Leu Ala Lys Glu Leu<br>    185                    190                    195 | | 630 |
| tac cct gga aac tac aag ccc aac gtc act cac tac ttt ctc cgg ctg<br>Tyr Pro Gly Asn Tyr Lys Pro Asn Val Thr His Tyr Phe Leu Arg Leu<br>200                    205                    210                    215 | | 678 |
| ctt cat gac aag ggg ctg ctt ctg cgg ctc tac acg cag aac atc gat<br>Leu His Asp Lys Gly Leu Leu Leu Arg Leu Tyr Thr Gln Asn Ile Asp<br>            220                    225                    230 | | 726 |
| ggg ctt gag aga gtg tcg ggc atc cct gcc tca aag ctg gtt gaa gct<br>Gly Leu Glu Arg Val Ser Gly Ile Pro Ala Ser Lys Leu Val Glu Ala<br>                235                    240                    245 | | 774 |
| cat gga acc ttt gcc tct gcc acc tgc aca gtc tgc caa aga ccc ttc<br>His Gly Thr Phe Ala Ser Ala Thr Cys Thr Val Cys Gln Arg Pro Phe<br>        250                    255                    260 | | 822 |
| cca ggg gag gac att cgg gct gac gtg atg gca gac agg gtt ccc cgc<br>Pro Gly Glu Asp Ile Arg Ala Asp Val Met Ala Asp Arg Val Pro Arg<br>    265                    270                    275 | | 870 |
| tgc ccg gtc tgc acc ggc gtt gtg aag ccc gac att gtg ttc ttt ggg<br>Cys Pro Val Cys Thr Gly Val Val Lys Pro Asp Ile Val Phe Phe Gly<br>280                      285                    290                    295 | | 918 |
| gag ccg ctg ccc cag agg ttc ttg ctg cat gtg gtt gat ttc ccc atg<br>Glu Pro Leu Pro Gln Arg Phe Leu Leu His Val Val Asp Phe Pro Met<br>            300                    305                    310 | | 966 |
| gca gat ctg ctg ctc atc ctt ggg acc tcc ctg gag gtg gag cct ttt<br>Ala Asp Leu Leu Leu Ile Leu Gly Thr Ser Leu Glu Val Glu Pro Phe<br>                315                    320                    325 | | 1014 |
| gcc agc ttg acc gag gcc gtg cgg agc tca gtt ccc cga ctg ctc atc<br>Ala Ser Leu Thr Glu Ala Val Arg Ser Ser Val Pro Arg Leu Leu Ile | | 1062 |

```
                  330                 335                 340
aac cgg gac ttg gtg ggg ccc ttg gct tgg cat cct cgc agc agg gac       1110
Asn Arg Asp Leu Val Gly Pro Leu Ala Trp His Pro Arg Ser Arg Asp
    345                 350                 355 gtg gcc cag ctg ggg gac gtg gtt cac ggc gtg gaa agc cta gtg gag       1158
Val Ala Gln Leu Gly Asp Val Val His Gly Val Glu Ser Leu Val Glu
360                 365                 370                 375 ctt ctg ggc tgg aca gaa gag atg cgg gac ctt gtg cag cgg gaa act       1206
Leu Leu Gly Trp Thr Glu Glu Met Arg Asp Leu Val Gln Arg Glu Thr
                380                 385                 390 ggg aag ctt gat gga cca gac aaa tag gatgatggct gcccccacac             1253
Gly Lys Leu Asp Gly Pro Asp Lys
                395 aataaatggt aacataggag acatccacat cccaattctg acaagacctc atgcctgaag    1313
acagcttggg caggtgaaac cagaatatgt gaactgagtg acacccgag gctgccactg     1373
gaatgtcttc tcaggccatg agctgcagtg actggtaggg ctgtgtttac agtcagggcc    1433
accccgtcac atatacaaag gagctgcctg cctgtttgct gtgttgaact cttcactctg    1493
ctgaagctcc taatggaaaa agctttcttc tgactgtgac cctcttgaac tgaatcagac    1553
caactggaat cccagaccga gtctgctttc tgtgcctagt tgaacggcaa gctcggcatc    1613
tgttggttac aagatccaga cttgggccga gcggtcccca gccctcttca tgttccgaag    1673
tgtagtcttg aggccctggt gccgcacttc tagcatgttg gtctccttta gtggggctat    1733
ttttaatgag agaaaatctg ttcttttccag catgaaatac atttagtctc ctcaaaggga   1793
ctgcaggtgt tgacatgagt tggaaaggga accctgggat acgtggcgtc ccctctattg    1853
gaacagtctg aggactgaag gcatttgtcc ctggatttat tggagacggc ccagctcctc    1913
cctctgaagg tggtcacatt ctgttgactc tccatactca gcctccctc cagaaacaga    1973
tctgttccag aacattccag cactttctat ctggcctcct tgtccccaca ctacgcccc     2033
ccaccctcgc cagggcttcc tctagtgaca ctgttagagc taatctctga cagggaag      2093
gcattactca cttaaaaccc aggctgagtc ctggccacct gctggattgt gacataggag    2153
gtggaatcca ctgaactgct acttctgcac aggctccttc tcctggggct gtacccaggc    2213
ccagccctga tggctcaccc tgtcaggcac cagctgctcc ctcctgggct ctcacccacc    2273
tgcacatcct ccttcctagc atcacattac ctgcgtgttt ccccagacaa aagcacttcc    2333
cattcttgaa ccttgcctac cctgggctga gctgacggca atagatttaa tgacagtgac    2393
tcccaggaag ggggtcctgt gactttgcgc cttaataaga acaaaaggtg gaattggtga    2453
cctaggaaaa ctgttgaatt ctaaaaagaa tgaagttagt ttctaaccct agttaatgtt    2513
cctttttat ttttgagtc ttgccctgtc actcagggtg gagtgcggtg ttatgatctc     2573
agctcactgc aacttccgcc tcccgggttt aagcgattct cctgggtagc tgggattaca    2633
ggtgtgtccc accacaccta gcacatgggc atatttgtaa tagagacaag gttttgctat    2693
gttggccagg ctggtctcga actcctggct tcaagtgatc cacccacctc ggcctcccaa    2753
agtgctggga ttacaggcat gagccactgt gcctggcccc tttatttgat aatttacaca    2813
tacattttg tccaaaactc ttcttattt caagatgatg tttctgtggc tatgtgtggt      2873
atgtggtata aatctcaatc tatggtc                                         2900
```

<210> SEQ ID NO 8
<211> LENGTH: 399
<212> TYPE: PRT
<213> ORGANISM: Homo sapiens

<400> SEQUENCE: 8

```
Met Ala Phe Trp Gly Trp Arg Ala Ala Ala Leu Arg Leu Trp Gly
 1               5                  10                  15

Arg Val Val Glu Arg Val Glu Ala Gly Gly Val Gly Pro Phe Gln
             20                  25                  30

Ala Cys Gly Cys Arg Leu Val Leu Gly Gly Arg Asp Asp Val Ser Ala
         35                  40                  45

Gly Leu Arg Gly Ser His Gly Ala Arg Gly Glu Pro Leu Asp Pro Ala
     50                  55                  60

Arg Pro Leu Gln Arg Pro Pro Arg Pro Glu Val Pro Arg Ala Phe Arg
 65                  70                  75                  80

Arg Gln Pro Arg Ala Ala Ala Pro Ser Phe Phe Ser Ser Ile Lys
                 85                  90                  95

Gly Gly Arg Arg Ser Ile Ser Phe Ser Val Gly Ala Ser Ser Val Val
                100                 105                 110

Gly Ser Gly Gly Ser Ser Asp Lys Gly Lys Leu Ser Leu Gln Asp Val
            115                 120                 125

Ala Glu Leu Ile Arg Ala Arg Ala Cys Gln Arg Val Val Val Met Val
    130                 135                 140

Gly Ala Gly Ile Ser Thr Pro Ser Gly Ile Pro Asp Phe Arg Ser Pro
145                 150                 155                 160

Gly Ser Gly Leu Tyr Ser Asn Leu Gln Gln Tyr Asp Leu Pro Tyr Pro
                165                 170                 175

Glu Ala Ile Phe Glu Leu Pro Phe Phe Phe His Asn Pro Lys Pro Phe
            180                 185                 190

Phe Thr Leu Ala Lys Glu Leu Tyr Pro Gly Asn Tyr Lys Pro Asn Val
        195                 200                 205

Thr His Tyr Phe Leu Arg Leu His Asp Lys Gly Leu Leu Leu Arg
    210                 215                 220

Leu Tyr Thr Gln Asn Ile Asp Gly Leu Glu Arg Val Ser Gly Ile Pro
225                 230                 235                 240

Ala Ser Lys Leu Val Glu Ala His Gly Thr Phe Ala Ser Ala Thr Cys
                245                 250                 255

Thr Val Cys Gln Arg Pro Phe Pro Gly Glu Asp Ile Arg Ala Asp Val
            260                 265                 270

Met Ala Asp Arg Val Pro Arg Cys Pro Val Cys Thr Gly Val Val Lys
        275                 280                 285

Pro Asp Ile Val Phe Phe Gly Glu Pro Leu Pro Gln Arg Phe Leu Leu
    290                 295                 300

His Val Asp Phe Pro Met Ala Asp Leu Leu Leu Ile Leu Gly Thr
305                 310                 315                 320

Ser Leu Glu Val Glu Pro Phe Ala Ser Leu Thr Glu Ala Val Arg Ser
                325                 330                 335

Ser Val Pro Arg Leu Leu Ile Asn Arg Asp Leu Val Gly Pro Leu Ala
            340                 345                 350

Trp His Pro Arg Ser Arg Asp Val Ala Gln Leu Gly Asp Val Val His
        355                 360                 365

Gly Val Glu Ser Leu Val Glu Leu Leu Gly Trp Thr Glu Glu Met Arg
    370                 375                 380

Asp Leu Val Gln Arg Glu Thr Gly Lys Leu Asp Gly Pro Asp Lys
385                 390                 395
```

```
<210> SEQ ID NO 9
<211> LENGTH: 2754
<212> TYPE: DNA
<213> ORGANISM: Homo sapiens
<220> FEATURE:
<221> NAME/KEY: CDS
<222> LOCATION: (314)..(1087)

<400> SEQUENCE: 9
cgagtccgga ggactcctcg gactgcgcgg aacatggcgt tctggggttg gcgcgccgcg     60
gcagccctcc ggctgtgggg ccgggtagtt gaacgggtcg aggccggggg aggcgtgggg    120
ccgtttcagg cctgcggctg tcggctggtg cttggcggca gggacgatta ttaaaggtgg    180
aagaaggtcc atatcttttt ctgtgggtgc ttcaagtgtt gttggaagtg gaggcagcag    240
tgacaagggg aagctttccc tgcaggatgt agctgagctg attcgggcca gagcctgcca    300
gagggtggtg gtc atg gtg ggg gcc ggc atc agc aca ccc agt ggc att       349
            Met Val Gly Ala Gly Ile Ser Thr Pro Ser Gly Ile
              1               5                  10 cca gac ttc aga tcg ccg ggg agt ggc ctg tac agc aac ctc cag cag      397
Pro Asp Phe Arg Ser Pro Gly Ser Gly Leu Tyr Ser Asn Leu Gln Gln
             15                  20                  25 tac gat ctc ccg tac ccc gag gcc att ttt gaa ctc cca ttc ttc ttt      445
Tyr Asp Leu Pro Tyr Pro Glu Ala Ile Phe Glu Leu Pro Phe Phe Phe
         30                  35                  40 cac aac ccc aag ccc ttt ttc act ttg gcc aag gag ctg tac cct gga      493
His Asn Pro Lys Pro Phe Phe Thr Leu Ala Lys Glu Leu Tyr Pro Gly
     45                  50                  55                  60 aac tac aag ccc aac gtc act cac tac ttt ctc cgg ctg ctt cat gac      541
Asn Tyr Lys Pro Asn Val Thr His Tyr Phe Leu Arg Leu Leu His Asp
                 65                  70                  75 aag ggg ctg ctt ctg cgg ctc tac acg cag aac atc gat ggg ctt gag      589
Lys Gly Leu Leu Leu Arg Leu Tyr Thr Gln Asn Ile Asp Gly Leu Glu
             80                  85                  90 aga gtg tcg ggc atc cct gcc tca aag ctg gtt gaa gct cat gga acc      637
Arg Val Ser Gly Ile Pro Ala Ser Lys Leu Val Glu Ala His Gly Thr
         95                 100                 105 ttt gcc tct gcc acc tgc aca gtc tgc caa aga ccc ttc cca ggg gag      685
Phe Ala Ser Ala Thr Cys Thr Val Cys Gln Arg Pro Phe Pro Gly Glu
    110                 115                 120 gac att cgg gct gac gtg atg gca gac agg gtt ccc cgc tgc ccg gtc      733
Asp Ile Arg Ala Asp Val Met Ala Asp Arg Val Pro Arg Cys Pro Val
125                 130                 135                 140 tgc acc ggc gtt gtg aag ccc gac att gtg ttc ttt ggg gag ccg ctg      781
Cys Thr Gly Val Val Lys Pro Asp Ile Val Phe Phe Gly Glu Pro Leu
                145                 150                 155 ccc cag agg ttc ttg ctg cat gtg gtt gat ttc ccc atg gca gat ctg      829
Pro Gln Arg Phe Leu Leu His Val Val Asp Phe Pro Met Ala Asp Leu
            160                 165                 170 ctg ctc atc ctt ggg acc tcc ctg gag gtg gag cct ttt gcc agc ttg      877
Leu Leu Ile Leu Gly Thr Ser Leu Glu Val Glu Pro Phe Ala Ser Leu
        175                 180                 185 acc gag gcc gtg cgg agc tca gtt ccc cga ctg ctc atc aac cgg gac      925
Thr Glu Ala Val Arg Ser Ser Val Pro Arg Leu Leu Ile Asn Arg Asp
    190                 195                 200 ttg gtg ggg ccc ttg gct tgg cat cct cgc agc agg gac gtg gcc cag      973
Leu Val Gly Pro Leu Ala Trp His Pro Arg Ser Arg Asp Val Ala Gln
205                 210                 215                 220 ctg ggg gac gtg gtt cac ggc gtg gaa agc cta gtg gag ctt ctg ggc     1021
Leu Gly Asp Val Val His Gly Val Glu Ser Leu Val Glu Leu Leu Gly
                225                 230                 235
```

```
tgg aca gaa gag atg cgg gac ctt gtg cag cgg gaa act ggg aag ctt    1069
Trp Thr Glu Glu Met Arg Asp Leu Val Gln Arg Glu Thr Gly Lys Leu
            240                 245                 250 gat gga cca gac aaa tag gatgatggct gccccacac aataaatggt             1117
Asp Gly Pro Asp Lys
        255 aacataggag acatccacat cccaattctg acaagacctc atgcctgaag acagcttggg   1177
caggtgaaac cagaatatgt gaactgagtg gacacccgag gctgccactg gaatgtcttc   1237
tcaggccatg agctgcagtg actggtaggg ctgtgtttac agtcagggcc accccgtcac   1297
atatacaaag gagctgcctg cctgtttgct gtgttgaact cttcactctg ctgaagctcc   1357
taatggaaaa agctttcttc tgactgtgac cctcttgaac tgaatcagac caactggaat   1417
cccagaccga gtctgctttc tgtgcctagt tgaacggcaa gctcggcatc tgttggttac   1477
aagatccaga cttgggccga gcggtcccca gccctcttca tgttccgaag tgtagtcttg   1537
aggccctggt gccgcacttc tagcatgttg gtctccttta gtggggctat ttttaatgag   1597
agaaaatctg ttctttccag catgaaatac atttagtctc ctcaaaggga ctgcaggtgt   1657
tgacatgagt tggaaaggga accctgggat acgtggcgtc ccctctattg aacagtctg    1717
aggactgaag gcatttgtcc ctggatttat tggagacggc ccagctcctc cctctgaagg   1777
tggtcacatt ctgttgactc tccatactca gcctctcctc cagaaacaga tctgttccag   1837
aacattccag cactttctat ctggcctcct tgtccccaca ctacgccccc ccaccctcgc   1897
cagggcttcc tctagtgaca ctgttagagc taatctctga gacagggaag gcattactca   1957
cttaaaaccc aggctgagtc ctggccacct gctggattgt gacataggag gtggaatcca   2017
ctgaactgct acttctgcac aggctccttc tcctggggct gtaccaggc ccagccctga   2077
tggctcaccc tgtcaggcac cagctgctcc ctcctgggct ctcacccacc tgcacatcct   2137
ccttcctagc atcacattac ctgcgtgttt ccccagacaa aagcacttcc cattcttgaa   2197
ccttgcctac cctgggctga gctgacggca atagatttaa tgacagtgac tcccaggaag   2257
ggggtcctgt gactttgcgc cttaataaga acaaaaggtg gaattggtga cctaggaaaa   2317
ctgttgaatt ctaaaagaa tgaagttagt ttctaaccct agttaatgtt cctttttat    2377
tttttgagtc ttgccctgtc actcagggtg gagtgcggtg ttatgatctc agctcactgc   2437
aacttccgcc tcccgggttt aagcgattct cctgggtagc tgggattaca ggtgtgtccc   2497
accacaccta gcacatgggc atatttgtaa tagagacaag gttttgctat gttggccagg   2557
ctggtctcga actcctggct tcaagtgatc cacccacctc ggcctcccaa agtgctggga   2617
ttacaggcat gagccactgt gcctggcccc tttatttgat aatttacaca tacattttg    2677
tccaaaactc ttctttattt caagatgatg tttctgtggc tatgtgtggt atgtggtata   2737
aatctcaatc tatggtc                                                  2754
```

<210> SEQ ID NO 10
<211> LENGTH: 257
<212> TYPE: PRT
<213> ORGANISM: Homo sapiens

<400> SEQUENCE: 10

```
Met Val Gly Ala Gly Ile Ser Thr Pro Ser Gly Ile Pro Asp Phe Arg
 1               5                  10                  15

Ser Pro Gly Ser Gly Leu Tyr Ser Asn Leu Gln Gln Tyr Asp Leu Pro
            20                  25                  30
```

```
Tyr Pro Glu Ala Ile Phe Glu Leu Pro Phe Phe His Asn Pro Lys
        35                  40                  45

Pro Phe Phe Thr Leu Ala Lys Glu Leu Tyr Pro Gly Asn Tyr Lys Pro
 50                  55                  60

Asn Val Thr His Tyr Phe Leu Arg Leu His Asp Lys Gly Leu Leu
 65                  70                  75                  80

Leu Arg Leu Tyr Thr Gln Asn Ile Asp Gly Leu Glu Arg Val Ser Gly
                 85                  90                  95

Ile Pro Ala Ser Lys Leu Val Glu Ala His Gly Thr Phe Ala Ser Ala
                100                 105                 110

Thr Cys Thr Val Cys Gln Arg Pro Phe Pro Gly Glu Asp Ile Arg Ala
                115                 120                 125

Asp Val Met Ala Asp Arg Val Pro Arg Cys Pro Val Cys Thr Gly Val
    130                 135                 140

Val Lys Pro Asp Ile Val Phe Phe Gly Glu Pro Leu Pro Gln Arg Phe
145                 150                 155                 160

Leu Leu His Val Val Asp Phe Pro Met Ala Asp Leu Leu Ile Leu
                165                 170                 175

Gly Thr Ser Leu Glu Val Glu Pro Phe Ala Ser Leu Thr Glu Ala Val
                180                 185                 190

Arg Ser Ser Val Pro Arg Leu Leu Ile Asn Arg Asp Leu Val Gly Pro
    195                 200                 205

Leu Ala Trp His Pro Arg Ser Arg Asp Val Ala Gln Leu Gly Asp Val
                210                 215                 220

Val His Gly Val Glu Ser Leu Val Glu Leu Leu Gly Trp Thr Glu Glu
225                 230                 235                 240

Met Arg Asp Leu Val Gln Arg Glu Thr Gly Lys Leu Asp Gly Pro Asp
                245                 250                 255

Lys

<210> SEQ ID NO 11
<211> LENGTH: 1174
<212> TYPE: DNA
<213> ORGANISM: Homo sapiens
<220> FEATURE:
<221> NAME/KEY: CDS
<222> LOCATION: (21)..(965)

<400> SEQUENCE: 11
gtccgtagag ctgtgagaga atg aag atg agc ttt gcg ttg act ttc agg tca       53
                     Met Lys Met Ser Phe Ala Leu Thr Phe Arg Ser
                      1               5                  10 gca aaa ggc cgt tgg atc gca aac ccc agc cag ccg tgc tcg aaa gcc      101
Ala Lys Gly Arg Trp Ile Ala Asn Pro Ser Gln Pro Cys Ser Lys Ala
            15                  20                  25 tcc att ggg tta ttt gtg cca gca agt cct cct ctg gac cct gag aag      149
Ser Ile Gly Leu Phe Val Pro Ala Ser Pro Pro Leu Asp Pro Glu Lys
         30                  35                  40 gtc aaa gag tta cag cgc ttc atc acc ctt tcc aag aga ctc ctt gtg      197
Val Lys Glu Leu Gln Arg Phe Ile Thr Leu Ser Lys Arg Leu Leu Val
     45                  50                  55 atg act ggg gca gga atc tcc acc gaa tcg ggg ata cca gac tac agg      245
Met Thr Gly Ala Gly Ile Ser Thr Glu Ser Gly Ile Pro Asp Tyr Arg
 60                  65                  70                  75 tca gaa aaa gtg ggg ctt tat gcc cgc act gac cgc agg ccc atc cag      293
Ser Glu Lys Val Gly Leu Tyr Ala Arg Thr Asp Arg Arg Pro Ile Gln
                 80                  85                  90
```

```
cat ggt gat ttt gtc cgg agt gcc cca atc cgc cag cgg tac tgg gcg     341
His Gly Asp Phe Val Arg Ser Ala Pro Ile Arg Gln Arg Tyr Trp Ala
            95                 100                 105 aga aac ttc gta ggc tgg cct caa ttc tcc tcc cac cag cct aac cct     389
Arg Asn Phe Val Gly Trp Pro Gln Phe Ser Ser His Gln Pro Asn Pro
        110                 115                 120 gca cac tgg gct ttg agc acc tgg gag aaa ctc gga aag ctg tac tgg     437
Ala His Trp Ala Leu Ser Thr Trp Glu Lys Leu Gly Lys Leu Tyr Trp
    125                 130                 135 ttg gtg acc caa aat gtg gat gct ttg cac acc aag gcg ggg agt cgg     485
Leu Val Thr Gln Asn Val Asp Ala Leu His Thr Lys Ala Gly Ser Arg
140                 145                 150                 155 cgc ctg aca gag ctc cac gga tgc atg gac agg gtc ctg tgc ttg gat     533
Arg Leu Thr Glu Leu His Gly Cys Met Asp Arg Val Leu Cys Leu Asp
            160                 165                 170 tgt ggg gaa cag act ccc cgg ggg gtg ctg caa gag cgt ttc caa gtc     581
Cys Gly Glu Gln Thr Pro Arg Gly Val Leu Gln Glu Arg Phe Gln Val
        175                 180                 185 ctg aac ccc acc tgg agt gct gag gcc cat ggc ctg gct cct gat ggt     629
Leu Asn Pro Thr Trp Ser Ala Glu Ala His Gly Leu Ala Pro Asp Gly
    190                 195                 200 gac gtc ttt ctc tca gag gag caa gtc cgg agc ttt cag gtc cca acc     677
Asp Val Phe Leu Ser Glu Glu Gln Val Arg Ser Phe Gln Val Pro Thr
205                 210                 215 tgc gtt caa tgt gga ggc cat ctg aaa cca gat gtc gtt ttc ttc ggg     725
Cys Val Gln Cys Gly Gly His Leu Lys Pro Asp Val Val Phe Phe Gly
220                 225                 230                 235 gac aca gtg aac cct gac aag gtt gat ttt gtg cac aag cgt gta aaa     773
Asp Thr Val Asn Pro Asp Lys Val Asp Phe Val His Lys Arg Val Lys
            240                 245                 250 gaa gcc gac tcc ctc ttg gtg gtg gga tca tcc ttg cag gta tac tct     821
Glu Ala Asp Ser Leu Leu Val Val Gly Ser Ser Leu Gln Val Tyr Ser
        255                 260                 265 ggt tac agg ttt atc ctc act gcc tgg gag aag aag ctc ccg att gca     869
Gly Tyr Arg Phe Ile Leu Thr Ala Trp Glu Lys Lys Leu Pro Ile Ala
    270                 275                 280 ata ctg aac att ggg ccc aca cgg tcg gat gac ttg gcg tgt ctg aaa     917
Ile Leu Asn Ile Gly Pro Thr Arg Ser Asp Asp Leu Ala Cys Leu Lys
285                 290                 295 ctg aat tct cgt tgt gga gag ttg ctg cct ttg ata gac cca tgc tga     965
Leu Asn Ser Arg Cys Gly Glu Leu Leu Pro Leu Ile Asp Pro Cys
300                 305                 310 ccacagcctg atattccaga acctggaaca gggactttca cttgaatctt gctgctaaat    1025
gtaaatgcct tctcaaatga cagattccag ttcccattca acagagtagg gtgcactgac    1085
aaagtataga aggttctagg tatcttaatg tgtggatatt cttaattaaa actcatttt     1145 tttaaataaa aaattgttca gctttaaaa                                      1174

<210> SEQ ID NO 12
<211> LENGTH: 314
<212> TYPE: PRT
<213> ORGANISM: Homo sapiens

<400> SEQUENCE: 12

Met Lys Met Ser Phe Ala Leu Thr Phe Arg Ser Ala Lys Gly Arg Trp
 1               5                  10                  15

Ile Ala Asn Pro Ser Gln Pro Cys Ser Lys Ala Ser Ile Gly Leu Phe
            20                  25                  30

Val Pro Ala Ser Pro Pro Leu Asp Pro Glu Lys Val Lys Glu Leu Gln
```

-continued

```
              35                  40                  45
Arg Phe Ile Thr Leu Ser Lys Arg Leu Leu Val Met Thr Gly Ala Gly
 50                  55                  60

Ile Ser Thr Glu Ser Gly Ile Pro Asp Tyr Arg Ser Glu Lys Val Gly
 65                  70                  75                  80

Leu Tyr Ala Arg Thr Asp Arg Arg Pro Ile Gln His Gly Asp Phe Val
                 85                  90                  95

Arg Ser Ala Pro Ile Arg Gln Arg Tyr Trp Ala Arg Asn Phe Val Gly
            100                 105                 110

Trp Pro Gln Phe Ser Ser His Gln Pro Asn Pro Ala His Trp Ala Leu
        115                 120                 125

Ser Thr Trp Glu Lys Leu Gly Lys Leu Tyr Trp Leu Val Thr Gln Asn
    130                 135                 140

Val Asp Ala Leu His Thr Lys Ala Gly Ser Arg Arg Leu Thr Glu Leu
145                 150                 155                 160

His Gly Cys Met Asp Arg Val Leu Cys Leu Asp Cys Gly Glu Gln Thr
                165                 170                 175

Pro Arg Gly Val Leu Gln Glu Arg Phe Gln Val Leu Asn Pro Thr Trp
            180                 185                 190

Ser Ala Glu Ala His Gly Leu Ala Pro Asp Gly Asp Val Phe Leu Ser
        195                 200                 205

Glu Glu Gln Val Arg Ser Phe Gln Val Pro Thr Cys Val Gln Cys Gly
    210                 215                 220

Gly His Leu Lys Pro Asp Val Val Phe Phe Gly Asp Thr Val Asn Pro
225                 230                 235                 240

Asp Lys Val Asp Phe Val His Lys Arg Val Lys Glu Ala Asp Ser Leu
                245                 250                 255

Leu Val Val Gly Ser Ser Leu Gln Val Tyr Ser Gly Tyr Arg Phe Ile
            260                 265                 270

Leu Thr Ala Trp Glu Lys Lys Leu Pro Ile Ala Ile Leu Asn Ile Gly
        275                 280                 285

Pro Thr Arg Ser Asp Asp Leu Ala Cys Leu Lys Leu Asn Ser Arg Cys
    290                 295                 300

Gly Glu Leu Leu Pro Leu Ile Asp Pro Cys
305                 310
```

<210> SEQ ID NO 13
<211> LENGTH: 1670
<212> TYPE: DNA
<213> ORGANISM: Homo sapiens
<220> FEATURE:
<221> NAME/KEY: CDS
<222> LOCATION: (297)..(1229)

<400> SEQUENCE: 13

```
ccggagcgcg gtcgggacac agcgcctcta ggagaaagcc tggaaggcgc tccgggggta      60
cccagagctc ttagcgggcc ggcagcatgt gcggggccca agtaaatgga aatgttttct     120
aacatataaa aacctacaga agaagaaaat aatttctgg  atcaaattag aagtctgtat     180
tatattgatg tctccagatt caaatatatt agaaagcagc cgtggagaca accatcttca     240
ttttgggaga ataactaaa  gcccgcctca agcattagaa ctacagacaa accctg atg     299
                                                                     Met
                                                                      1 cga cct ctc cag att gtc cca agt cga ttg att tcc cag cta tat tgt      347
Arg Pro Leu Gln Ile Val Pro Ser Arg Leu Ile Ser Gln Leu Tyr Cys
              5                  10                  15
```

-continued

```
ggc ctg aag cct cca gcg tcc aca cga aac cag att tgc ctg aaa atg      395
Gly Leu Lys Pro Pro Ala Ser Thr Arg Asn Gln Ile Cys Leu Lys Met
         20                  25                  30 gct cgg cca agt tca agt atg gca gat ttt cga aag ttt ttt gca aaa      443
Ala Arg Pro Ser Ser Ser Met Ala Asp Phe Arg Lys Phe Phe Ala Lys
     35                  40                  45 gca aag cac ata gtc atc atc tca gga gct ggt gtt agt gca gaa agt      491
Ala Lys His Ile Val Ile Ile Ser Gly Ala Gly Val Ser Ala Glu Ser
 50                  55                  60                  65 ggt gtt ccg acc ttc aga gga gct gga ggt tat tgg aga aaa tgg caa      539
Gly Val Pro Thr Phe Arg Gly Ala Gly Gly Tyr Trp Arg Lys Trp Gln
                 70                  75                  80 gcc cag gac ctg gcg act ccc ctg gcc ttt gcc cac aac ccg tcc cgg      587
Ala Gln Asp Leu Ala Thr Pro Leu Ala Phe Ala His Asn Pro Ser Arg
             85                  90                  95 gtg tgg gag ttc tac cac tac cgg cgg gag gtc atg ggg agc aag gag      635
Val Trp Glu Phe Tyr His Tyr Arg Arg Glu Val Met Gly Ser Lys Glu
        100                 105                 110 ccc aac gcc ggg cac cgc gcc ata gcc gag tgt gag acc cgg ctg ggc      683
Pro Asn Ala Gly His Arg Ala Ile Ala Glu Cys Glu Thr Arg Leu Gly
    115                 120                 125 aag cag ggc cgg cga gtc gtg gtc atc acc cag aac atc gat gag ctg      731
Lys Gln Gly Arg Arg Val Val Val Ile Thr Gln Asn Ile Asp Glu Leu
130                 135                 140                 145 cac cgc aag gct ggc acc aag aac ctt ctg gag atc cat ggt agc tta      779
His Arg Lys Ala Gly Thr Lys Asn Leu Leu Glu Ile His Gly Ser Leu
                150                 155                 160 ttt aaa act cga tgt acc tct tgt gga gtt gtg gct gag aat tac aag      827
Phe Lys Thr Arg Cys Thr Ser Cys Gly Val Val Ala Glu Asn Tyr Lys
            165                 170                 175 agt cca att tgt cca gct tta tca gga aaa ggt gct cca gaa cct gga      875
Ser Pro Ile Cys Pro Ala Leu Ser Gly Lys Gly Ala Pro Glu Pro Gly
        180                 185                 190 act caa gat gcc agc atc cca gtt gag aaa ctt ccc cgg tgt gaa gag      923
Thr Gln Asp Ala Ser Ile Pro Val Glu Lys Leu Pro Arg Cys Glu Glu
    195                 200                 205 gca ggc tgc ggg ggc ttg ctg cga cct cac gtc gtg tgg ttt gga gaa      971
Ala Gly Cys Gly Gly Leu Leu Arg Pro His Val Val Trp Phe Gly Glu
210                 215                 220                 225 aac ctg gat cct gcc att ctg gag gag gtt gac aga gag ctc gcc cac     1019
Asn Leu Asp Pro Ala Ile Leu Glu Glu Val Asp Arg Glu Leu Ala His
                230                 235                 240 tgt gat tta tgt cta gtg gtg ggc act tcc tct gtg gtg tac cca gca     1067
Cys Asp Leu Cys Leu Val Val Gly Thr Ser Ser Val Val Tyr Pro Ala
            245                 250                 255 gcc atg ttt gcc ccc cag gtg gct gcc agg ggc gtg cca gtg gct gaa     1115
Ala Met Phe Ala Pro Gln Val Ala Ala Arg Gly Val Pro Val Ala Glu
        260                 265                 270 ttt aac acg gag acc acc cca gct acg aac aga ttc agg ttt cat ttc     1163
Phe Asn Thr Glu Thr Thr Pro Ala Thr Asn Arg Phe Arg Phe His Phe
    275                 280                 285 cag gga ccc tgt gga acg act ctt cct gaa gcc ctt gcc tgt cat gaa     1211
Gln Gly Pro Cys Gly Thr Thr Leu Pro Glu Ala Leu Ala Cys His Glu
290                 295                 300                 305 aat gaa act gtt tct taa gtgtcctggg gaagaaagaa attacagtat            1259
Asn Glu Thr Val Ser
                310 atctaagaac taggccacac gcagaggaga aatggtctta tgggtggtga gctgagtact   1319
```

```
gaacaatcta aaaatagcct ctgattccct cgctggaatc caacctgttg ataagtgatg    1379
ggggtttaga agtagcaaag agcacccaca ttcaaaagtc acagaactgg aaagttaatt    1439
catattattt ggtttgaact gaaacgtgag gtatctttga tgtgtatggt tggttattgg    1499
gagggaaaaa ttttgtaaat tagattgtct aaaaaaaata gttattctga ttatattttt    1559
gttatctggg caaagtagaa gtcaagggt aaaaaccta ctattctgat ttttgcacaa     1619
gttttagtgg aaaataaaat cacactctac agtaaaaaaa aaaaaaaaa a              1670
```

<210> SEQ ID NO 14
<211> LENGTH: 310
<212> TYPE: PRT
<213> ORGANISM: Homo sapiens

<400> SEQUENCE: 14

```
Met Arg Pro Leu Gln Ile Val Pro Ser Arg Leu Ile Ser Gln Leu Tyr
  1               5                  10                  15

Cys Gly Leu Lys Pro Pro Ala Ser Thr Arg Asn Gln Ile Cys Leu Lys
                 20                  25                  30

Met Ala Arg Pro Ser Ser Met Ala Asp Phe Arg Lys Phe Phe Ala
             35                  40                  45

Lys Ala Lys His Ile Val Ile Ile Ser Gly Ala Gly Val Ser Ala Glu
 50                  55                  60

Ser Gly Val Pro Thr Phe Arg Gly Ala Gly Gly Tyr Trp Arg Lys Trp
 65                  70                  75                  80

Gln Ala Gln Asp Leu Ala Thr Pro Leu Ala Phe Ala His Asn Pro Ser
                 85                  90                  95

Arg Val Trp Glu Phe Tyr His Tyr Arg Arg Glu Val Met Gly Ser Lys
            100                 105                 110

Glu Pro Asn Ala Gly His Arg Ala Ile Ala Glu Cys Glu Thr Arg Leu
            115                 120                 125

Gly Lys Gln Gly Arg Arg Val Val Ile Thr Gln Asn Ile Asp Glu
            130                 135                 140

Leu His Arg Lys Ala Gly Thr Lys Asn Leu Leu Glu Ile His Gly Ser
145                 150                 155                 160

Leu Phe Lys Thr Arg Cys Thr Ser Cys Gly Val Val Ala Glu Asn Tyr
                165                 170                 175

Lys Ser Pro Ile Cys Pro Ala Leu Ser Gly Lys Gly Ala Pro Glu Pro
            180                 185                 190

Gly Thr Gln Asp Ala Ser Ile Pro Val Glu Lys Leu Pro Arg Cys Glu
            195                 200                 205

Glu Ala Gly Cys Gly Gly Leu Leu Arg Pro His Val Val Trp Phe Gly
        210                 215                 220

Glu Asn Leu Asp Pro Ala Ile Leu Glu Glu Val Asp Arg Glu Leu Ala
225                 230                 235                 240

His Cys Asp Leu Cys Leu Val Val Gly Thr Ser Ser Val Val Tyr Pro
                245                 250                 255

Ala Ala Met Phe Ala Pro Gln Val Ala Arg Gly Val Pro Val Ala
            260                 265                 270

Glu Phe Asn Thr Glu Thr Thr Pro Ala Thr Asn Arg Phe Arg Phe His
            275                 280                 285

Phe Gln Gly Pro Cys Gly Thr Thr Leu Pro Glu Ala Leu Ala Cys His
            290                 295                 300

Glu Asn Glu Thr Val Ser
305                 310
```

<210> SEQ ID NO 15
<211> LENGTH: 2350
<212> TYPE: DNA
<213> ORGANISM: Homo sapiens
<220> FEATURE:
<221> NAME/KEY: CDS
<222> LOCATION: (219)..(1118)

<400> SEQUENCE: 15

```
attcggggc gcgagctgcc ccagtaaatg gaaatgtttt ctaacatata aaaacctaca      60
gaagaagaaa ataattttct ggatcaaatt agaagtctgt attatattga tgtctccaga    120
ttcaaatata ttagaaagca gccgtggaga caaccatctt cattttgggc gaaataacta    180
aagcccgcct caagcattag aactacagac aaaccctg atg cga cct ctc cag att    236
                                          Met Arg Pro Leu Gln Ile
                                            1               5 gtc cca agt cga ttg att tcc cag cta tat tgt ggc ctg aag cct cca     284
Val Pro Ser Arg Leu Ile Ser Gln Leu Tyr Cys Gly Leu Lys Pro Pro
         10                  15                  20 gcg tcc aca cga aac cag att tgc ctg aaa atg gct cgg cca agt tca     332
Ala Ser Thr Arg Asn Gln Ile Cys Leu Lys Met Ala Arg Pro Ser Ser
     25                  30                  35 agt atg gca gat ttt cga aag ttt ttt gca aaa gca aag cac ata gtc     380
Ser Met Ala Asp Phe Arg Lys Phe Phe Ala Lys Ala Lys His Ile Val
 40                  45                  50 atc atc tca gga gct ggt gtt agt gca gaa agt ggt gtt ccg acc ttc     428
Ile Ile Ser Gly Ala Gly Val Ser Ala Glu Ser Gly Val Pro Thr Phe
 55                  60                  65                  70 aga gga gct gga ggt tat tgg aga aaa tgg caa gcc cag gac ctg gcg     476
Arg Gly Ala Gly Gly Tyr Trp Arg Lys Trp Gln Ala Gln Asp Leu Ala
                 75                  80                  85 act ccc ctg gcc ttt gcc cac aac ccg tcc cgg gtg tgg gag ttc tac     524
Thr Pro Leu Ala Phe Ala His Asn Pro Ser Arg Val Trp Glu Phe Tyr
             90                  95                 100 cac tac cgg cgg gag gtc atg ggg agc aag gag ccc aac gcc ggg cac     572
His Tyr Arg Arg Glu Val Met Gly Ser Lys Glu Pro Asn Ala Gly His
        105                 110                 115 cgc gcc ata gcc gag tgt gag acc cgg ctg ggc aag cag ggc cgg cga     620
Arg Ala Ile Ala Glu Cys Glu Thr Arg Leu Gly Lys Gln Gly Arg Arg
    120                 125                 130 gtc gtg gtc atc acc cag aac atc gat gag ctg cac cgc aag gct ggc     668
Val Val Val Ile Thr Gln Asn Ile Asp Glu Leu His Arg Lys Ala Gly
135                 140                 145                 150 acc aag aac ctt ctg gag atc cat ggt agc tta ttt aaa act cga tgt     716
Thr Lys Asn Leu Leu Glu Ile His Gly Ser Leu Phe Lys Thr Arg Cys
                155                 160                 165 acc tct tgt gga gtt gtg gct gag aat tac aag agt cca att tgt cca     764
Thr Ser Cys Gly Val Val Ala Glu Asn Tyr Lys Ser Pro Ile Cys Pro
            170                 175                 180 gct tta tca gga aaa ggt gct cca gaa cct gga act caa gat gcc agc     812
Ala Leu Ser Gly Lys Gly Ala Pro Glu Pro Gly Thr Gln Asp Ala Ser
        185                 190                 195 atc cca gtt gag aaa ctt ccc cgg tgt gaa gag gca ggc tgc ggg ggc     860
Ile Pro Val Glu Lys Leu Pro Arg Cys Glu Glu Ala Gly Cys Gly Gly
    200                 205                 210 ttg ctg cga cct cac gtc gtg tgg ttt gga gaa aac ctg gat cct gcc     908
Leu Leu Arg Pro His Val Val Trp Phe Gly Glu Asn Leu Asp Pro Ala
215                 220                 225                 230 att ctg gag gag gtt gac aga gag ctc gcc cac tgt gat tta tgt cta     956
Ile Leu Glu Glu Val Asp Arg Glu Leu Ala His Cys Asp Leu Cys Leu
```

```
Ile Leu Glu Glu Val Asp Arg Glu Leu Ala His Cys Asp Leu Cys Leu
            235                 240                 245 gtg gtg ggc act tcc tct gtg gtg tac cca gca gcc atg ttt gcc ccc     1004
Val Val Gly Thr Ser Ser Val Val Tyr Pro Ala Ala Met Phe Ala Pro
            250                 255                 260 cag gtg gct gcc agg ggc gtg cca gtg gct gaa ttt aac acg gag acc     1052
Gln Val Ala Ala Arg Gly Val Pro Val Ala Glu Phe Asn Thr Glu Thr
            265                 270                 275 acc cca gct acg aac aga ttc agt cat ttg atc tcc atc tca tct cta     1100
Thr Pro Ala Thr Asn Arg Phe Ser His Leu Ile Ser Ile Ser Ser Leu
        280                 285                 290 att att ata aag aat taa aacaagtcat cattgtagaa aagcaagaaa             1148
Ile Ile Ile Lys Asn
295 atgcagatag agaaaaagaa gaaaataaaa ctggagtatt tccacaaccc aagtttagag   1208
ttggccccca cctcccatgc catggactga gcagcagggg cccagcatcc cttggatatg   1268
gtggctgtgt cttcatgtga agaaactga acttggtggt ttttcctgcc agttcaggag    1328
agattcttgg catgtaatat atatcactgc tcaagtcaag cctcctaaaa ccacagacct   1388
gtttcagctg ctacttcagc caaaattctt cagcttcata ttgtcttgaa acctatgat    1448
tgtctctaac aaacaggcta cttgctagtt agaaattctt atcaatttgg caagctactt   1508
atcaaccaga ctgaccacaa gaactgtcat ctcatcaatg aaggagtaac tgatcaatga   1568
agccagcaat gctttttct tggcatcatc aaagctgaca tttagaagag atgctggtga    1628
tagtcatctc atcctactca attttttcaaa ggcagaaacc aaccctggag caattgagag  1688
gactgtttaa acacagagct taacaatggc agaattgtat atctcgtgct taacagattt   1748
tggttgaact ttaccctagg tcaggggtca gcaaactact gcctgtgggc caaatttgcc   1808
caccacctgt atctgtaaat aaggtttcat tggaacacag ctgtggccat atgtttgtat   1868
attgtgtgtg gctgcttttg cattaggatg acagaggtga atagttgcaa cagagactgg   1928
ctggtctgca aagcctaaaa tatgtcctgt gtggcccttt acagaaaaag ttttctaacc   1988
cctgctctag gttacggaga aaaaaaaatg gaataatgtt ctctgctact tttaacctga   2048
ttttctttgt acctaaatag gcagctagaa tgctgcctat atttaataa ggatttggat    2108
ctcacaagac accttaggcc tacacaagtt gttcagattc tttgcccag ttctaatcta    2168
gtgacaaagg catagaattc tcctcccaca ggaatgtatt tctattttca aggtgttaat   2228
tagttccagt tttggttttg tcgttttccc catgtccgat gcttatattg gatgatttct   2288
gataaacctg actattccaa taaaccctag gcattttga atttaaaaaa aaaaaaaaaaa  2348
aa                                                                  2350
```

<210> SEQ ID NO 16
<211> LENGTH: 299
<212> TYPE: PRT
<213> ORGANISM: Homo sapiens

<400> SEQUENCE: 16

```
Met Arg Pro Leu Gln Ile Val Pro Ser Arg Leu Ile Ser Gln Leu Tyr
1               5                   10                  15

Cys Gly Leu Lys Pro Pro Ala Ser Thr Arg Asn Gln Ile Cys Leu Lys
            20                  25                  30

Met Ala Arg Pro Ser Ser Met Ala Asp Phe Arg Lys Phe Phe Ala
        35                  40                  45

Lys Ala Lys His Ile Val Ile Ile Ser Gly Ala Gly Val Ser Ala Glu
```

-continued

```
                    50                  55                  60
Ser Gly Val Pro Thr Phe Arg Gly Ala Gly Gly Tyr Trp Arg Lys Trp
 65                  70                  75                  80

Gln Ala Gln Asp Leu Ala Thr Pro Leu Ala Phe Ala His Asn Pro Ser
                 85                  90                  95

Arg Val Trp Glu Phe Tyr His Tyr Arg Arg Glu Val Met Gly Ser Lys
            100                 105                 110

Glu Pro Asn Ala Gly His Arg Ala Ile Ala Glu Cys Glu Thr Arg Leu
        115                 120                 125

Gly Lys Gln Gly Arg Arg Val Val Ile Thr Gln Asn Ile Asp Glu
    130                 135                 140

Leu His Arg Lys Ala Gly Thr Lys Asn Leu Leu Glu Ile His Gly Ser
145                 150                 155                 160

Leu Phe Lys Thr Arg Cys Thr Ser Cys Gly Val Val Ala Glu Asn Tyr
                165                 170                 175

Lys Ser Pro Ile Cys Pro Ala Leu Ser Gly Lys Gly Ala Pro Glu Pro
            180                 185                 190

Gly Thr Gln Asp Ala Ser Ile Pro Val Glu Lys Leu Pro Arg Cys Glu
        195                 200                 205

Glu Ala Gly Cys Gly Gly Leu Leu Arg Pro His Val Val Trp Phe Gly
    210                 215                 220

Glu Asn Leu Asp Pro Ala Ile Leu Glu Glu Val Asp Arg Glu Leu Ala
225                 230                 235                 240

His Cys Asp Leu Cys Leu Val Val Gly Thr Ser Ser Val Val Tyr Pro
                245                 250                 255

Ala Ala Met Phe Ala Pro Gln Val Ala Arg Gly Val Pro Val Ala
            260                 265                 270

Glu Phe Asn Thr Glu Thr Thr Pro Ala Thr Asn Arg Phe Ser His Leu
        275                 280                 285

Ile Ser Ile Ser Ser Leu Ile Ile Ile Lys Asn
    290                 295
```

<210> SEQ ID NO 17
<211> LENGTH: 1638
<212> TYPE: DNA
<213> ORGANISM: Homo sapiens
<220> FEATURE:
<221> NAME/KEY: CDS
<222> LOCATION: (61)..(1128)

<400> SEQUENCE: 17

```
gcttccggcg gaagcggcct caacaaggga aactttattg ttcccgtggg gcagtcgagg      60 atg tcg gtg aat tac gcg gcg ggg ctg tcg ccg tac gcg gac aag ggc     108
Met Ser Val Asn Tyr Ala Ala Gly Leu Ser Pro Tyr Ala Asp Lys Gly
 1               5                  10                  15 aag tgc ggc ctc ccg gag atc ttc gac ccc ccg gag gag ctg gag cgg     156
Lys Cys Gly Leu Pro Glu Ile Phe Asp Pro Pro Glu Glu Leu Glu Arg
             20                  25                  30 aag gtg tgg gaa ctg gcg agg ctg gtc tgg cag tct tcc agt gtg gtg     204
Lys Val Trp Glu Leu Ala Arg Leu Val Trp Gln Ser Ser Ser Val Val
         35                  40                  45 ttc cac acg ggt gcc ggc atc agc act gcc tct ggc atc ccc gac ttc     252
Phe His Thr Gly Ala Gly Ile Ser Thr Ala Ser Gly Ile Pro Asp Phe
     50                  55                  60 agg ggt ccc cac gga gtc tgg acc atg gag gag cga ggt ctg gcc ccc     300
Arg Gly Pro His Gly Val Trp Thr Met Glu Glu Arg Gly Leu Ala Pro
 65                  70                  75                  80
```

```
aag ttc gac acc acc ttt gag agc gcg cgg ccc acg cag acc cac atg    348
Lys Phe Asp Thr Thr Phe Glu Ser Ala Arg Pro Thr Gln Thr His Met
                85                  90                  95 gcg ctg gtg cag ctg gag cgc gtg ggc ctc ctc cgc ttc ctg gtc agc    396
Ala Leu Val Gln Leu Glu Arg Val Gly Leu Leu Arg Phe Leu Val Ser
            100                 105                 110 cag aac gtg gac ggg ctc cat gtg cgc tca ggc ttc ccc agg gac aaa    444
Gln Asn Val Asp Gly Leu His Val Arg Ser Gly Phe Pro Arg Asp Lys
        115                 120                 125 ctg gca gag ctc cac ggg aac atg ttt gtg gaa gaa tgt gcc aag tgt    492
Leu Ala Glu Leu His Gly Asn Met Phe Val Glu Glu Cys Ala Lys Cys
    130                 135                 140 aag acg cag tac gtc cga gac aca gtc gtg ggc acc atg ggc ctg aag    540
Lys Thr Gln Tyr Val Arg Asp Thr Val Val Gly Thr Met Gly Leu Lys
145                 150                 155                 160 gcc acg ggc cgg ctc tgc acc gtg gct aag gca agg ggg ctg cga gcc    588
Ala Thr Gly Arg Leu Cys Thr Val Ala Lys Ala Arg Gly Leu Arg Ala
                165                 170                 175 tgc agg gga gag ctg agg gac acc atc cta gac tgg gag gac tcc ctg    636
Cys Arg Gly Glu Leu Arg Asp Thr Ile Leu Asp Trp Glu Asp Ser Leu
            180                 185                 190 ccc gac cgg gac ctg gca ctc gcc gat gag gcc agc agg aac gcc gac    684
Pro Asp Arg Asp Leu Ala Leu Ala Asp Glu Ala Ser Arg Asn Ala Asp
        195                 200                 205 ctg tcc atc acg ctg ggt aca tcg ctg cag atc cgg ccc agc ggg aac    732
Leu Ser Ile Thr Leu Gly Thr Ser Leu Gln Ile Arg Pro Ser Gly Asn
    210                 215                 220 ctg ccg ctg gct acc aag cgc cgg gga ggc cgc ctg gtc atc gtc aac    780
Leu Pro Leu Ala Thr Lys Arg Arg Gly Gly Arg Leu Val Ile Val Asn
225                 230                 235                 240 ctg cag ccc acc aag cac gac cgc cat gct gac ctc cgc atc cat ggc    828
Leu Gln Pro Thr Lys His Asp Arg His Ala Asp Leu Arg Ile His Gly
                245                 250                 255 tac gtt gac gag gtc atg acc cgg ctc atg gag cac ctg ggg ctg gag    876
Tyr Val Asp Glu Val Met Thr Arg Leu Met Glu His Leu Gly Leu Glu
            260                 265                 270 atc ccc gcc tgg gac ggc ccc cgt gtg ctg gag agg gcg ctg cca ccc    924
Ile Pro Ala Trp Asp Gly Pro Arg Val Leu Glu Arg Ala Leu Pro Pro
        275                 280                 285 ctg ccc cgc ccg ccc acc ccc aag ctg gag ccc aag gag gaa tct ccc    972
Leu Pro Arg Pro Pro Thr Pro Lys Leu Glu Pro Lys Glu Glu Ser Pro
    290                 295                 300 acc cgg atc aac ggc tct atc ccc gcc ggc ccc aag cag gag ccc tgc   1020
Thr Arg Ile Asn Gly Ser Ile Pro Ala Gly Pro Lys Gln Glu Pro Cys
305                 310                 315                 320 gcc cag cac aac ggc tca gag ccc gcc agc ccc aaa cgg gag cgg ccc   1068
Ala Gln His Asn Gly Ser Glu Pro Ala Ser Pro Lys Arg Glu Arg Pro
                325                 330                 335 acc agc cct gcc ccc cac aga ccc ccc aaa agg gtg aag gcc aag gcg   1116
Thr Ser Pro Ala Pro His Arg Pro Pro Lys Arg Val Lys Ala Lys Ala
            340                 345                 350 gtc ccc agc tga ccagggtgct tggggagggt ggggcttttt gtagaaactg        1168
Val Pro Ser
        355 tggattcttt ttctctcgtg gtctcacttt gttacttgtt tctgtccccg ggagcctcag  1228 ggctctgaga gctgtgctcc aggccagggg ttacacctgc cctccgtggt ccctccctgg  1288 gctccagggg cctctggtgc ggttccggga agaagccaca ccccagaggt gacagctgag  1348
```

```
cccctgccac accccagcct ctgacttgct gtgttgtcca gaggtgaggc tgggccctcc    1408
ctggtctcca gcttaaacag gagtgaactc cctctgtccc cagggcctcc cttctgggcc    1468
ccctacagcc caccctaccc ctcctccatg ggccctgcag gaggggagac ccaccttgaa    1528 gtggggatc agtagaggct tgcactgcct ttggggctgg agggagacgt gggtccacca     1588
ggcttctgga aaagtcctca atgcaataaa aacaatttct ttcttgcaaa               1638
```

<210> SEQ ID NO 18
<211> LENGTH: 355
<212> TYPE: PRT
<213> ORGANISM: Homo sapiens

<400> SEQUENCE: 18

```
Met Ser Val Asn Tyr Ala Ala Gly Leu Ser Pro Tyr Ala Asp Lys Gly
 1               5                  10                  15

Lys Cys Gly Leu Pro Glu Ile Phe Asp Pro Pro Glu Glu Leu Glu Arg
            20                  25                  30

Lys Val Trp Glu Leu Ala Arg Leu Val Trp Gln Ser Ser Ser Val Val
        35                  40                  45

Phe His Thr Gly Ala Gly Ile Ser Thr Ala Ser Gly Ile Pro Asp Phe
    50                  55                  60

Arg Gly Pro His Gly Val Trp Thr Met Glu Glu Arg Gly Leu Ala Pro
65                  70                  75                  80

Lys Phe Asp Thr Thr Phe Glu Ser Ala Arg Pro Thr Gln Thr His Met
                85                  90                  95

Ala Leu Val Gln Leu Glu Arg Val Gly Leu Leu Arg Phe Leu Val Ser
            100                 105                 110

Gln Asn Val Asp Gly Leu His Val Arg Ser Gly Phe Pro Arg Asp Lys
        115                 120                 125

Leu Ala Glu Leu His Gly Asn Met Phe Val Glu Glu Cys Ala Lys Cys
    130                 135                 140

Lys Thr Gln Tyr Val Arg Asp Thr Val Val Gly Thr Met Gly Leu Lys
145                 150                 155                 160

Ala Thr Gly Arg Leu Cys Thr Val Ala Lys Ala Arg Gly Leu Arg Ala
                165                 170                 175

Cys Arg Gly Glu Leu Arg Asp Thr Ile Leu Asp Trp Glu Asp Ser Leu
            180                 185                 190

Pro Asp Arg Asp Leu Ala Leu Ala Asp Glu Ala Ser Arg Asn Ala Asp
        195                 200                 205

Leu Ser Ile Thr Leu Gly Thr Ser Leu Gln Ile Arg Pro Ser Gly Asn
    210                 215                 220

Leu Pro Leu Ala Thr Lys Arg Gly Gly Arg Leu Val Ile Val Asn
225                 230                 235                 240

Leu Gln Pro Thr Lys His Asp Arg His Ala Asp Leu Arg Ile His Gly
                245                 250                 255

Tyr Val Asp Glu Val Met Thr Arg Leu Met Glu His Leu Gly Leu Glu
            260                 265                 270

Ile Pro Ala Trp Asp Gly Pro Arg Val Leu Glu Arg Ala Leu Pro Pro
        275                 280                 285

Leu Pro Arg Pro Pro Thr Pro Lys Leu Glu Pro Lys Glu Glu Ser Pro
    290                 295                 300

Thr Arg Ile Asn Gly Ser Ile Pro Ala Gly Pro Lys Gln Glu Pro Cys
305                 310                 315                 320

Ala Gln His Asn Gly Ser Glu Pro Ala Ser Pro Lys Arg Glu Arg Pro
```

```
                    325                 330                 335
Thr Ser Pro Ala Pro His Arg Pro Pro Lys Arg Val Lys Ala Lys Ala
            340                 345                 350

Val Pro Ser
        355

<210> SEQ ID NO 19
<211> LENGTH: 1718
<212> TYPE: DNA
<213> ORGANISM: Homo sapiens
<220> FEATURE:
<221> NAME/KEY: CDS
<222> LOCATION: (34)..(1236)

<400> SEQUENCE: 19
gcggaagcgg aagagcaggt ctccagggga gcg atg gca gcc ggg ggt ctg agc        54
                                    Met Ala Ala Gly Gly Leu Ser
                                      1               5 cgc tcc gag cgc aaa gcg gcg gag cgg gtc cgg agg ttg cgg gag gag       102
Arg Ser Glu Arg Lys Ala Ala Glu Arg Val Arg Arg Leu Arg Glu Glu
         10                  15                  20 cag cag agg gag cgc ctc cgc cag gtg tcg cgc atc ctg agg aag gcg       150
Gln Gln Arg Glu Arg Leu Arg Gln Val Ser Arg Ile Leu Arg Lys Ala
 25                  30                  35 gcg gcg gag cgc agc gcc gag gag ggc cgg ctg ctg gcc gag agc gcg       198
Ala Ala Glu Arg Ser Ala Glu Glu Gly Arg Leu Leu Ala Glu Ser Ala
 40                  45                  50                  55 gac ctg gta acg gag ctg cag ggc cgg agc cgg cgc gag ggc ctg           246
Asp Leu Val Thr Glu Leu Gln Gly Arg Ser Arg Arg Glu Gly Leu
             60                  65                  70 aag cgg cgg cag gag gag gtg tgc gac gac ccg gag gag ctg cgg ggg       294
Lys Arg Arg Gln Glu Glu Val Cys Asp Asp Pro Glu Glu Leu Arg Gly
         75                  80                  85 aag gtc cgg gag ctg gcc agc gcc gtc cgg aac gcc aaa tac ttg gtc       342
Lys Val Arg Glu Leu Ala Ser Ala Val Arg Asn Ala Lys Tyr Leu Val
 90                  95                 100 gtc tac aca ggc gcg gga atc agc acg gca gcg tct atc cca gac tac       390
Val Tyr Thr Gly Ala Gly Ile Ser Thr Ala Ala Ser Ile Pro Asp Tyr
        105                 110                 115 cgg ggc cct aat gga gtg tgg aca ctg ctt cag aaa ggg aga agc gtt       438
Arg Gly Pro Asn Gly Val Trp Thr Leu Leu Gln Lys Gly Arg Ser Val
120                 125                 130                 135 agt gct gcc gac ctg agc gag gcc gag cca acc ctc acc cac atg agc       486
Ser Ala Ala Asp Leu Ser Glu Ala Glu Pro Thr Leu Thr His Met Ser
                140                 145                 150 atc acc cgt ctg cat gag cag aag ctg gtg cag cat gtg gtg tct cag       534
Ile Thr Arg Leu His Glu Gln Lys Leu Val Gln His Val Val Ser Gln
            155                 160                 165 aac tgt gac ggg ctc cac ctg agg agt ggg ctg ccg cgc acg gcc atc       582
Asn Cys Asp Gly Leu His Leu Arg Ser Gly Leu Pro Arg Thr Ala Ile
        170                 175                 180 tcc gag ctc cac ggg aac atg tac att gaa gtc tgt acc tcc tgc gtt       630
Ser Glu Leu His Gly Asn Met Tyr Ile Glu Val Cys Thr Ser Cys Val
185                 190                 195 ccc aac agg gag tac gtg cgg gtg ttc gat gtg acg gag cgc act gcc       678
Pro Asn Arg Glu Tyr Val Arg Val Phe Asp Val Thr Glu Arg Thr Ala
200                 205                 210                 215 ctc cac aga cac cag aca ggc cgg acc tgc cac aag tgt ggg acc cag       726
Leu His Arg His Gln Thr Gly Arg Thr Cys His Lys Cys Gly Thr Gln
                220                 225                 230
```

```
ctg cgg gac acc att gtg cac ttt ggg gag agg ggg acg ttg ggg cag    774
Leu Arg Asp Thr Ile Val His Phe Gly Glu Arg Gly Thr Leu Gly Gln
        235                 240                 245 cct ctg aac tgg gaa gcg gcg acc gag gct gcc agc aga gca gac acc    822
Pro Leu Asn Trp Glu Ala Ala Thr Glu Ala Ala Ser Arg Ala Asp Thr
            250                 255                 260 atc ctg tgt cta ggg tcc agc ctg aag gtt cta aag aag tac cca cgc    870
Ile Leu Cys Leu Gly Ser Ser Leu Lys Val Leu Lys Lys Tyr Pro Arg
265                 270                 275 ctc tgg tgc atg acc aag ccc cct agc cgg cgg ccg aag ctt tac atc    918
Leu Trp Cys Met Thr Lys Pro Pro Ser Arg Arg Pro Lys Leu Tyr Ile
280                 285                 290                 295 gtg aac ctg cag tgg acc ccg aag gat gac tgg gct gcc ctg aag cta    966
Val Asn Leu Gln Trp Thr Pro Lys Asp Asp Trp Ala Ala Leu Lys Leu
        300                 305                 310 cat ggg aag tgt gat gac gtc atg cgg ctc ctc atg gcc gag ctg ggc   1014
His Gly Lys Cys Asp Asp Val Met Arg Leu Leu Met Ala Glu Leu Gly
            315                 320                 325 ttg gag atc ccc gcc tat agc agg tgg cag gat ccc att ttc tca ctg   1062
Leu Glu Ile Pro Ala Tyr Ser Arg Trp Gln Asp Pro Ile Phe Ser Leu
                330                 335                 340 gcg act ccc ctg cgt gct ggt gaa gaa ggc agc cac agt cgg aag tcg   1110
Ala Thr Pro Leu Arg Ala Gly Glu Glu Gly Ser His Ser Arg Lys Ser
345                 350                 355 ctg tgc aga agc aga gag gag gcc ccg cct ggg gac cgg ggt gca ccg   1158
Leu Cys Arg Ser Arg Glu Glu Ala Pro Pro Gly Asp Arg Gly Ala Pro
360                 365                 370                 375 ctt agc tcg gcc ccc atc cta ggg ggc tgg ttt ggc agg ggc tgc aca   1206
Leu Ser Ser Ala Pro Ile Leu Gly Gly Trp Phe Gly Arg Gly Cys Thr
                380                 385                 390 aaa cgc aca aaa agg aag aaa gtg acg taa tcacgtgctc gatgaagaac     1256
Lys Arg Thr Lys Arg Lys Lys Val Thr
                395                 400 agttggcact ttgcagatgg ccagtgtcac ggtgaaggct gggttgcccc cacgggtcta  1316
gggagaacga actctttggg gatgacattt tcaccgtgac attttagcc atttgtcctt   1376 gaggaagccc cttgcactgc tgcggttgta ccctgatacg gcctggccat cgaggacacc  1436
tgcccatccg gcctctgtgt caagaggtgg cagccgcacc tttctgtgag aacggaactc  1496
gggttatttc agccccggcc tgcagagtgg aagcgcccag cggcctttcc tcgctcacca  1556
ggccagtctc agggcctcac cgtatttcta ctactactta atgaaaaagt gtgaacttta  1616
tagaatcctc tctgtactgg atgtgcggca gaggggtggc tccgagcctc ggctctatgc  1676
agaccttttt atttctatta aacgtttctg cactggcaaa aa                    1718
```

<210> SEQ ID NO 20
<211> LENGTH: 400
<212> TYPE: PRT
<213> ORGANISM: Homo sapiens

<400> SEQUENCE: 20

```
Met Ala Ala Gly Gly Leu Ser Arg Ser Glu Arg Lys Ala Ala Glu Arg
1               5                   10                  15

Val Arg Arg Leu Arg Glu Glu Gln Gln Arg Glu Arg Leu Arg Gln Val
            20                  25                  30

Ser Arg Ile Leu Arg Lys Ala Ala Ala Glu Arg Ser Ala Glu Glu Gly
        35                  40                  45

Arg Leu Leu Ala Glu Ser Ala Asp Leu Val Thr Glu Leu Gln Gly Arg
    50                  55                  60
```

-continued

```
Ser Arg Arg Arg Glu Gly Leu Lys Arg Arg Gln Glu Val Cys Asp
 65              70                  75                  80

Asp Pro Glu Glu Leu Arg Gly Lys Val Arg Glu Leu Ala Ser Ala Val
             85                  90                  95

Arg Asn Ala Lys Tyr Leu Val Val Tyr Thr Gly Ala Gly Ile Ser Thr
            100                 105                 110

Ala Ala Ser Ile Pro Asp Tyr Arg Gly Pro Asn Gly Val Trp Thr Leu
            115                 120                 125

Leu Gln Lys Gly Arg Ser Val Ser Ala Ala Asp Leu Ser Glu Ala Glu
130             135                 140

Pro Thr Leu Thr His Met Ser Ile Thr Arg Leu His Glu Gln Lys Leu
145                 150                 155                 160

Val Gln His Val Val Ser Gln Asn Cys Asp Gly Leu His Leu Arg Ser
                165                 170                 175

Gly Leu Pro Arg Thr Ala Ile Ser Glu Leu His Gly Asn Met Tyr Ile
            180                 185                 190

Glu Val Cys Thr Ser Cys Val Pro Asn Arg Glu Tyr Val Arg Val Phe
        195                 200                 205

Asp Val Thr Glu Arg Thr Ala Leu His Arg His Gln Thr Gly Arg Thr
    210                 215                 220

Cys His Lys Cys Gly Thr Gln Leu Arg Asp Thr Ile Val His Phe Gly
225                 230                 235                 240

Glu Arg Gly Thr Leu Gly Gln Pro Leu Asn Trp Glu Ala Ala Thr Glu
                245                 250                 255

Ala Ala Ser Arg Ala Asp Thr Ile Leu Cys Leu Gly Ser Ser Leu Lys
            260                 265                 270

Val Leu Lys Lys Tyr Pro Arg Leu Trp Cys Met Thr Lys Pro Pro Ser
            275                 280                 285

Arg Arg Pro Lys Leu Tyr Ile Val Asn Leu Gln Trp Thr Pro Lys Asp
290                 295                 300

Asp Trp Ala Ala Leu Lys Leu His Gly Lys Cys Asp Asp Val Met Arg
305                 310                 315                 320

Leu Leu Met Ala Glu Leu Gly Leu Glu Ile Pro Ala Tyr Ser Arg Trp
                325                 330                 335

Gln Asp Pro Ile Phe Ser Leu Ala Thr Pro Leu Arg Ala Gly Glu Glu
            340                 345                 350

Gly Ser His Ser Arg Lys Ser Leu Cys Arg Ser Arg Glu Glu Ala Pro
            355                 360                 365

Pro Gly Asp Arg Gly Ala Pro Leu Ser Ser Ala Pro Ile Leu Gly Gly
    370                 375                 380

Trp Phe Gly Arg Gly Cys Thr Lys Arg Thr Lys Arg Lys Lys Val Thr
385                 390                 395                 400
```